(12) United States Patent
Griffioen et al.

(10) Patent No.: US 8,618,138 B2
(45) Date of Patent: Dec. 31, 2013

(54) INDOLE AMIDE DERIVATIVES AND RELATED COMPOUNDS FOR USE IN THE TREATMENT OF NEURODEGENERATIVE DISEASES

(75) Inventors: Gerard Griffioen, Linden (BE); Tom Van Dooren, Koningshooikt (BE); Veronica Rojas De La Parra, Haasrode (BE); Arnaud Marchand, Korbeek/Lo (BE); Sara Allasia, Mechelen (BE); Amuri Kilonda, Roosbeek-Boutersem (BE); Patrick Chaltin, Jodoigne (BE)

(73) Assignees: Katholieke Universiteit Leuven, K.U. Leuven R&D, Leuven (BE); reMYND, Heverlee (BE)

( * ) Notice: Subject to any disclaimer, the term of this patent is extended or adjusted under 35 U.S.C. 154(b) by 0 days.

(21) Appl. No.: 13/377,505

(22) PCT Filed: Jun. 11, 2010

(86) PCT No.: PCT/EP2010/058271
§ 371 (c)(1),
(2), (4) Date: Dec. 9, 2011

(87) PCT Pub. No.: WO2010/142801
PCT Pub. Date: Dec. 16, 2010

(65) Prior Publication Data
US 2012/0083475 A1   Apr. 5, 2012

(30) Foreign Application Priority Data
Jun. 11, 2009   (GB) .................................. 0910003.3

(51) Int. Cl.
*A61K 31/4439* (2006.01)
*A61K 31/422* (2006.01)
*C07D 413/14* (2006.01)
*C07D 261/18* (2006.01)

(52) U.S. Cl.
USPC ......... 514/339; 514/378; 546/272.1; 548/248

(58) Field of Classification Search
None
See application file for complete search history.

(56) References Cited

U.S. PATENT DOCUMENTS

| | | | |
|---|---|---|---|
| 5,314,886 A | 5/1994 | Becker | |
| 7,101,878 B1 * | 9/2006 | Anderson et al. | 514/231.5 |
| 7,666,888 B2 * | 2/2010 | Bartberger et al. | 514/378 |
| 2005/0239689 A1 | 10/2005 | Thorson | |
| 2007/0105937 A1 | 5/2007 | Pappolla | |
| 2009/0005359 A1 | 1/2009 | Cossrow et al. | |

FOREIGN PATENT DOCUMENTS

| | | |
|---|---|---|
| JP | 9 087237 | 3/1997 |
| JP | 09087237 A | 3/1997 |
| WO | 0055144 A1 | 9/2000 |
| WO | WO 00/55144 | 9/2000 |
| WO | 2005115977 A1 | 12/2005 |
| WO | WO 2005/115977 | 12/2005 |
| WO | WO 2006/062224 | 6/2006 |
| WO | WO 2008/152099 | 12/2008 |
| WO | WO 2009/037244 | 3/2009 |
| WO | 2010142801 A1 | 12/2010 |

OTHER PUBLICATIONS

Antonio R. Damasio, Alzheimer's Disease and Related Dementias, Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL: http://www.cnn.com/2003/HEALTH/conditions/09/24/alzheimers.drug.ap/indez.html, pp. 1 and 2.*
Chemcats Accession No. 2041655837; CAS Registry No. 92483838-0; Chemcats Accession No. 2041655832; CAS Registry No. 924824-73-7; Chemcats Accession No. 2041653100; CAS Registry No. 924841-23-6; TimTIc Stock Library; Nov. 20, 2007.
Chemcats Acdession No. 2068130438; CAS Registry No. 1111459-60-9; Enamine ScreeningLibrary; Apr. 3, 2009.
Chemcats Accession No. 2038047808; CAS Registry No. 832332-82-6; Aurora Screening Library; Feb. 9, 2009.
Answer 1 of 10 CAPLUS WO 2009/047240; SmithklineBeechem; 2009.
International Search Report; PCT/EP2010/058271 dated Aug. 4, 2010.

* cited by examiner

*Primary Examiner* — Alicia L Otton
(74) *Attorney, Agent, or Firm* — TraskBritt

(57) ABSTRACT

This invention provides novel compounds and the novel compounds for use as a medicine, more in particular for the prevention or treatment of neurodegenerative disorders, more specifically certain neurological disorders, such as disorders collectively known as tauopathies, and disorders characterized by cytotoxic α-synuclein amyloidogenesis. The present invention also relates to the use of said novel compounds for the manufacture of medicaments useful for treating such neurodegenerative disorders. The present invention further relates to pharmaceutical compositions including said novel compounds and to methods for the preparation of said novel compounds.

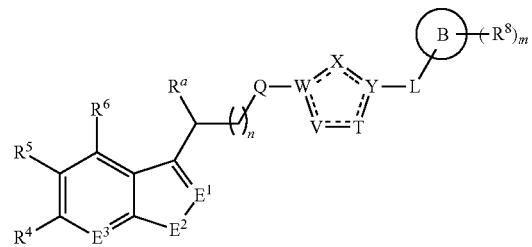

18 Claims, 2 Drawing Sheets

INDOLE AMIDE DERIVATIVES AND RELATED COMPOUNDS FOR USE IN THE TREATMENT OF NEURODEGENERATIVE DISEASES

CROSS-REFERENCE TO RELATED APPLICATIONS

This is a national phase entry under 35 U.S.C. §371 of international Patent Application PCT/EP2010/058271, filed Jun. 11, 2010, published in English as International Patent Publication WO 2010/142801 A1 on Dec. 16, 2010, which claims the benefit under Article 8 of the Patent Cooperation Treaty to the United Kingdom Patent Application Serial No. 0910003.3, filed Jun. 11, 2009.

FIELD OF THE INVENTION

The present invention relates to novel compounds and to the novel compounds for use as a medicine, more in particular for the prevention or treatment of neurodegenerative disorders, more specifically certain neurological disorders, such as disorders collectively known as tauopathies, and disorders characterised by cytotoxic α-synuclein amyloidogenesis. The present invention also relates to the compounds for use as a medicaments and to the use of said compounds for the manufacture of medicaments useful for treating such neurodegenerative disorders. The present invention further relates to pharmaceutical compositions including said novel compounds and to methods for the preparation of said novel compounds.

BACKGROUND OF THE INVENTION

TAU is an intracellular protein with the ability to bind and consequently stabilise and define microtubule structure and function. Apart from this physiological function TAU also plays a direct role in numerous neurodegenerative disorders collectively known as "tauopathies" with the most notable examples being Alzheimer's disease, Pick's disease, corticobasal degeneration, progressive supranuclear palsy, frontotemporal dementia and parkinsonism linked to chromosome 17 (FTDP-17).

Tauopathies are characterised by insoluble aggregates or polymers of tau which are formed by self-polymerisation of tau monomers. The precise molecular mechanisms involved in TAU aggregation is not clearly known but may involve partial denaturation or misfolding of the TAU protein in conformations with a high propensity to self-organise into higher order structures. An important aspect of the TAU aggregation is its inherent cytotoxicity, which reduces cellular integrity or even triggers cell death. In case of neurodegenerative diseases, loss of affected neurons leads to cognitive and/or motor dysfunctioning. A direct role of TAU in disease onset has been established unequivocally by the elucidation of familial mutations in TAU which appear to be responsible for a very early and sometimes aggressive form of tauopathy. Such mutations comprise changes in the amino acid sequence of TAU that promote toxic aggregation and thereby provoke loss of cellular integrity.

Treatments aimed to suppress cytotoxic TAU pathology are presently not available. Currently used treatments for Alzheimer's disease offer a small symptomatic benefit, but no treatments to delay or halt the progression of the disease are available. Thus there is a need in the art for designing new drugs for therapeutic treatments that target the underlying molecular mechanism of TAU-related pathologies such as Alzheimer's disease, or at least retard the onset of the most disabilitating manifestations thereof.

α-Synuclein is a neuronal protein which originally has been associated with neuronal plasticity during Zebra finch song learning. Although its role at the molecular level is at present largely elusive it appears to have lipid bi-layer (or membrane) with binding properties important for preserving proper transport of neurotransmitter vesicles to the axonal ends of neurons presumably to ensure proper signalling at the synapse. Apart from its physiological role in brain cells, human α-synuclein also possesses pathological features that underlies a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist, which aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a need in the art for designing new drugs for therapeutic treatments that target the underlying molecular mechanism of α-synuclein related pathologies in order to reduce neuronal cell death and/or degeneration.

It is also known to the skilled in the art that the physicochemical properties of known drugs as well as their ADME-Tox (administration, distribution, metabolism, excretion) properties may limit or prohibit their use in the treatment of diseases. Therefore, a problem of existing drugs that can be overcome with the compounds of the invention can be selected from a poor or inadequate physicochemical or ADME-Tox properties such as solubility, LogP, CYP inhibition, hepatic stability, plasmatic stability, among others.

SUMMARY OF THE INVENTION

The present invention is based on the unexpected finding that at least one of the above-mentioned problems can be solved by a novel class of compounds. The present invention provides compounds which are useful for preventing or treating neurodegenerative disorders, especially tauopathies. The present invention demonstrates that these compounds efficiently inhibit the tau-aggregation induced toxicity which is responsible for neurodegeneration. Therefore, these novel compounds constitute a useful class of compounds that can be used in the treatment and/or prevention of neurodegenerative disorders in animals, more specifically in humans.

A first aspect of the present invention therefore provides compounds according to formula (AA1),

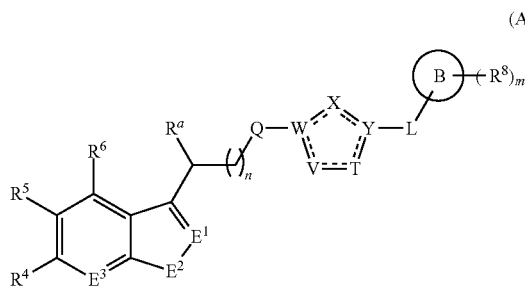

(AA1)

wherein,
each dotted line individually represents an optional double bond, wherein maximally two dotted lines selected from the five dotted lines are a double bond;
$E^1$ is independently selected from $CR^1$; and N;
$E^2$ is independently selected from $NR^2$; and O;
$E^3$ is independently selected from $CR^3$; and N;

$R^a$ is hydrogen or can be taken together with $R^b$ to form a substituted or unsubstituted 4, 5, 6, 7 or 8 membered ring containing one N atom, preferably a piperidine ring;
$R^b$ is hydrogen or can be taken together with $R^a$ to form a substituted or unsubstituted 4, 5, 6, 7 or 8 membered ring containing one N atom, preferably a piperidine ring;
Q is independently selected from $NR^b$—C(O); C(O); and C(O)NH;
each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$—$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
$R^2$ is selected from hydrogen; alkyl; alkenyl; and alkynyl;
n is selected from 0; 1 or 2;
each of X, Y, T, W and V is independently selected from —$CZ^1H$—; —$CZ^1$—; —C—; —N—; $NR^{101}$; —O—; —S—; or —CO—; wherein at least one of X, Y, T; W or V is selected from —$CZ^1H$— or —$CZ^1$— or —C—; and whereby Y is selected from —$CZ^1$—; —C—; or —N—;
L is independently selected from being not present; —O—; —NH—; —$NR^{10}$—; $C_{1-6}$alkylene; $C_{1-6}$alkenylene; $C_{1-6}$alkynylene;
wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or $S(O)_2$;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$;

—NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; cyano; —COOH; —COOR$^{10}$; —C(O)NR$^{12}$R$^{13}$; —C(O)R$^{11}$;

each Z$^1$ is independently selected from hydrogen; alkyl; and Z;

each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein R$^{12}$ and R$^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

In another particular embodiment of the present invention, L is selected from —O—; —NH—; —NR$^{10}$—; C$_{1-3}$alkylene; C$_{1-3}$alkenylene; C$_{1-3}$alkynylene; yet more in particular L is selected from —O—; —NH—; —NR$^{10}$—; C$_{1-2}$alkylene; C$_{1-2}$alkenylene; C$_{1-2}$alkynylene; still more in particular L is selected from —O—; —NH—; —NR$^{10}$—; and —CH$_2$—; yet still more in particular L is —CH$_2$—.

In another particular embodiment, the compounds of the invention are not selected from N-[2-(5-chloro-2-methyl-1H-indol-3-yl)ethyl]-1-(tetrahydro-2-furanylmethyl)-1H-1,2,3-triazole-4-carboxamide.

In another particular embodiment, R$^5$ is halogen. In yet another particular embodiment, R$^5$ can not be Cl, while R$^2$ is Me.

In a particular embodiment of the present invention and of all formulas herein, each of X, Y, T, W and V is independently selected from —CZ$^1$H—; —CZ$^1$—; —C—; —N—; NR$^{101}$; —O—; —S—; or —CO—; and form with the dotted lines one of the cycles having one of the structural formula (Ia), (IIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa):

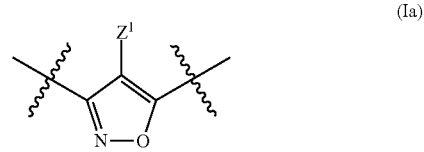

(Ia)

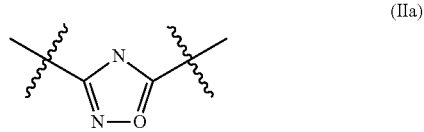

(IIa)

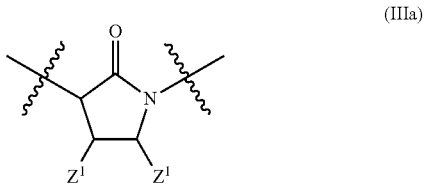

(IIIa)

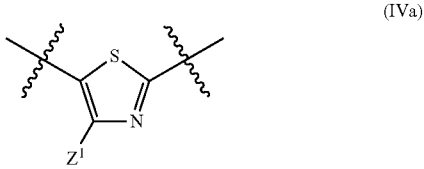

(IVa)

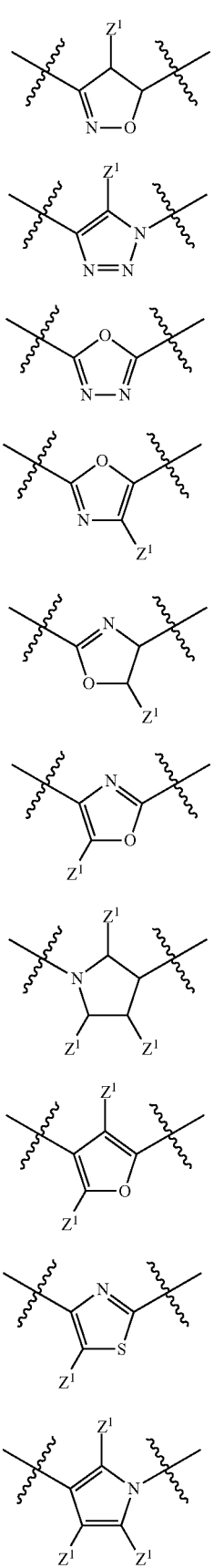
(Va)
(VIa)
(VIIa)
(VIIIa)
(IXa)
(Xa)
(XIa)
(XIIa)
(XIIIa)
(XIVa)
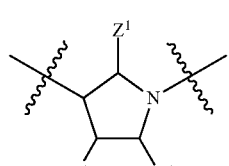
(XVa)
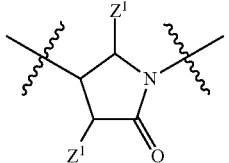
(XVIa)
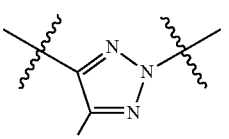
(XVIIa)
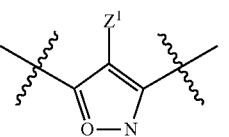
(XVIIIa)
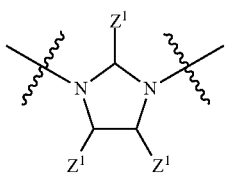
(XIXa)
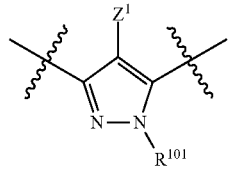
(XXa)
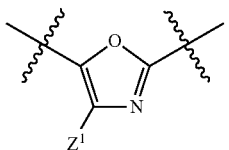
(XXIa)
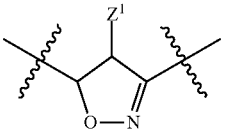
(XXIIa)
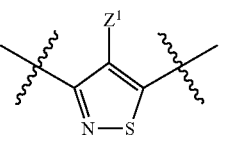
(XXIIIa)

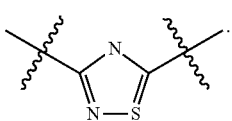

In another particular embodiment, the present invention concerns compound of formula (AA1), or a stereoisomer, enantiomer or tautomer thereof wherein
  each dotted line individually represents an optional double bond, wherein maximally two dotted lines selected from the five dotted lines are a double bond;
  $E^1$ is independently selected from $CR^1$; and N;
  $E^2$ is independently selected from $NR^2$; and O;
  $E^3$ is independently selected from $CR^3$; and N;
  Q is independently selected from $NR^b$—C(O); C(O); and C(O)NH;
  $R^a$ is hydrogen or can be taken together with $R^b$ to form a substituted or unsubstituted unsaturated 4, 5, 6, 7 or 8 membered ring containing one N atom;
  $R^b$ is hydrogen or can be taken together with $R^a$ to form a substituted or unsubstituted unsaturated 4, 5, 6, 7 or 8 membered ring containing one N atom;
  each $R^1$, $R^3$, $R^4$, and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; cyano; —COOH; —$COOR^{10}$—$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
    and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
  $R^2$ is selected from hydrogen; alkyl; alkenyl; and alkynyl;
  $R^5$ is selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
    and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
  n is selected from 0; 1 or 2;
  B represents a cyclic structure selected from cycloalkyl; cycloalkenyl; cycloalkynyl; aryl; and heterocycle;
  m is selected from 0; 1; 2; 3; 4 and 5;
  $R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
    wherein said alkyl, alkenyl and alkynyl optionally includes one or more heteroatoms, said heteroatoms being selected from the atoms O, S and N;
    and wherein said alkyl, alkenyl and alkynyl can be unsubstituted or substituted with Z;
    and wherein a carbon atom or heteroatom of said alkyl, alkenyl and alkynyl, can be oxidized to form a C=O, C=S, N=O, N=S, S=O or $S(O)_2$;
  each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
  each $Z^1$ is independently selected from hydrogen; alkyl; and Z;
  each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
    and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
  each $R^{101}$ is independently selected from hydrogen and $R^{10}$;
  each $R^{11}$ is independently selected from hydroxyl; alkyl; alkenyl; alkynyl; aryl; heterocycle; arylalkylene; arylalkenylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

wherein L is independently selected from —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=S, N=O, N=S, S=O or $S(O)_2$;

and each of X, Y, T, W and V is independently selected from —$CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa) as described herein.

In another particular embodiment of the present invention, L is a straight unbranched linking chain of atoms linking B with the five membered ring, whereby said straight linking chain of atoms is maximally three, more specifically two, yet more specifically one atom long, whereby said atoms are selected from C, O and N.

In another particular embodiment of the present invention, L is selected from —O—; —NH—; —$NR^{10}$—; $C_{1-3}$alkylene; $C_{1-3}$alkenylene; $C_{1-3}$alkynylene; yet more in particular L is selected from —O—; —NH—; —$NR^{10}$—; $C_{1-2}$alkylene; $C_{1-2}$alkenylene; $C_{1-2}$alkynylene; still more in particular L is selected from —O—; —NH—; —$NR^{10}$—; and —$CH_2$—; yet still more in particular L is —$CH_2$—.

In another particular embodiment, the compounds of the invention are not selected from N-[2-(5-chloro-2-methyl-1H-indol-3-yl)ethyl]-1-(tetrahydro-2-furanylmethyl)-1H-1,2,3-triazole-4-carboxamide.

In another particular embodiment, L is a single bond or is not present for a selection of compounds whereby X, Y, T, W and V form with the dotted lines formulae described herein, such as for formula (III).

In another particular embodiment, $R^5$ is halogen. In yet another particular embodiment, $R^5$ cannot be Cl, while $R^1$ is Me.

In another particular embodiment, specifically when each of X, Y, T, W and V form with the dotted lines formula (VI), the $Z^1$ substituent in such formula (VI) is selected from hydrogen. In another particular embodiment, each of X, Y, T, W and V can not form with the dotted lines formula (VI). In another particular embodiment, each of X, Y, T, W and V can not form with the dotted lines formula (IV), (XVI), or (XX).

In another particular embodiment, each of X, Y, T, W and V is independently selected from —$CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (Va), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa), more in particular having one of the structural formula (Ia), (IIa), (Va), (XVIIIa), (XXIIa), (XXIIIa) or (XXIVa) as described herein.

In a particular embodiment, each $R^1$, $R^3$, $R^4$, and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; and alkynyl. More in particular, each $R^1$, $R^3$, $R^4$, and $R^6$ is independently selected from hydrogen; halogen; —OH; —$OR^{10}$; —SH; —$SR^{10}$; trifluoromethyl; trifluoromethoxy; nitro; alkyl; alkenyl; and alkynyl.

In another particular embodiment, $R^1$ is hydrogen or alkyl, more in particular is hydrogen. In another particular embodiment, $R^2$ is hydrogen or alkyl, yet more in particular is hydrogen. In another particular embodiment, $R^3$ is hydrogen. In another particular embodiment, $R^4$ is hydrogen. In another particular embodiment, $R^6$ is hydrogen. In another particular embodiment, $R^3$, $R^4$ and $R^6$ are hydrogen.

In another particular embodiment, $R^1$ and $R^2$ are each hydrogen when X, Y, T, W and V form the cycle of formulae (VI), (XVI) or (XX).

In another particular embodiment, $R^8$ is not selected from —$NHC(O)R^{10}$. In another particular embodiment, $R^8$ is not 2-methylenetetrahydrofuranyl. In another particular embodiment, $R^8$ is selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C=S, N=O, N=S, S=O or S(O)$_2$.

In another particular embodiment, R$^8$ is selected from hydrogen; halogen; alkyl; alkenyl; alkynyl; —OH; —OR$^{10}$; —SH; —SR$^{10}$; trifluoromethyl; trifluoromethoxy; —NR$^{12}$R$^{13}$; -cyano. In another particular embodiment, R$^8$ is selected from hydrogen; halogen; linear alkyl; linear alkenyl; linear alkynyl; —OH; —OR$^{10}$; —SH; —SR$^{10}$; trifluoromethyl; trifluoromethoxy; —NR$^{12}$R$^{13}$; -cyano. In another particular embodiment, R$^8$ does not comprise a cyclic ring structure (for example selected from cyclic alkyl, cyclic alkenyl, cyclic alkynyl, aryl or heterocycle). In a particular embodiment, R$^8$ is halogen, yet more in particular is fluor.

In another particular embodiment, R$^8$ is not 2-methylenetetrahydrofuranyl and R$^2$ is hydrogen when X, Y, T, W and V form the cycle of formula (VI).

In another particular embodiment, m is 2.

In yet another particular embodiment, the compounds of the invention comprise maximally three monocyclic or cyclic fused ring systems selected from aryl or heterocycle. In yet another particular embodiment, the compounds of the invention comprise maximally ring systems, whereby said three ring systems consist of:
indole;
the five-membered ring comprising X, Y, T, W and V; and
B.

In another particular embodiment, each of X, Y, T, W and V is independently selected from —CZ$^1$H—; —CZ$^1$—; —C—; —N—; NR$^{101}$; —O—; —S—; or —CO—; and are more in particular selected from (Ia), (IIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa): wherein
Z$^1$ is independently selected from hydrogen, alkyl and Z;
Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; NR$^{12}$R$^{13}$; -cyano; —COOH; —COOR$^{10}$; —C(O)NR$^{12}$R$^{13}$; —C(O)R$^{11}$;

each R$^{10}$ is independently selected from alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;

each R$^{12}$ and R$^{13}$ is independently selected from hydrogen; alkyl; alkenyl; alkynyl; wherein said alkyl, alkenyl, alkynyl, optionally include one or more heteroatoms in the alkyl, alkenyl or alkynyl moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$.

In another particular embodiment, each of X, Y, T, W and V is independently selected from —CZ$^1$H—; —CZ$^1$—; —C—; —N—; NR$^{101}$; —O—; —S—; or —CO—; and are more in particular selected from (Ia), (IIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa): wherein
Z$^1$ is independently selected from hydrogen; alkyl; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each R$^{10}$ is independently selected from alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;

each R$^{12}$ and R$^{13}$ is independently selected from hydrogen; alkyl; alkenyl; alkynyl; wherein said alkyl, alkenyl, alkynyl, optionally include one or more heteroatoms in the alkyl, alkenyl or alkynyl moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$.

In another particular embodiment, each of X, Y, T, W and V is independently selected from —CH$_2$—; —CH—; —C—; —N—; NH; —O—; —S—; or —CO—.

In another particular embodiment, each of X, Y, T, W and V is independently selected from —CH$_2$—; —CH—; —C—; —N—; NH; —O—; —S—; or —CO— and form with the dotted lines one of the cycles having one of the structural formula (Ia'), (IIa'), (IIIa'), (Va'), (VIIa'), (VIIIa'), (Ixa'), (Xa'), (XIa'), (XIIa'), (XIIIa'), (XIVa'), (Xva'), (XVIa'), (XVIIa'), (XVIIIa'), (XIXa'), (Xxa'), (XXIa'), (XXIIa'), (XXIIIa') or (XXIVa'):

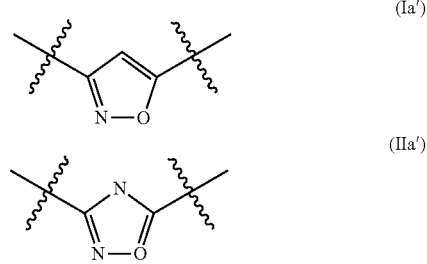

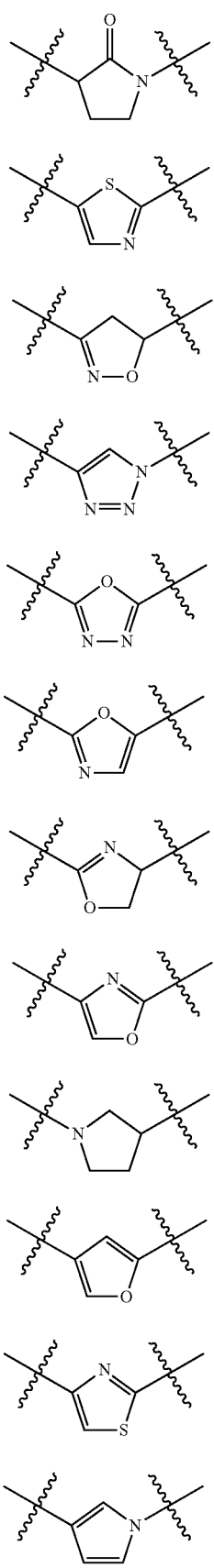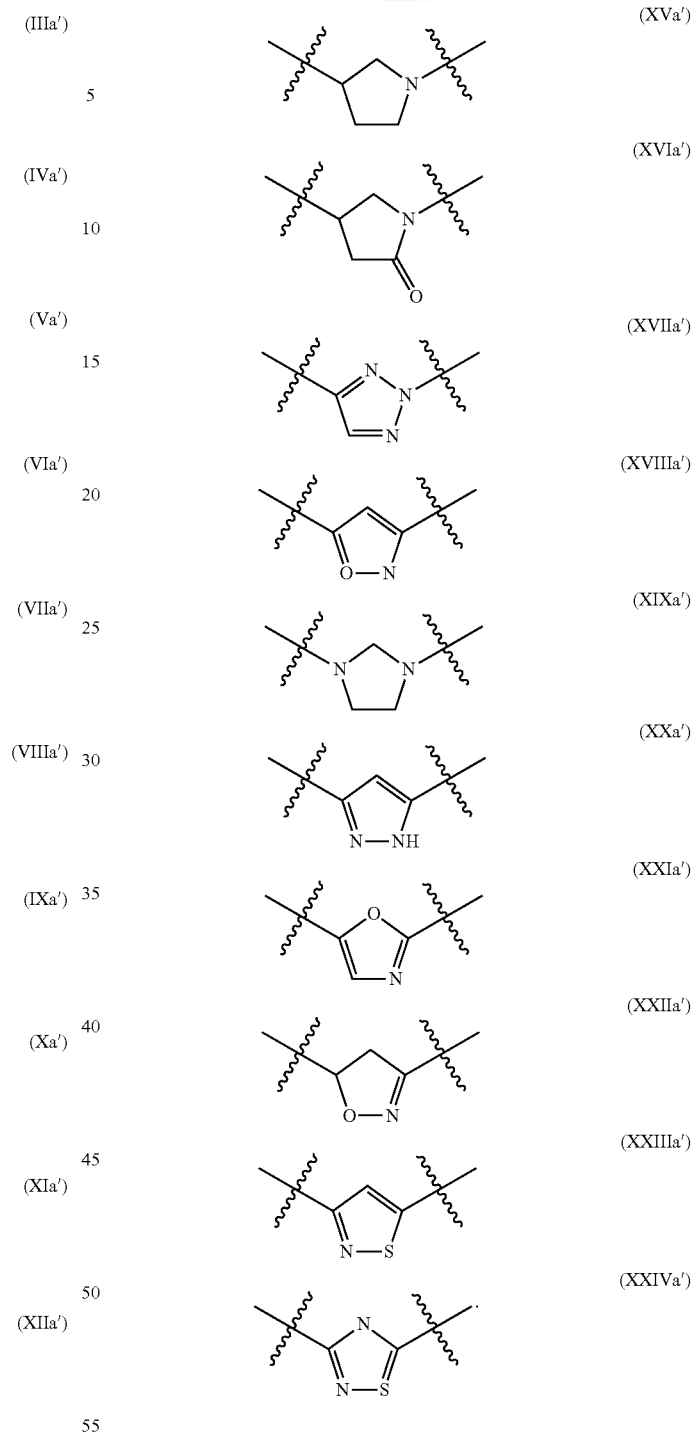

In an embodiment, the present invention concerns compound of formula (AA1), or a stereoisomer, enantiomer or tautomer thereof wherein each dotted line individually represents an optional double bond, wherein maximally two dotted lines selected from the five dotted lines are a double bond;

$E^1$ is independently selected from $CR^1$; and N;

$E^2$ is independently selected from $NR^2$; and O;

$E^3$ is independently selected from $CR^3$; and N;

Q is independently selected from $NR^b$—C(O); C(O); and C(O)NH;

$R^a$ is hydrogen or can be taken together with $R^b$ to form a substituted or unsubstituted unsaturated 4, 5, 6, 7 or 8 membered ring containing one N atom;

$R^b$ is hydrogen or can be taken together with $R^a$ to form a substituted or unsubstituted unsaturated 4, 5, 6, 7 or 8 membered ring containing one N atom;

each $R^1$, $R^3$, $R^4$, and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^2$ is selected from hydrogen; alkyl; alkenyl; and alkynyl;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; -alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

n is selected from 0; 1 or 2;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

wherein L is independently selected from —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=S, N=O, N=S, S=O or $S(O)_2$;

and each of X, Y, T, W and V is independently selected from —$CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), (XIXa), (XXIa), (XXIIa), (XXIIIa) or (XXIVa), (Ia)

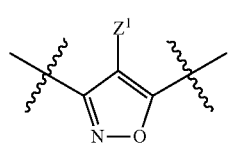

(IIa)

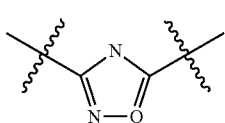

(IIIa)

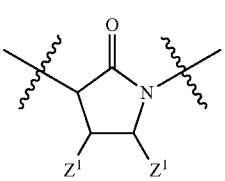

(IVa)

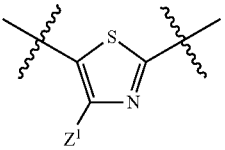

(Va)

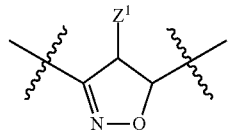

(VIIa)

(VIIIa)

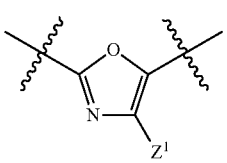

(IXa)

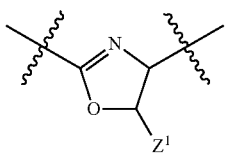

(Xa)

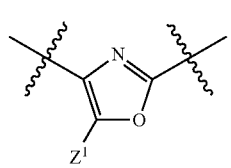

(XIa)

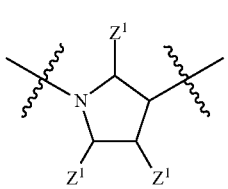

(XIIa)

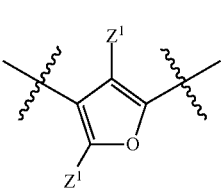

(XIIIa)

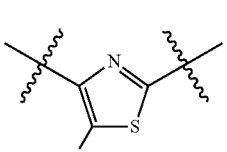

(XIVa)

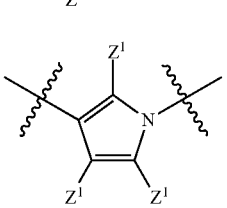

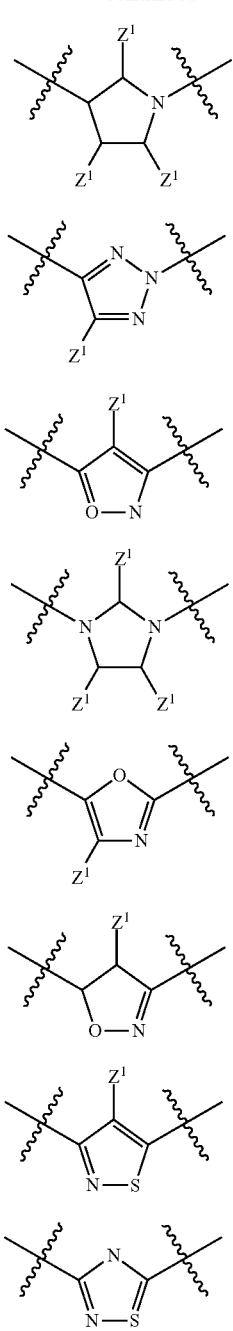

or wherein L is selected from a single bond, and X, Y, T, W and V form with the dotted lines a cycle of formula (IIIa),

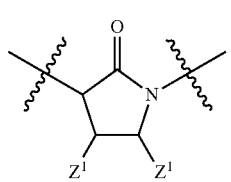

wherein the left side of the formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), (XIXa), (XXIa), (XXIIa), (XXIIIa), (XXIVa) is attached to Q and the right side thereof is attached to L; or a solvate, hydrate, salt or prodrug thereof.

In a particular embodiment of the present invention, the compounds have a structure according to formula (AA1) or other formulae herein, wherein $E^1$ is $CR^1$, $E^2$ is $NR^2$, and $E^3$ is $CR^3$; or $E^1$ is N, $E^2$ is $NR^2$, and $E^3$ is $CR^3$; or $E^1$ is $CR^1$, $E^2$ is $NR^2$, and $E^3$ is N; or $E^1$ is $CR^1$, $E^2$ is O, and $E^3$ is $CR^3$.

In a particular embodiment of the present invention, the compounds have a structure according to the formulas (AA2), (AA3), or (AA4):

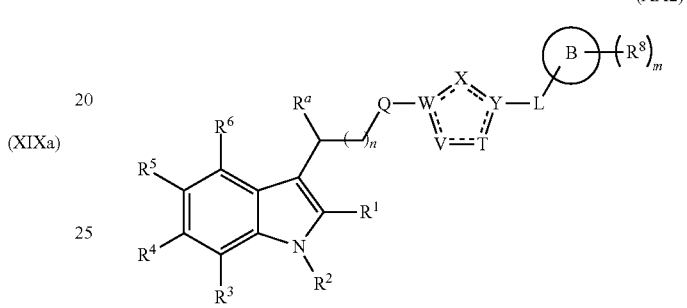

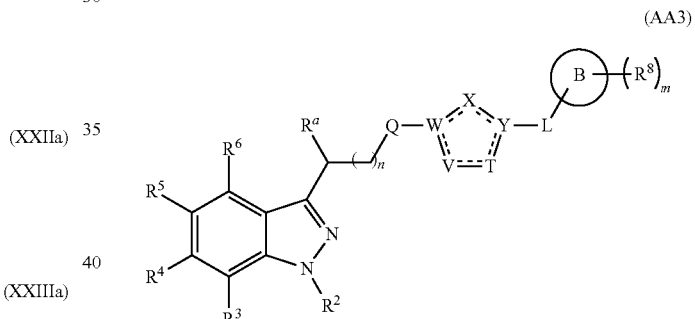

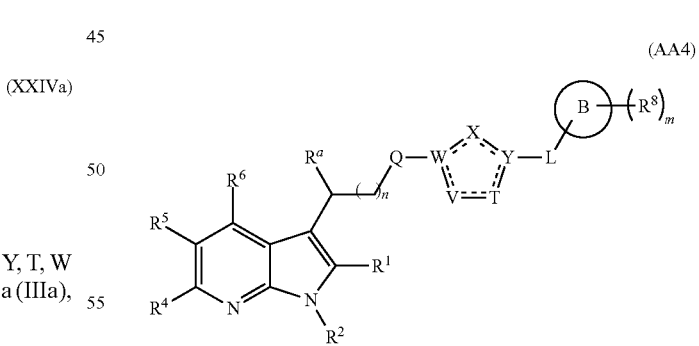

wherein $R^1$, $R^2$, $R^3$, $R^4$, $R^5$, $R^6$, $R^8$, $R^a$, Q, W, X, Y, V, T, L, B, m, n have the same meaning as that defined herein.

In another particular embodiment of the invention, the compounds have a structure according to the formulas (AA1), (AA2), (AA3), or (AA4), wherein Q is $NR^b$—C(O). In yet another particular embodiment, both $R^a$ and $R^b$ are hydrogen.

In a more particular embodiment the present invention therefore provides compounds according to formula (A1), (A1)

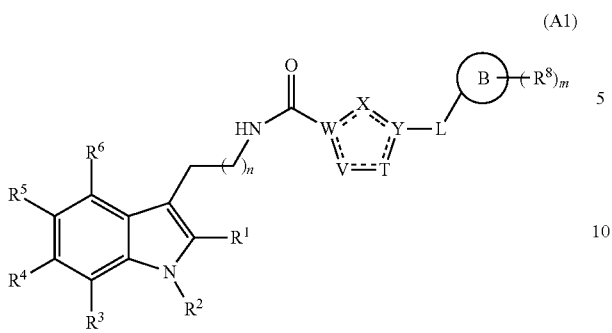

wherein,
  each dotted line individually represents an optional double bond, wherein maximally two dotted lines selected from the five dotted lines are a double bond;
  each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
    and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;
  $R^2$ is selected from hydrogen; alkyl; alkenyl; and alkynyl;
  n is selected from 0; 1 or 2;
  each of X, Y, T, W and V is independently selected from —$CZ^1H$—; —$CZ^1$—; —C—; —N—; $NR^{101}$; —O—; —S—; or —CO—; wherein at least one of X, Y, T; W or V is selected from —$CZ^1H$— or —$CZ^1$— or —C—;
  L is independently selected from being not present; —O—; —NH—; —$NR^{10}$—; $C_{1-6}$alkylene; $C_{1-6}$alkenylene; $C_{1-6}$alkynylene;
    wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
    and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;
  B represents a cyclic structure selected from cycloalkyl; cycloalkenyl; cycloalkynyl; aryl; and heterocycle;
  m is selected from 0; 1; 2; 3; 4 and 5;
  $R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
    wherein said alkyl, alkenyl and alkynyl optionally includes one or more heteroatoms, said heteroatoms being selected from the atoms O, S and N;
    and wherein said alkyl, alkenyl and alkynyl can be unsubstituted or substituted with Z;
    and wherein two or more hydrogen atoms on a carbon atom or heteroatom of said alkyl, alkenyl and alkynyl, can be taken together to form a C=O, C=S, N=O, N=S, S=O or $S(O)_2$;
  each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
  each $Z^1$ is independently selected from hydrogen; alkyl; and Z;
  each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
    and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;
  each $R^{101}$ is independently selected from hydrogen and $R^{10}$;
  each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
    and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
    and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl (ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

and wherein R$^{12}$ and R$^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

In a more particular embodiment the present invention therefore provides compounds according to formula (A1),

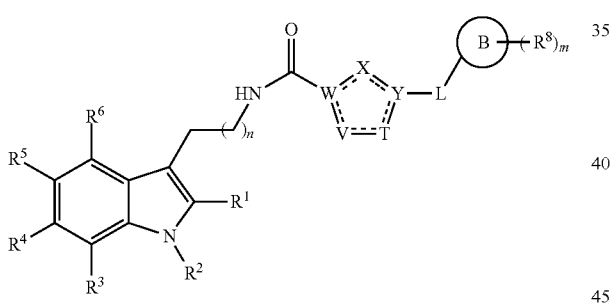

(A1)

wherein, each dotted line individually represents an optional double bond, wherein maximally two dotted lines selected from the five dotted lines are a double bond;

each R$^1$, R$^3$, R$^4$, R$^5$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl (ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

R$^2$ is selected from hydrogen; alkyl; alkenyl; and alkynyl;

n is selected from 0; 1 or 2;

each of X, Y, T, W and V is independently selected from —CZ$^1$H—; —CZ$^1$—; NR$^{101}$; —O—; —S—; or —CO—; wherein at least one of X, Y, T; W or V is selected from —CZ$^1$H— or —CZ$^1$—;

L is independently selected from being not present; —O—; —NR$^{10}$—; C$_{1-6}$alkylene; C$_{1-6}$alkenylene; C$_{1-6}$alkynylene;

wherein each of said C$_{1-6}$alkylene, C$_{1-6}$alkenylene or C$_{1-6}$alkynylene optionally includes one or more heteroatoms, said heteroatoms being selected from the heteroatoms consisting of O, S and N, and wherein each of said C$_{1-6}$alkylene, C$_{1-6}$alkenylene or C$_{1-6}$alkynylene, can be unsubstituted or substituted;

and wherein two or more hydrogen atoms on a carbon atom or heteroatom of said C$_{1-6}$alkylene, C$_{1-6}$alkenylene or C$_{1-6}$alkynylene, can be taken together to form a C=O, C=S, N=O, N=S, S=O or S(O)$_2$;

B represents a cyclic structure selected from cycloalkyl; cycloalkenyl; cycloalkynyl; aryl; and heterocycle;

m is selected from 0; 1; 2; 3; 4 and 5;

R$^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein two or more hydrogen atoms on a carbon atom or heteroatom of said alkyl, alkenyl and alkynyl, can be taken together to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)R$^{10}$; —NR$^{10}$S(O)$_2$R$^{10}$; —NR$^{10}$C (O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each Z$^1$ is independently selected from hydrogen and Z;

each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

In a yet more particular embodiment, the compounds of the invention have a structure according to the formulas (AA1), (AA2) (AA3), (AA4), or (A1) or any subgroup thereof, whereby V is N. Yet more in particular, the compounds of the invention have a structure according to the formulas (AA1), (AA2) (AA3), (AA4), or (A1) or any subgroup thereof, whereby T is O. In a still more particular embodiment, the compounds of the invention have a structure according to the formulas (AA1), (AA2) (AA3), (AA4), or (A1) or any subgroup thereof, whereby V is N and T is O. In another more particular embodiment, the compounds of the invention have a structure according to the formulas (AA1), (AA2) (AA3), (AA4), or (A1) or any subgroup thereof, whereby W and Y are C.

In a particular embodiment of the invention, the compounds have a structure according to the formulas (AA1), (AA2) (AA3), (AA4), or (A1) or any subgroup thereof, wherein the dotted lines and X, Y, T, W and V are selected from —CZ$^1$H—; —CZ$^1$—; —C—; —N—; NR$^{101}$; —O—; —S—; or —CO—; to form one of the following cycles:

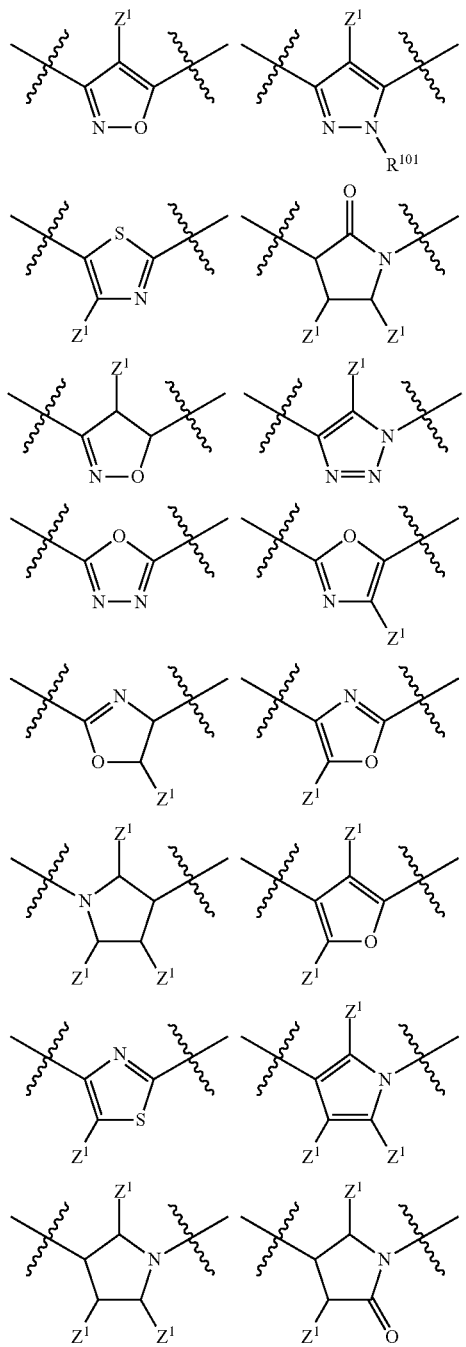

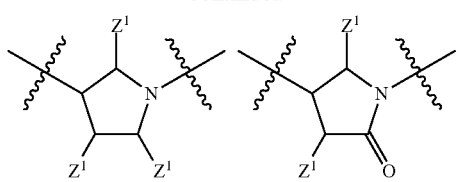
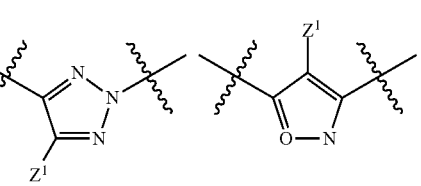

In a particular embodiment of the invention, the compounds have a structure according to the formulas (AA1), (AA2) (AA3), (AA4), or (A1) or any subgroup thereof, wherein the dotted lines and X, Y, T, W and V are selected from —CZ$^1$H—; —CZ$^1$—; NR$^{101}$; —O—; —S—; or —CO—; to form one of the following cycles:

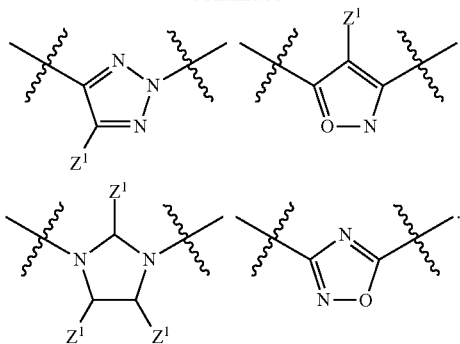
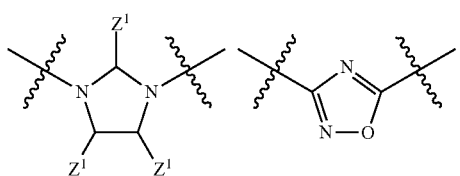
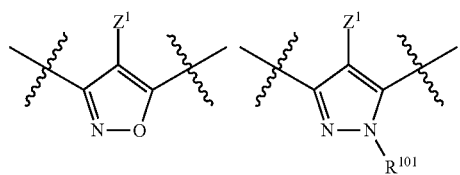

In another preferred embodiment, the compounds have a structure according to formula (A2), (A2'), (AB2) or (AB2');

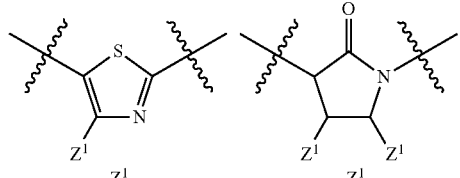
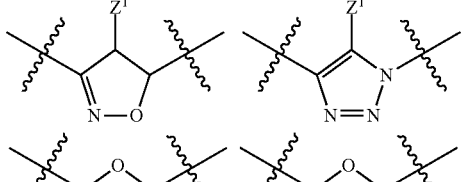
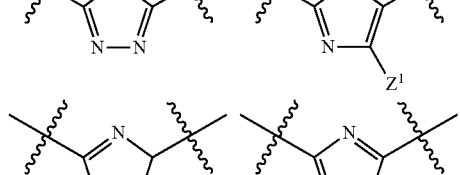
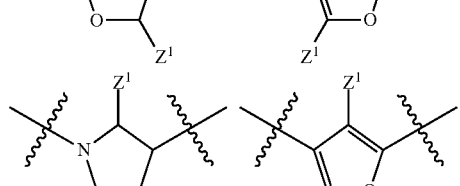

(AB2)
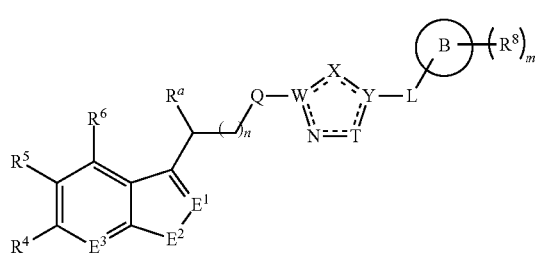

(AB2')
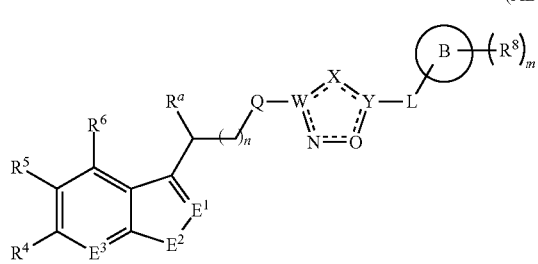

(A2)
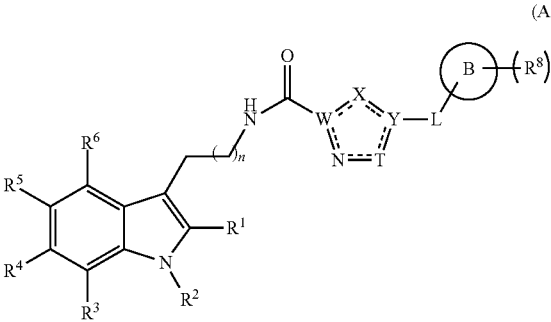

-continued

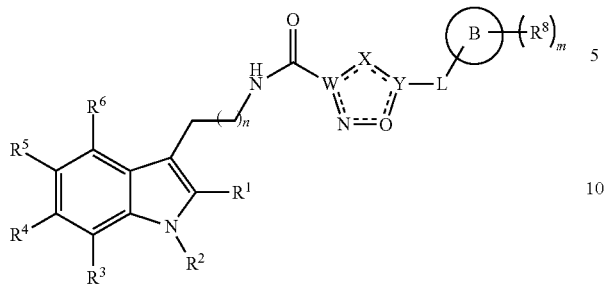

(A2')

wherein $E^1$, $E^2$, $E^3$, $R^4$, $R^5$, $R^6$, $R^8$, $R^a$, Q, W, X, Y, L, B, m, n have the same meaning as defined herein or embodiments described herein.

In another embodiment, the compounds have a structure according to formula (A2'), wherein, each dotted line individually represents an optional double bond, wherein maximally two dotted lines selected from the five dotted lines are a double bond;

each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

$R^2$ is selected from hydrogen; alkyl; alkenyl; and alkynyl;
n is selected from 0; 1 or 2;

each of X, Y and W is independently selected from —$CZ^1H$—; —$CZ^1$—; —C—; —N—; $NR^{101}$; —O—; —S—; or —CO—; wherein at least one of X, Y or W is selected from —$CZ^1H$— or —$CZ^1$— or —C—;

L is independently selected from being not present; —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein two or more hydrogen atoms on a carbon atom or heteroatom of said alkyl, alkenyl and alkynyl, can be taken together to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof, provided that the compounds are not selected from:

3-Isoxazolecarboxamide, 5-cyclopropyl-N-[2-(1H-indol-3-yl)ethyl]-;
3-Isoxazolecarboxamide, 5-(2-furanyl)-N-[2-(1H-indol-3-yl)ethyl]-;
3-Isoxazolecarboxamide, 5-[(2,4-difluorophenoxy)methyl]-N-[2-(1H-indol-3-yl)ethyl]-;
3-Isoxazolecarboxamide, N-[2-(1H-indol-3-yl)ethyl]-5-(2-thienyl)-;
3-Isoxazolecarboxamide, N-[2-(1H-indol-3-yl)ethyl]-5-[[(6-methyl-3-pyridinyl)oxy]methyl]-;
3-Isoxazolecarboxamide, N-[2-(5-chloro-2,7-dimethyl-1H-indol-3-yl)ethyl]-5-(4-chlorophenyl)-;
3-Isoxazolecarboxamide, 5-(4-chlorophenyl)-N-[2-(5-methyl-1H-indol-3-yl)ethyl]-;
3-Isoxazolecarboxamide, N-[2-(1H-indol-3-yl)ethyl]-5-(4-morpholinylmethyl)-;
3-Isoxazolecarboxamide, N-[2-(1H-indol-3-yl)ethyl]-5-(1-pyrrolidinylmethyl)-;
3-Isoxazolecarboxamide, N-[2-(1H-indol-3-yl)ethyl]-5-phenyl-.

In a particular embodiment, the compounds of the invention are not selected from:
3-Isoxazolecarboxamide, 5-cyclopropyl-N-[2-(1H-indol-3-yl)ethyl]-;
3-Isoxazolecarboxamide, 5-(2-furanyl)-N-[2-(1H-indol-3-yl)ethyl]-;
3-Isoxazolecarboxamide, 5-[(2,4-difluorophenoxy)methyl]-N-[2-(1H-indol-3-yl)ethyl]-;
3-Isoxazolecarboxamide, N-[2-(1H-indol-3-yl)ethyl]-5-(2-thienyl)-;
3-Isoxazolecarboxamide, N-[2-(1H-indol-3-yl)ethyl]-5-[[(6-methyl-3-pyridinyl)oxy]methyl]-;
3-Isoxazolecarboxamide, N-[2-(5-chloro-2,7-dimethyl-1H-indol-3-yl)ethyl]-5-(4-chlorophenyl)-;
3-Isoxazolecarboxamide, 5-(4-chlorophenyl)-N-[2-(5-methyl-1H-indol-3-yl)ethyl]-;
3-Isoxazolecarboxamide, N-[2-(1H-indol-3-yl)ethyl]-5-(4-morpholinylmethyl)-;
3-Isoxazolecarboxamide, N-[2-(1H-indol-3-yl)ethyl]-5-(1-pyrrolidinylmethyl)-;
3-Isoxazolecarboxamide, N-[2-(1H-indol-3-yl)ethyl]-5-phenyl-.

In another embodiment, the compounds have a structure according to formula (A2'), wherein,
each dotted line individually represents an optional double bond, wherein maximally two dotted lines selected from the five dotted lines are a double bond;
each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

$R^2$ is selected from hydrogen; alkyl; alkenyl; and alkynyl;
n is selected from 0; 1 or 2;
each of X, Y and W is independently selected from —$CZ^1H$—; —$CZ^1$—; $NR^{101}$; —O—; —S—; or —CO—; wherein at least one of X, Y or W is selected from —$CZ^1H$— or —$CZ^1$—;
L is independently selected from being not present; —O—; —$NR^{10}$—; $C_{1-6}$alkylene; $C_{1-6}$alkenylene; $C_{1-6}$alkynylene;
wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;
- wherein said alkyl, alkenyl and alkynyl optionally includes one or more heteroatoms, said heteroatoms being selected from the atoms O, S and N;
- and wherein said alkyl, alkenyl and alkynyl can be unsubstituted or substituted with Z;
- and wherein two or more hydrogen atoms on a carbon atom or heteroatom of said alkyl, alkenyl and alkynyl, can be taken together to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each Z$^1$ is independently selected from hydrogen and Z;

each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;
- and wherein R$^{12}$ and R$^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof, provided that the compounds are not selected from:

3-Isoxazolecarboxamide, 5-cyclopropyl-N-[2-(1H-indol-3-yl)ethyl]-;

3-Isoxazolecarboxamide, 5-(2-furanyl)-N-[2-(1H-indol-3-yl)ethyl]-;

3-Isoxazolecarboxamide, 5-[(2,4-difluorophenoxy)methyl]-N-[2-(1H-indol-3-yl)ethyl]-;

3-Isoxazolecarboxamide, N-[2-(1H-indol-3-yl)ethyl]-5-(2-thienyl)-;

3-Isoxazolecarboxamide, N-[2-(1H-indol-3-yl)ethyl]-5-[[(6-methyl-3-pyridinyl)oxy]methyl]-;

3-Isoxazolecarboxamide, N-[2-(5-chloro-2,7-dimethyl-1H-indol-3-yl)ethyl]-5-(4-chlorophenyl)-;

3-Isoxazolecarboxamide, 5-(4-chlorophenyl)-N-[2-(5-methyl-1H-indol-3-yl)ethyl]-;

3-Isoxazolecarboxamide, N-[2-(1H-indol-3-yl)ethyl]-5-(4-morpholinylmethyl)-;

3-Isoxazolecarboxamide, N-[2-(1H-indol-3-yl)ethyl]-5-(1-pyrrolidinylmethyl)-;

3-Isoxazolecarboxamide, N-[2-(1H-indol-3-yl)ethyl]-5-phenyl-.

In a particular embodiment, the compounds of the invention are not selected from:

3-Isoxazolecarboxamide, 5-cyclopropyl-N-[2-(1H-indol-3-yl)ethyl]-;

3-Isoxazolecarboxamide, 5-(2-furanyl)-N-[2-(1H-indol-3-yl)ethyl]-;

3-Isoxazolecarboxamide, 5-[(2,4-difluorophenoxy)methyl]-N-[2-(1H-indol-3-yl)ethyl]-;

3-Isoxazolecarboxamide, N-[2-(1H-indol-3-yl)ethyl]-5-(2-thienyl)-;

3-Isoxazolecarboxamide, N-[2-(1H-indol-3-yl)ethyl]-5-[[(6-methyl-3-pyridinyl)oxy]methyl]-;

3-Isoxazolecarboxamide, N-[2-(5-chloro-2,7-dimethyl-1H-indol-3-yl)ethyl]-5-(4-chlorophenyl)-;

3-Isoxazolecarboxamide, 5-(4-chlorophenyl)-N-[2-(5-methyl-1H-indol-3-yl)ethyl]-;

3-Isoxazolecarboxamide, N-[2-(1H-indol-3-yl)ethyl]-5-(4-morpholinylmethyl)-;

3-Isoxazolecarboxamide, N-[2-(1H-indol-3-yl)ethyl]-5-(1-pyrrolidinylmethyl)-;

3-Isoxazolecarboxamide, N-[2-(1H-indol-3-yl)ethyl]-5-phenyl-.

In yet another preferred embodiment, the compounds have a structure according to formula (A3), (A4), (A4') or (A4"), (A3)
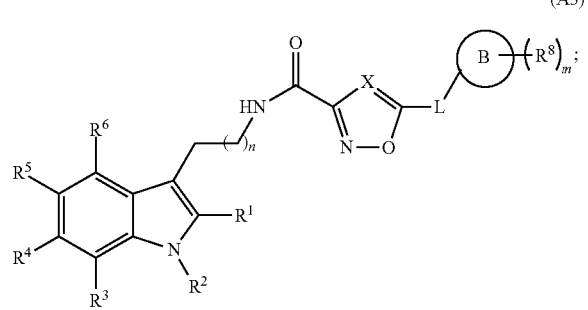

(A4)
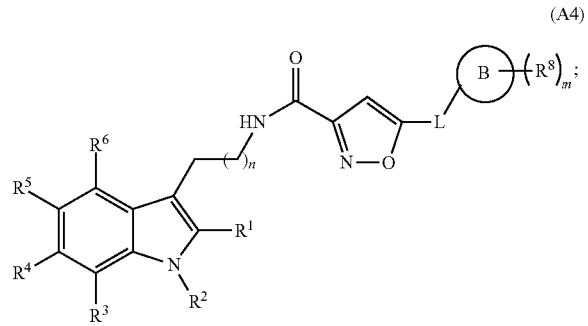

(A4')
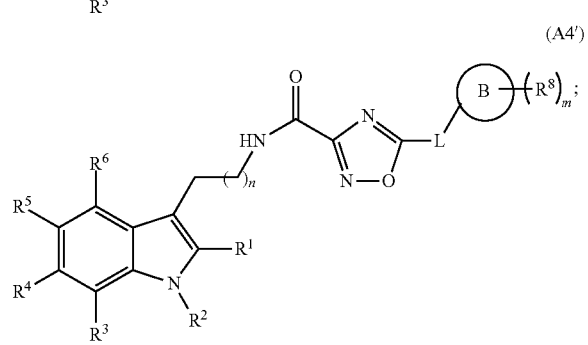

(A4")
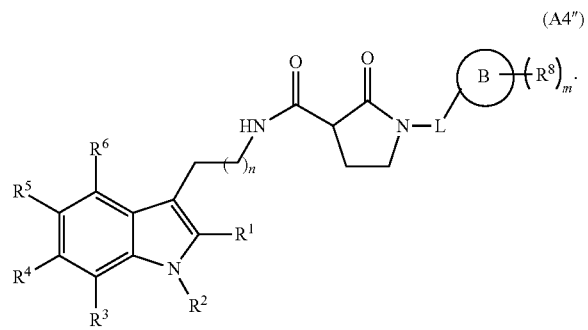

In yet another preferred embodiment, the compounds have a structure according to formula (AB3), (AB4), (AB4') or (AB4"), (AB3)
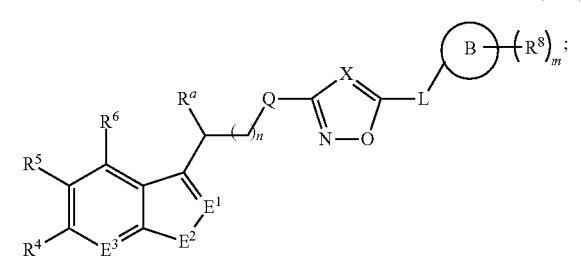

(AB4)
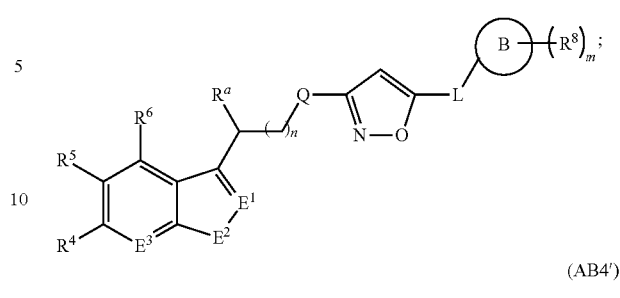

(AB4')
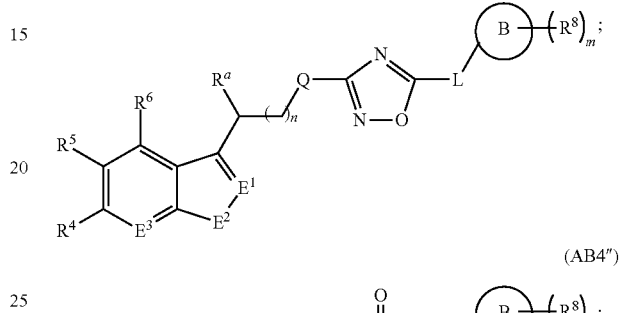

(AB4")
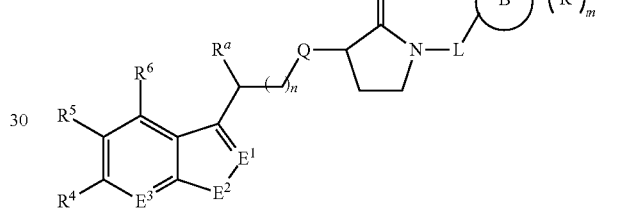

In a particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, wherein n is 1.

In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, whereby $R^2$ is H. In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, whereby $R^3$ is H.

In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, B is $C_{3-8}$cycloalkyl or $C_{6-10}$aryl and $R^8$ is selected from hydrogen, halogen, cyano, $C_{1-6}$alkoxy, trifluoromethyl; trifluoromethoxy.

In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, whereby the cycle B is phenyl.

In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, whereby L is selected from being not present; —O—; —NH—; —NR$^{10}$—; and C$_{1-6}$alkylene, yet more in particular, whereby L is selected from —O—; —NH—; —NR$^{10}$—; and C$_{1-6}$alkylene, and still more in particular, L is C$_{1-6}$alkylene, optionally substituted by one or more substituents each independently selected from halogen; C$_{1-6}$alkyl; haloC$_{1-6}$alkyl; haloC$_{1-6}$alkyloxy and still more in particular, whereby L is —CH$_2$—.

In another particular embodiment of the present invention, the compounds have a structure according to the formulas (AA1), (AA2), (AA3), (AA4), (A1), (A2), (A2'), (AB2), (AB2'), (A3), (A4), (A4'), (A4"), (AB3), (AB4), (AB4') or (AB4") or any subgroup thereof, whereby L is selected from being not present; —O—; —NR$^{10}$—; and C$_{1-6}$alkylene, yet more in particular, whereby L is selected from —O—; —NR$^{10}$—; and C$_{1-6}$alkylene, and still more in particular, L is C$_{1-6}$alkylene, optionally substituted by one or more substituents each independently selected from halogen; C$_{1-6}$alkyl, haloC$_{1-6}$alkyl; haloC$_{1-6}$alkyloxy and still more in particular, whereby L is —CH$_2$—.

In another particular embodiment of the present invention, the compounds have a structure according to the formulas herein, whereby R$^8$ is selected from hydrogen and halogen.

In another particular embodiment of the present invention, the compounds have a structure according to the formulas herein, whereby R$^1$, R$^3$, R$^4$ and R$^6$ are hydrogen.

A particular embodiment of the invention relates to compounds with a structure according to formula (A5), (A6), (A5'), (A5"), (A6') or (A6"):

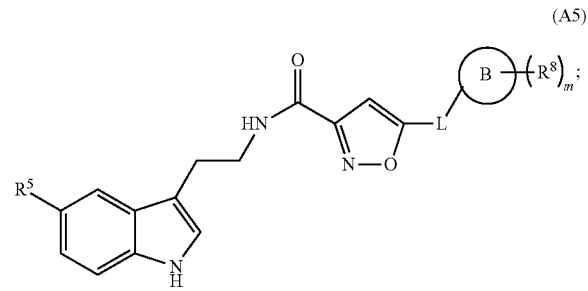
(A5)

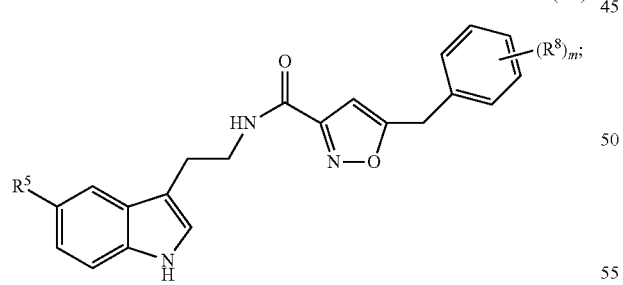
(A6)

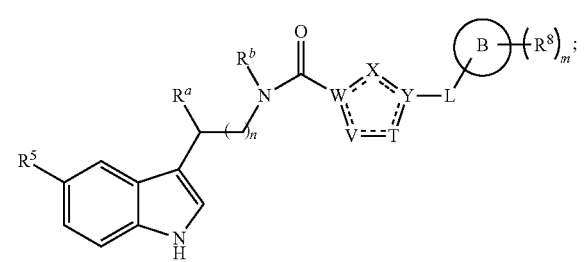
(A5')

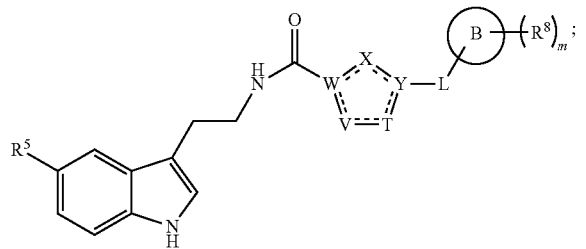
(A5")

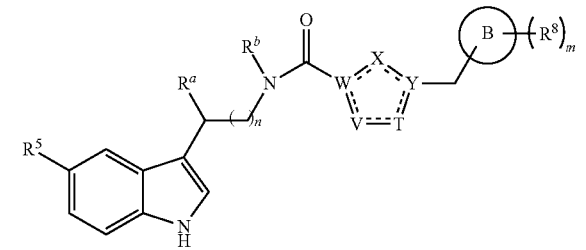
(A6')

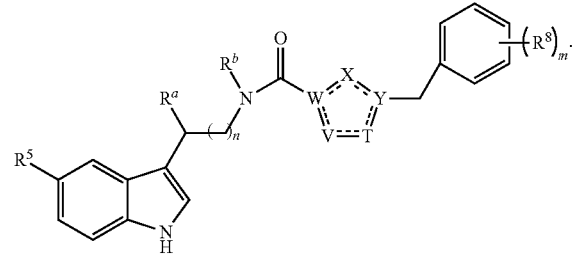
(A6")

whereby all the remaining variables are as in formula (A1), (AA1) or other formula or all embodiments described herein.

Another particular embodiment of the invention relates to compounds with a structure according to formula (A7) or (A8)

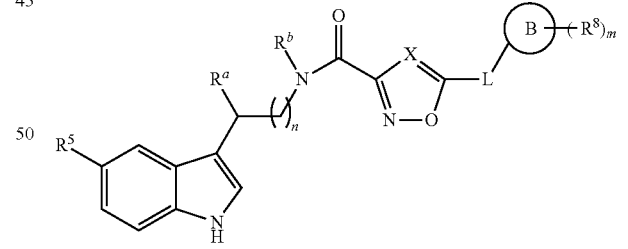
(A7)

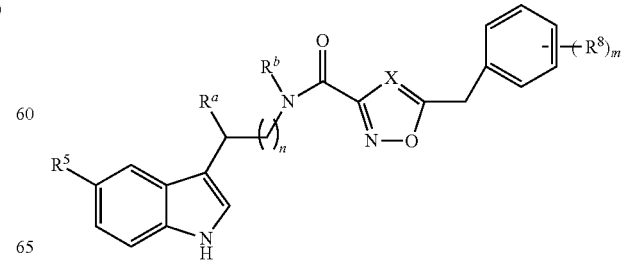
(A8)

whereby all the remaining variables are as in formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6') or (A6"), or any subgroup thereof, all other formulas or all embodiments described herein.

Another particular embodiment of the invention relates to compounds with a structure according to formula (A9) or (A10)

(A9)

(A10)

whereby all the remaining variables are as in formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6') or (A6"), (A7) or (A8) or any subgroup thereof, all other formulas or all embodiments described herein.

Another particular embodiment of the invention relates to compounds with a structure according to formula (A11) or (A12)

(A11)

(A12)

whereby all the remaining variables are as in formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6'), (A6"), (A7), (A8), (A9), (A10) or any subgroup thereof, all other formulas or all embodiments described herein.

In a particular embodiment, the compounds of the present invention are selected from the list of: N-(2-(5-chloro-1H-indol-3-yl)ethyl)-5-(3-methoxybenzyl)isoxazole-3-carboxamide;
N-(2-(5-chloro-1H-indol-3-yl)ethyl)-5-cyclopentylisoxazole-3-carboxamide;
N-(2-(5-chloro-1H-indol-3-yl)ethyl)-5-(3-cyanobenzyl) isoxazole-3-carboxamide;
N-(2-(5-chloro-1H-indol-3-yl)ethyl)-5-(4-cyanobenzyl) isoxazole-3-carboxamide;
N-(2-(5-chloro-1H-indol-3-yl)ethyl)-5-(2,5-difluorobenzyl) isoxazole-3-carboxamide;
N-(2-(5-chloro-1H-indol-3-yl)ethyl)-5-cyclopropylisoxazole-3-carboxamide;
5-benzyl-N-(2-(5-chloro-1H-indol-3-yl)ethyl)isoxazole-3-carboxamide;
N-(2-(5-chloro-1H-indol-3-yl)ethyl)-5-(2-methoxybenzyl) isoxazole-3-carboxamide;
N-(2-(5-chloro-1H-indol-3-yl)ethyl)-5-(4-(trifluoromethyl) benzyl)isoxazole-3-carboxamide;
N-(2-(5-chloro-1H-indol-3-yl)ethyl)-5-(4-methoxybenzyl) isoxazole-3-carboxamide;
N-(2-(5-chloro-1H-indol-3-yl)ethyl)-5-(furan-2-yl)isoxazole-3-carboxamide;
N-(2-(5-chloro-1H-indol-3-yl)ethyl)-5-(4-methylbenzyl) isoxazole-3-carboxamide;
N-(2-(5-chloro-1H-indol-3-yl)ethyl)-5-cyclohexylisoxazole-3-carboxamide;
5-(3-fluorobenzyl)-N-(2-(5-methyl-1H-indol-3-yl)ethyl) isoxazole-3-carboxamide;
N-(2-(5-chloro-1H-indol-3-yl)ethyl)-1-methyl-5-(thiophen-2-yl)-1H-pyrazole-3-carboxamide;
N-(2-(5-chloro-1H-indol-3-yl)ethyl)-5-(thiophen-2-yl)isoxazole-3-carboxamide;
N-(2-(5-chloro-1H-indol-3-yl)ethyl)-5-(furan-2-ylmethyl) isoxazole-3-carboxamide;
N-(2-(5-chloro-1H-indol-3-yl)ethyl)-5-(furan-2-yl)-1-methyl-1H-pyrazole-3-carboxamide;
N-(2-(5-chloro-1H-indol-3-yl)ethyl)-5-(3-methylbenzyl) isoxazole-3-carboxamide;
N-(2-(5-chloro-1H-indol-3-yl)ethyl)-5-(2-fluoro-3-methoxybenzyl)isoxazole-3-carboxamide;
N-(2-(5-chloro-1H-indol-3-yl)ethyl)-5-(furan-3-ylmethyl) isoxazole-3-carboxamide;
N-(2-(5-chloro-1H-indol-3-yl)ethyl)-5-(3-fluorobenzyl) isoxazole-3-carboxamide;

N-(2-(1H-indol-3-yl)ethyl)-4-methyl-2-p-tolylthiazole-5-carboxamide;
N-(2-(5-chloro-1H-indol-3-yl)ethyl)-5-(thiophen-3-ylmethyl)isoxazole-3-carboxamide;
N-(2-(5-chloro-1H-indol-3-yl)ethyl)-1-methyl-5-phenyl-1H-pyrazole-3-carboxamide;
N-(2-(5-chloro-1H-indol-3-yl)ethyl)-5-(thiophen-2-ylmethyl)isoxazole-3-carboxamide;
N-(2-(5-fluoro-1H-indol-3-yl)ethyl)-5-(3-fluorobenzyl)isoxazole-3-carboxamide;
tert-butyl 3-(2-(5-chloro-1H-indol-3-yl)ethylcarbamoyl)isoxazol-5-ylcarbamate;
N-(2-(5-chloro-1H-indol-3-yl)ethyl)-5-(3-(trifluoromethyl)benzyl)isoxazole-3-carboxamide;
N-(2-(1H-indol-3-yl)ethyl)-5-(3-fluorobenzyl)isoxazole-3-carboxamide;
N-(2-(5-methoxy-1H-indol-3-yl)ethyl)-4-methyl-2-p-tolylthiazole-5-carboxamide;
N-(2-(1H-indol-3-yl)ethyl)-4-methyl-2-(2-propylpyridin-4-yl)thiazole-5-carboxamide;
N-((5-chloro-1H-indol-3-yl)methyl)-5-(3-fluorobenzyl)isoxazole-3-carboxamide;
N-(3-(5-chloro-1H-indol-3-yl)propyl)-5-(3-fluorobenzyl)isoxazole-3-carboxamide;
N-(2-(5-chloro-1H-indol-3-yl)ethyl)-5-phenylisoxazole-3-carboxamide;
N-(2-(5-fluoro-1H-indol-3-yl)ethyl)-4-methyl-2-p-tolylthiazole-5-carboxamide;
N-(2-(5-chloro-1H-indol-3-yl)ethyl)-5-(2,3-dihydrobenzo[b][1,4]dioxin-5-yl)isoxazole-3-carboxamide;
N-(2-(1H-indol-3-yl)ethyl)-4-methyl-2-(phenethylamino)thiazole-5-carboxamide;
N-(2-(5-chloro-1H-indol-3-yl)ethyl)-1-(4-ethylphenyl)-2-oxopyrrolidine-3-carboxamide;
N-(2-(5-chloro-1H-indol-3-yl)ethyl)-5-(pyridin-4-ylmethyl)isoxazole-3-carboxamide;
5-((1H-pyrazol-1-yl)methyl)-N-(2-(5-chloro-1H-indol-3-yl)ethyl)isoxazole-3-carboxamide;
5-benzyl-N-(2-(5-chloro-1H-indol-3-yl)ethyl)-4,5-dihydroisoxazole-3-carboxamide;
N-(2-(5-chloro-1H-indol-3-yl)ethyl)-1-cyclohexyl-1H-1,2,3-triazole-4-carboxamide;
N-(2-(5-chloro-1H-indol-3-yl)ethyl)-4-methyl-2-p-tolylthiazole-5-carboxamide;
N-(2-(5-chloro-1H-indol-3-yl)ethyl)-4-methyl-2-phenylthiazole-5-carboxamide;
N-(2-(6-fluoro-1H-indol-3-yl)ethyl)-5-(3-fluorobenzyl)isoxazole-3-carboxamide;
1-(4-ethylphenyl)-N-(2-(5-methyl-1H-indol-3-yl)ethyl)-2-oxopyrrolidine-3-carboxamide;
N-(2-(5-chloro-1H-indol-3-yl)ethyl)-5-(4-methoxyphenyl)isoxazole-3-carboxamide;
N-(2-(5-chloro-1H-indol-3-yl)ethyl)-3-phenyl-4,5-dihydroisoxazole-5-carboxamide;
N-(2-(5-chloro-1-methyl-1H-indol-3-yl)ethyl)-5-(3-fluorobenzyl)isoxazole-3-carboxamide;
N-(2-(5-chloro-1H-indol-3-yl)ethyl)-5-phenyl-1,3,4-oxadiazole-2-carboxamide;
N-(2-(5-chloro-1H-indol-3-yl)ethyl)-5-phenyloxazole-2-carboxamide;
1-benzyl-N-(2-(5-chloro-1H-indol-3-yl)ethyl)-1H-1,2,3-triazole-4-carboxamide;
N-(2-(5-chloro-1H-indol-3-yl)ethyl)-5-phenyl-4,5-dihydroisoxazole-3-carboxamide;
N-(2-(5-chloro-1H-indol-3-yl)ethyl)-5-(4-chlorophenyl)isoxazole-3-carboxamide;
N-(2-(5-chloro-1H-indol-3-yl)ethyl)-5-p-tolylisoxazole-3-carboxamide;
(R)—N-(2-(5-chloro-1H-indol-3-yl)ethyl)-4-cyclohexyl-4,5-dihydrooxazole-2-carboxamide;
(S)—N-(2-(5-chloro-1H-indol-3-yl)ethyl)-4-cyclohexyl-4,5-dihydrooxazole-2-carboxamide;
5-benzyl-N-(2-(5-chloro-1H-indol-3-yl)ethyl)-1,3,4-oxadiazole-2-carboxamide;
N-(2-(5-chloro-1H-indol-3-yl)ethyl)-5-(pyrrolidin-1-ylmethyl)isoxazole-3-carboxamide;
N-(2-(5-chloro-1H-indol-3-yl)ethyl)-5-methyl-2-phenyloxazole-4-carboxamide;
N-(2-(5-chloro-1H-indol-3-yl)ethyl)-3-phenylpyrrolidine-1-carboxamide;
N-(2-(5-chloro-1H-indol-3-yl)ethyl)-2-oxo-1-phenylpyrrolidine-3-carboxamide;
N-(2-(5-chloro-1H-indol-3-yl)ethyl)-1-(3-fluorophenyl)-2-oxopyrrolidine-3-carboxamide;
N-(2-(5-chloro-1H-indol-3-yl)ethyl)-5-((ethylamino)methyl)isoxazole-3-carboxamide;
N-(2-(5-chloro-1H-indol-3-yl)ethyl)-2-phenylthiazole-4-carboxamide;
N-(2-(5-chloro-1H-indol-3-yl)ethyl)-5-(4-chlorophenyl)-2-(trifluoromethyl)furan-3-carboxamide 3-benzyl-N-(2-(5-chloro-1H-indol-3-yl)ethyl)imidazolidine-1-carboxamide;
N-(2-(5-chloro-1H-indol-3-yl)ethyl)-1-(4-methoxyphenyl)-2-oxopyrrolidine-3-carboxamide;
N-(2-(5-chloro-1H-indol-3-yl)ethyl)-1-(4-isopropylphenyl)-2-oxopyrrolidine-3-carboxamide;
N-(2-(1H-indol-3-yl)ethyl)-1-cyclopropyl-2,5-dimethyl-1H-pyrrole-3-carboxamide;
N-(2-(5-chloro-1H-indol-3-yl)ethyl)-4-methyl-2-(pyrazin-2-yl)thiazole-5-carboxamide;
5-(3-fluorobenzyl)-N-(2-(6-methoxy-1H-indol-3-yl)ethyl)isoxazole-3-carboxamide;
3-benzyl-N-(2-(5-chloro-1H-indol-3-yl)ethyl)pyrrolidine-1-carboxamide;
N-(2-(5-chloro-1H-indol-3-yl)ethyl)-1-cyclohexyl-2-oxopyrrolidine-3-carboxamide;
N-(2-(5-chloro-1H-indol-3-yl)ethyl)-5-cyclohexyl-1,3,4-oxadiazole-2-carboxamide;
N-(2-(5-chloro-1H-indol-3-yl)ethyl)-1-(4-fluorophenyl)-2-oxopyrrolidine-3-carboxamide;
N-(2-(5-chloro-1H-indol-3-yl)ethyl)-1-(2-fluorophenyl)-2-oxopyrrolidine-3-carboxamide;
(S)-4-benzyl-N-(2-(5-chloro-1H-indol-3-yl)ethyl)-4,5-dihydrooxazole-2-carboxamide;
(R)-4-benzyl-N-(2-(5-chloro-1H-indol-3-yl)ethyl)-4,5-dihydrooxazole-2-carboxamide;
N-(2-(5-chloro-1H-indol-3-yl)ethyl)-1-(3-ethylphenyl)-2-oxopyrrolidine-3-carboxamide;
N-(2-(5-chloro-1H-indol-3-yl)ethyl)-4-phenyl-4,5-dihydrooxazole-2-carboxamide;
N-(2-(5-chloro-1H-indol-3-yl)ethyl)-5-oxo-1-phenylpyrrolidine-3-carboxamide;
N-(2-(5-chloro-1H-indol-3-yl)ethyl)-5-(4-chlorophenyl)-2-methylfuran-3-carboxamide;
N-(2-(1H-indol-3-yl)ethyl)-1-(furan-2-ylmethyl)-5-oxopyrrolidine-3-carboxamide;
N-(2-(1H-indol-3-yl)ethyl)-1-(2,3-dihydrobenzo[b][1,4]dioxin-6-yl)-5-oxopyrrolidine-3-carboxamide;
N-(2-(1H-indol-3-yl)ethyl)-1-(naphthalen-1-yl)-5-oxopyrrolidine-3-carboxamide;
N-(2-(1H-indol-3-yl)ethyl)-1-(2-chlorobenzyl)-5-oxopyrrolidine-3-carboxamide;

N-(2-(1H-indol-3-yl)ethyl)-1-(4-(N,N-diethylsulfamoyl) phenyl)-5-oxopyrrolidine-3-carboxamide;
N-(2-(1H-indol-3-yl)ethyl)-5-oxo-1-phenethylpyrrolidine-3-carboxamide;
N-(2-(1H-indol-3-yl)ethyl)-1-benzyl-5-oxopyrrolidine-3-carboxamide;
N-(2-(5-chloro-1H-indol-3-yl)ethyl)-5-methyl-2-phenyl-2H-1,2,3-triazole-4-carboxamide;
5-amino-N-(2-(5-chloro-1H-indol-3-yl)ethyl)isoxazole-3-carboxamide;
N-(2-(5-chloro-1H-indol-3-yl)ethyl)-5-cyclohexyl-4,5-dihydroisoxazole-3-carboxamide;
1-benzyl-N-(2-(5-chloro-1H-indol-3-yl)ethyl)-2-oxopyrrolidine-3-carboxamide;
(S)-1-benzyl-N-(2-(5-chloro-1H-indol-3-yl)ethyl)pyrrolidine-3-carboxamide;
(R)-1-benzyl-N-(2-(5-chloro-1H-indol-3-yl)ethyl)pyrrolidine-3-carboxamide;
N-(2-(5-chloro-1H-indol-3-yl)ethyl)-1-cyclohexyl-5-oxopyrrolidine-3-carboxamide;
5-(3-fluorobenzyl)-N-(2-(5-methoxy-1H-indol-3-yl)ethyl)isoxazole-3-carboxamide;
N-(2-(5-chloro-1H-indol-3-yl)ethyl)-3-phenylisoxazole-5-carboxamide;
N-(2-(5-chloro-1H-indol-3-yl)ethyl)-1-phenylpyrrolidine-3-carboxamide;
N-(2-(benzofuran-3-yl)ethyl)-5-(3-fluorobenzyl)isoxazole-3-carboxamide;
N-(2-(5-chloro-1H-indol-3-yl)ethyl)-1-(4-cyanophenyl)-2-oxopyrrolidine-3-carboxamide;
N-(2-(5-chloro-1H-indol-3-yl)ethyl)-5-(2,5-difluorobenzyl)-1,2,4-oxadiazole-3-carboxamide;
N-(2-(5-chloro-1H-indol-3-yl)ethyl)-5-(2,3-difluorobenzyl)-1,2,4-oxadiazole-3-carboxamide;
N-(2-(5-chloro-1H-indol-3-yl)ethyl)-5-(3,4-difluorobenzyl)-1,2,4-oxadiazole-3-carboxamide;
N-(2-(5-chloro-2-methyl-1H-indol-3-yl)ethyl)-5-(2,5-difluorobenzyl)isoxazole-3-carboxamide;
N-(2-(5-methoxy-1H-indol-3-yl)ethyl)-5-methyl-3-phenylisoxazole-4-carboxamide;
N-(2-(1H-indol-3-yl)ethyl)-2-(p-tolylamino)thiazole-4-carboxamide;
N-(2-(5-chloro-1H-indol-3-yl)ethyl)-5-methyl-3-phenylisoxazole-4-carboxamide;
N-(2-(5-chloro-1H-indol-3-yl)ethyl)-4-methyloxazole-5-carboxamide;
N-(2-(5-chloro-1H-indol-3-yl)ethyl)-5-phenyloxazole-4-carboxamide;
N-(2-(5-chloro-1H-indol-3-yl)ethyl)-5-methylisoxazole-3-carboxamide;
N-(2-(5-chloro-1H-indol-3-yl)ethyl)-3-methyl-5-phenylisoxazole-4-carboxamide;
N-(2-(5-chloro-1H-indol-3-yl)ethyl)-2,5-dimethyloxazole-4-carboxamide;
N-(2-(5-chloro-1H-indol-3-yl)ethyl)-1-phenyl-1H-pyrazole-5-carboxamide;
N-(2-(5-chloro-1H-indol-3-yl)ethyl)-1-methyl-1H-pyrazole-3-carboxamide;
N-(2-(5-chloro-1H-indol-3-yl)ethyl)-1-methyl-1H-pyrazole-5-carboxamide;
1-benzyl-3-tert-butyl-N-(2-(5-chloro-1H-indol-3-yl)ethyl)-1H-pyrazole-5-carboxamide;
N-(2-(5-chloro-1H-indol-3-yl)ethyl)-5-(hydroxymethyl)isoxazole-3-carboxamide;
N-(2-(5-chloro-1H-indol-3-yl)ethyl)-5-methyl-2-phenylfuran-3-carboxamide;
N-(2-(5-chloro-1H-indol-3-yl)ethyl)-5-(ethoxymethyl)isoxazole-3-carboxamide;
N-(2-(5-chloro-1H-indol-3-yl)ethyl)-5-(dimethylamino)isoxazole-3-carboxamide;
N-(2-(5-chloro-1H-indol-3-yl)ethyl)-5-((diethylamino)methyl)isoxazole-3-carboxamide;
1-(3-benzylimidazolidin-1-yl)-3-(5-chloro-1H-indol-3-yl)propan-1-one;
N-(2-(5-chloro-1H-pyrrolo[2,3-b]pyridin-3-yl)ethyl)-5-(2,5-difluorobenzoyl)isoxazole-3-carboxamide;
N-(2-(5-chloro-1H-pyrrolo[2,3-b]pyridin-3-yl)ethyl)-5-(2,5-difluorobenzyl)isoxazole-3-carboxamide;
N-(2-(5-chloro-1H-indol-3-yl)ethyl)-5-(3,4-difluorobenzyl)isoxazole-3-carboxamide;
N-(2-(5-chloro-1H-indol-3-yl)ethyl)-5-(2,3-difluorobenzyl)isoxazole-3-carboxamide;
N-(2-(5-chloro-1H-indol-3-yl)ethyl)-5-(3,5-difluorobenzyl)isoxazole-3-carboxamide;
N-(2-(5-chloro-1H-indol-3-yl)ethyl)-2-oxo-1-(4-(trifluoromethyl)phenyl)pyrrolidine-3-carboxamide;
N-(2-(5-chloro-1H-indol-3-yl)ethyl)-2-oxo-1-p-tolylpyrrolidine-3-carboxamide;
1-(4-acetylphenyl)-N-(2-(5-chloro-1H-indol-3-yl)ethyl)-2-oxopyrrolidine-3-carboxamide;
5-(2,5-difluorobenzyl)-N-(2-(5-(trifluoromethyl)-1H-indol-3-yl)ethyl)isoxazole-3-carboxamide;
N-(2-(6-chloro-5-methyl-1H-indol-3-yl)ethyl)-5-(2,5-difluorobenzyl)isoxazole-3-carboxamide;
N-(2-(5-cyano-1H-indol-3-yl)ethyl)-5-(2,5-difluorobenzyl)isoxazole-3-carboxamide;
(4-(1H-indol-3-yl)piperidin-1-yl)(5-(2,5-difluorobenzyl)isoxazol-3-yl)methanone;
(4-(5-chloro-1H-indol-3-yl)piperidin-1-yl)(5-(2,5-difluorobenzyl)isoxazol-3-yl)methanone;
5-(2,5-difluorobenzyl)-N-(2-(5-phenyl-1H-indol-3-yl)ethyl)isoxazole-3-carboxamide;
N-(2-(5-chloro-7-fluoro-1H-indol-3-yl)ethyl)-5-(2,5-difluorobenzyl)isoxazole-3-carboxamide;
N-(2-(5-chloro-1H-indol-3-yl)ethyl)-1-(4-chloro-3-fluorophenyl)-2-oxopyrrolidine-3-carboxamide;
N-(2-(5-chloro-1H-indol-3-yl)ethyl)-1-(3,4-dimethylphenyl)-2-oxopyrrolidine-3-carboxamide;
N-(2-(5-chloro-1H-indol-3-yl)ethyl)-1-(3,5-difluorophenyl)-2-oxopyrrolidine-3-carboxamide;
N-(2-(5-chloro-1H-indol-3-yl)ethyl)-1-(2,3-dihydro-1H-inden-5-yl)-2-oxopyrrolidine-3-carboxamide;
N-(2-(5-chloro-1H-indol-3-yl)ethyl)-1-(1,3-dihydroisobenzofuran-5-yl)-2-oxopyrrolidine-3-carboxamide;
N-(2-(5-chloro-1H-indol-3-yl)ethyl)-1-(3-fluoro-4-methoxyphenyl)-2-oxopyrrolidine-3-carboxamide;
N-(2-(5-chloro-1H-indol-3-yl)ethyl)-1-(3,4-difluorophenyl)-2-oxopyrrolidine-3-carboxamide;
N-(2-(5-chloro-1H-indol-3-yl)ethyl)-1-cyclopropyl-2-oxopyrrolidine-3-carboxamide;
N-(2-(5-chloro-1H-indol-3-yl)ethyl)-1-(3-fluoro-4-(trifluoromethyl)phenyl)-2-oxopyrrolidine-3-carboxamide;
N-(2-(5-chloro-1H-indol-3-yl)ethyl)-1-(2,6-difluorophenyl)-2-oxopyrrolidine-3-carboxamide
N-(2-(5-chloro-1H-indol-3-yl)ethyl)-1-(3-fluoro-4-methylphenyl)-2-oxopyrrolidine-3-carboxamide;
N-(2-(5-chloro-1H-indol-3-yl)ethyl)-1-(4-chlorophenyl)-2-oxopyrrolidine-3-carboxamide;
N-(2-(5-chloro-1H-indol-3-yl)ethyl)-1-(3-chlorophenyl)-2-oxopyrrolidine-3-carboxamide;
1-(3-(1H-pyrrol-1-yl)phenyl)-N-(2-(5-chloro-1H-indol-3-yl)ethyl)-2-oxopyrrolidine-3-carboxamide;

N-(2-(5-chloro-1H-indol-3-yl)ethyl)-2-oxo-1-(1-phenylethyl)pyrrolidine-3-carboxamide;
N-(2-(5-chloro-1H-indol-3-yl)ethyl)-1-(2-ethylphenyl)-2-oxopyrrolidine-3-carboxamide;
N-(2-(5-chloro-1H-indol-3-yl)ethyl)-2-oxo-1-o-tolylpyrrolidine-3-carboxamide;
N-(2-(5-chloro-1H-indol-3-yl)ethyl)-2-oxo-1-m-tolylpyrrolidine-3-carboxamide;
N-(2-(5-chloro-1H-indol-3-yl)ethyl)-1-(1-methyl-1H-pyrazol-3-yl)-2-oxopyrrolidine-3-carboxamide;
N-(2-(5-chloro-1H-indol-3-yl)ethyl)-1-(2-chlorophenyl)-2-oxopyrrolidine-3-carboxamide;
N-(2-(5-chloro-1H-indol-3-yl)ethyl)-1-(3-methoxyphenyl)-2-oxopyrrolidine-3-carboxamide;
N-(2-(5-chloro-1H-indol-3-yl)ethyl)-1-(2-methoxyphenyl)-2-oxopyrrolidine-3-carboxamide;
N-(2-(5-chloro-1H-indol-3-yl)ethyl)-1-(cyclohexylmethyl)-2-oxopyrrolidine-3-carboxamide;
N-(2-(5-chloro-1H-indol-3-yl)ethyl)-1-p-tolylpyrrolidine-3-carboxamide;
N-(2-(1H-indazol-3-yl)ethyl)-5-(2,5-difluorobenzyl)isoxazole-3-carboxamide;
N-(2-(5-chloro-1H-indol-3-yl)ethyl)-1-(1-methyl-1H-indol-5-yl)-2-oxopyrrolidine-3-carboxamide;
5-benzyl-N-(2-(5-chloro-1H-indol-3-yl)ethyl)-1,2,4-oxadiazole-3-carboxamide;
N-(2-(5-chloro-1H-indol-3-yl)ethyl)-5-(3-fluorobenzyl)-1,2,4-oxadiazole-3-carboxamide;
N-(2-(5-chloro-1H-indol-3-yl)ethyl)-5-(2-fluorobenzyl)-1,2,4-oxadiazole-3-carboxamide;
N-(2-(5-chloro-1H-indol-3-yl)ethyl)-5-(4-fluorobenzyl)-1,2,4-oxadiazole-3-carboxamide;
N-(2-(5-chloro-1H-indol-3-yl)ethyl)-5-(4-chlorobenzyl)-1,2,4-oxadiazole-3-carboxamide;
N-(2-(5-chloro-1H-indol-3-yl)ethyl)-5-(4-methoxybenzyl)-1,2,4-oxadiazole-3-carboxamide;
N-(2-(5-chloro-1H-indol-3-yl)ethyl)-5-(3,4-dichlorobenzyl)-1,2,4-oxadiazole-3-carboxamide;
N-(2-(5-chloro-1H-indol-3-yl)ethyl)-5-(4-chloro-3-fluorobenzyl)-1,2,4-oxadiazole-3-carboxamide;
5-(4-tert-butylbenzyl)-N-(2-(5-chloro-1H-indol-3-yl)ethyl)-1,2,4-oxadiazole-3-carboxamide;
N-(2-(5-chloro-1H-indol-3-yl)ethyl)-5-(3-methoxybenzyl)-1,2,4-oxadiazole-3-carboxamide;
N-(2-(5-chloro-1H-indol-3-yl)ethyl)-5-(3,4-dimethoxybenzyl)-1,2,4-oxadiazole-3-carboxamide;
N-(2-(5-chloro-1H-indol-3-yl)ethyl)-5-(2,5-dimethoxybenzyl)-1,2,4-oxadiazole-3-carboxamide;
N-(2-(5-chloro-1H-indol-3-yl)ethyl)-5-(thiophen-2-ylmethyl)-1,2,4-oxadiazole-3-carboxamide;
N-(2-(5-chloro-1H-indol-3-yl)ethyl)-5-(4-methylbenzyl)-1,2,4-oxadiazole-3-carboxamide;
N-(2-(5-chloro-1H-indol-3-yl)ethyl)-5-(3,5-difluorobenzyl)-1,2,4-oxadiazole-3-carboxamide;
N-(2-(5-chloro-1H-indol-3-yl)ethyl)-5-(2-methoxybenzyl)-1,2,4-oxadiazole-3-carboxamide;
N-(2-(5-chloro-1H-indol-3-yl)ethyl)-5-(3-methylbenzyl)-1,2,4-oxadiazole-3-carboxamide;
N-(2-(5-chloro-1H-indol-3-yl)ethyl)-5-(4-(trifluoromethoxy)benzyl)-1,2,4-oxadiazole-3-carboxamide;
N-(2-(5-chloro-1H-indol-3-yl)ethyl)-5-(3-(trifluoromethyl)benzyl)-1,2,4-oxadiazole-3-carboxamide;
N-(2-(5-chloro-1H-indol-3-yl)ethyl)-5-(4-(trifluoromethyl)benzyl)-1,2,4-oxadiazole-3-carboxamide;
N-(2-(5-chloro-1H-indol-3-yl)ethyl)-5-(2,6-difluorobenzyl)-1,2,4-oxadiazole-3-carboxamide;
N-(2-(5-chloro-1H-indol-3-yl)ethyl)-5-(2,4-difluorobenzyl)-1,2,4-oxadiazole-3-carboxamide;
N-(2-(5-chloro-1H-indol-3-yl)ethyl)-5-(3-chlorobenzyl)-1,2,4-oxadiazole-3-carboxamide;
N-(2-(5-chloro-1H-indol-3-yl)ethyl)-5-(2-chlorobenzyl)-1,2,4-oxadiazole-3-carboxamide;
N-(2-(5-chloro-1H-indol-3-yl)ethyl)-5-(2-methylbenzyl)-1,2,4-oxadiazole-3-carboxamide;
N-(2-(5-chloro-1H-indol-3-yl)ethyl)-5-(thiophen-3-ylmethyl)-1,2,4-oxadiazole-3-carboxamide;
N-(2-(5-chloro-1H-indol-3-yl)ethyl)-5-(2,5-difluorobenzoyl)isoxazole-3-carboxamide;
N-(2-(5-chloro-1H-indol-3-yl)ethyl)-5-(hydroxy(phenyl)methyl)isoxazole-3-carboxamide;
N-(2-(5-chloro-1H-indol-3-yl)ethyl)oxazole-5-carboxamide;
N-(2-(5-chloro-1H-indol-3-yl)ethyl)-4-methyl-2-phenyloxazole-5-carboxamide;
N-(2-(5-chloro-1H-indol-3-yl)ethyl)-2-phenyloxazole-5-carboxamide;
N-(2-(5-chloro-1H-indol-3-yl)ethyl)-4-phenylisoxazole-3-carboxamide;
N-(2-(5-chloro-1H-indol-3-yl)ethyl)-5-phenyl-1,2,4-oxadiazole-3-carboxamide;
N-(2-(5-chloro-1H-indol-3-yl)ethyl)-5-(2,5-difluorophenyl)-1,2,4-oxadiazole-3-carboxamide;
N-(2-(5-chloro-1H-indol-3-yl)ethyl)-5-((5-methyl-2-phenyloxazol-4-yl)methyl)-1,2,4-oxadiazole-3-carboxamide;
N-(2-(5-chloro-1H-indol-3-yl)ethyl)-5-(2-fluoro-3-(trifluoromethyl)benzyl)-1,2,4-oxadiazole-3-carboxamide;
N-(2-(5-chloro-1H-indol-3-yl)ethyl)-5-(2-fluoro-5-(trifluoromethyl)benzyl)-1,2,4-oxadiazole-3-carboxamide;
N-(2-(5-chloro-1H-indol-3-yl)ethyl)-5-(4-fluoro-2-(trifluoromethyl)benzyl)-1,2,4-oxadiazole-3-carboxamide;
N-(2-(5-chloro-1H-indol-3-yl)ethyl)-5-(2,3,4-trifluorobenzyl)-1,2,4-oxadiazole-3-carboxamide;
N-(2-(5-chloro-1H-indol-3-yl)ethyl)-5-(2,4,6-trifluorobenzyl)-1,2,4-oxadiazole-3-carboxamide;
N-(2-(5-chloro-1H-indol-3-yl)ethyl)-5-((2,5-difluorophenyl)difluoromethyl)isoxazole-3-carboxamide;
N-(2-(5-chloro-1H-indol-3-yl)ethyl)-5-((2,5-difluorophenyl)fluoromethyl)isoxazole-3-carboxamide;
5-benzyl-N-(2-(5-chloro-1H-indol-3-yl)ethyl)-1,2,4-thiadiazole-3-carboxamide;
5-benzyl-N-(2-(5-chloro-1H-indol-3-yl)ethyl)isothiazole-3-carboxamide;
N-(2-(5-bromo-1H-indol-3-yl)ethyl)-5-(2,5-difluorobenzyl)isoxazole-3-carboxamide;
N-(2-(5-chloro-1H-indol-3-yl)ethyl)-1-phenyl-1H-1,2,3-triazole-4-carboxamide;
N-(2-(5-chloro-1H-indol-3-yl)ethyl)-2-oxo-1-(4-(trifluoromethoxy)phenyl)pyrrolidine-3-carboxamide;
N-(2-(5-chloro-1H-indol-3-yl)ethyl)-5-((2,5-difluorophenyl)(hydroxy)methyl)isoxazole-3-carboxamide;
N-(2-(5-chloro-1H-indol-3-yl)ethyl)-5-(ethoxymethyl)-4,5-dihydroisoxazole-3-carboxamide.

Another aspect of the present invention provides A pharmaceutical composition comprising one or more pharmaceutically acceptable excipients and a therapeutically effective amount of a compound according to the invention.

Another aspect of the present invention provides the compounds according to formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6'), (A6"), (A7), (A8), (A9), (A10), (A11), (A12) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, for use as a medicine or a medicament.

In a particular embodiment, the invention provides the compounds for use a medicine for the prevention or treatment of neurodegenerative disorders, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The present invention also provides for the use of the compounds according to formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6'), (A6"), (A7), (A8), (A9), (A10), (A11), (A12) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, for the manufacture of a medicament for the prevention or treatment of a disorder in an animal, more in particular a mammal or a human.

In a particular embodiment, the invention provides for the use of the compounds as described herein for the manufacture of a medicament for the prevention or treatment of a neurodegenerative disorder in an animal, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the invention relates to a method for the prevention or treatment of a disorder in animals, more particularly mammals or humans, by the administration of one or more such compounds according to formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A6), (A5'), (A5"), (A6'), (A6"), (A7), (A8), (A9), (A10), (A11), (A12) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof to a patient in need thereof. In a particular embodiment, said disorder is a neurodegenerative disorder, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the present invention provides a pharmaceutical composition comprising one or more pharmaceutically acceptable carriers or excipients and a therapeutically effective amount of a compound according to formula (AA1), (AA2), (AA3), (AA4), (A1), (A2), (A2'), (AB2), (AB2'), (A3), (A4), (A4'), (A4"), (AB3), (AB4), (AB4'), (AB4"), (A5), (A5"), (A6), (A5'), (A6'), (A6"), (A7), (A8), (A9), (A10), (A11), (A12) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof.

In a particular embodiment, the present invention relates to pharmaceutical compositions comprising the compounds of the invention according to formulae, embodiments and claims herein in admixture with at least a pharmaceutically acceptable carrier, the active compounds preferably being in a concentration range of about 0.1 to 100% by weight.

The invention further relates to the use of a composition comprising (a) one or more compounds of the invention (of formulae, embodiments and claims herein), and (b) one or more drugs known for the (symptomatic) prevention or treatment of neurodegenerative disorders.

Yet another aspect of the invention provides a method for the preparation of the compounds of the invention which comprises the following steps (with the knowledge that where indole is described, the same counts for the corresponding heterocycles as described herein i.e. aza-indole, indazole, benzoxazole):

reacting a substituted or unsubstituted (1H-indol-3-yl)methanamine, 2-(1H-indol-3-yl)ethanamine or 3-(1H-indol-3-yl)propan-1-amine with a correctly substituted five membered ring derivative bearing one acid chloride function in a polar aprotic solvent in the presence of a strong base at a temperature between −10° C. to 50° C.

reacting a substituted or unsubstituted (1H-indol-3-yl)methanamine, 2-(1H-indol-3-yl)ethanamine or 3-(1H-indol-3-yl)propan-1-amine with a correctly substituted five membered ring derivative bearing one carboxylic acid function in a polar aprotic solvent in the presence of a strong base at a temperature between 20° C. to 50° C. and in the presence of a peptide bond formation coupling agent.

optionally reacting the compound obtain in the previous step wherein the 5 membered ring bears a halogen atom or a —CH$_2$LG radical wherein LG is a leaving group with suitable nucleophiles or with derivatives such as boronic acid, stannane or organozinc derivatives.

Also the intermediates used in the preparation methods described herein are aspects of the present invention.

Particular embodiments of the inventions are also described in the claims and relate to especially useful subtypes of the compounds of the invention. In particular embodiments, the terms alkyl, alkenyl or alkynyl can be restricted to refer to their cyclic or linear subgroups (such as the linear alkyl or cycloalkyl for alkyl).

More generally, the invention relates to the compounds of formula and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

Figure 1:
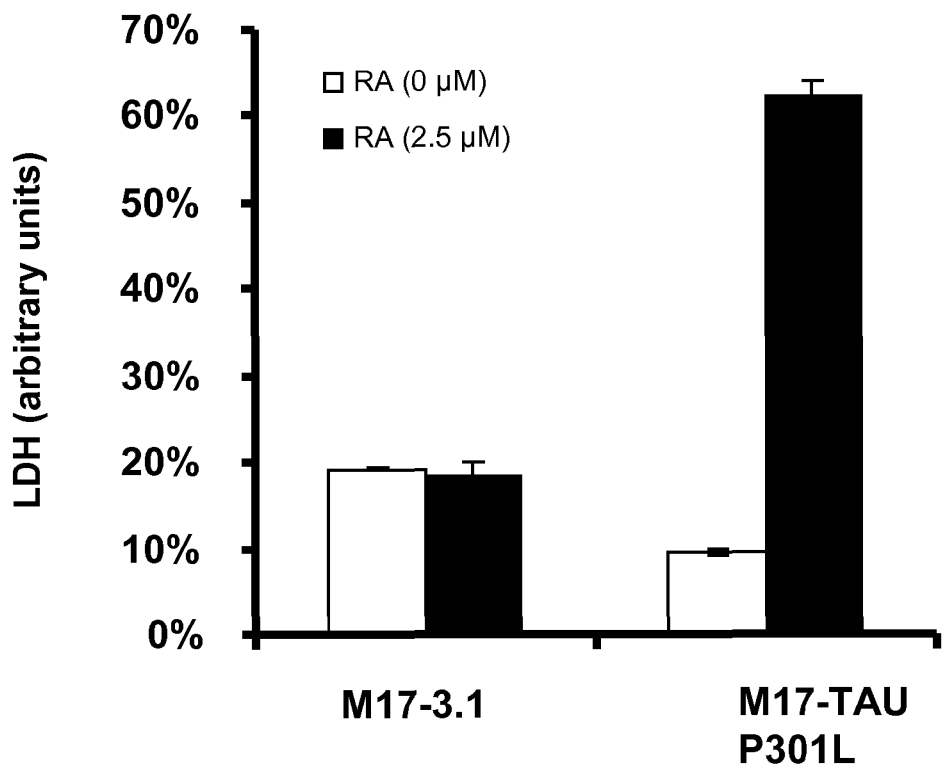
FIG. 1 shows the sensitivity of a TAU(301) expressing neuroblastoma cell line to retinoic acid-instigated differentiation.

(A) pan-TAU (anti-TAU monoclonal antibody (mAb) HT7, Thermo Scientific; detects all tau species independent of phosphorylation status), (B) phosphorylated tau on pS202, T205 (AD2 anti-TAU antibody, Biorad) and unphosphorylated tau on pS202 (anti-TAU-1 antibody, clone PC1C6, Millipore), the graph depicts the ratio of AD2/TAU-1;

(C) phosphorylated tau on pT231 (AT180 anti-TAU mAb, Thermo Scientific), and (D) phosphorylated tau on pT181 (AT270 anti-TAU mAb, Thermo Scientific).

Statistics: students two-tailed T-test*p<0.05, **p<0.01.

DETAILED DESCRIPTION OF THE INVENTION

The terminology "L is independently selected from being not present" and other possibilities as used herein refers to the situation that the two groups which are linked by L are directly coupled to each other via a single bond. As used herein the term "not being present" and "single bond" are synonyms and used interchangeably. As an example, if the invention refers to a compound comprising the following formula

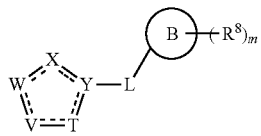

wherein L is independently selected from being not present; —O—; —NH—; —NR$^{10}$—; $C_{1-6}$alkylene; $C_{1-6}$alkenylene; and $C_{1-6}$alkynylene; then this comprises compounds with the following structure

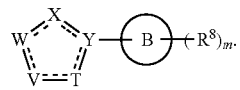

The terminology "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl(ene), heteroarylheteroalkenyl(ene), arylheteroalkynyl(ene), heteroarylheteroalkynyl(ene), heteroarylheteroalkynyl(ene), among others. In other words, this term means that —CH$_3$ can be replaced by —NH$_2$; —CH$_2$— by —NH—, —O— or —S—; a —CH= by —N=; and =CH by =N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, CH$_3$—O—CH$_2$—, CH$_3$—S—CH$_2$—, CH$_3$—CH$_2$—O—CH$_2$—, CH$_3$—NH—, (CH$_3$)$_2$—N—, (CH$_3$)$_2$—CH$_2$—NH—CH$_2$—CH$_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-CH$_2$—S—CH$_2$—, aryl-CH$_2$—O—CH$_2$—, aryl-NH—CH$_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a C=O, C=S, N=O, N=S, S=O or S(O)$_2$" as used herein, refers to a group where two or more hydrogen atoms on a carbon atom or heteroatom of said group are taken together to form C=O, C=S, N=O, N=S, S=O or S(O)$_2$. In other words, the expression means that a carbon atom or heteroatom of said group can be oxidized to form a C=O, C=S, N=O, N=S, S=O or S(O)$_2$. As an example, the terminology refers to "an alkyl wherein optionally two or more hydrogen atoms on a carbon atom or heteroatom of said alkyl can be taken together to form a C=O, C=S, N=O, N=S, S=O or S(O)$_2$", includes among other examples CH$_3$—C(O)—CH$_2$—, CH$_3$—C(O)—, CH$_3$—C(S)—CH$_2$— and (CH$_3$)$_2$—CH$_2$—C(O)—CH$_2$—CH$_2$—. As another example, as used herein and unless otherwise stated, the expression "two or more hydrogen atoms on a carbon atom or heteroatom of said heterocycle can be taken together to form a C=O, C=S, N=O, N=S, S=O or S(O)$_2$" means that a carbon atom or heteroatom of the ring can be oxidized to form a C=O, C=S, N=O, N=S, S=O or S(O)$_2$.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a C=O, C=S, N=O, N=S, S=O or S(O)$_2$" can combine the two aspects described herein above and includes, if the group referred to is alkyl, among other examples CH$_3$—COO—, CH$_3$—COO—CH$_2$—, CH$_3$—NH—CO—, CH$_3$—NH—CO—CH$_2$—, CH$_3$—NH—CS—CH$_2$—, CH$_3$—NH—CS—NH—CH$_2$—, CH$_3$—NH—S(O)$_2$— and CH$_3$—NH—S(O)$_2$—NH—CH$_2$—.

The term "leaving group" as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl (i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$), cyclopentenyl (—$C_5H_7$), cyclohexenyl (—$C_6H_9$) and 5-hexenyl (—$CH_2CH_2CH_2CH_2$CH=$CH_2$). The double bond may be in the cis or trans configuration. In a particular embodiment, the term alkenyl refers to $C_{1-12}$ hydrocarbons, yet more in particular to $C_{1-6}$ hydrocarbons as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$) and 5-hexenyl (—$CH_2CH_2CH_2CH_2$CH=$CH_2$). The double bond may be in the cis or trans configuration.

The term "cycloalkenyl" as used herein refers to $C_2$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—$C_5H_7$) and cyclohexenyl (—$C_6H_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH). In a particular embodiment, the term alkenyl refers to $C_{1-12}$ hydrocarbons, yet more in particular to $C_{1-6}$ hydrocarbons as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH).

The term "cycloalkynyl" as used herein refers to $C_2$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like.

"Arylalkylene" as used herein refers to an alkyl radical in which one of the hydrogen atoms bonded to a carbon atom, typically a terminal or sp3 carbon atom, is replaced with an aryl radical. Typical arylalkylene groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkylene group comprises 6 to 20 carbon atoms, e.g. the alkylene moiety of the arylalkylene group is 1 to 6 carbon atoms and the aryl moiety is 5 to 14 carbon atoms.

"Arylalkenylene" as used herein refers to an alkenylene radical in which one of the hydrogen atoms bonded to a carbon atom, is replaced with an aryl radical. The arylalkenylene group comprises 6 to 20 carbon atoms, e.g. the alkenylene moiety of the arylalkenylene group is 1 to 6 carbon atoms and the aryl moiety is 5 to 14 carbon atoms.

"Arylalkynylene" as used herein refers to an alkynyl radical in which one of the hydrogen atoms bonded to a carbon atom, is replaced with an aryl radical. The arylalkynylene group comprises 6 to 20 carbon atoms, e.g. the alkynylene moiety of the arylalkynylene group is 1 to 6 carbon atoms and the aryl moiety is 5 to 14 carbon atoms.

The term "heterocycle" as used herein means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

"Heterocycle-alkylene" as used herein refers to an alkyl radical in which one of the hydrogen atoms bonded to a carbon atom, typically a terminal or sp3 carbon atom, is replaced with a heterocycle radical. An example of a heterocycle-alkylene group is 2-pyridyl-methylene. The heterocycle-alkylene group comprises 6 to 20 carbon atoms, e.g. the alkylene moiety of the heterocycle-alkyl group is 1 to 6 carbon atoms and the heterocycle moiety is 5 to 14 carbon atoms.

"Heterocycle-alkenylene" as used herein refers to an alkenyl radical in which one of the hydrogen atoms bonded to a carbon atom, is replaced with an heterocycle radical. The heterocycle-alkenylene group comprises 6 to 20 carbon atoms, e.g. the alkenylene moiety of the heterocycle-alkenylene group is 1 to 6 carbon atoms and the heterocycle moiety is 5 to 14 carbon atoms.

"Heterocycle-alkynylene" as used herein refers to an alkynylene radical in which one of the hydrogen atoms bonded to a carbon atom, is replaced with a heterocycle radical. The heterocycle-alkynylene group comprises 6 to 20 carbon atoms, e.g. the alkynylene moiety of the heterocycle-alkynylene group is 1 to 6 carbon atoms and the heterocycle moiety is 5 to 14 carbon atoms.

"Heteroaryl" means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkylene" as used herein refers to an alkyl radical in which one of the hydrogen atoms bonded to a carbon atom, typically a terminal or sp3 carbon atom, is replaced with a heterocycle radical. An example of a heteroaryl-alkylene group is 2-pyridyl-methylene. The heteroaryl-alkylene group comprises 6 to 20 carbon atoms, e.g. the alkylene moiety of the heteroaryl-alkylene group is 1 to 6 carbon atoms and the heteroaryl moiety is 5 to 14 carbon atoms.

"Heteroaryl-alkenylene" as used herein refers to an alkenyl radical in which one of the hydrogen atoms bonded to a carbon atom, is replaced with an heteroaryl radical. The heteroaryl-alkenylene group comprises 6 to 20 carbon atoms, e.g. the alkenylene moiety of the heteroaryl-alkenylene group is 1 to 6 carbon atoms and the heteroaryl moiety is 5 to 14 carbon atoms.

"Heteroaryl-alkynylene" as used herein refers to an alkynyl radical in which one of the hydrogen atoms bonded to a carbon atom, is replaced with a heteroaryl radical. The heteroaryl-alkynylene group comprises 6 to 20 carbon atoms, e.g. the alkynylene moiety of the heteroaryl-alkynylene group is 1 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocycle" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Whenever the term "substituted" is used in the present invention, and unless otherwise stated, it is meant to indicate that one or more hydrogens on the atom, or group indicated in the expression using "substituted" is replaced with one or more group each independently selected from halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$, -cyano; —COOH; —COOR$^{10}$; —C(O)NR$^{12}$R$^{13}$; —C(O)R$^{11}$; wherein R$^{10}$, R$^{11}$, R$^{12}$, R$^{13}$ have the same meaning as that defined herein.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

In an embodiment, the present invention encompasses compounds of formula (AA1) or any subgroup thereof, wherein, each dotted line individually represents an optional double bond, wherein maximally two dotted lines selected from the five dotted lines are a double bond;

$E^1$ is independently selected from $CR^1$; and N; preferably $E^1$ is $CR^1$;

$E^2$ is independently selected from $NR^2$; and O; preferably $E^2$ is $NR^2$;

$E^3$ is independently selected from $CR^3$; and N; preferably $E^3$ is $CR^3$;

Q is independently selected from $NR^b$—C(O); or C(O)NH; preferably Q is selected $NR^b$—C(O);

$R^a$ is hydrogen or can be taken together with $R^b$ to form a substituted or unsubstituted unsaturated 4, 5, 6, 7 or 8 membered ring containing one N atom, for example a piperidine ring; preferably $R^a$ is hydrogen;

$R^b$ is hydrogen or can be taken together with $R^a$ to form a substituted or unsubstituted unsaturated 4, 5, 6, 7 or 8 membered ring containing one N atom, for example a piperidine ring; preferably $R^b$ is hydrogen;

$R^1$ is selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl (ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; preferably $R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably $R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{6-10}$aryl; wherein said $C_{1-6}$alkyl, $C_{3-8}$cycloalkyl, or $C_{6-10}$aryl, can be unsubstituted or substituted with Z; preferably $R^1$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{6-10}$aryl; preferably $R^1$ is selected from hydrogen; halogen; —OH; $C_{1-6}$alkyloxy; trifluoromethyl; trifluoromethoxy; nitro; —$NH_2$; -cyano; —COOH; —$COOC_{1-6}$ alkyl; $C_{1-6}$alkyl, $C_{3-8}$cycloalkyl; preferably $R^1$ is selected from hydrogen; halogen; $C_{1-6}$alkyl; preferably $R^1$ is hydrogen;

$R^3$ is selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl (ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; preferably $R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably $R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{6-10}$aryl; wherein said $C_{1-6}$alkyl, $C_{3-8}$cycloalkyl; or $C_{6-10}$aryl, can be unsubstituted or substituted with Z; preferably $R^3$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{6-10}$aryl; preferably $R^3$ is selected from hydrogen; halogen; —OH; $C_{1-6}$alkyloxy; trifluoromethyl; trifluoromethoxy; nitro; —$NH_2$; -cyano; —COOH; —$COOC_{1-}$ $_6$alkyl; $C_{1-6}$alkyl; $C_{3-8}$cycloalkyl; preferably $R^3$ is selected from hydrogen; halogen; $C_{1-6}$alkyl; preferably $R^3$ is hydrogen;

$R^4$ is selected from hydrogen; halogen; —OH; —OR$^{10}$; —SH; —SR$^{10}$; —S(O)R$^{11}$; —S(O)$_2$R$^{11}$; —S(O)$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)$_2$; preferably $R^4$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably $R^4$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{6-10}$aryl; wherein said $C_{1-6}$alkyl, $C_{3-8}$cycloalkyl, or $C_{6-10}$aryl, can be unsubstituted or substituted with Z; preferably $R^4$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{6-10}$aryl; preferably $R^4$ is selected from hydrogen; halogen; —OH; $C_{1-6}$alkyloxy; trifluoromethyl; trifluoromethoxy; nitro; —NH$_2$; -cyano; —COOH; —COOC$_{1-6}$alkyl; $C_{1-6}$alkyl; $C_{3-8}$cycloalkyl; preferably $R^4$ is selected from hydrogen; halogen; $C_{1-6}$alkyl; preferably $R^4$ is hydrogen;

$R^6$ is selected from hydrogen; halogen; —OH; —OR$^{10}$; —SH; —SR$^{10}$; —S(O)R$^{11}$; —S(O)$_2$—; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)$_2$; preferably $R^6$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably $R^6$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{6-10}$aryl; wherein said $C_{1-6}$alkyl, $C_{3-8}$cycloalkyl, or $C_{6-10}$aryl, can be unsubstituted or substituted with Z; preferably $R^6$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{6-10}$aryl; preferably $R^6$ is selected from hydrogen; halogen; —OH; $C_{1-6}$alkyloxy; trifluoromethyl; trifluoromethoxy; nitro; —NH$_2$; -cyano; —COOH; —COOC$_{1-6}$alkyl; $C_{1-6}$alkyl; $C_{3-8}$cycloalkyl; preferably $R^6$ is selected from hydrogen; halogen; $C_{1-6}$alkyl; preferably $R^6$ is hydrogen;

$R^2$ is selected from hydrogen; alkyl; alkenyl; and alkynyl; preferably $R^2$ is selected from hydrogen; $C_{1-6}$alkyl; $C_{3-8}$cycloalkyl; $C_{1-6}$alkenyl; and $C_{1-6}$alkynyl; preferably $R^2$ is selected from hydrogen, $C_{1-6}$alkyl, or $C_{3-8}$cycloalkyl; preferably $R^2$ is hydrogen;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)$_2$; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-8}$alkyl; $C_{3-8}$cycloalkyl; $C_{6-10}$aryl; wherein said $C_{1-8}$alkyl, $C_{3-8}$cycloalkyl, or $C_{6-10}$aryl, can be unsubstituted or substituted with Z; preferably $R^5$ is selected from halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-8}$cycloalkyl; $C_{6-10}$aryl; preferably R⁵ is selected from halogen; —OH; $C_{1-6}$alkyloxy; trifluoromethyl; trifluoromethoxy; nitro; —NH₂; -cyano; —COOH; —COOC$_{1-6}$alkyl; $C_{1-6}$alkyl; $C_{3-8}$cycloalkyl; preferably R⁵ is selected from halogen or $C_{1-6}$alkyl; preferably R⁵ is halogen; preferably R⁵ is chloro or fluoro, preferably R⁵ is chloro;

n is selected from 0; 1 or 2; preferably n is 1 or 2, preferably n is 1;

B represents a cyclic structure selected from cycloalkyl; cycloalkenyl; cycloalkynyl; aryl; or heterocycle; preferably B is selected from $C_{3-8}$cycloalkyl; $C_{5-8}$cycloalkenyl; $C_{6-10}$aryl; or heterocycle; preferably B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from $C_{3-6}$cycloalkyl; $C_{6-10}$aryl; or pyridyl, dihydroypyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;

m is selected from 0; 1; 2; 3; 4 and 5; preferably m is selected from 0, 1, 2, 3, preferably m is 0, 1, or 2;

R⁸ is independently selected from hydrogen; halogen; aryl; alkyl; alkenyl; alkynyl; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C═O, C═S, N═O, N═S, S═O or S(O)₂; preferably R⁸ is independently selected from hydrogen; halogen; $C_{1-6}$alkyl; $C_{3-8}$cycloalkyl; $C_{2-6}$alkenyl; $C_{2-6}$alkynyl; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; wherein said $C_{1-6}$alkyl, $C_{3-8}$cycloalkyl; $C_{2-6}$alkenyl and $C_{2-6}$alkynyl optionally includes one or more heteroatoms, said heteroatoms being selected from the atoms O, S and N; and wherein said $C_{1-6}$alkyl, $C_{3-8}$cycloalkyl; $C_{2-6}$alkenyl and $C_{2-6}$alkynyl can be unsubstituted or substituted with Z; preferably R⁸ is independently selected from hydrogen; halogen; $C_{1-6}$alkyl; $C_{3-8}$cycloalkyl; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; wherein said $C_{1-6}$alkyl or $C_{3-8}$cycloalkyl, can be unsubstituted or substituted with Z; preferably R⁸ is independently selected from hydrogen; halogen; $C_{1-6}$alkyl; —OH; —OR¹⁰; —SH; —SR¹⁰; —S(O)₂R¹¹; trifluoromethyl; trifluoromethoxy; nitro; —NHC(O)R¹⁰; —NR¹⁰C(O)R¹⁰; —NR¹²R¹³; -cyano; —COOH; —COOR¹⁰; —C(O)NR¹²R¹³; wherein said $C_{1-6}$alkyl can be unsubstituted or substituted with Z; preferably R⁸ is independently selected from hydrogen; halogen; $C_{1-6}$alkyl; —OH; —OR¹⁰; —SH; trifluoromethyl; trifluoromethoxy; nitro; —NR¹²R¹³; -cyano; —COOH; —COOR¹⁰;

each Z is independently selected from halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; preferably each Z is independently selected from halogen; —OH; —OR¹⁰; —SH; —SR¹⁰; —S(O)R¹¹; —S(O)₂R¹¹; trifluoromethyl; trifluoromethoxy; nitro; —NHC(O)R¹⁰; —NR¹⁰C(O)R¹⁰; —NR¹²R¹³; -cyano; —COOH; —COOR¹⁰; preferably each Z is independently selected from halogen; —OH; —OR¹⁰; —SH; —SR¹⁰; trifluoromethyl; trifluoromethoxy; nitro; —NR¹²R¹³; -cyano; —COOH; —COOR¹⁰; preferably each Z is independently selected from halogen; —OH; —OR¹⁰; trifluoromethyl; trifluoromethoxy; nitro; NH₂; -cyano; —COOH; or —COO$_{1-6}$ alkyl;

each Z¹ is independently selected from hydrogen; alkyl; or Z; preferably each Z¹ is independently selected from hydrogen, $C_{1-6}$alkyl, $C_{3-8}$cycloalkyl or Z; preferably each Z¹ is independently selected from hydrogen, $C_{1-6}$alkyl, or Z; preferably each Z¹ is independently selected from hydrogen, or Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; preferably each $R^{10}$ is independently selected from $C_{1-6}$alkyl; $C_{3-8}$cycloalkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene or heterocycle-$C_{2-6}$alkynylene; wherein said $C_{1-6}$alkyl, $C_{3-8}$cycloalkyl; $C_{2-6}$alkenyl, $C_{2-6}$alkynyl, $C_{6-10}$aryl, $C_{6-10}$aryl$C_{1-6}$alkylene, $C_{6-10}$aryl$C_{2-6}$alkenylene, heterocycle, $C_{6-10}$aryl$C_{2-6}$ alkynylene, heterocycle-$C_{1-6}$alkylene, heterocycle-$C_{2-6}C_{2-6}$ alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; wherein a carbon atom or heteroatom of said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$alkenylene or heterocycle-$C_{2-6}$alkynylene, can be oxidized to form a C=O, C=S, N=O, N=S, S=O or $S(O)_2$; preferably each $R^{10}$ is independently selected from $C_{1-6}$alkyl; $C_{3-8}$cycloalkyl; $C_{6-10}$aryl; heterocycle; $C_{6-10}$aryl$C_{1-6}$alkylene; heterocycle-$C_{1-6}$alkylene; preferably each $R^{10}$ is independently selected from $C_{1-6}$alkyl; $C_{3-8}$cycloalkyl; $C_{6-10}$aryl; or heterocycle; preferably each $R^{10}$ is independently selected from $C_{1-6}$alkyl; or $C_{6-10}$aryl; preferably each $R^{10}$ is $C_{1-6}$alkyl;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; preferably $R^{11}$ is independently selected from hydroxyl; $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$ alkynylene and wherein said $C_{1-6}$alkyl, $C_{3-8}$cycloalkyl; $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl; $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$alkenylene or heterocycle-$C_{2-6}$alkynylene can be oxidized to form a C=O, C=S, N=O, N=S, S=O or $S(O)_2$; preferably $R^{11}$ is independently selected from hydroxyl; $C_{1-6}$alkyl, $C_{3-8}$cycloalkyl; $C_{6-10}$aryl, heterocycle, $C_{6-10}$aryl$C_{1-6}$alkylene, heterocycle-$C_{1-6}$alkylene; preferably $R^{11}$ is independently selected from hydroxyl; $C_{1-6}$alkyl, $C_{3-8}$cycloalkyl; $C_{6-10}$aryl, heterocycle, preferably $R^{11}$ is independently selected from hydroxyl; $C_{1-6}$alkyl, or $C_{6-10}$aryl, preferably $R^{11}$ is independently selected from hydroxyl or $C_{1-6}$alkyl, each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; and wherein $R^{12}$ and $R^{13}$ can be taken together in order to form a (5-, 6-, or 7-membered) heterocycle which can be unsubstituted or substituted; preferably each $R^{12}$ and $R^{13}$ is independently selected from hydrogen; $C_{1-6}$alkyl, $C_{3-8}$cycloalkyl; $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene; and wherein said $C_{1-6}$alkyl, $C_{3-8}$cycloalkyl; $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl; $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene can be oxidized to form a C=O, C=S, N=O, N=S, S=O or $S(O)_2$; and wherein $R^{12}$ and $R^{13}$ can be taken together in order to form a (5-, 6-, or 7-membered) heterocycle which can be unsubstituted or substituted; preferably each $R^{12}$ and $R^{13}$ is independently selected from hydrogen; $C_{1-6}$alkyl, $C_{3-8}$cycloalkyl; $C_{6-10}$aryl, heterocycle, $C_{6-10}$aryl$C_{1-6}$alkylene, heterocycle-$C_{1-6}$alkylene; preferably each $R^{12}$ and $R^{13}$ is independently selected from hydrogen; $C_{1-6}$alkyl, $C_{3-8}$cycloalkyl; $C_{6-10}$aryl, heterocycle, preferably each $R^{12}$ and $R^{13}$ is independently selected from hydrogen; $C_{1-6}$alkyl, $C_{3-6}$cycloalkyl, or $C_{6-10}$aryl, preferably each $R^{12}$ and $R^{13}$ is independently selected from hydrogen; or $C_{1-6}$alkyl, wherein L is independently selected from —O—; —NH—; —NR$^{10}$—; $C_{1-6}$alkylene; $C_{1-6}$alkenylene; $C_{1-6}$alkynylene; wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted; and wherein a carbon atom or heteroatom of said $C_{1-6}$alkylene, $C_{1-6}$alkenylene or $C_{1-6}$alkynylene, can be oxidized to form a C=S, N=O, N=S, S=O or S(O)$_2$; preferably L is independently selected from —O—; —NH—; —NR$^{10}$—; $C_{1-6}$alkylene; $C_{1-6}$alkenylene; $C_{1-6}$alkynylene; preferably L is independently selected from —O—; —NH—; —NR$^{10}$—; $C_{1-6}$alkylene; preferably L is independently selected from —O—; or $C_{1-6}$alkylene; preferably L is $C_{1-6}$alkylene;

and each of X, Y, T, W and V is independently selected from —CZ$^1$H—; —CZ$^1$—; —C—; —N—; NR$^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa) preferably X, Y, T, W and V form with the dotted lines one of the cycles having one of the structural formula (Ia), (IIa), (IIIa), (IVa), (Va), (VIa), (VIIa), (VIIIa), (IXa), preferably X, Y, T, W and V form with the dotted lines one of the cycles having one of the structural formula (Ia), (IIa), (IIIa), (IVa), (Va), preferably X, Y, T, W and V form with the dotted lines one of the cycles having one of the structural formula (Ia) or (IIa) or (IIIa),

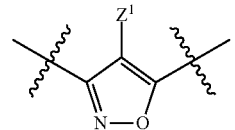

(Ia)

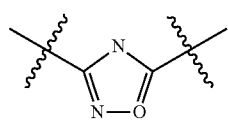

(IIa)

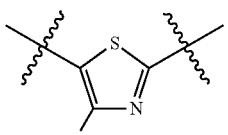

(IVa)

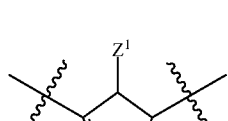

(Va)

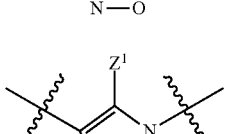

(VIa)

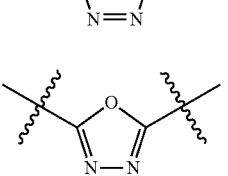

(VIIa)

-continued

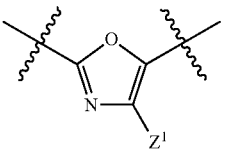

(VIIIa)

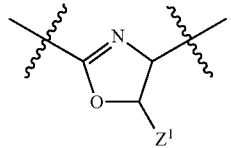

(IXa)

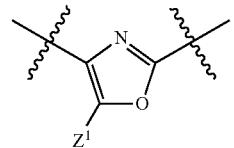

(Xa)

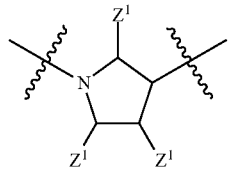

(XIa)

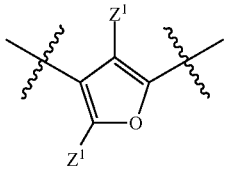

(XIIa)

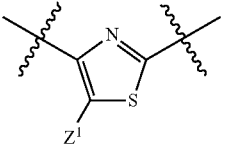

(XIIIa)

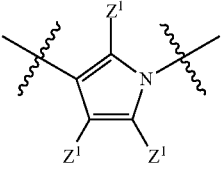

(XIVa)

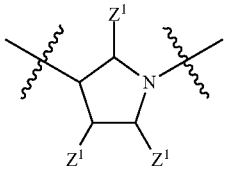

(XVa)

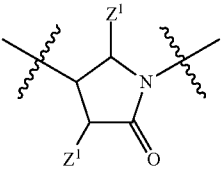

(XVIa)

(XVIIa) 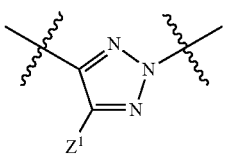

(XVIIIa) 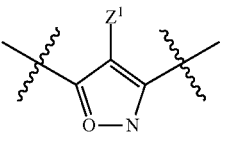

(XIXa) 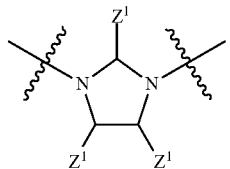

(XXa) 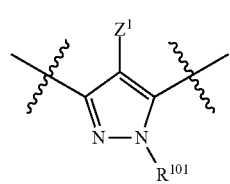

(XXIa) 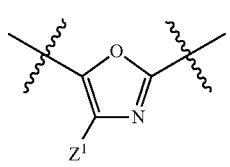

(XXIIa) 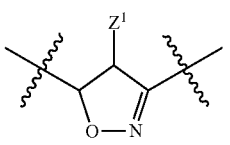

(XXIIIa) 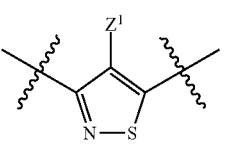

(XXIVa) 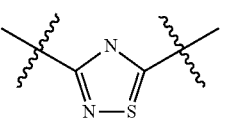

(IIIa) 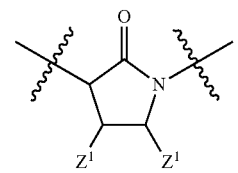

or wherein L is a single bond; and X, Y, T, W and V form with the dotted lines a cycle of formula (IIIa), (IIIa) 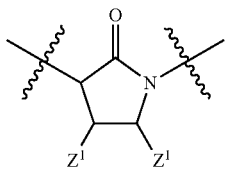

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

In an embodiment, the present invention encompasses compounds of formula (AA1) or any subgroup thereof, wherein, $E^1$ is $CR^1$;
$E^2$ is $NR^2$;
$E^3$ is $CR^3$;
Q is selected $NR^b$—C(O);
$R^a$ is hydrogen;
$R^b$ is hydrogen;
$R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^4$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^6$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^2$ is selected from hydrogen; $C_{1-6}$alkyl; $C_{3-6}$cycloalkyl; $C_{1-6}$alkenyl; and $C_{1-6}$alkynyl;
$R^5$ is selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
n is 1 or 2, preferably n is 1;
B is selected from $C_{3-8}$cycloalkyl; $C_{6-8}$cycloalkenyl; $C_{6-10}$aryl; or heterocycle; preferably B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;

m is selected from 0, 1, 2, 3, $R^8$ is independently selected from hydrogen; halogen; $C_{1-6}$alkyl; $C_{3-8}$cycloalkyl; $C_{2-6}$alkenyl; $C_{2-6}$alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said $C_{1-6}$alkyl, $C_{3-8}$cycloalkyl, $C_{2-6}$alkenyl and $C_{2-6}$alkynyl optionally includes one or more heteroatoms, said heteroatoms being selected from the atoms O, S and N; and wherein said $C_{1-6}$alkyl, $C_{3-8}$cycloalkyl, $C_{2-6}$alkenyl and $C_{2-6}$alkynyl can be unsubstituted or substituted with Z;

each Z is independently selected from halogen; —OH; —$OR^{10}$; —SH; —$SR^{10}$; —$S(O)R^{11}$; —$S(O)_2R^{11}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{12}R^{13}$; -cyano; —COOH; —$COOR^{10}$;

each $Z^1$ is independently selected from hydrogen; alkyl; or Z;

each $R^{10}$ is independently selected from $C_{1-6}$alkyl; $C_{3-8}$cycloalkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene or heterocycle-$C_{2-6}$alkynylene; wherein said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; wherein a carbon atom or heteroatom of said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$alkenylene or heterocycle-$C_{2-6}$alkynylene, can be oxidized to form a C=O, C=S, N=O, N=S, S=O or $S(O)_2$;

each $R^{101}$ is independently selected from hydrogen and $R^{10}$;

$R^{11}$ is independently selected from hydroxyl; $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene and wherein said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl, $C_{2-6}$alkenyl, heterocycle, $C_{2-6}$alkenyl, $C_{6-10}$aryl, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene can be oxidized to form a C=O, C=S, N=O, N=S, S=O or $S(O)_2$;

each $R^{12}$ and $R^{13}$ is independently selected from hydrogen; $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene; and wherein said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}C_{2-6}$alkenylene or heterocycle-$C_{2-6}$alkynylene can be oxidized to form a C=O, C=S, N=O, N=S, S=O or $S(O)_2$; and wherein $R^{12}$ and $R^{13}$ can be taken together in order to form a (5-, 6-, or 7-membered) heterocycle which can be unsubstituted or substituted;

L is independently selected from —O—; —NH—; —$NR^{10}$—; $C_{1-6}$alkylene; $C_{1-6}$alkenylene; $C_{1-6}$alkynylene;

X, Y, T, W and V form with the dotted lines one of the cycles having one of the structural formula (Ia), (IIa), (IIIa), (IVa), (Va), (VIa), (VIIa), (VIIIa), (IXa), or more particularly form with the dotted lines one of the cycles having one of the structural formula (Ia) or (IIa), or (IIIa), or wherein L is a single bond; and X, Y, T, W and V form with the dotted lines a cycle of formula (IIIa), wherein the left side of the formula (Ia), (IIa), (IIIa), (IVa), (Va), (VIa), (VIIa), (VIIIa), (IXa), is attached to Q and the right side thereof is attached to L.

In an embodiment, the present invention encompasses compounds of formula (A1) or any subgroup thereof wherein, $R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^4$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^6$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^2$ is selected from hydrogen or $C_{1-6}$alkyl;
$R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;
n is 1,
B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;
m is 0, 1, or 2;
$R^8$ is independently selected from hydrogen; halogen; $C_{1-6}$alkyl; $C_{3-6}$cycloalkyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein said $C_{1-6}$alkyl or $C_{3-6}$cycloalkyl can be unsubstituted or substituted with Z;
each $Z^1$ is independently selected from halogen; —OH; —OR$^{10}$; —SH; —SR$^{10}$; —S(O)R$^{11}$; —S(O)$_2$R$^{11}$; trifluoromethyl; trifluoromethoxy; nitro; —NHC(O)R$^{10}$; —NR$^{10}$C(O)R$^{10}$; —NR$^{12}$R$^{13}$; -cyano; —COOH; —COOR$^{10}$;
each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen; or Z;
each $R^{10}$ is independently selected from $C_{1-6}$alkyl; $C_{3-6}$cycloalkyl; $C_{6-10}$aryl; heterocycle; $C_{6-10}$aryl$C_{1-6}$alkylene; heterocycle-$C_{1-6}$alkylene;
each $R^{101}$ is independently selected from hydrogen and $R^{10}$;
$R^{11}$ is independently selected from hydroxyl; $C_{1-6}$alkyl, $C_{3-6}$cycloalkyl, $C_{6-10}$aryl, heterocycle, $C_{6-10}$aryl$C_{1-6}$alkylene, heterocycle-$C_{1-6}$alkylene;
each $R^{12}$ and $R^{13}$ is independently selected from hydrogen; $C_{1-6}$alkyl, $C_{3-6}$cycloalkyl, $C_{6-10}$aryl, heterocycle, $C_{6-10}$aryl$C_{1-6}$alkylene, heterocycle-$C_{1-6}$alkylene;
L is independently selected from —O—; —NH—; —NR$^{10}$—; $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa),
or wherein L is a single bond; and X, Y, T, W and V form with the dotted lines a cycle of formula (IIIa), wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

In an embodiment, the present invention encompasses compounds of formula (A1) or any subgroup thereof wherein,
$R^1$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl;
$R^3$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl;
$R^4$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl;
$R^6$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl;
$R^2$ is hydrogen;
$R^5$ is selected from halogen; —OH; —OR$^{10}$; trifluoromethyl; trifluoromethoxy; nitro; —NR$^{12}$R$^{13}$; -cyano; —COOH; —COOR$^{10}$; $C_{1-6}$alkyl; $C_{3-6}$cycloalkyl; $C_{6-10}$aryl;
n is 1;
B is selected from $C_{3-6}$cycloalkyl; $C_{6-10}$aryl; or pyridyl, dihydroypyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;
m is 0, 1, or 2;
$R^8$ is independently selected from hydrogen; halogen; $C_{1-6}$alkyl; $C_{3-6}$cycloalkyl; —OH; —OR$^{10}$; —SH; —SR$^{10}$; —S(O)$_2$R$^{11}$; trifluoromethyl; trifluoromethoxy; nitro; —NHC(O)R$^{10}$; —NR$^{10}$C(O)R$^{10}$; —NR$^{12}$R$^{13}$; -cyano; —COOH; —COOR$^{10}$; —C(O)NR$^{12}$R$^{13}$; wherein said $C_{1-6}$alkyl or $C_{3-6}$cycloalkyl can be unsubstituted or substituted with Z;
each Z is independently selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$;
each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen; or Z;
each $R^{10}$ is independently selected from $C_{1-6}$alkyl; $C_{3-6}$cycloalkyl; $C_{6-10}$aryl; or heterocycle;
each $R^{101}$ is independently selected from hydrogen and $R^{10}$;
$R^{11}$ is independently selected from hydroxyl; $C_{1-6}$alkyl, $C_{3-6}$cycloalkyl, $C_{6-10}$aryl, heterocycle,
each $R^{12}$ and $R^{13}$ is independently selected from hydrogen; $C_{1-6}$alkyl, $C_{3-6}$cycloalkyl, $C_{6-10}$aryl, heterocycle, L is independently selected from —O—; or $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa), or wherein L is a single bond; and X, Y, T, W and V form with the dotted lines a cycle of formula (IIIa), wherein the left side of the formula (Ia), (IIa), (IIIa), (IVa), (Va), (VIa), (VIIa), (VIIIa), (IXa), is attached to Q and the right side thereof is attached to L.

In an embodiment, the present invention encompasses compounds of formula (A1) or any subgroup thereof wherein, $R^1$ is selected from hydrogen; halogen; $C_{1-6}$alkyl; $R^3$ is selected from hydrogen; halogen; $C_{1-6}$alkyl; $R^4$ is selected from hydrogen; halogen; $C_{1-6}$alkyl; $R^6$ is selected from hydrogen; halogen; $C_{1-6}$alkyl; $R^2$ is hydrogen; $R^5$ is selected from halogen or $C_{1-6}$alkyl; n is 1; B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; m is 0, 1, or 2; $R^8$ is independently selected from hydrogen; halogen; $C_{1-6}$alkyl; —OH; —OR$^{10}$; —SH; trifluoromethyl; trifluoromethoxy; nitro; —NR$^{12}$R$^{13}$; -cyano; —COOH; —COOR$^{10}$;

each Z is independently selected from halogen; —OH; —OR$^{10}$; trifluoromethyl; trifluoromethoxy; nitro; NH$_2$; -cyano; —COOH; or —COO$_{1-6}$alkyl;

each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen; or Z;

each $R^{10}$ is independently selected from $C_{1-6}$alkyl; or $C_{6-10}$aryl;

each $R^{101}$ is independently selected from hydrogen and $R^{10}$;

$R^{11}$ is independently selected from hydroxyl; $C_{1-6}$alkyl, or $C_{6-10}$aryl, each $R^{12}$ and $R^{13}$ is independently selected from hydrogen; $C_{1-6}$alkyl, or $C_{6-10}$aryl, L is $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa), preferably X, Y, T, W and V form with the dotted lines one of the cycles having one of the structural formula (Ia), (IIa), (IVa), (Va), preferably X, Y, T, W and V form with the dotted lines one of the cycles having one of the structural formula (Ia) or (IIa), or wherein L is a single bond; and X, Y, T, W and V form with the dotted lines a cycle of formula (IIIa), wherein the left side of the formula (Ia), (IIa), (IIIa), (IVa), (Va), (VIa), (VIIa), (VIIIa), (IXa), is attached to Q and the right side thereof is attached to L.

In an embodiment, the present invention encompasses compounds of formula (A1) or any subgroup thereof wherein, $R^1$ is hydrogen; $R^3$ is hydrogen; $R^4$ is hydrogen; $R^6$ is hydrogen; $R^2$ is hydrogen; $R^5$ is selected from halogen or $C_{1-6}$alkyl; n is 1; B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; m is 0, 1, or 2; $R^8$ is independently selected from hydrogen; halogen; $C_{1-6}$alkyl; —OH; —OR$^{10}$; —SH; trifluoromethyl; trifluoromethoxy; nitro; —NR$^{12}$R$^{13}$; -cyano; —COOH; each Z is independently selected from halogen; —OH; —OR$^{10}$; trifluoromethyl; trifluoromethoxy; nitro; NH$_2$; -cyano; —COOH; each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen, or Z; each $R^{10}$ is $C_{1-6}$ alkyl; each $R^{101}$ is independently selected from hydrogen and $R^{10}$; $R^{11}$ is independently selected from hydroxyl or $C_{1-6}$alkyl, each $R^{12}$ and $R^{13}$ is independently selected from hydrogen; or $C_{1-6}$alkyl, L is $C_{1-6}$alkylene; and X, Y, T, W and V form with the dotted lines one of the cycles having one of the structural formula (Ia), (IIa), (IIIa), (IVa), or wherein L is a single bond; and X, Y, T, W and V form with the dotted lines a cycle of formula (IIIa), wherein the left side of the formula (Ia), (IIa), (IIIa), (IVa), is attached to Q and the right side thereof is attached to L.

The present invention also encompasses a pharmaceutical composition comprising one or more pharmaceutically acceptable excipients and a therapeutically effective amount of a compound according to formula (AA1) or any subgroup thereof or a stereoisomer, enantiomer or tautomer thereof.

In an embodiment, the present invention also encompasses a pharmaceutical composition comprising one or more pharmaceutically acceptable excipients and a therapeutically effective amount of a compound according to formula (AA1) or any subgroup thereof or a stereoisomer, enantiomer or tautomer thereof, wherein, each dotted line individually represents an optional double bond, wherein maximally two dotted lines selected from the five dotted lines are a double bond;

$E^1$ is independently selected from $CR^1$; and N;

$E^2$ is independently selected from $NR^2$; and O;

$E^3$ is independently selected from $CR^3$; and N;

Q is independently selected from $NR^b$—C(O); and C(O) NH;

$R^a$ is hydrogen or can be taken together with $R^b$ to form a substituted or unsubstituted unsaturated 4, 5, 6, 7 or 8 membered ring containing one N atom;

$R^b$ is hydrogen or can be taken together with $R^a$ to form a substituted or unsubstituted unsaturated 4, 5, 6, 7 or 8 membered ring containing one N atom;

$R^1$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; r<cyano; —COOH; —COOR$^{10}$; —C(O)NR$^{12}$R$^{13}$; —C(O)R$^{11}$; alkyl; alkenyl; and alkynyl;

each $R^3$, $R^4$, and $R^6$ is independently selected from hydrogen; halogen; —OH; —OR$^{10}$; —SH; —SR$^{10}$; —S(O)R$^{11}$; —S(O)$_2$R$^{11}$; SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano;

—COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^2$ is selected from hydrogen; alkyl; alkenyl; and alkynyl;
$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

n is selected from 0; 1 or 2;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each $Z^1$ is independently selected from hydrogen; alkyl; and Z;
each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{101}$ is independently selected from hydrogen and $R^{10}$;
each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein $R^{12}$ and $R^{13}$ can be taken together in order to form a (5-, 6-, or 7-membered) heterocycle which can be unsubstituted or substituted;

wherein L is independently selected from being not present; —O—; —NH—; —NR$^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=S, N=O, N=S, S=O or S(O)$_2$;

and each of X, Y, T, W and V is independently selected from —CZ$^1$H—; —CZ$^1$—; —C—; —N—; NR$^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa), wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

The present invention also encompasses compounds of formula (AA1) or any subgroup thereof or a stereoisomer, enantiomer, tautomer, solvate, hydrate, salt or prodrug thereof for use as a medicine.

The present invention also encompasses compounds of formula (AA1) or any subgroup thereof or a stereoisomer, enantiomer, tautomer, solvate, hydrate, salt or prodrug thereof for use as a medicine for the prevention or treatment of neurodegenerative disorders, wherein, each dotted line individually represents an optional double bond, wherein maximally two dotted lines selected from the five dotted lines are a double bond;

$E^1$ is independently selected from CR$^1$; and N;

$E^2$ is independently selected from NR$^2$; and O;

$E^3$ is independently selected from CR$^3$; and N;

$R^a$ is hydrogen or can be taken together with $R^b$ to form a substituted or unsubstituted 4, 5, 6, 7 or 8 membered ring containing one N atom, preferably a piperidine ring;

$R^b$ is hydrogen or can be taken together with $R^a$ to form a substituted or unsubstituted 4, 5, 6, 7 or 8 membered ring containing one N atom, preferably a piperidine ring;

Q is independently selected from NR$^b$—C(O); C(O); and C(O)NH;

each $R^1$, $R^3$, $R^4$, and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^5$ is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^2$ is selected from hydrogen; alkyl; alkenyl; and alkynyl;

n is selected from 0; 1 or 2;

each of X, Y, T, W and V is independently selected from —CZ$^1$H—; —CZ$^1$—; —C—; —N—; NR$^{101}$; —O—; —S—; or —CO—; wherein at least one of X, Y, T; W or V is selected from —CZ$^1$H— or —CZ— or —C—; and whereby Y is selected from —CZ$^1$—; —C—; or —N—;

L is independently selected from being not present; —O—; —NH—; —NR$^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or S(O)$_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein $R^{12}$ and $R^{13}$ can be taken together in order to form a (5-, 6-, or 7-membered) heterocycle which can be unsubstituted or substituted.

In an embodiment, the present invention also encompasses compounds of formula (AA1) or any subgroup thereof or a stereoisomer, enantiomer, tautomer, solvate, hydrate, salt or prodrug thereof for use as a medicine for the prevention or treatment of neurodegenerative disorders, wherein, each dotted line individually represents an optional double bond, wherein maximally two dotted lines selected from the five dotted lines are a double bond;

$E^1$ is independently selected from CR$^1$; and N;

$E^2$ is independently selected from NR$^2$; and O;

$E^3$ is independently selected from CR$^3$; and N;

Q is independently selected from NR$^b$—C(O); and C(O)NH;

$R^a$ is hydrogen or can be taken together with $R^b$ to form a substituted or unsubstituted unsaturated 4, 5, 6, 7 or 8 membered ring containing one N atom;

$R^b$ is hydrogen or can be taken together with $R^a$ to form a substituted or unsubstituted unsaturated 4, 5, 6, 7 or 8 membered ring containing one N atom;

each $R^1$, $R^3$, $R^4$, and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^2$ is selected from hydrogen; alkyl; alkenyl; and alkynyl;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)

$R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

n is selected from 0; 1 or 2;

L is independently selected from being not present, —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or $S(O)_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{18}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

and each of X, Y, T, W and V is independently selected from —$CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa),

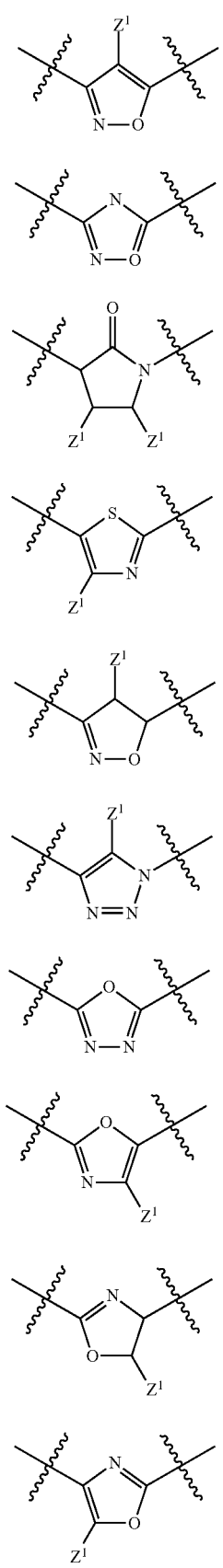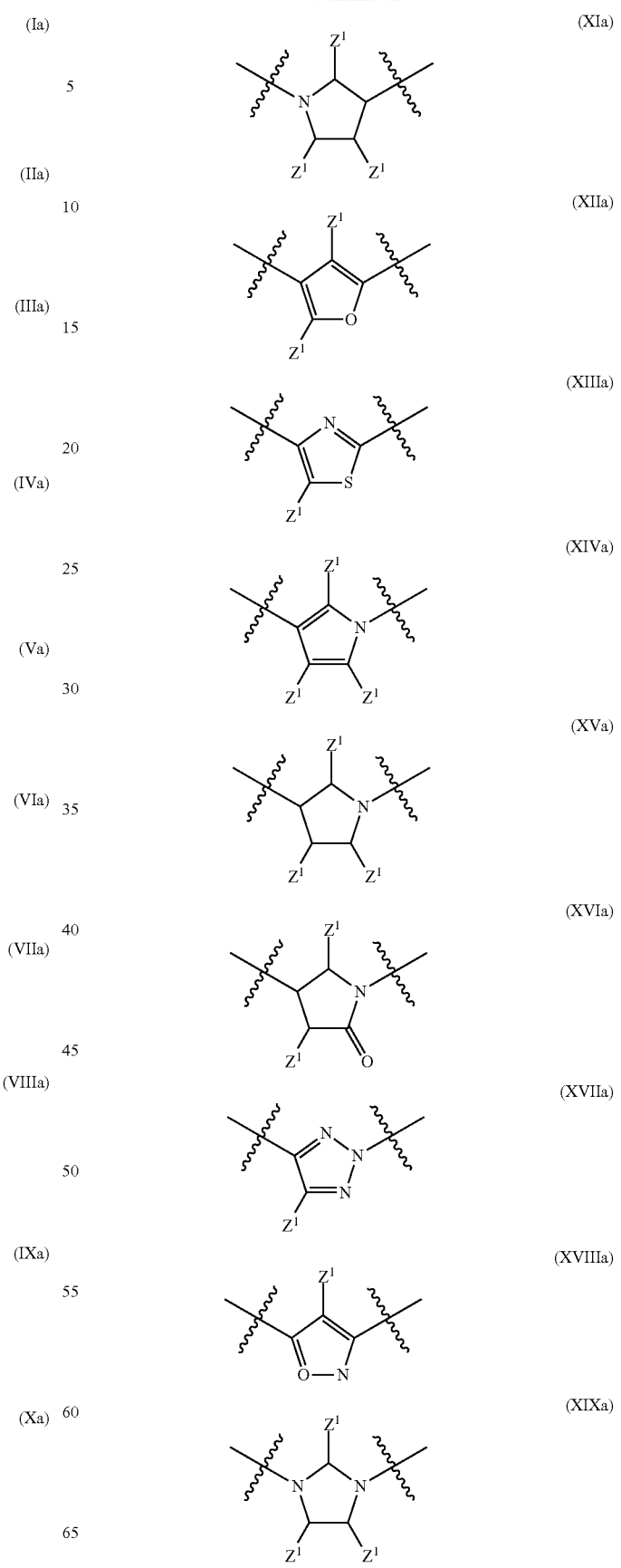

-continued

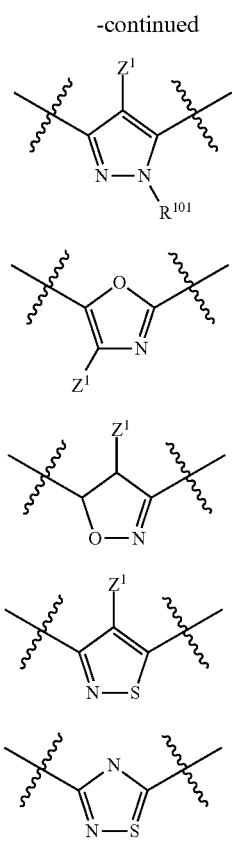

(XXa)

(XXIa)

(XXIIa)

(XXIIIa)

(XXIVa)

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

Another aspect of the present invention provides compounds according to formula (BB1),

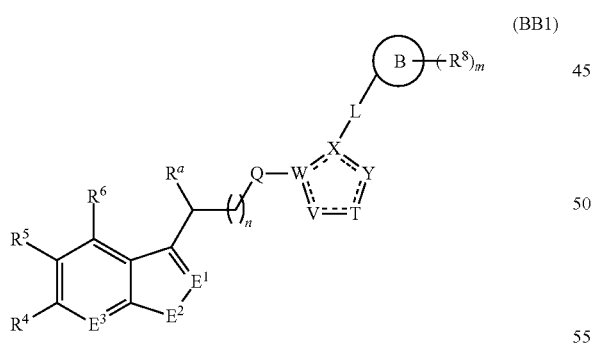

(BB1)

wherein,
each dotted line individually represents an optional double bond, wherein maximally two dotted lines selected from the five dotted lines are a double bond;

$E^1$ is independently selected from $CR^1$; and N;

$E^2$ is independently selected from $NR^2$; and O;

$E^3$ is independently selected from $CR^3$; and N;

$R^a$ is hydrogen or can be taken together with $R^b$ to form a substituted or unsubstituted 4, 5, 6, 7 or 8 membered ring containing one N atom, preferably a piperidine ring;

$R^b$ is hydrogen or can be taken together with $R^a$ to form a substituted or unsubstituted 4, 5, 6, 7 or 8 membered ring containing one N atom, preferably a piperidine ring;

Q is independently selected from $NR^b$—C(O); C(O); and C(O)NH;

each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; $NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

$R^2$ is selected from hydrogen; alkyl; alkenyl; and alkynyl;

n is selected from 0; 1 or 2;

each of X, Y, T, W and V is independently selected from —$CZ^1H$—; —$CZ^1$—; —C—; —N—; $NR^{101}$; —O—; —S—; or —CO—; wherein at least one of X, Y, T; W or V is selected from —$CZ^1H$— or —$CZ^1$— or —C1-;

L is independently selected from being not present; —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or $S(O)_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;
and wherein a carbon atom or heteroatom of said alkyl, alkenyl and alkynyl, can be oxidized to form a C=O, C=S, N=O, N=S, S=O or S(O)$_2$;
each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;
each Z$^1$ is independently selected from hydrogen; alkyl; and Z;
each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
each R$^{101}$ is independently selected from hydrogen and R$^{10}$;
each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein R$^{12}$ and R$^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

In a particular embodiment of this aspect of the invention, the compounds have a structure according to the formulae (BB2), (BB3), (BB4), (BB5), (BB6), or (BB7),

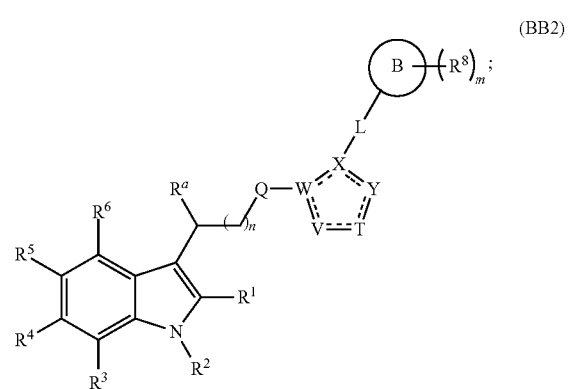

(BB2)

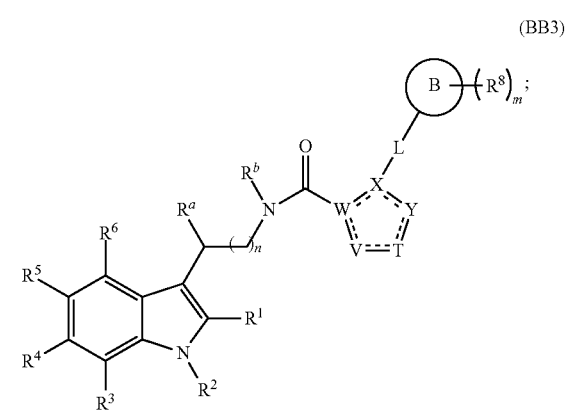

(BB3)

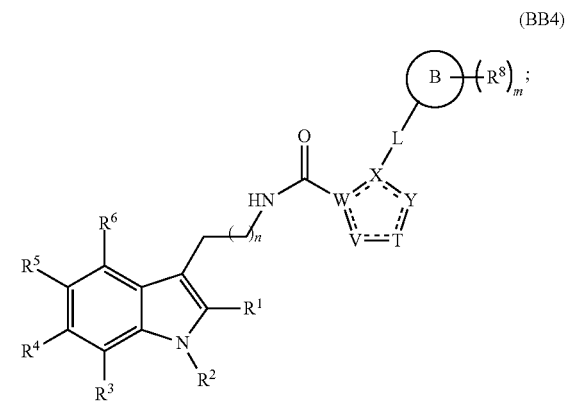

(BB4)

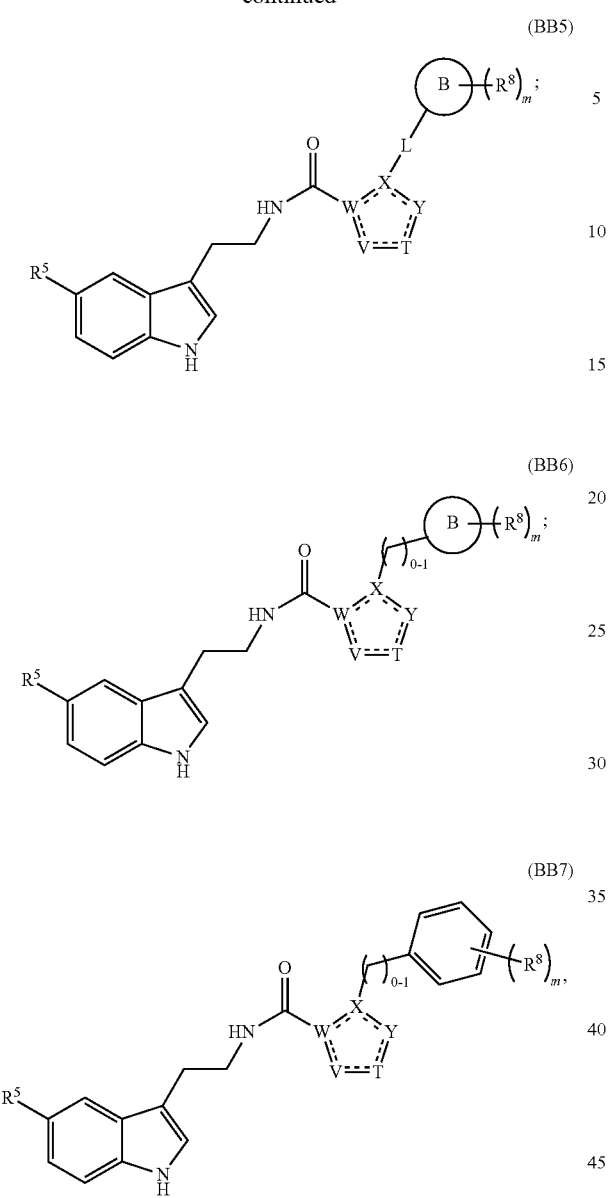

(BB5)

(BB6)

(BB7)

whereby all variables are as provided for formula (BB1).

In a more particular embodiment of this aspect of the invention each of X, Y, T, W and V is independently selected from —CZ$^1$H—; —CZ$^1$—; —C—; —N—; NR$^{101}$; —O—; —S—; or —CO—; and form with the dotted lines one of the cycles having one of the structural formula (Ib), (IIb), (IIIb), (IVb), or (Vb).

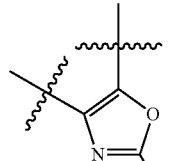

(IIb)

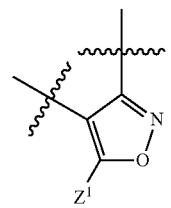

(IIIb)

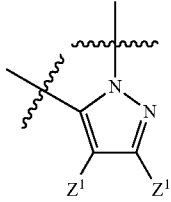

(IVb)

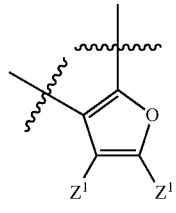

(Vb)

In a particular embodiment, the invention provides the compounds of formulae (BB1), (BB2), (BB3), (BB4), (BB5), (BB6) and (BB7) and embodiments thereof described herein for use as a medicine, more in particular for the prevention or treatment of neurodegenerative disorders, such as disorders collectively known as tauopathies, and disorders characterised by cytotoxic α-synuclein amyloidogenesis. The invention also provides for pharmaceutical compositions of the compounds of the formulae (BB1), (BB2), (BB3), (BB4), (BB5), (BB6) and (BB7) and embodiments thereof described herein and methods for the treatment or prevention of neurodegenerative disorders by using said compounds of the formulae (BB1), (BB2), (BB3), (BB4), (BB5), (BB6) and (BB7) and embodiments thereof.

Another aspect of the present invention provides compounds according to formula (CC1),

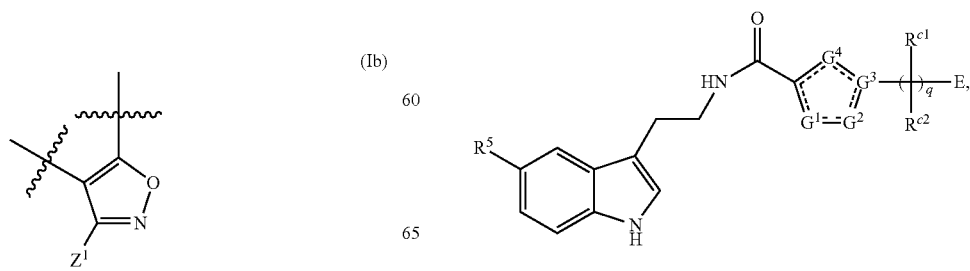

(CC1)

(Ib)

wherein,
each dotted line individually represents an optional double bond, wherein maximally two dotted lines selected from the five dotted lines are a double bond;
each of $G^1$, $G^2$, $G^3$ and $G^4$ is independently selected from N; $NR^{c3}$; O; $CHR^{c3}$; and $CR^{c3}$; wherein at least two of $G^1$, $G^2$, $G^3$ and $G^4$ are selected from N; $NR^{c3}$; and O; while the other two of $G^1$, $G^2$, $G^3$ and $G^4$ are selected from $CHR^{c3}$; and $CR^{c3}$;
each $R^{c3}$ is selected from hydrogen; and alkyl;
$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
q is selected from 0; 1; 2; or 3; preferably q is 0 or 1;
E is selected from hydrogen; halogen; —OH; —$OR^{10}$; —SH; —$SR^{10}$; trifluoromethoxy; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$;
each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
and wherein $R^{12}$ and $R^{13}$ can be taken together in order to form a (5-, 6-, or 7-membered) heterocycle which can be unsubstituted or substituted;
each of $R^{1c}$ and $R^{2c}$ is independently selected from hydrogen; halogen; alkyl; alkenyl or alkynyl;
and isomers (in particular stereoisomers, enantiomers or tautomers), solvates, hydrates, salts (in particular pharmaceutically acceptable salts) or prodrugs thereof.

In a particular embodiment of this aspect of the invention each of $G^1$, $G^2$, $G^3$ and $G^4$ is independently selected from N; $NR^{c3}$; O; $CHR^{c3}$; and $CR^{c3}$; and form with the dotted lines one of the cycles having one of the structural formula (Ic), (IIc), (IIIc), (IVc), or (Vc):

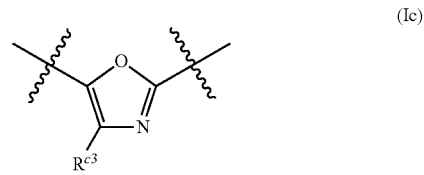
(Ic)

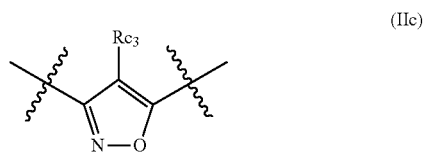
(IIc)

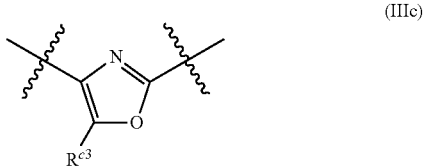
(IIIc)

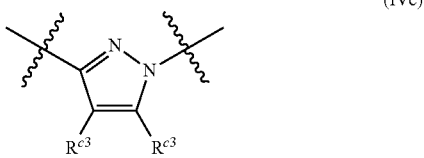
(IVc)

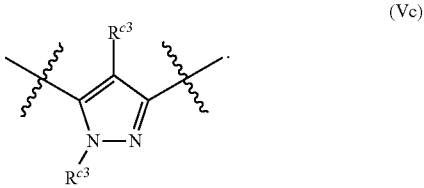
(Vc)

A particular embodiment of this aspect of the present invention provides compounds according to formula (CC2),

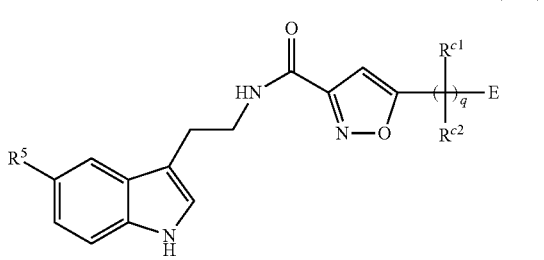

(CC2)

wherein,

R⁵ is independently selected from halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;

q is selected from 0; 1; 2; or 3; preferably q is 0 or 1;

E is selected from hydrogen; halogen; —OH; —OR¹⁰; —SH; —SR¹⁰; trifluoromethoxy; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³;

each R¹⁰ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;

each R¹² and R¹³ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;

and wherein R¹² and R¹³ can be taken together in order to form a (5-, 6-, or 7-membered) heterocycle which can be unsubstituted or substituted;

each of R¹ᶜ and R² is independently selected from hydrogen; halogen; alkyl; alkenyl or alkynyl;

and isomers (in particular stereoisomers, enantiomers or tautomers), solvates, hydrates, salts (in particular pharmaceutically acceptable salts) or prodrugs thereof.

In a particular embodiment of the present aspect of the invention, E is selected from hydrogen; —OH; —NR¹²R¹³ (preferably NH₂, NHMe, N(Me)₂, NHethyl or N(ethyl)₂); —O-alkyl; NHC(O)O-alkyl.

In a particular embodiment, each of R¹ᶜ and R²ᶜ is independently selected from hydrogen; halogen; or alkyl; yet more particularly is hydrogen.

In a particular embodiment, R⁵ is selected from hydrogen, halogen and alkyl (more preferably $C_{1-6}$ alkyl, yet more preferably methyl).

In a particular embodiment, the invention provides the compounds of formulae (CC1) and (CC2) and embodiments thereof described herein for use as a medicine, more in particular for the prevention or treatment of neurodegenerative disorders, such as disorders collectively known as tauopathies, and disorders characterised by cytotoxic α-synuclein amyloidogenesis. The invention also provides for pharmaceutical compositions of the compounds of the formulae (CC1) and (CC2) and embodiments thereof described herein and methods for the treatment or prevention of neurodegenerative disorders by using said compounds of the formulae (CC1) and (CC2) and embodiments thereof.

In a particular embodiment, the invention provides the compounds described herein for use as a medicine for the prevention or treatment of neurodegenerative disorders, such as disorders collectively known as tauopathies, and disorders characterised by cytotoxic α-synuclein amyloidogenesis. The invention also provides for pharmaceutical compositions of the compounds described herein and methods for the treatment or prevention of neurodegenerative disorders.

The term "Tauopathy" as used herein, unless otherwise stated, refers to a disease characterised by dysfunctioning of the TAU protein, for instance manifested by insoluble aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17).

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The term "neurodegenerative disorders" as used herein, unless otherwise stated, refers to tauopathy and α-synucleopathy, and thereby includes, but is not limited to Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "Alzheimer's disease" as used herein, also called Alzheimer disease, Senile Dementia of the Alzheimer Type (SDAT) or simply Alzheimer's refers to a chronic progressive nervous disease characterised by neurodegeneration with as most important (early) symptom being memory loss. As the disease advances, symptoms include confusion, irritability and aggression, mood swings, language breakdown, long-term memory loss, and the general withdrawal of the sufferer as their senses decline.

The term "neuroprotective" agent, as used herein, refers to drugs or chemical agents intended to prevent neurodegeneration, including drugs that slow down or stop the progression of neuronal degeneration.

The present invention relates to a group of novel compounds which have desirable biological properties such as an inhibitory effect on TAU-instigated cytotoxicity. Based on this inhibitory activity, and the fact that these compounds are not toxic to neural cells, these derivatives are useful in the manufacture of a medicament for the prevention and/or treatment of a tauopathy. The novel compounds have a structure according to formulae and embodiments thereof as described herein.

The term "pharmaceutically acceptable carrier" or "pharmaceutically acceptable excipient" as used herein in relation to pharmaceutical compositions and combined preparations means any material or substance with which the active principle may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

These novel compounds of the invention can be prepared by the following methods which are exemplified further in the examples.

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention can be prepared according to the following general procedures:

Scheme 1:

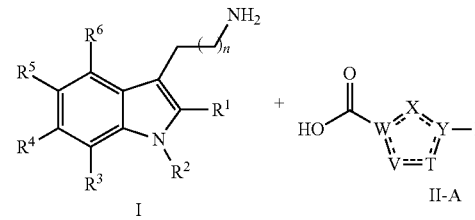

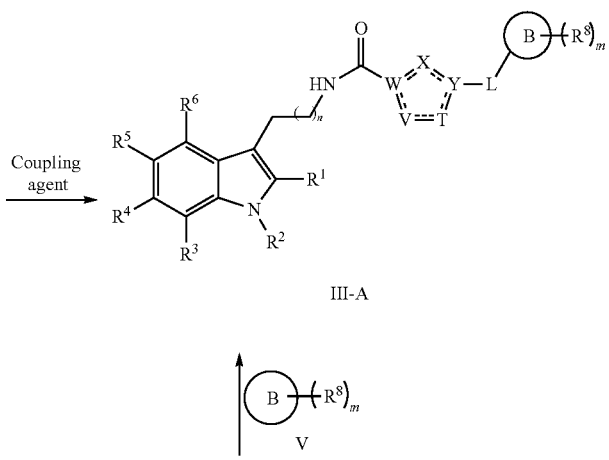

-continued

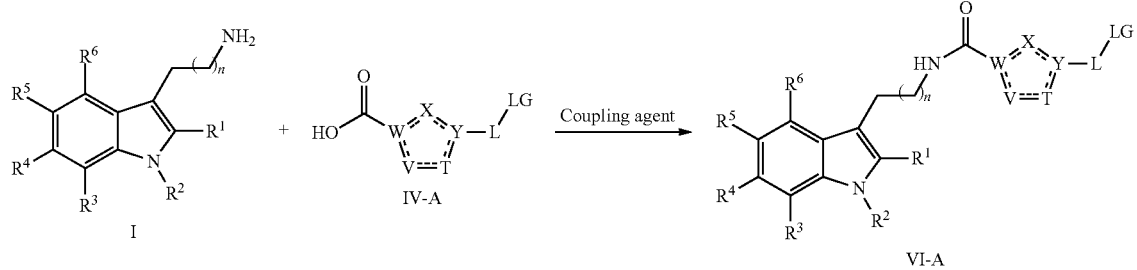

Scheme 1: all $R^1, R^2, R^3, R^4, R^5, R^6, R^8, L, B, n, m$ and LG are as described for the compounds of the present invention and its embodiments and formulae.

Intermediates of formula I are commercially available or synthesized by procedures known to the skilled in the art or as set forth in the examples below. More detailed information can be found in the following references (e.g., Journal of Fluorine Chemistry, 127(9), 1256-1260, 2006; Medicinal Chemistry, 3(6), 561-571, 2007; WO 2006007542; J. Org. Chem., 71(18), 7028-7034, 2006; Organic Letters, 4(16), 2613-2615, 2002; Tetrahedron Letters, 43(5), 787-790, 2002; Synlett, 8, 1311-1315, 2005; Journal of the American Chemical Society, 130(12), 3853-3865, 2008; Journal of Medicinal Chemistry, 49(21), 6408-6411, 2006; Journal of Medicinal Chemistry, 47(15), 3823-3842, 2004 . . . ). Condensation of intermediates of formula I with intermediates of formula II-A (commercially available or synthesized by procedures known to the skilled in the art or as set forth in the examples below), by procedures known to the skilled in the art or as set forth in the examples below provides compounds of formula III-A. In a similar manner, condensation of intermediates of formula I with intermediates of formula IV-A (commercially available or synthesized by procedures known to the skilled in the art or as set forth in the examples below), by procedures known to the skilled in the art or as set forth in the examples below, provides intermediates of formula VI-A, which can be subsequently converted in compounds of formula II-A with a suitable precursor of intermediate of formula V by procedures known to the skilled in the art or as set forth in the examples below.

These strategies can be applied for the synthesis of any 5 membered ring systems (e.g., furane, thiophene, pyrrole, imidazole, oxazole, oxadiazole, isoxazole, isothiazole, thiazole, triazole, pyrazole, pyrrolidine, pyrrolidinone, imidazoline, . . . ) and is not limited to these examples.

Synthesis of 5-substituted isoxazole 3-carboxamide derivatives

This class of compounds can be prepared following the general procedure outlined hereunder.

Scheme 2:

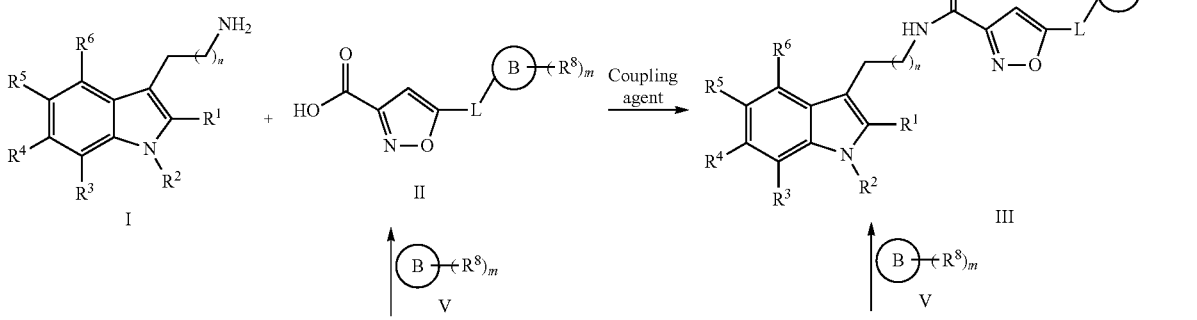

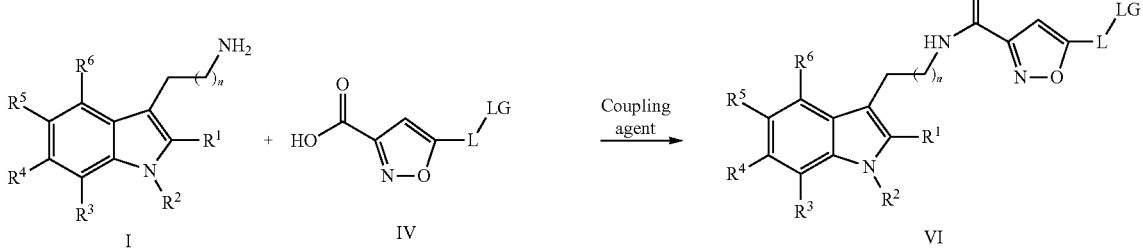

Scheme 2: all $R^1, R^2, R^3, R^4, R^5, R^6, R^8, L, B, n, m$ and LG are as described for the compounds of the present invention and its embodiments and formulae.

Compounds of general formula III can be prepared by reacting a compound of general formula I (commercially available or synthesized by procedures known to the skilled in the art or as set forth in the examples below) with a compound of general formula II in the presence of coupling agent (e.g., thionyl chloride, DCC, EDCI, HATU, PyBop, . . . ) following standard procedures that are known to the skilled in the art or as set forth in the examples below. Compounds of general formula III can also be prepared from intermediates with general formula VI and a suitable precursor of intermediate with general formula V by procedures known to the skilled in the art or as set forth in the examples below. The preparation of intermediates with general formula II and IV are described hereunder.

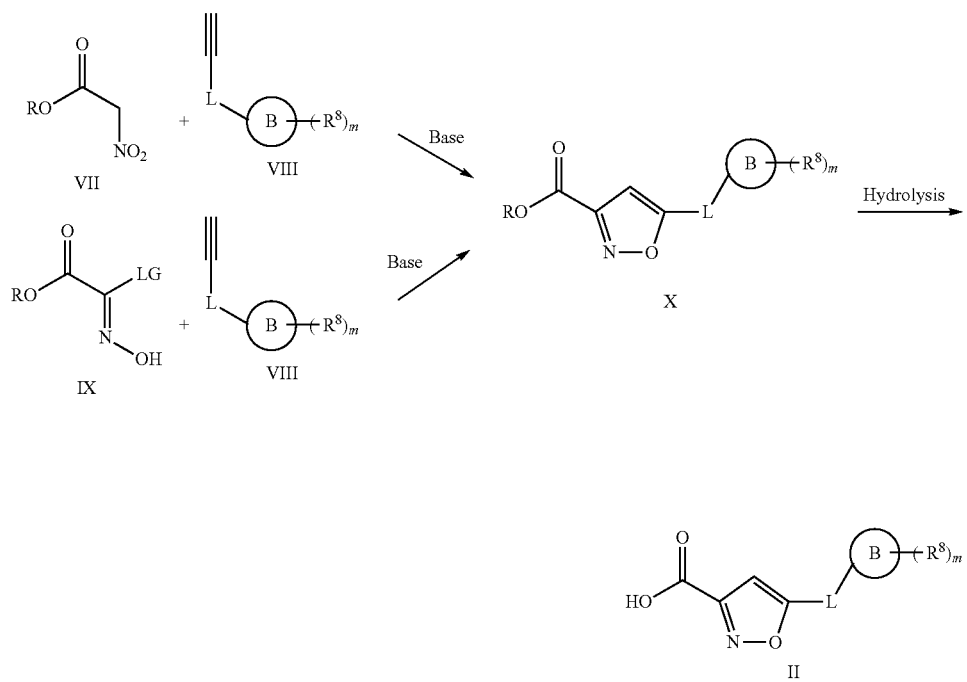

Scheme 3: all $R^8$, L, B, m and LG are as described for the compounds of the present invention and its embodiments and formulae.

Intermediates of general formula VII or IX (commercially available or synthesized by procedures known to the skilled in the art or as set forth in the examples below) wherein R is an ester protecting group such as methyl or ethyl and wherein LG is a leaving group only selected from halogen (e.g., Chlorine, bromine or iodine) are reacted with intermediates of general formula VIII (commercially available or synthesized by procedures known to the skilled in the art or as set forth in the examples below) in the presence of a base (e.g., DABCO, NaHCO$_3$, . . . ) at a temperature raising from room temperature to 90° C., in a polar protic and/or aprotic solvent (e.g., EtOH, H$_2$O, ethyl acetate, . . . ) to furnish the intermediates of general formula X. A pressurized reaction vessel (ace pressure tube) might be required to carry out such a reaction. Intermediates X are finally converted into the desired intermediates of general formula II under standard basic hydrolysis conditions that are known to the skilled In the art or as set forth in the examples below.

Alternatively, intermediates of general formula II and IV can also be prepared following the procedures depicted in scheme 4.

Scheme 4:

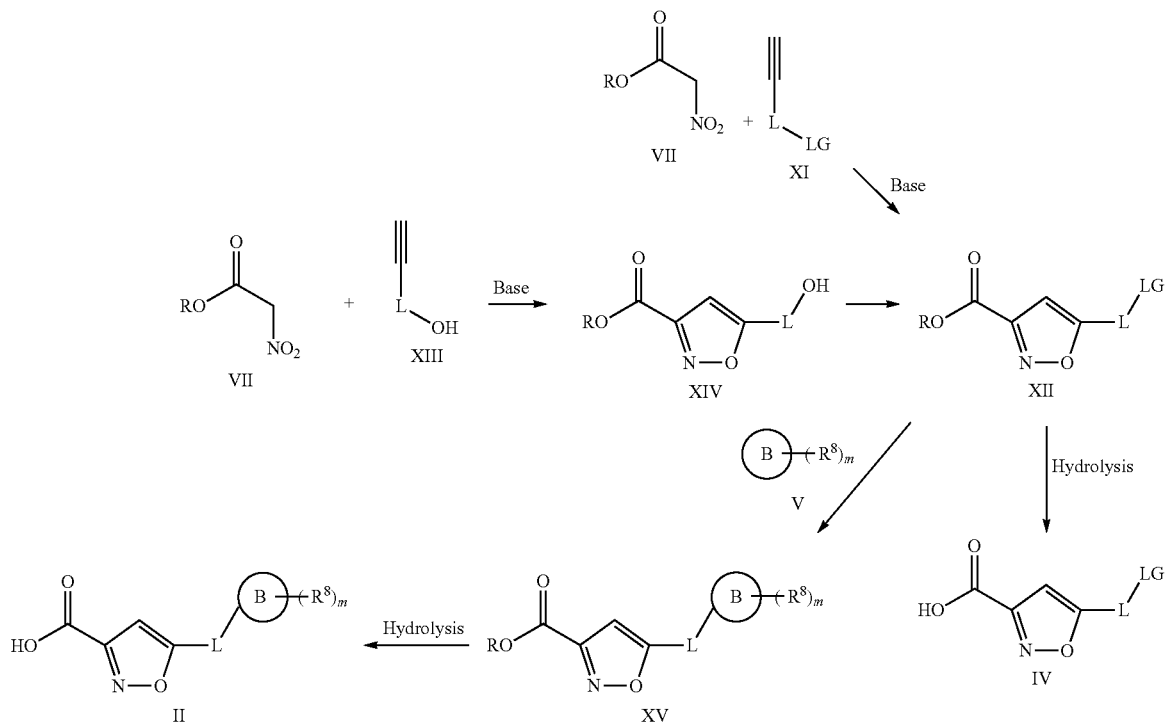

Scheme 4: all $R^8$, L, B, m, and LG are as described for the compounds of the present invention and its embodiments and formulae.

As outlined in the scheme 4, the preparation of intermediates II and IV are based on the use of the same key intermediate of general formula XII. These intermediates XII can be obtained by reacting intermediates VII (commercially available or synthesized by procedures known to the skilled in the art or as set forth in the examples below) wherein R is an ester protecting group such as methyl or ethyl with intermediates of general formula XI (commercially available or synthesized by procedures known to the skilled in the art or as set forth in the examples below) in the presence of a base (e.g., DABCO, $NaHCO_3$, ...) at a temperature raising from room temperature to 90° C., in a polar protic and/or aprotic solvent (e.g., EtOH, $H_2O$, ethyl acetate, ...). In a similar manner, intermediates with general formula XII can also be prepared from intermediates VII and an intermediates of general formula XIII in the presence of a base (e.g., DABCO, $NaHCO_3$, ...) at a temperature raising from room temperature to 90° C., in a polar protic and/or aprotic solvent (e.g., EtOH, $H_2O$, ethyl acetate, ...) to furnish new intermediates of general formula XIV. These intermediates XIV are converted into the desired intermediates of formula XII with classical methods that are known to the skilled in the art or as set forth in the examples below. The intermediates XII are then submitted to standard basic hydrolysis conditions to afford the desired intermediates IV. Alternatively, coupling of intermediates XII with a suitable precursor of intermediates V by procedures known to the skilled in the art or as set forth in the examples below, provides intermediates of formula XV which are hydrolyzed to intermediates of formula II.

Synthesis of
5-substituted-1,2,4-oxadiazole-3-carboxamide
derivatives

This class of compounds can be prepared following the general procedure outlined hereunder in scheme 5

Scheme 5:

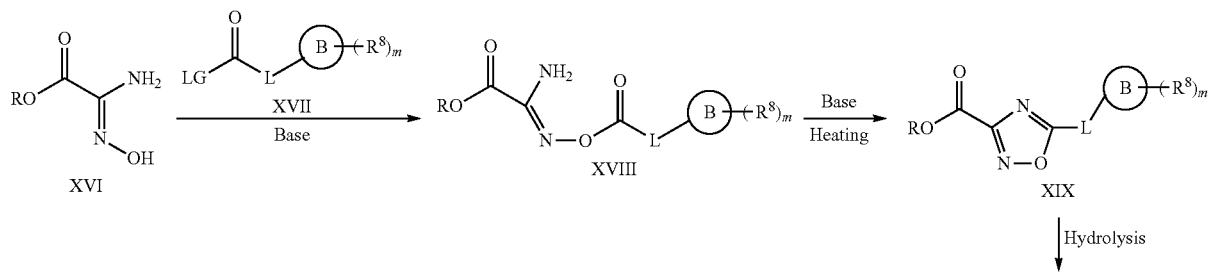

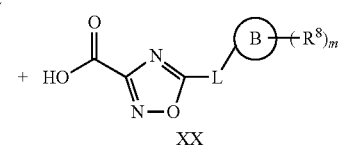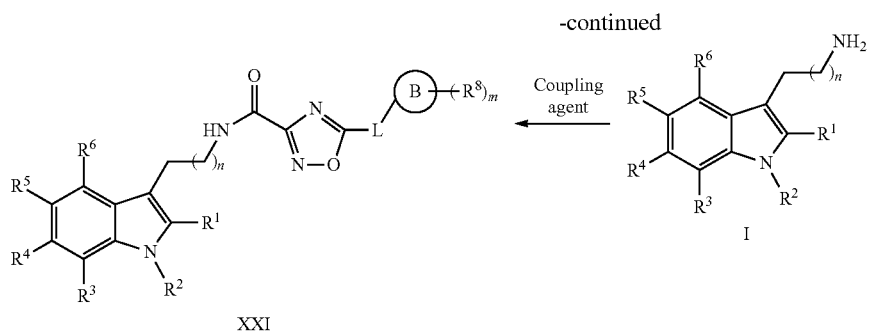

Scheme 5: all $R^1, R^2, R^3, R^4, R^5, R^6, R^8, L, B, n, m$ and LG are as described for the compounds of the present invention and its embodiments and formulae.

Condensation of intermediates XVI (commercially available or synthesized by procedures known to the skilled in the art or as set forth in the examples below) wherein R is an ester protecting group such as methyl or ethyl with intermediates of general formula XVII (commercially available or synthesized by procedures known to the skilled in the art or as set forth in the examples below) wherein LG is a leaving group only selected from halogen in the presence of a base (e.g., triethylamine, diisopropylethylamine, pyridine, . . . ) at a temperature raising from –10° C. to room temperature, in a polar aprotic solvent (e.g., dichloromethane, DMF, . . . ) provides intermediates XVIII which are directly converted in intermediates of formula XIX by heating at high temperature (most preferably 120° C.) in the presence of base such as pyridine. The ester protecting group R is hydrolyzed under standard basic conditions and the intermediates of formula XX are reacted with intermediates I following procedures that are known to the skilled in the art or as set forth in the examples below, provides the desired compounds of formula XXI.

Synthesis of 5-substituted-4,5-dihydroisoxazole 3-carboxamide derivatives

Scheme 6:

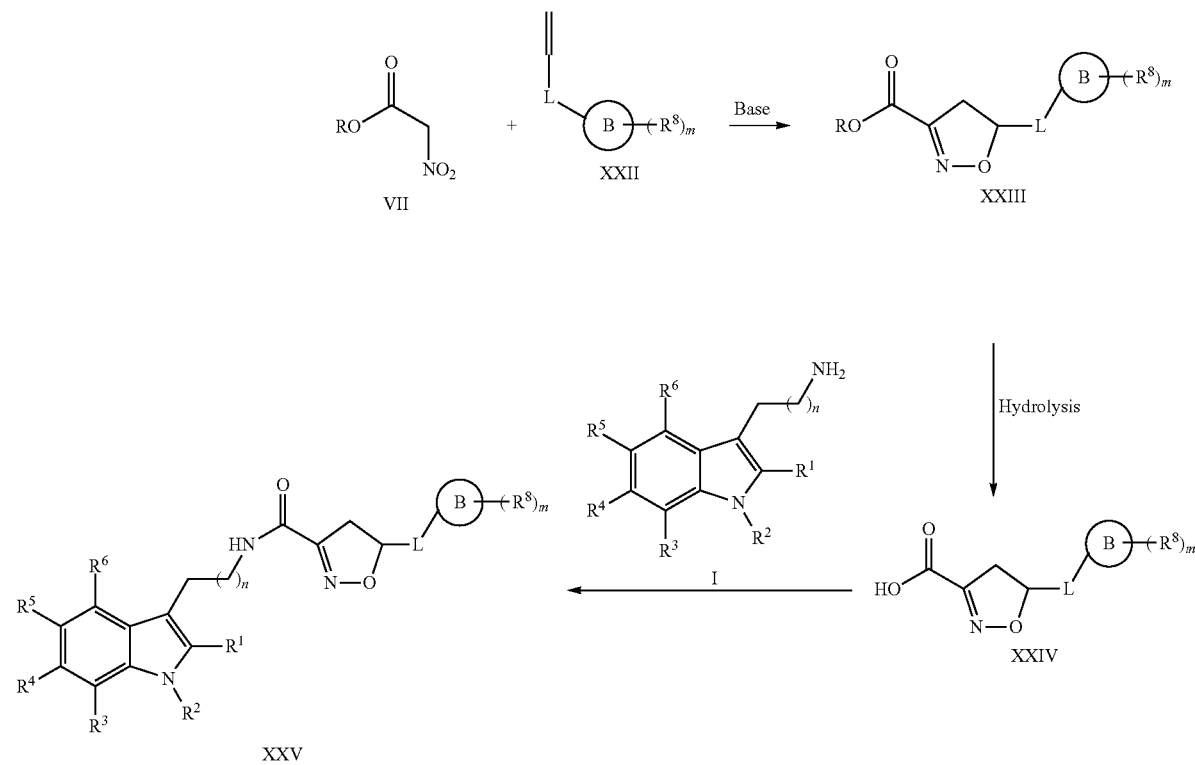

105

Scheme 6: all $R^1$, $R^2$, $R^3$, $R^4$, $R^5$, $R^6$, $R^8$, L, B, n and m are as described for the compounds of the present invention and its embodiments and formulae.

Condensation of intermediates VII (commercially available or synthesized by procedures known to the skilled in the art or as set forth in the examples below) wherein R is an ester protecting group such as methyl or ethyl with intermediates of general formula XXII (commercially available or synthesized by procedures known to the skilled in the art or as set forth in the examples below) in the presence of a base (e.g., DABCO, $NaHCO_3$, . . . ) at a temperature raising from room temperature to 90° C., in a polar protic and/or aprotic solvent (e.g., EtOH, $H_2O$, ethyl acetate, . . . ) provides intermediates of formula XXIII. The ester protecting group R is hydrolyzed under standard basic conditions and the intermediates of formula XXIV are reacted with intermediates I following procedures that are known to the skilled in the art or as set forth in the examples below to provide the desired compounds of formula XXV.

Synthesis of 3-substituted-4,5-dihydroisoxazole
5-carboxamide derivatives

Scheme 7:

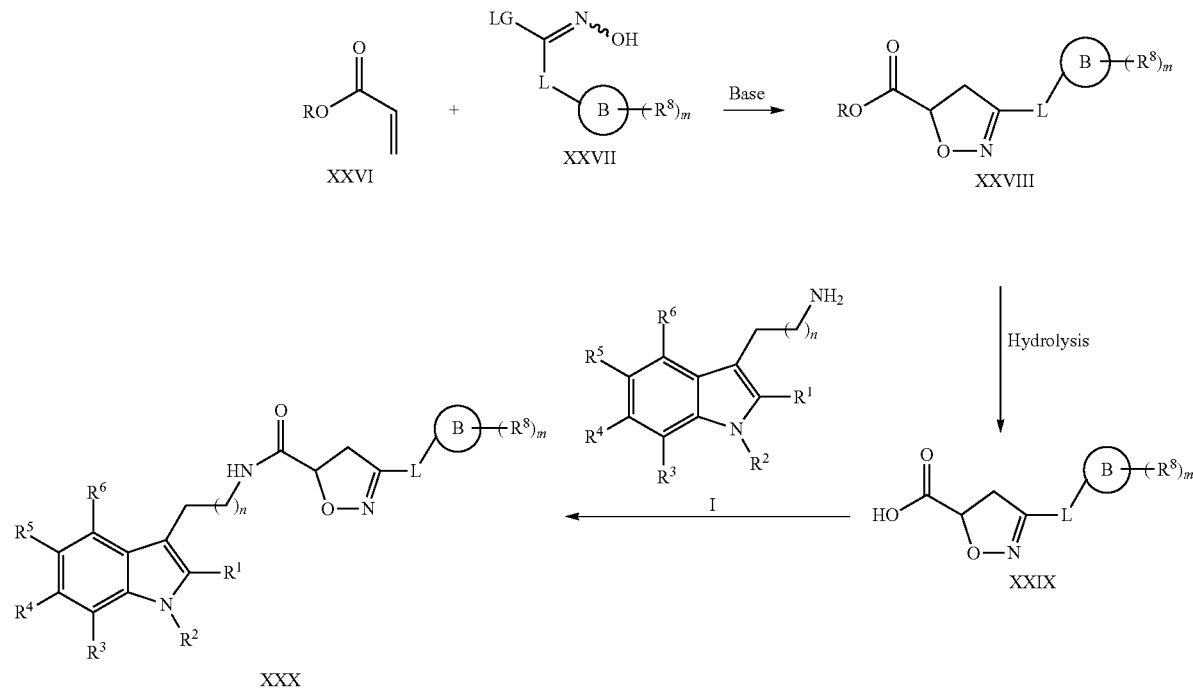

Scheme 7: all $R^1$, $R^2$, $R^3$, $R^4$, $R^5$, $R^6$, $R^8$, L, B, n, m and LG are as described for the compounds of the present invention and its embodiments and formulae.

Condensation of intermediates XXVI (commercially available or synthesized by procedures known to the skilled in the art or as set forth in the examples below) wherein R is an ester protecting group such as methyl or ethyl with intermediates of general formula XXVII (commercially available or synthesized by procedures known to the skilled in the art or as set forth in the examples below) and wherein LG is a leaving group only selected from halogen (e.g., chlorine, bromine and iodine) in the presence of a base (e.g., DABCO, $NaHCO_3$, . . . ) at a temperature raising from room temperature to 90° C., in a polar protic and/or aprotic solvent (e.g., EtOH, $H_2O$, ethyl acetate, . . . ) provides intermediates of formula XXVIII. The ester protecting group R is hydrolyzed under standard basic conditions and intermediates of formula XXIX are reacted with intermediates I following procedures that are known to the skilled in the art or as set forth in the examples below to provide the desired compounds of formula XXX.

Synthesis of 4-substituted-4,5-dihydroisooxazole-3-carboxamide derivatives

Scheme 8:

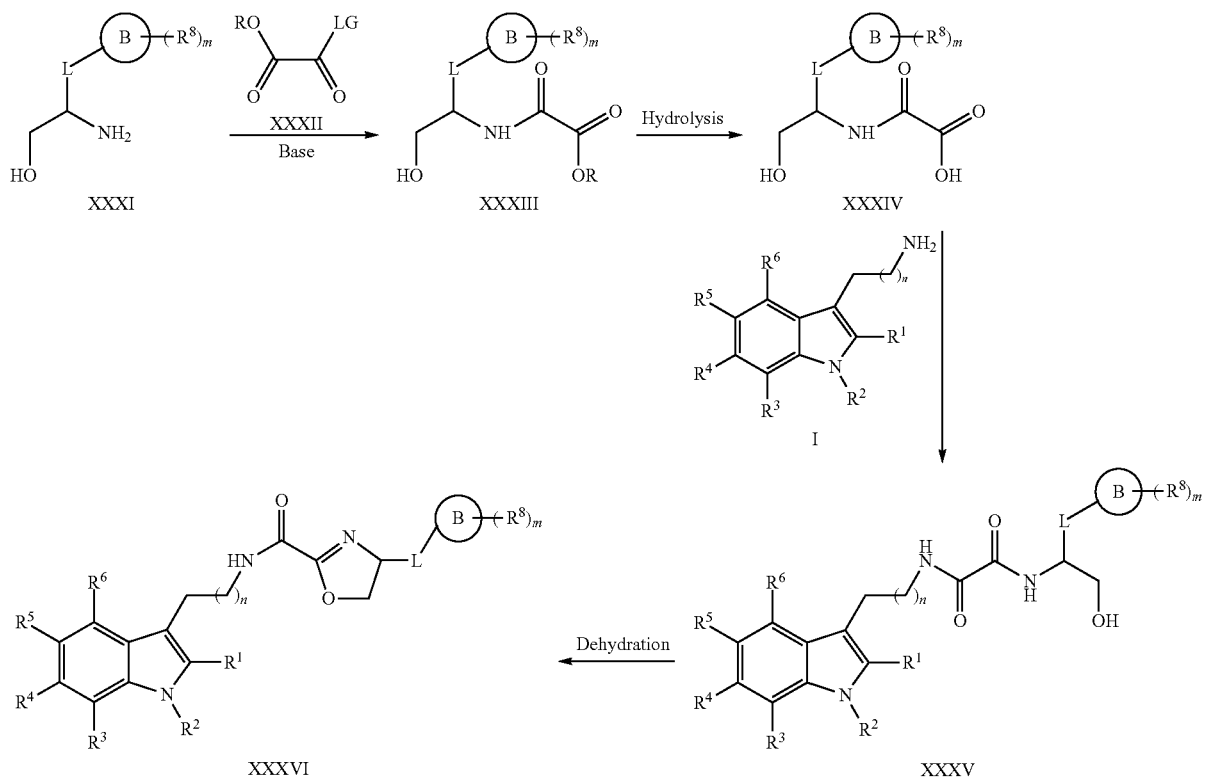

Scheme 8: all $R^1, R^2, R^3, R^4, R^5, R^6, R^8, L, B, n, m$ and LG are as described for the compounds of the present invention and its embodiments and formulae.

Condensation of intermediates XXXI (commercially available or synthesized by procedures known to the skilled in the art or as set forth in the examples below) with intermediates of general formula XXXII (commercially available or synthesized by procedures known to the skilled in the art or as set forth in the examples below) and wherein R is an ester protecting group such as methyl or ethyl and LG is a leaving group only selected from halogen in the presence of a base (e.g., triethylamine, pyridine, . . . ) at a temperature raising from −10° C. to room temperature, in a polar aprotic solvent (e.g., dichloromethane, DMF, THF . . . ) provides intermediates of formula XXXIII. The ester protecting group R is hydrolyzed under standard basic conditions and the intermediates of formula XXXIV are reacted with intermediates I following procedures that are known to the skilled in the art or as set forth in the examples below to provide intermediates of formula XXXV. Intermediates XXXV are then subjected to dehydration condition (e.g., burgess reagent; see J. Med. Chem., 51(7), 2321-25, 2008) in order to obtain the desired compounds of general formula XXXVI.

Synthesis of 5-substituted-oxazole-2-carboxamide derivatives

Scheme 9:

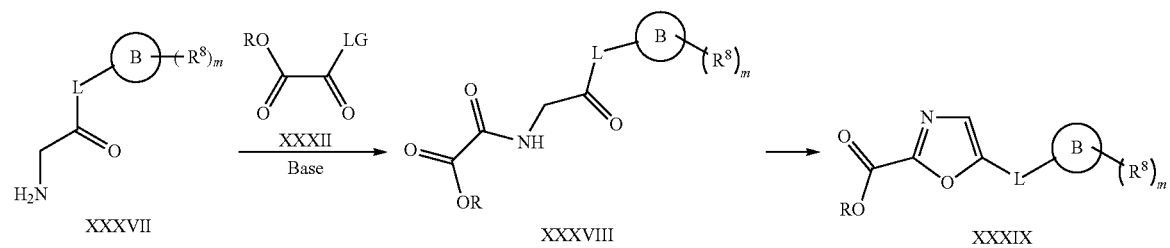

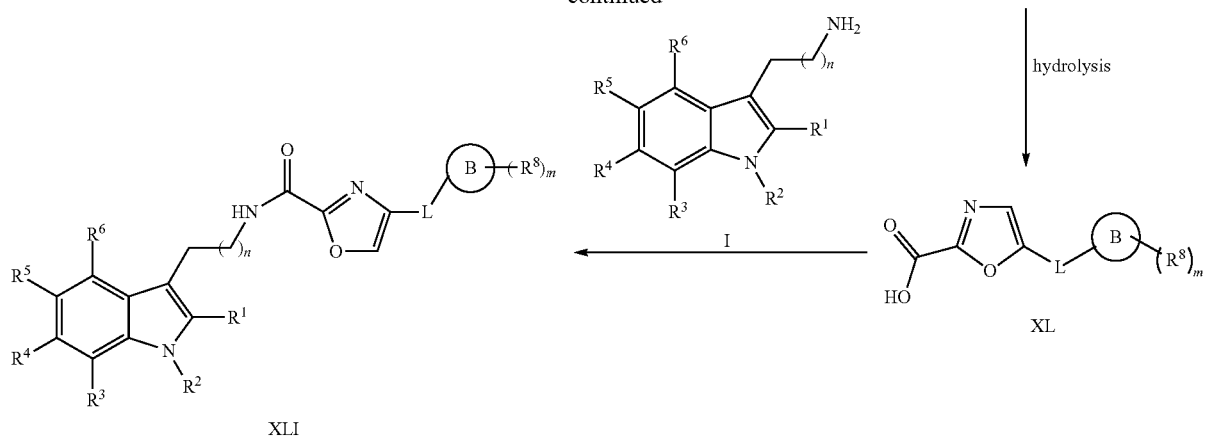

Scheme 9: all $R^1, R^2, R^3, R^4, R^5, R^6, R^8, L, B, n, m$ and LG are as described for the compounds of the present invention and its embodiments and formulae.

Condensation of intermediates XXXVII (commercially available or synthesized by procedures known to the skilled in the art or as set forth in the examples below) with intermediates of general formula XXXII (commercially available or synthesized by procedures known to the skilled in the art or as set forth in the examples below) and wherein R is an ester protecting group such as methyl or ethyl and LG is a leaving group only selected from halogen in the presence of a base (e.g., triethylamine, pyridine, . . . ) at a temperature raising from –10° C. to 50° C., in a polar aprotic solvent (e.g., dichloromethane, DMF, THF . . . ) provides intermediates of formula XXXVIII. These intermediates are then subjected to dehydration conditions (e.g., $POCl_3$) preferably carried out at high temperature (90 to 110° C.) in order to obtain the desired intermediates XXXIX. The ester protecting group R is hydrolyzed under standard basic conditions and the intermediates of formula XL are reacted with intermediates I following procedures that are known to the skilled in the art or as set forth in the examples below to provide intermediates of formula XLI.

Synthesis of 1-substituted-2-oxopyrrolidine-3-carboxamide derivatives

Scheme 10:

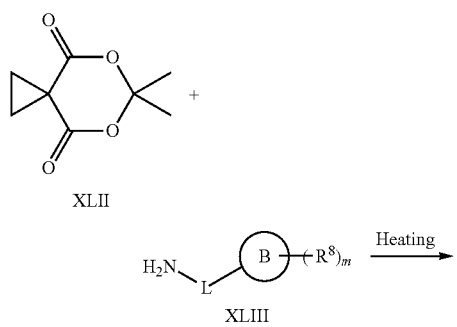

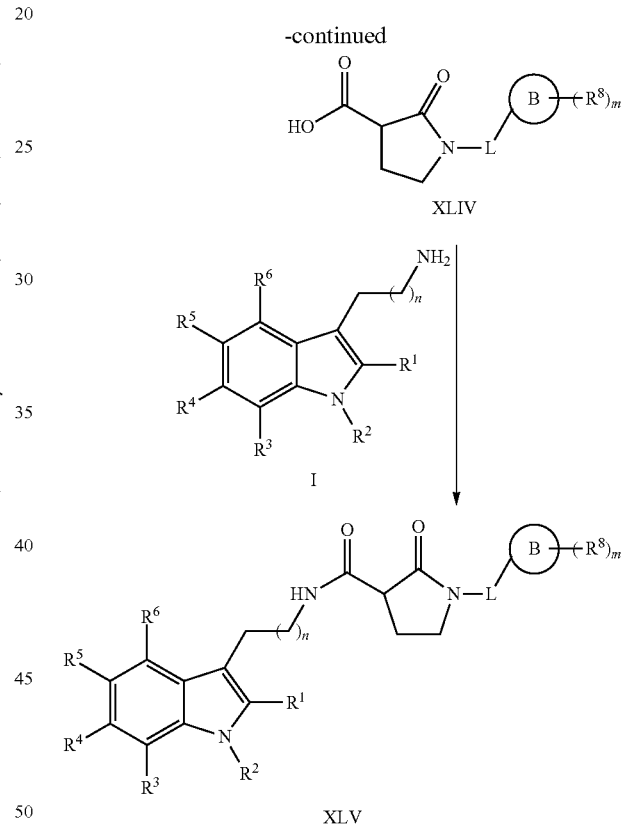

Scheme 10: all $R^1, R^2, R^3, R^4, R^5, R^6, K R^8, L, B, n,$ and $m$ are as described for the compounds of the present invention and its embodiments and formulae.

Condensation of the intermediate XLII (commercially available) with intermediates of general formula XLIII (commercially available or synthesized by procedures known to the skilled in the art or as set forth in the examples below) in a polar protic solvent (most preferably ethanol) at high temperature (most preferably 100° C.) under microwave irradiation provides intermediates of formula XLIV. These intermediates XL are reacted with intermediates I following procedures that are known to the skilled in the art or as set forth in the examples below to provide intermediates of formula XLV.

Synthesis of
1-substituted-1H-1,2,3-triazole-4-carboxamide
derivatives

The preparation of compounds with general formula LI is based on the synthesis of the key intermediates IL and is depicted in scheme 11.

Scheme 11:

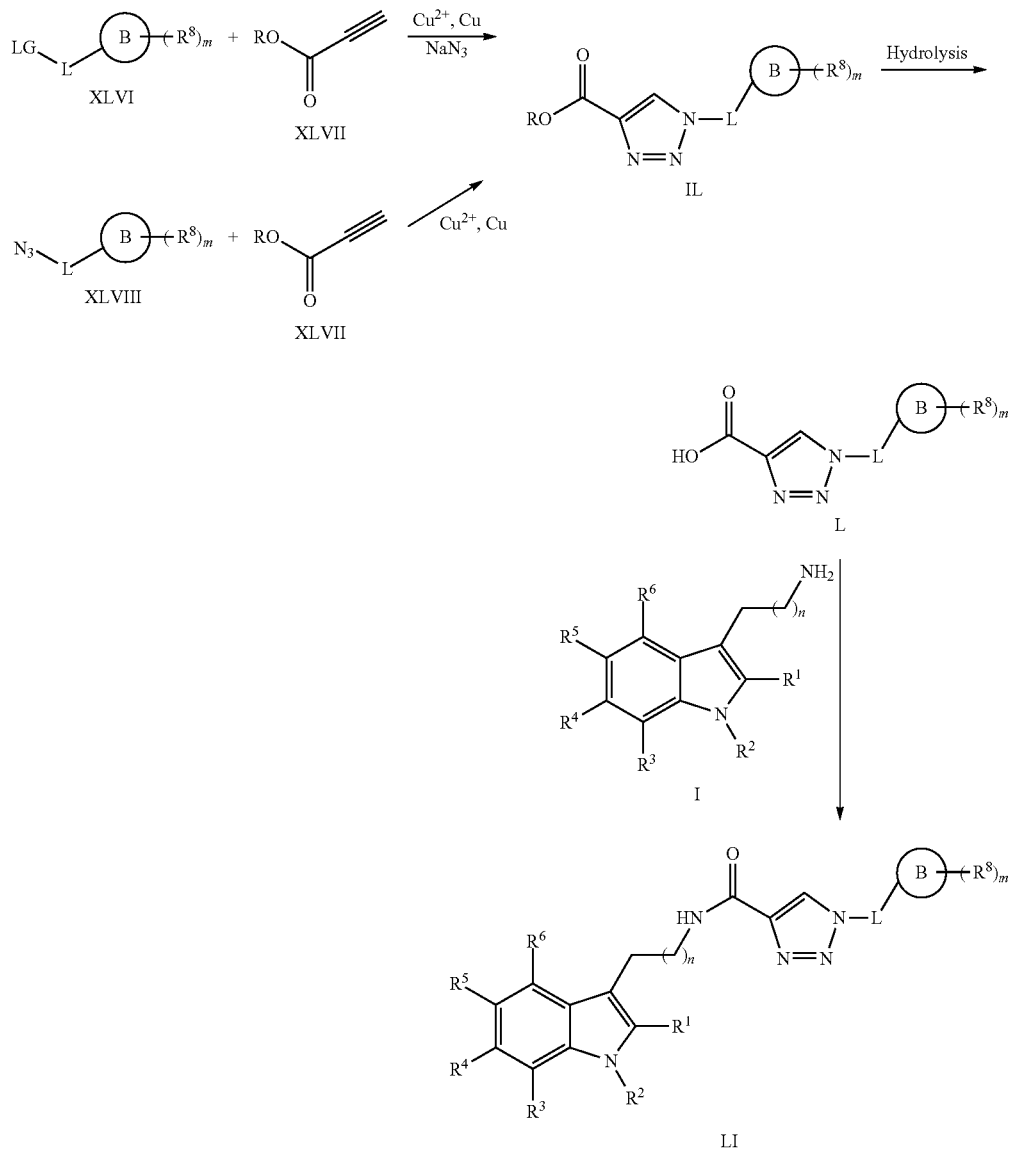

Scheme 11: all $R^1$, $R^2$, $R^3$, $R^4$, $R^5$, $R^6$, $R^8$, L, B, n, m and LG are as described for the compounds of the present invention and its embodiments and formulae.

Condensation of intermediates XLVI (commercially available or synthesized by procedures known to the skilled in the art or as set forth in the examples below) with intermediates of formula XLVII wherein R is an ester protecting group such as methyl or ethyl and in the presence of sodium azide in a polar protic solvent mixture (e.g., propanol, tert-butanol, $H_2O$, ...) and with a cupper based catalysis provides the desired intermediates with formula IL. Similarly, Condensation of intermediates XLVIII (commercially available or synthesized by procedures known to the skilled in the art or as set forth in the examples below) with intermediates of formula XLVII wherein R is an ester protecting group such as methyl or ethyl and in a polar protic solvent mixture (e.g., propanol, tert-butanol, $H_2O$, ...) and with a cupper based catalysis provides the desired intermediates with formula IL. The ester protecting group R is hydrolyzed under standard basic conditions and the intermediates of formula L are reacted with intermediates I following procedures that are known to the skilled in the art or as set forth in the examples below to provide intermediates of formula LI.

Synthesis of 1-substituted-2-oxopyrrolidine-4-carboxamide derivatives

Scheme 12:

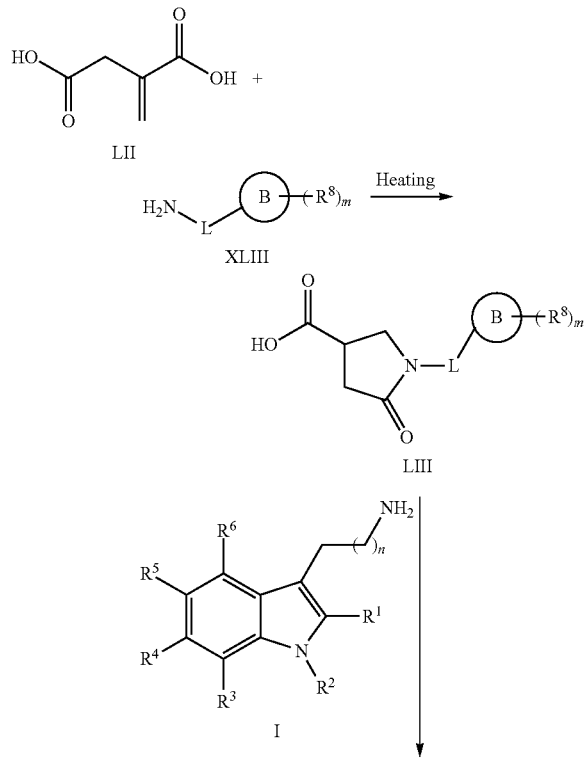

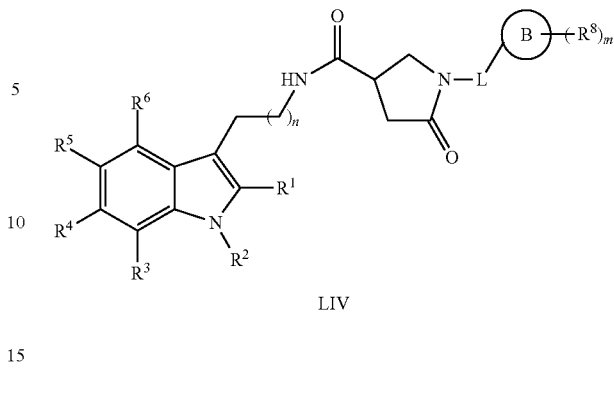

Scheme 12: all $R^1$, $R^2$, $R^3$, $R^4$, $R^5$, $R^6$, $R^8$, L, B, n and m are as described for the compounds of the present invention and its embodiments and formulae.

Condensation of the intermediate LII (commercially available) with intermediates of general formula XLIII (commercially available or synthesized by procedures known to the skilled in the art or as set forth in the examples below) in a polar protic solvent (most preferably $H_2O$) at high temperature (most preferably 100° C.) as described in the following reference (ARKIVOC, (XV), 303-314, 2007) provides intermediates of formula LIII. These intermediates LIII are reacted with intermediates I following procedures that are known to the skilled in the art or as set forth in the examples below to provide intermediates of formula LIV.

Synthesis of 1-substituted-pyrrolidine-3-carboxamide derivatives

Scheme 13:

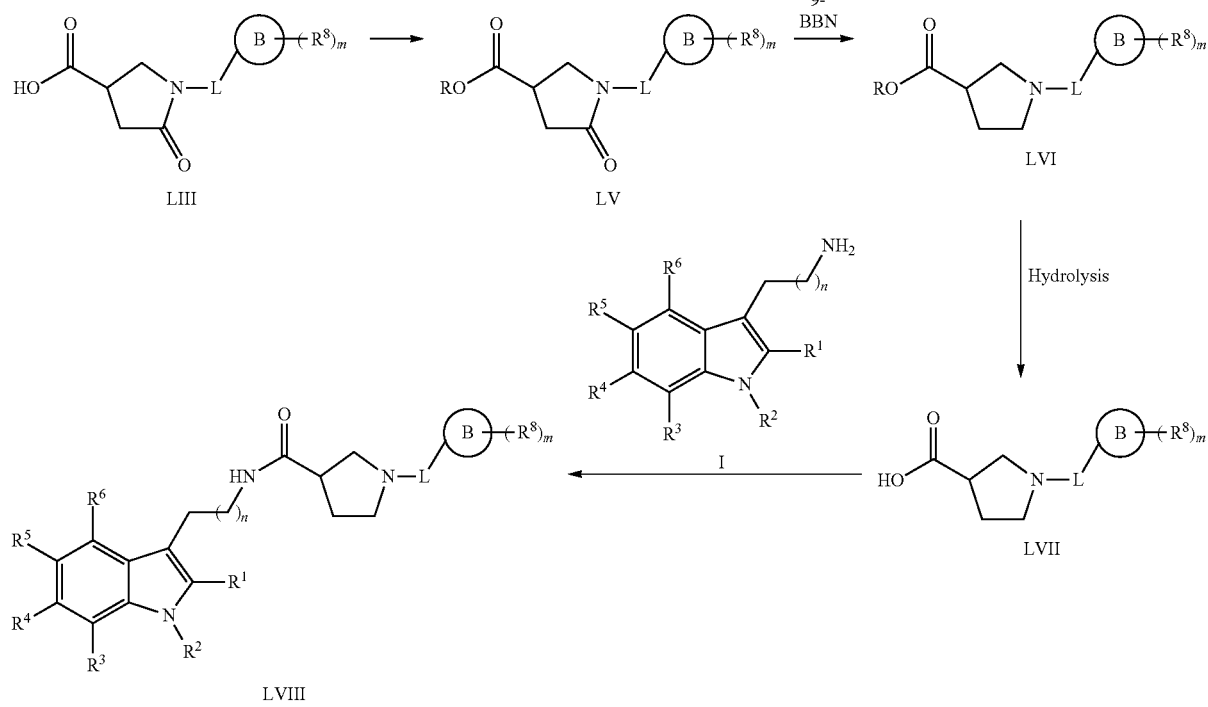

Scheme 13: all $R^1$, $R^2$, $R^3$, $R^4$, $R^5$, $R^6$, $R^8$, L, B, n and m are as described for the compounds of the present invention and its embodiments and formulae.

Intermediates of formula LIII are converted into intermediates of formula LV wherein R is an ester protecting group such as methyl or ethyl under standard esterification procedures known to the skilled in the art or as set forth in the examples below. The lactam function from intermediates LV is then reduced in the presence of 9-borabicyclo[3.3.1]nonane (9-BBN) in a polar aprotic solvent (e.g., THF) at a temperature raising from RT to 65° C. (most preferably 65° C.) in order to obtain the desired intermediates LVI. More information can be found in the following references (Tetrahedron Lett., 40, 3673-76, 1999; Tetrahedron, 64(21), 4803-4816; 2008). The ester protecting group R is hydrolyzed under standard basic conditions and the intermediates of formula LVII are reacted with intermediates I following procedures that are known to the skilled in the art or as set forth in the examples below to provide intermediates of formula LVIII.

Synthesis of
3-substituted-pyrrolidine-1-carboxamide derivatives

Scheme 14:

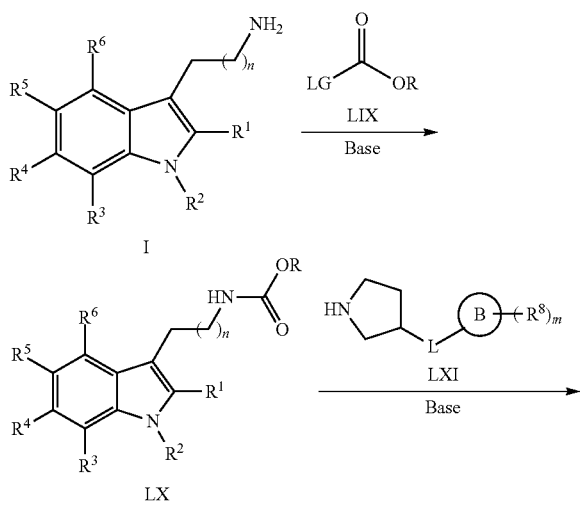

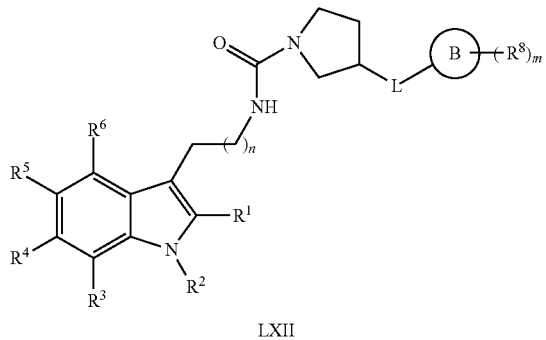

Scheme 14: all $R^1$, $R^2$, $R^3$, $R^4$, $R^5$, $R^6$, $R^8$, L, B, n, m and LG are as described for the compounds of the present invention and its embodiments and formulae.

Condensation of intermediates of formula I with intermediates of formula LIX (commercially available or synthesized by procedures known to the skilled in the art or as set forth in the examples below) and wherein R is an ester protecting group such as methyl or ethyl and LG is a leaving group only selected from halogen in the presence of a base (e.g., triethylamine, pyridine, . . . ) at a temperature raising from −10° C. to room temperature, in a polar aprotic solvent (e.g., dichloromethane, DMF, THF . . . ) provides intermediates of formula LX. These intermediates LX are subsequently reacted with intermediates of formula LXI (commercially available or synthesized by procedures known to the skilled in the art or as set forth in the examples below) in order to obtain the desired compounds with formula LXII. Beforehand, intermediates LXI can be activated by treatment with a strong base (most preferably NaH) in a polar aprotic solvent (e.g., THF, DMF, . . . ) at a temperature raising from 0° C. to RT, in order to enhance the reactivity of the amine.

Synthesis of
5-substituted-1,3,4-oxadiazole-2-carboxamide derivatives

Scheme 15:

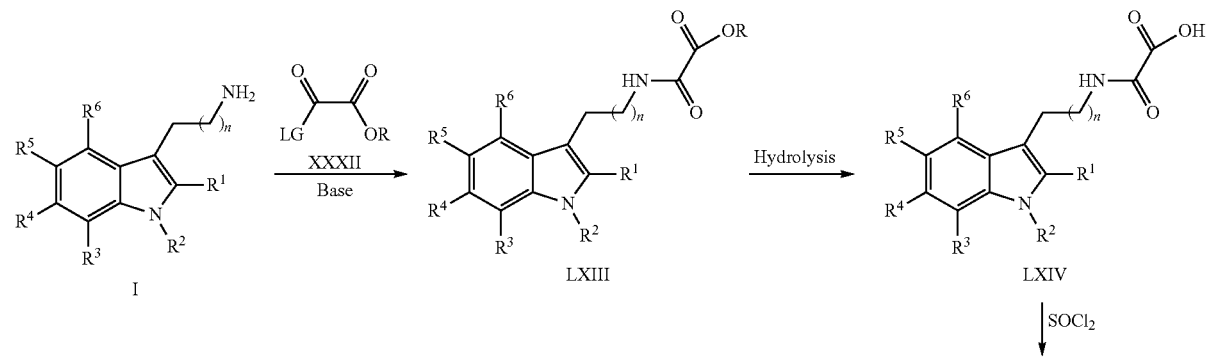

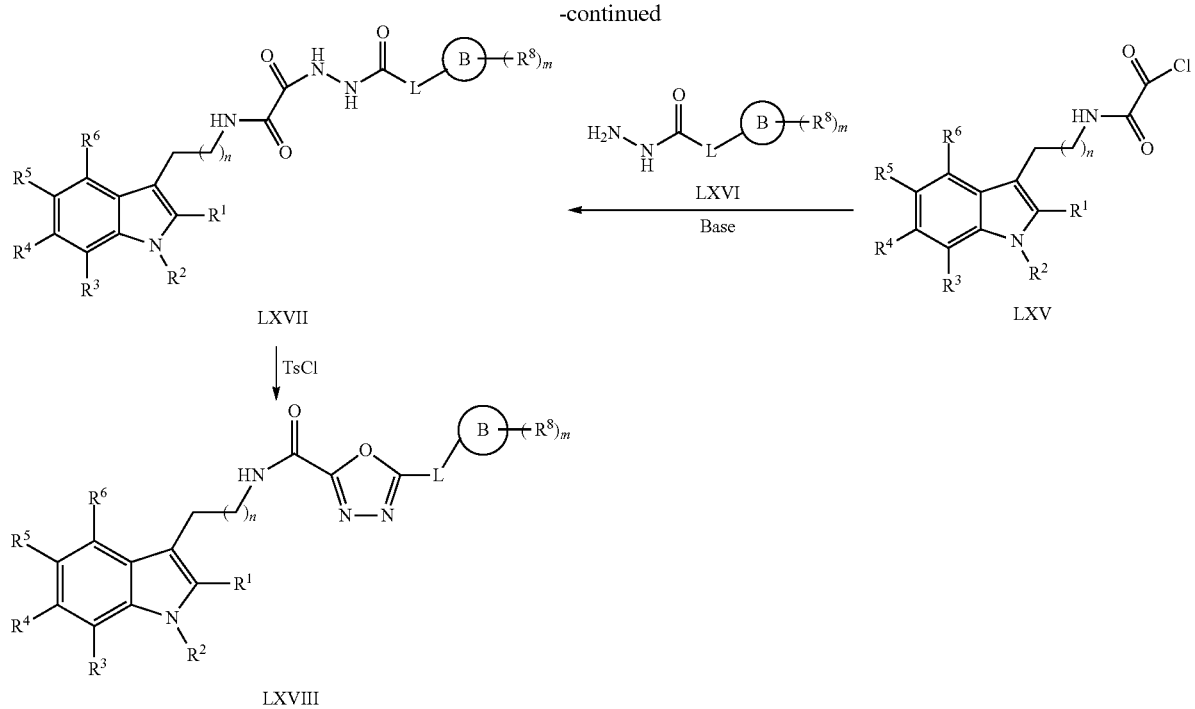

LXVII  LXV

LXVIII

Scheme 15: all $R^1$, $R^2$, $R^3$, $R^4$, $R^5$, $R^6$, $R^8$, L, B, n, m and LG are as described for the compounds of the present invention and its embodiments and formulae.

Condensation of intermediates I with intermediates of general formula XXXII (commercially available or synthesized by procedures known to the skilled in the art or as set forth in the examples below) and wherein R is an ester protecting group such as methyl or ethyl and LG is a leaving group only selected from halogen, in the presence of a base (e.g., triethylamine, pyridine, . . . ) at a temperature raising from −10° C. to 50° C., in a polar aprotic solvent (e.g., dichloromethane, DMF, THF . . . ) provides intermediates of formula LXIII. The ester protecting group R is hydrolyzed under standard basic conditions and intermediates of formula LXIV are converted in intermediates of general formula LXV. These intermediates are reacted with hydrazide derivatives of formula LXVI (commercially available or synthesized by procedures known to the skilled in the art or as set forth in the examples below) in a polar aprotic solvent (e.g. dichloromethane, THF, DMF . . . ) in the presence of a base (e.g. triethylamine, $K_2CO_3$, Pyridine, . . . ) at a temperature raising from 0° C. to room temperature to furnish the intermediates of formula LXVII which is engaged in a cyclization reaction in the presence of p-toluensulfonyl chloride to provide the expected compounds of general formula LXVIII.

Synthesis of 3-substituted isoxazole 5-carboxamide derivatives

Scheme 16:

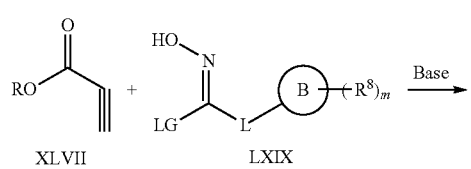

XLVII  LXIX

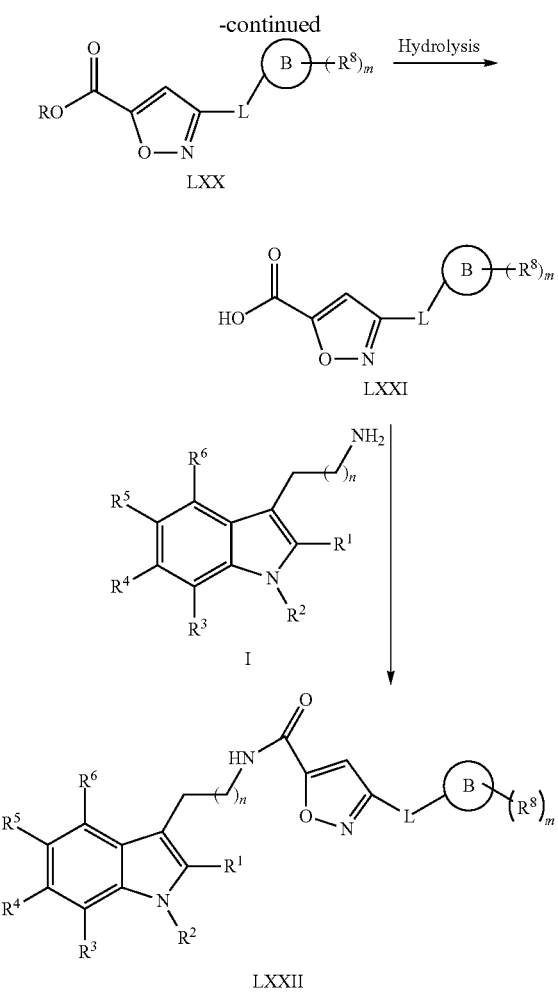

LXX

LXXI

I

LXXII

Scheme 16: all $R^1$, $R^2$, $R^3$, $R^4$, $R^5$, $R^6$, $R^8$, L, B, n, m and LG are as described for the compounds of the present invention and its embodiments and formulae.

Intermediates of general formula XLVII (commercially available or synthesized by procedures known to the skilled in the art or as set forth in the examples below) wherein R is an ester protecting group such as methyl or ethyl are reacted with intermediates of general formula LXIX (commercially available or synthesized by procedures known to the skilled in the art or as set forth in the examples below) wherein LG is a leaving group only selected from halogen in the presence of a base (e.g., DABCO, $NaHCO_3$, ... ) at a temperature raising from room temperature to 90° C., in a polar protic and/or aprotic solvent (e.g., EtOH, $H_2O$, Ethyl acetate, ... ) to provide intermediates of general formula LXX. The ester protecting group R is hydrolyzed under standard basic conditions and intermediates of formula LXXI are reacted with intermediates I following procedures that are known to the skilled in the art or as set forth in the examples below to provide intermediates of formula LXXII.

EXAMPLES

The following examples are provided for the purpose of illustrating the present invention and by no means should be interpreted to limit the scope of the present invention.
Part A represents the preparation of the compounds (intermediates and final compounds) whereas Part B represents the pharmacological examples.
All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector. The separations were performed with a X-Bridge Prep C18, 100×19 mm, 5 μm column equipped with a X-Bridge C18, 5 μm, 19×10 mm Guard column.
Elution were carried out with the methods described in the following tables, and detection wavelengths were fixed at 210 and 254 nm.
Solvent A: Ammonium Acetate puriss p.a. for HPLC 10 mM in milliQ water, adjusted at pH10 with ammonium hydroxide puriss p.a. for HPLC.
Solvent B: acetonitrile HPLC grade.

HPLC Method 1

| Time (min) | Flow Rate ml/min | Solvent A % | Solvent B % |
|---|---|---|---|
| 0 | 20 | 60 | 40 |
| 2.00 | 20 | 60 | 40 |
| 7.00 | 20 | 20 | 80 |
| 7.10 | 20 | 10 | 90 |
| 10.00 | 20 | 10 | 90 |
| 10.50 | 20 | 60 | 40 |
| 16.00 | 20 | 60 | 40 |

HPLC Method 2

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

HPLC Method 3

Solvent A: Formic Acid LC-MS grade 0.1% in milliQ water
Solvent B: Acetonitrile HPLC grade.

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

HPLC Method 4

Solvent A: Ammonium Acetate puriss p.a. for HPLC 10 mM in milliQ water, adjusted at pH10 with Ammonium Hydroxyde puriss p.a. for HPLC.
Solvent B: Acetonitrile HPLC grade.

| Time (min) | Flow Rate ml/min | Solvent A % | Solvent B % |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

HPLC Method 5

Solvent A: Formic Acid LC-MS grade 0.1% in milliQ water
Solvent B: Formic Acid LC-MS grade 0.1% in Acetonitrile HPLC grade.

| Time (min) | Flow Rate ml/min | Solvent A % | Solvent B % |
|---|---|---|---|
| 0 | 20 | 80 | 20 |
| 2.00 | 20 | 80 | 20 |
| 7.00 | 20 | 40 | 60 |
| 8.00 | 20 | 10 | 90 |
| 10.80 | 20 | 10 | 90 |
| 11.00 | 20 | 80 | 20 |
| 16.00 | 20 | 80 | 20 |

Exemplary compounds of the present invention are shown in table 1 (Table 1A and 1B)
Table 1
TABLE 1A
| Compound code | STRUCTURE |
|---|---|
| D1 | 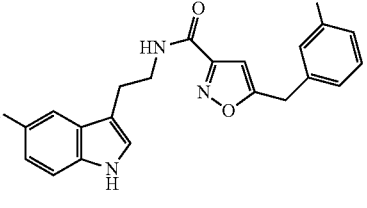 |
| D2 | 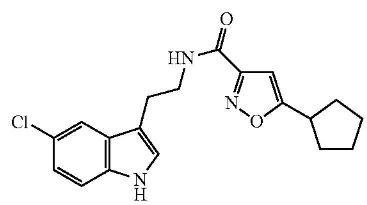 [SMILES: O=C(NCCc1c[nH]c2ccc(Cl)cc12)c1cc(C2CCCC2)on1] |
| D3 | 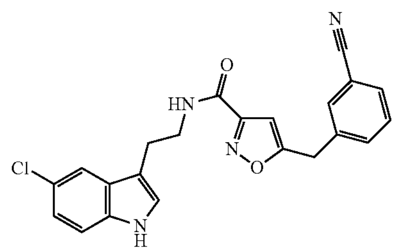 [SMILES: N#Cc1cccc(Cc2cc(C(=O)NCCc3c[nH]c4ccc(Cl)cc34)no2)c1] |
| D4 | 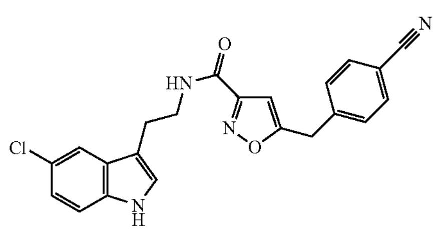 [SMILES: N#Cc1ccc(Cc2cc(C(=O)NCCc3c[nH]c4ccc(Cl)cc34)no2)cc1] |
| D5 | 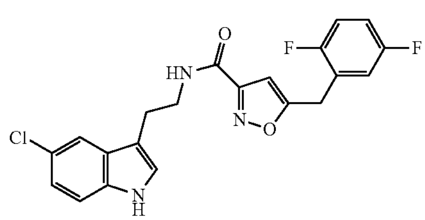 [SMILES: O=C(NCCc1c[nH]c2ccc(Cl)cc12)c1cc(Cc2cc(F)ccc2F)on1] |
| D6 | 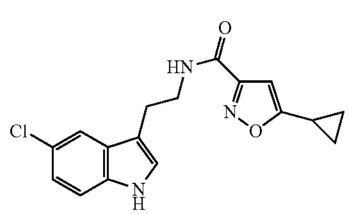 [SMILES: O=C(NCCc1c[nH]c2ccc(Cl)cc12)c1cc(C2CC2)on1] |
TABLE 1A-continued
| Compound code | STRUCTURE |
|---|---|
| D7 | 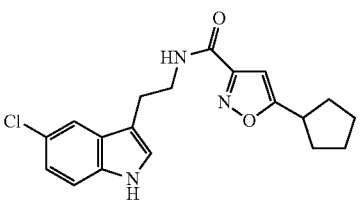 |
| D8 | 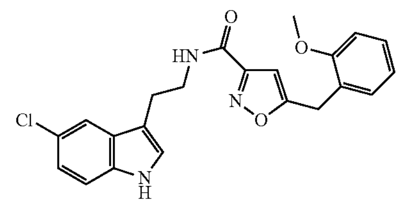 [SMILES: COc1ccccc1Cc1cc(C(=O)NCCc2c[nH]c3ccc(Cl)cc23)no1] |
| D9 | 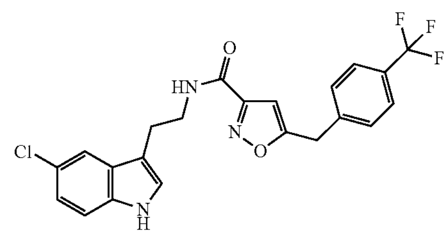 [SMILES: O=C(NCCc1c[nH]c2ccc(Cl)cc12)c1cc(Cc2ccc(C(F)(F)F)cc2)on1] |
| D10 | 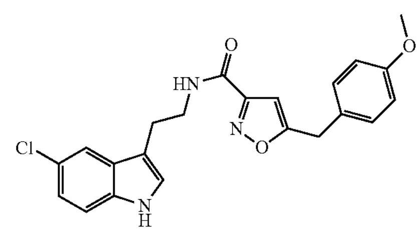 [SMILES: COc1ccc(Cc2cc(C(=O)NCCc3c[nH]c4ccc(Cl)cc34)no2)cc1] |
| D11 | 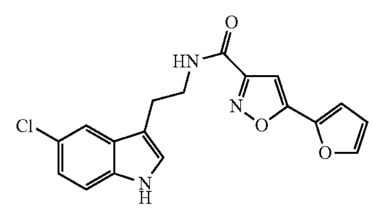 [SMILES: O=C(NCCc1c[nH]c2ccc(Cl)cc12)c1cc(-c2ccco2)on1] |
| D12 | 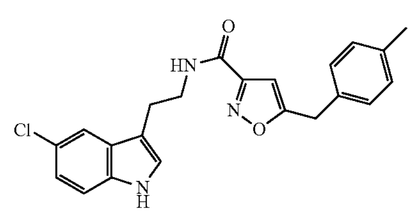 [SMILES: Cc1ccc(Cc2cc(C(=O)NCCc3c[nH]c4ccc(Cl)cc34)no2)cc1] |
| D13 | 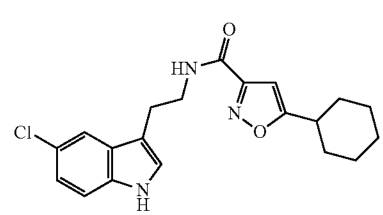 [SMILES: O=C(NCCc1c[nH]c2ccc(Cl)cc12)c1cc(C2CCCCC2)on1] |

TABLE 1A-continued

| Compound code | STRUCTURE |
|---|---|
| D14 | (5-methylindole-ethyl)-NH-C(O)-isoxazole-CH2-(3-fluorophenyl) |
| D15 | (5-chloroindole-ethyl)-NH-C(O)-(1-methylpyrazole)-thiophene |
| D16 | (5-chloroindole-ethyl)-NH-C(O)-isoxazole-thiophene |
| D17 | (5-chloroindole-ethyl)-NH-C(O)-isoxazole-CH2-furan |
| D19 | (5-chloroindole-ethyl)-NH-C(O)-(1-methylpyrazole)-furan |
| D20 | (5-chloroindole-ethyl)-NH-C(O)-isoxazole-CH2-(3-methylphenyl) |
| D21 | (5-chloroindole-ethyl)-NH-C(O)-isoxazole-CH2-(2-fluoro-3-methoxyphenyl) |
| D22 | (5-chloroindole-ethyl)-NH-C(O)-isoxazole-CH2-furan |
| D23 | (5-chloroindole-ethyl)-NH-C(O)-isoxazole-CH2-(3-fluorophenyl) |
| D24 | (indole-ethyl)-NH-C(O)-(4-methylthiazole)-(4-methylphenyl) |
| D25 | (5-chloroindole-ethyl)-NH-C(O)-isoxazole-CH2-thiophene |
| D26 | (5-chloroindole-ethyl)-NH-C(O)-(1-methylpyrazole)-phenyl |
| D27 | (5-chloroindole-ethyl)-NH-C(O)-isoxazole-CH2-thiophene |
| D28 | (5-fluoroindole-ethyl)-NH-C(O)-isoxazole-CH2-(3-fluorophenyl) |

TABLE 1A-continued

| Compound code | STRUCTURE |
|---|---|
| D29 | |
| D30 | |
| D31 | |
| D32 | |
| D33 | |
| D34 | 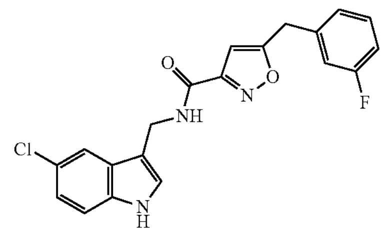 [SMILES: O=C(NCc1c[nH]c2ccc(Cl)cc12)c1cc(Cc2cccc(F)c2)on1] |
| D35 | 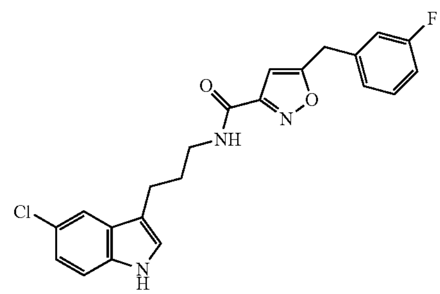 [SMILES: O=C(NCCCc1c[nH]c2ccc(Cl)cc12)c1cc(Cc2cccc(F)c2)on1] |
| D36 | 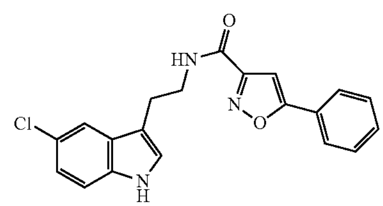 [SMILES: O=C(NCCc1c[nH]c2ccc(Cl)cc12)c1cc(-c2ccccc2)on1] |
| D37 | 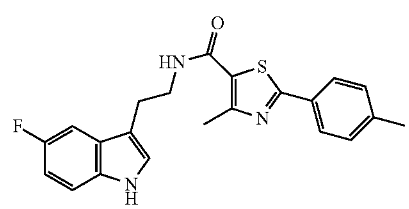 [SMILES: Cc1ccc(-c2nc(C)c(C(=O)NCCc3c[nH]c4ccc(F)cc34)s2)cc1] |
| D38 | 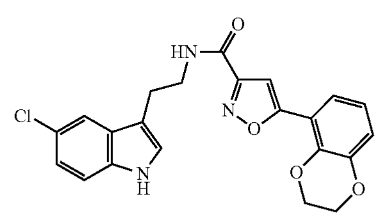 [SMILES: O=C(NCCc1c[nH]c2ccc(Cl)cc12)c1cc(-c2cccc3c2OCCO3)on1] |
| D39 | 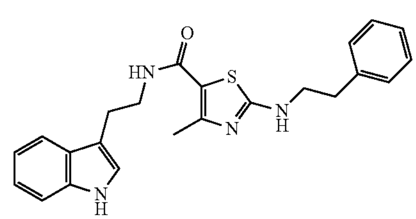 [SMILES: Cc1nc(NCCc2ccccc2)sc1C(=O)NCCc1c[nH]c2ccccc12] |
| D40 | 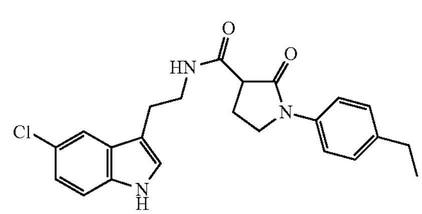 [SMILES: CCc1ccc(N2CCC(C(=O)NCCc3c[nH]c4ccc(Cl)cc34)C2=O)cc1] |

TABLE 1A-continued

| Compound code | STRUCTURE |
|---|---|
| D41 | (structure) |
| D42 | (structure) |
| D43 | (structure) |
| D44 | (structure) |
| D45 | (structure) |
| D46 | (structure) |
| D47 | (structure) |
| D48 | (structure) |
| D49 | (structure) |
| D50 | (structure) |
| D51 | (structure) |
| D52 | (structure) |
| D53 | (structure) |
| D54 | (structure) |

TABLE 1A-continued

| Compound code | STRUCTURE |
|---|---|
| D55 | (5-chloro-1H-indol-3-yl)ethyl 5-phenyl-4,5-dihydroisoxazole-3-carboxamide |
| D56 | (5-chloro-1H-indol-3-yl)ethyl 5-(4-chlorophenyl)isoxazole-3-carboxamide |
| D57 | (5-chloro-1H-indol-3-yl)ethyl 5-(p-tolyl)isoxazole-3-carboxamide |
| D58 | (5-chloro-1H-indol-3-yl)ethyl (S)-4-cyclohexyl-4,5-dihydrooxazole-2-carboxamide |
| D59 | (5-chloro-1H-indol-3-yl)ethyl (R)-4-cyclohexyl-4,5-dihydrooxazole-2-carboxamide |
| D60 | (5-chloro-1H-indol-3-yl)ethyl 5-benzyl-1,3,4-oxadiazole-2-carboxamide |
| D61 | (5-chloro-1H-indol-3-yl)ethyl 5-(pyrrolidin-1-ylmethyl)isoxazole-3-carboxamide |
| D62 | (5-chloro-1H-indol-3-yl)ethyl 5-methyl-2-phenyloxazole-4-carboxamide |
| D63 | (5-chloro-1H-indol-3-yl)ethyl 3-phenylpyrrolidine-1-carboxamide |
| D64 | (5-chloro-1H-indol-3-yl)ethyl 2-oxo-1-phenylpyrrolidine-3-carboxamide |
| D65 | (5-chloro-1H-indol-3-yl)ethyl 1-(3-fluorophenyl)-2-oxopyrrolidine-3-carboxamide |
| D66 | (5-chloro-1H-indol-3-yl)ethyl 5-((ethylamino)methyl)isoxazole-3-carboxamide |
| D67 | (5-chloro-1H-indol-3-yl)ethyl 2-phenylthiazole-4-carboxamide |
| D68 | (5-chloro-1H-indol-3-yl)ethyl 5-(4-chlorophenyl)-2-(trifluoromethyl)furan-3-carboxamide |

TABLE 1A-continued

| Compound code | STRUCTURE |
|---|---|
| D69 | 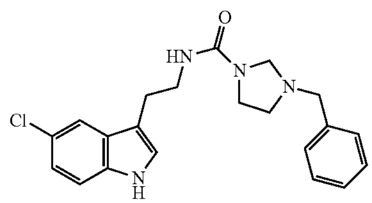 [SMILES: O=C(NCCc1c[nH]c2ccc(Cl)cc12)N1CCN(Cc2ccccc2)C1] |
| D70 | 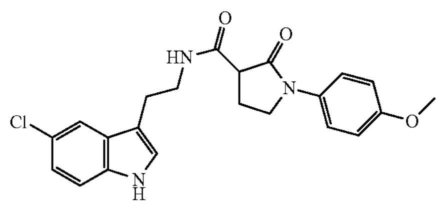 [SMILES: COc1ccc(N2CCC(C(=O)NCCc3c[nH]c4ccc(Cl)cc34)C2=O)cc1] |
| D71 | 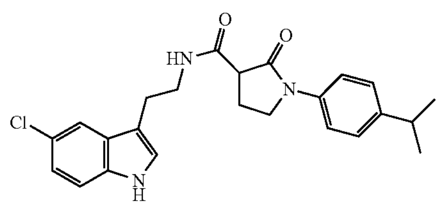 [SMILES: CC(C)c1ccc(N2CCC(C(=O)NCCc3c[nH]c4ccc(Cl)cc34)C2=O)cc1] |
| D72 | 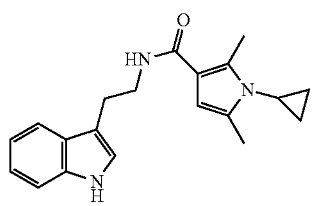 [SMILES: Cc1cc(C(=O)NCCc2c[nH]c3ccccc23)c(C)n1C1CC1] |
| D73 | 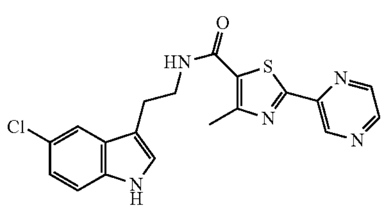 [SMILES: Cc1nc(-c2cnccn2)sc1C(=O)NCCc1c[nH]c2ccc(Cl)cc12] |
| D74 | 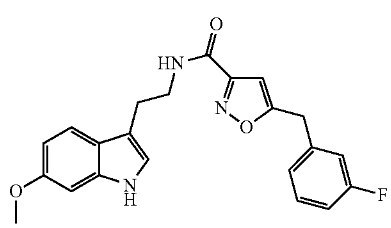 [SMILES: COc1ccc2c(CCNC(=O)c3cc(Cc4cccc(F)c4)on3)c[nH]c2c1] |
| D75 | 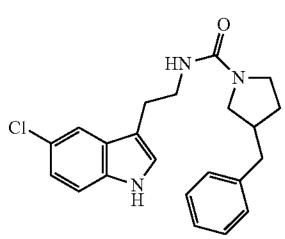 [SMILES: O=C(NCCc1c[nH]c2ccc(Cl)cc12)N1CCC(Cc2ccccc2)C1] |
| D76 | |
| D77 | |
| D78 | |
| D79 | |
| D80 | |
| D81 | |
| D82 | |

TABLE 1A-continued
| Compound code | STRUCTURE |
|---|---|
| D83 | 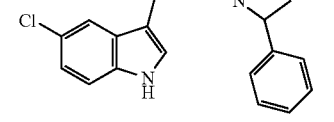 |
| D84 | 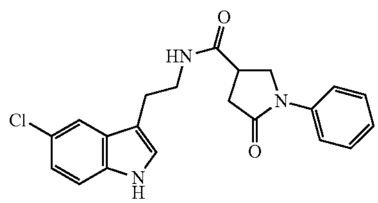 [SMILES: O=C(NCCc1c[nH]c2ccc(Cl)cc12)C1CC(=O)N(c2ccccc2)C1] |
| D85 | 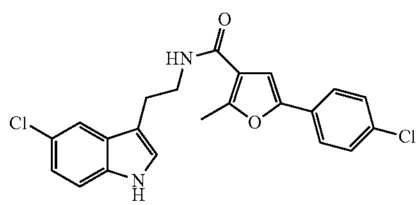 [SMILES: Cc1oc(-c2ccc(Cl)cc2)cc1C(=O)NCCc1c[nH]c2ccc(Cl)cc12] |
| D86 | 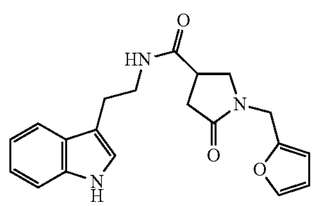 [SMILES: O=C(NCCc1c[nH]c2ccccc12)C1CC(=O)N(Cc2ccco2)C1] |
| D87 | 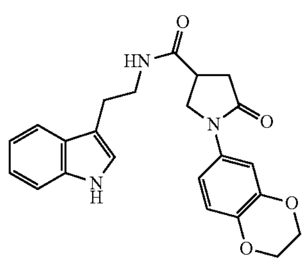 [SMILES: O=C(NCCc1c[nH]c2ccccc12)C1CC(=O)N(c2ccc3c(c2)OCCO3)C1] |
| D88 | 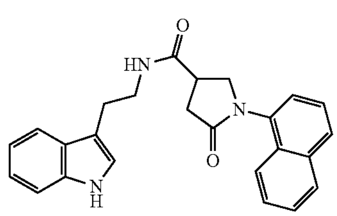 [SMILES: O=C(NCCc1c[nH]c2ccccc12)C1CC(=O)N(c2cccc3ccccc23)C1] |
| D89 | 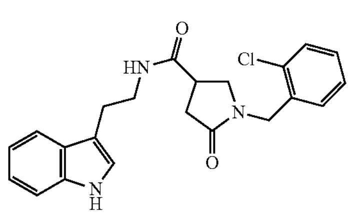 [SMILES: O=C(NCCc1c[nH]c2ccccc12)C1CC(=O)N(Cc2ccccc2Cl)C1] |
| D90 | 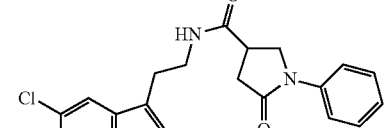 |
| D91 | |
| D92 | |
| D93 | |
| D94 | |
| D95 | |
| D96 | |

TABLE 1A-continued
| Compound code | STRUCTURE |
|---|---|
| D97 | 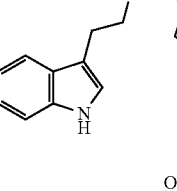 |
| D98 | 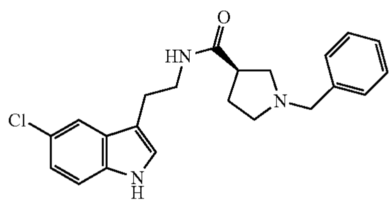 [SMILES: O=C(NCCc1c[nH]c2ccc(Cl)cc12)[C@@H]1CCN(Cc2ccccc2)C1] |
| D99 | 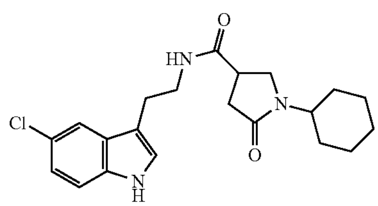 [SMILES: O=C(NCCc1c[nH]c2ccc(Cl)cc12)C1CC(=O)N(C2CCCCC2)C1] |
| D100 | 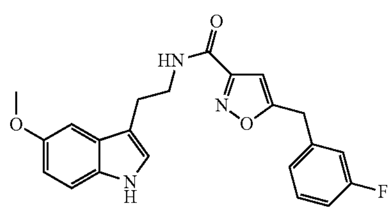 [SMILES: COc1ccc2[nH]cc(CCNC(=O)c3cc(Cc4cccc(F)c4)on3)c2c1] |
| D101 | 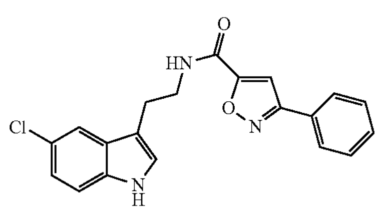 [SMILES: O=C(NCCc1c[nH]c2ccc(Cl)cc12)c1cc(-c2ccccc2)no1] |
| D102 | 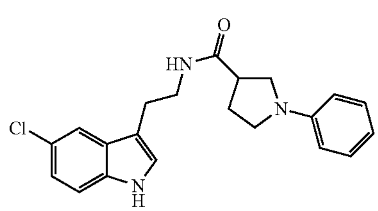 [SMILES: O=C(NCCc1c[nH]c2ccc(Cl)cc12)C1CCN(c2ccccc2)C1] |
| D103 | 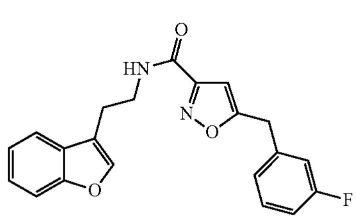 [SMILES: O=C(NCCc1coc2ccccc12)c1cc(Cc2cccc(F)c2)on1] |
| D104 | 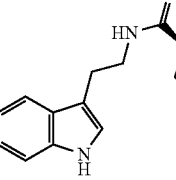 |
| D105 | 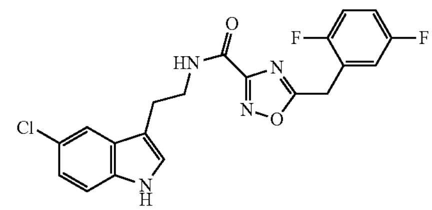 [SMILES: O=C(NCCc1c[nH]c2ccc(Cl)cc12)c1noc(Cc2cc(F)ccc2F)n1] |
| D106 | 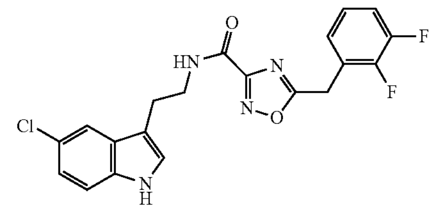 [SMILES: O=C(NCCc1c[nH]c2ccc(Cl)cc12)c1noc(Cc2cccc(F)c2F)n1] |
| D107 | 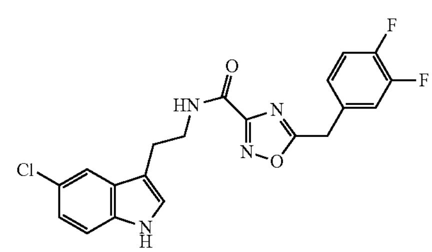 [SMILES: O=C(NCCc1c[nH]c2ccc(Cl)cc12)c1noc(Cc2ccc(F)c(F)c2)n1] |
| D108 | 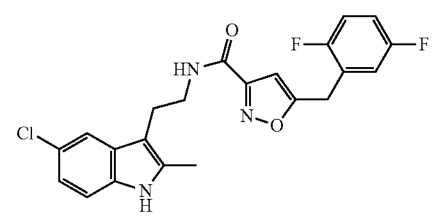 [SMILES: Cc1[nH]c2ccc(Cl)cc2c1CCNC(=O)c1cc(Cc2cc(F)ccc2F)on1] |

TABLE 1B
| Compound code | STRUCTURE |
|---|---|
| D109 | 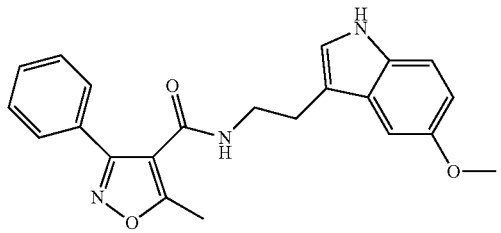 [SMILES: COc1ccc2[nH]cc(CCNC(=O)c3c(-c4ccccc4)noc3C)c2c1] |
| D110 | 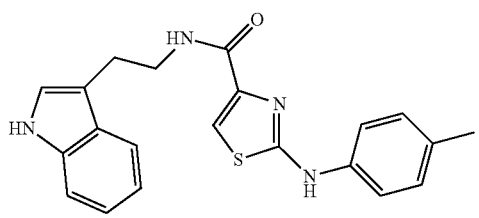 [SMILES: Cc1ccc(Nc2nc(C(=O)NCCc3c[nH]c4ccccc34)cs2)cc1] |
| D111 | 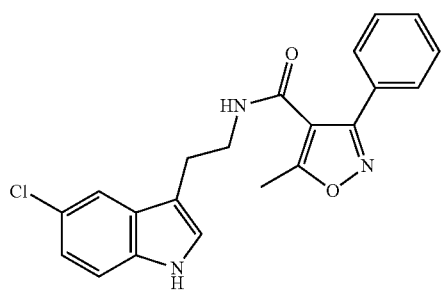 [SMILES: Cc1onc(-c2ccccc2)c1C(=O)NCCc1c[nH]c2ccc(Cl)cc12] |
| D112 | 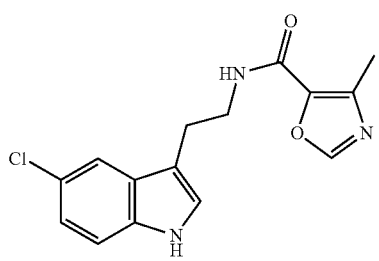 [SMILES: Cc1ncoc1C(=O)NCCc1c[nH]c2ccc(Cl)cc12] |
| D113 | 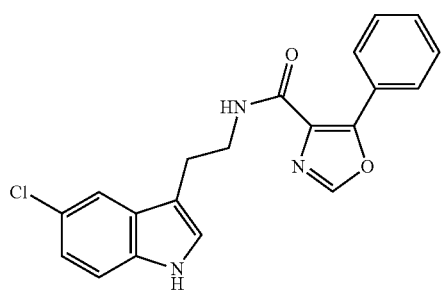 [SMILES: O=C(NCCc1c[nH]c2ccc(Cl)cc12)c1ncoc1-c1ccccc1] |
| D114 | 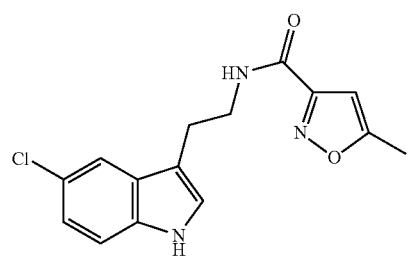 [SMILES: Cc1cc(C(=O)NCCc2c[nH]c3ccc(Cl)cc23)no1] |

TABLE 1B-continued
| Compound code | STRUCTURE |
|---|---|
| D115 | 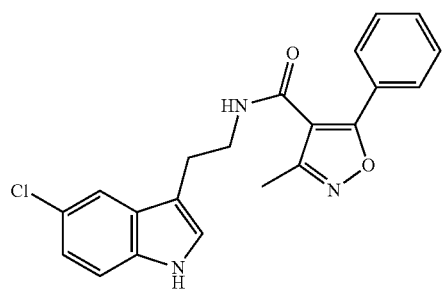 [SMILES: Cc1noc(-c2ccccc2)c1C(=O)NCCc1c[nH]c2ccc(Cl)cc12] |
| D116 | 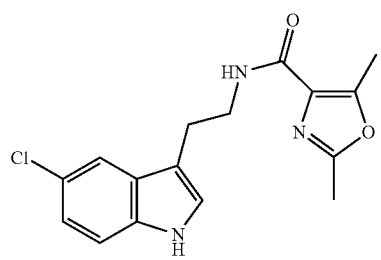 [SMILES: Cc1nc(C(=O)NCCc2c[nH]c3ccc(Cl)cc23)c(C)o1] |
| D117 | 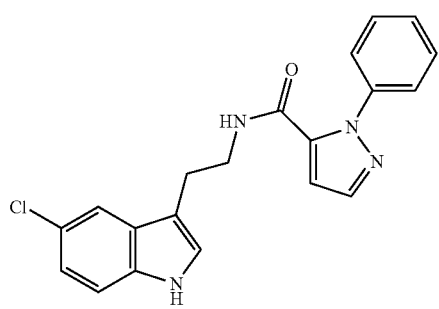 [SMILES: O=C(NCCc1c[nH]c2ccc(Cl)cc12)c1ccnn1-c1ccccc1] |
| D118 | 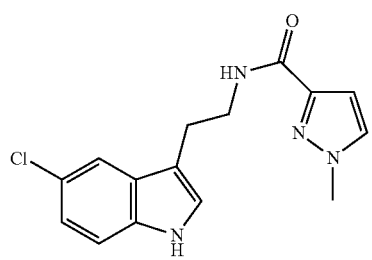 [SMILES: Cn1ccc(C(=O)NCCc2c[nH]c3ccc(Cl)cc23)n1] |
| D119 | 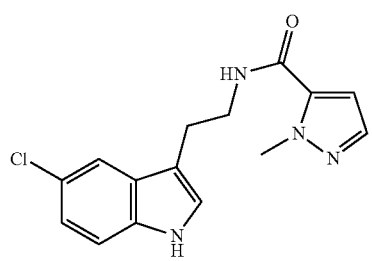 [SMILES: Cn1nccc1C(=O)NCCc1c[nH]c2ccc(Cl)cc12] |

TABLE 1B-continued
| Compound code | STRUCTURE |
|---|---|
| D120 | 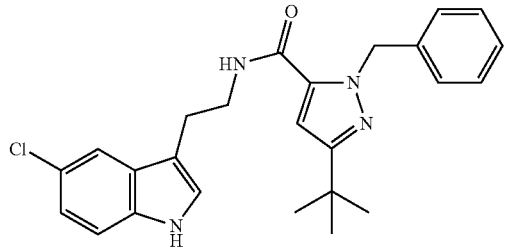 [SMILES: CC(C)(C)c1cc(C(=O)NCCc2c[nH]c3ccc(Cl)cc23)n(Cc2ccccc2)n1] |
| D121 | 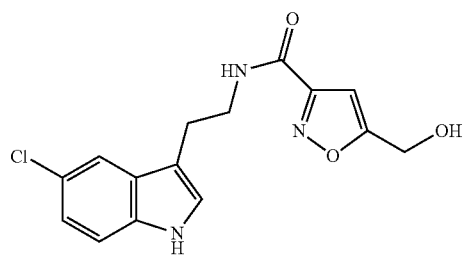 [SMILES: O=C(NCCc1c[nH]c2ccc(Cl)cc12)c1cc(CO)on1] |
| D122 | 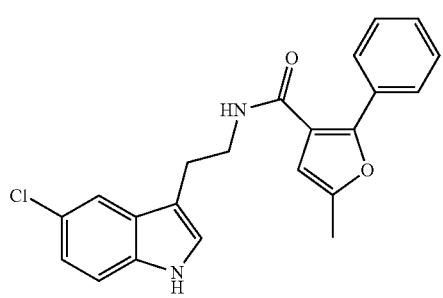 [SMILES: Cc1cc(C(=O)NCCc2c[nH]c3ccc(Cl)cc23)c(-c2ccccc2)o1] |
| D123 | 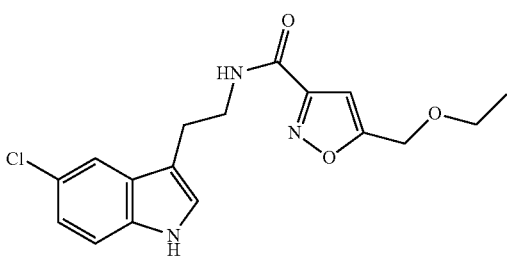 [SMILES: CCOCc1cc(C(=O)NCCc2c[nH]c3ccc(Cl)cc23)no1] |
| D124 | 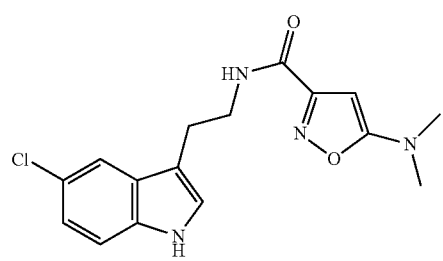 [SMILES: CN(C)c1cc(C(=O)NCCc2c[nH]c3ccc(Cl)cc23)no1] |
| D125 | 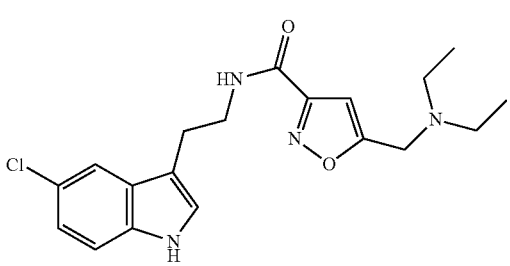 [SMILES: CCN(CC)Cc1cc(C(=O)NCCc2c[nH]c3ccc(Cl)cc23)no1] |

TABLE 1B-continued
| Compound code | STRUCTURE |
|---|---|
| D126 | 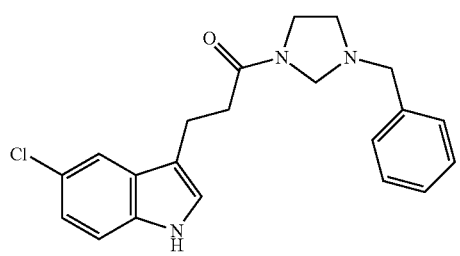 [SMILES: O=C(CCc1c[nH]c2ccc(Cl)cc12)N1CCN(Cc2ccccc2)C1] |
| D127 | 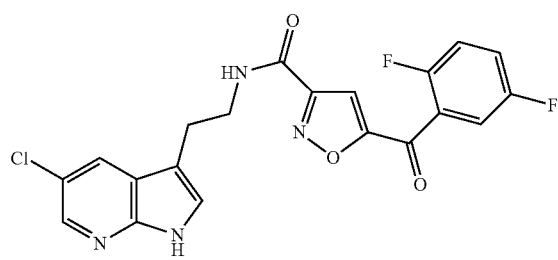 [SMILES: O=C(NCCc1c[nH]c2ncc(Cl)cc12)c1cc(C(=O)c2cc(F)ccc2F)on1] |
| D128 | 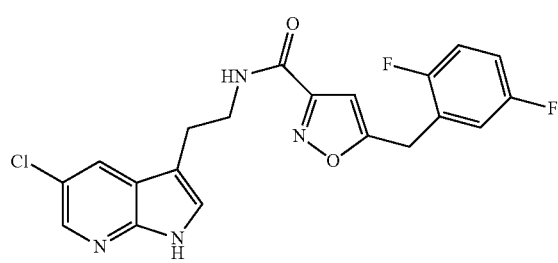 [SMILES: O=C(NCCc1c[nH]c2ncc(Cl)cc12)c1cc(Cc2cc(F)ccc2F)on1] |
| D129 | 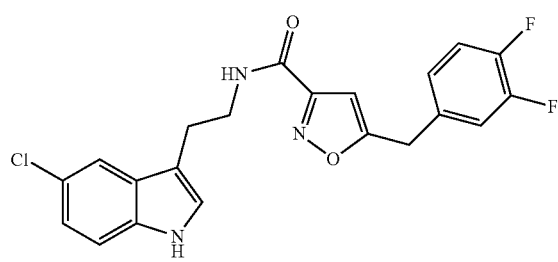 [SMILES: O=C(NCCc1c[nH]c2ccc(Cl)cc12)c1cc(Cc2ccc(F)c(F)c2)on1] |
| D130 | 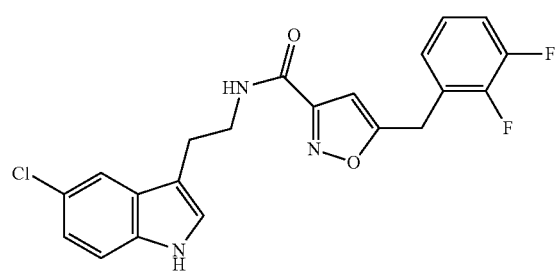 [SMILES: O=C(NCCc1c[nH]c2ccc(Cl)cc12)c1cc(Cc2cccc(F)c2F)on1] |

TABLE 1B-continued
| Compound code | STRUCTURE |
|---|---|
| D131 | 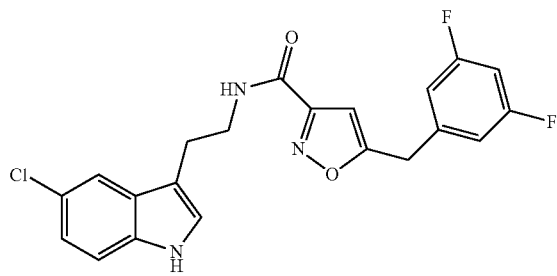 [SMILES: O=C(NCCc1c[nH]c2ccc(Cl)cc12)c1cc(Cc2cc(F)cc(F)c2)on1] |
| D132 | 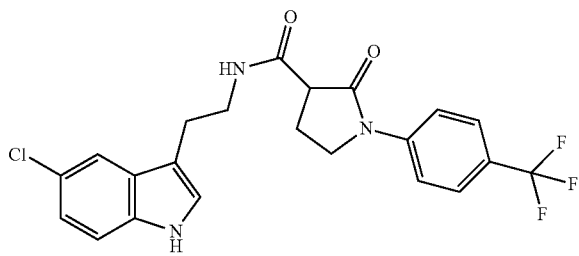 [SMILES: O=C(NCCc1c[nH]c2ccc(Cl)cc12)C1CCN(c2ccc(C(F)(F)F)cc2)C1=O] |
| D133 | 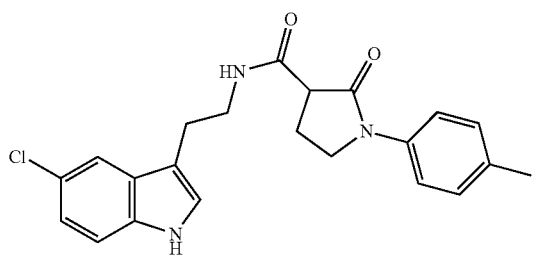 [SMILES: Cc1ccc(N2CCC(C(=O)NCCc3c[nH]c4ccc(Cl)cc34)C2=O)cc1] |
| D134 | 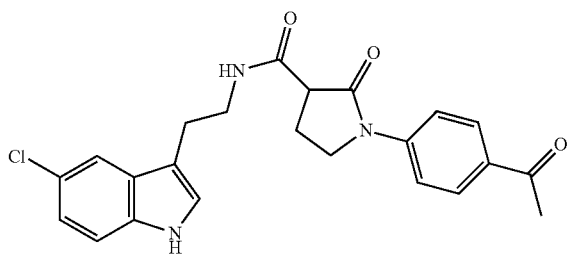 [SMILES: CC(=O)c1ccc(N2CCC(C(=O)NCCc3c[nH]c4ccc(Cl)cc34)C2=O)cc1] |
| D135 | 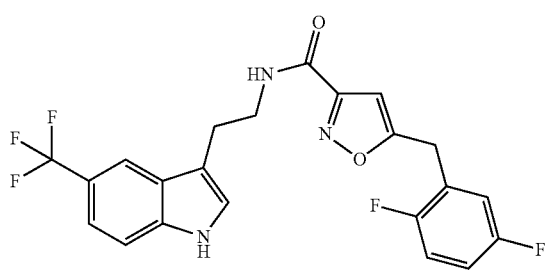 [SMILES: O=C(NCCc1c[nH]c2ccc(C(F)(F)F)cc12)c1cc(Cc2cc(F)ccc2F)on1] |

TABLE 1B-continued
| Compound code | STRUCTURE |
|---|---|
| D136 | 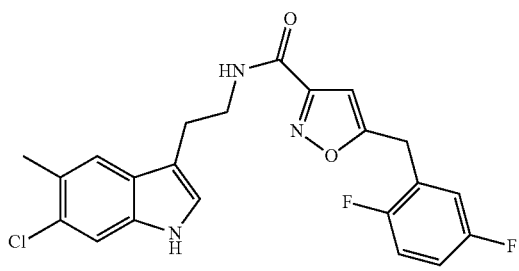 [SMILES: Cc1cc2c(CCNC(=O)c3cc(Cc4cc(F)ccc4F)on3)c[nH]c2cc1Cl] |
| D137 | 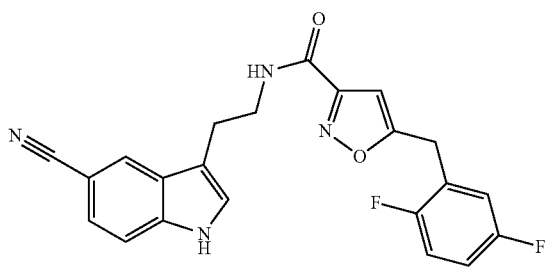 [SMILES: N#Cc1ccc2[nH]cc(CCNC(=O)c3cc(Cc4cc(F)ccc4F)on3)c2c1] |
| D138 | 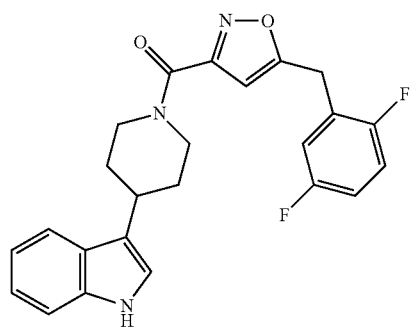 [SMILES: O=C(c1cc(Cc2cc(F)ccc2F)on1)N1CCC(c2c[nH]c3ccccc23)CC1] |
| D139 | 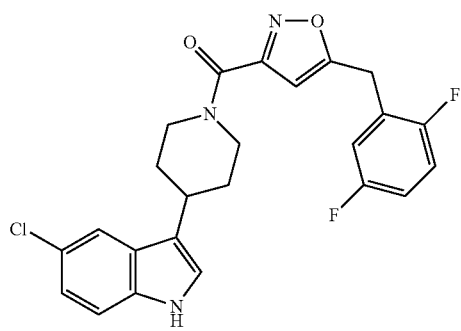 [SMILES: O=C(c1cc(Cc2cc(F)ccc2F)on1)N1CCC(c2c[nH]c3ccc(Cl)cc23)CC1] |
| D140 | 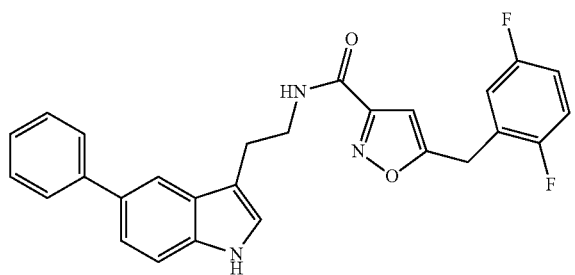 [SMILES: O=C(NCCc1c[nH]c2ccc(-c3ccccc3)cc12)c1cc(Cc2cc(F)ccc2F)on1] |

TABLE 1B-continued
| Compound code | STRUCTURE |
|---|---|
| D141 | 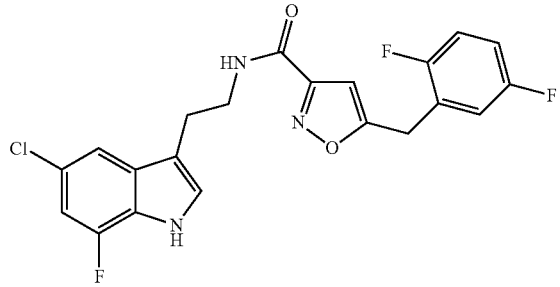 [SMILES: O=C(NCCc1c[nH]c2c(F)cc(Cl)cc12)c1cc(Cc2cc(F)ccc2F)on1] |
| D142 | 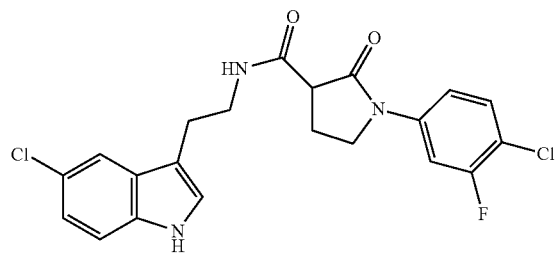 [SMILES: O=C(NCCc1c[nH]c2ccc(Cl)cc12)C1CCN(c2ccc(Cl)c(F)c2)C1=O] |
| D143 | 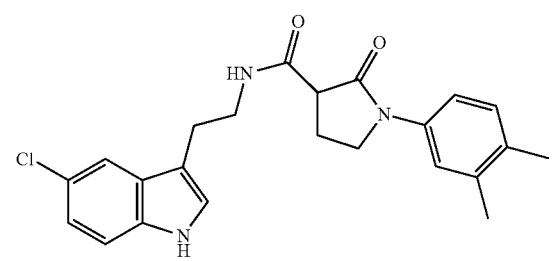 [SMILES: Cc1ccc(N2CCC(C(=O)NCCc3c[nH]c4ccc(Cl)cc34)C2=O)cc1C] |
| D144 | 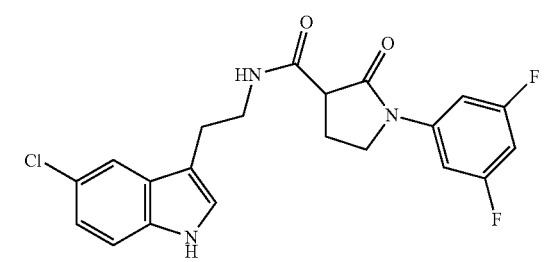 [SMILES: O=C(NCCc1c[nH]c2ccc(Cl)cc12)C1CCN(c2cc(F)cc(F)c2)C1=O] |
| D145 | 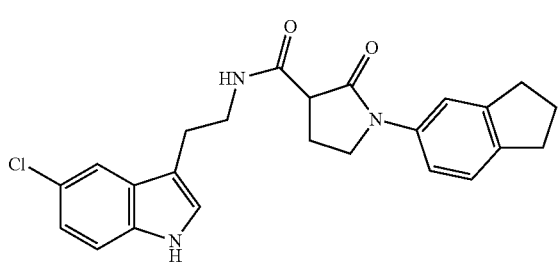 [SMILES: O=C(NCCc1c[nH]c2ccc(Cl)cc12)C1CCN(c2ccc3c(c2)CCC3)C1=O] |
| D146 | 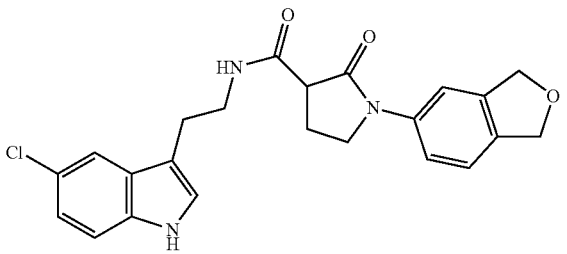 [SMILES: O=C(NCCc1c[nH]c2ccc(Cl)cc12)C1CCN(c2ccc3c(c2)COC3)C1=O] |

TABLE 1B-continued
| Compound code | STRUCTURE |
|---|---|
| D147 | 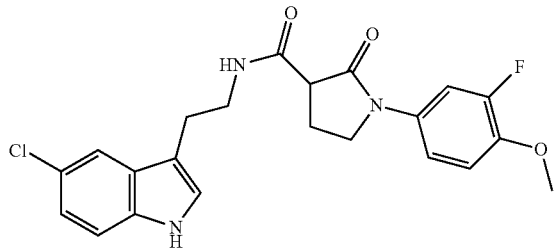 [SMILES: COc1ccc(N2CCC(C(=O)NCCc3c[nH]c4ccc(Cl)cc34)C2=O)cc1F] |
| D148 | 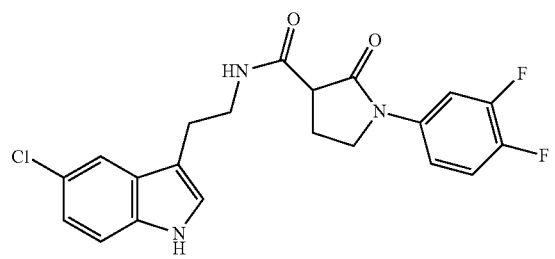 [SMILES: O=C(NCCc1c[nH]c2ccc(Cl)cc12)C1CCN(c2ccc(F)c(F)c2)C1=O] |
| D149 | 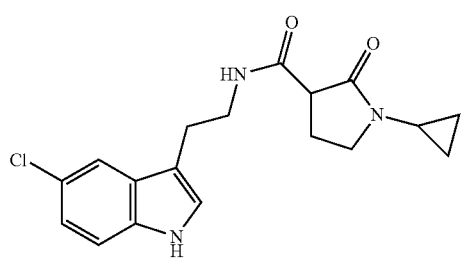 [SMILES: O=C(NCCc1c[nH]c2ccc(Cl)cc12)C1CCN(C2CC2)C1=O] |
| D150 | 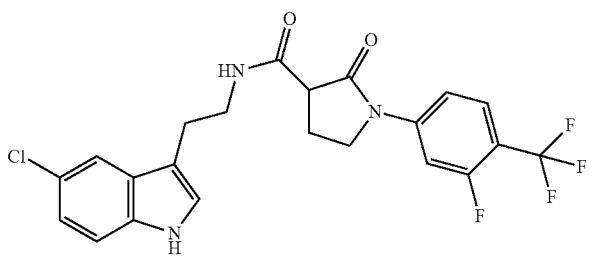 [SMILES: O=C(NCCc1c[nH]c2ccc(Cl)cc12)C1CCN(c2ccc(C(F)(F)F)c(F)c2)C1=O] |
| D151 | 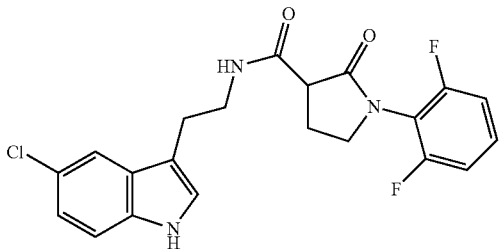 [SMILES: O=C(NCCc1c[nH]c2ccc(Cl)cc12)C1CCN(c2c(F)cccc2F)C1=O] |
| D152 | 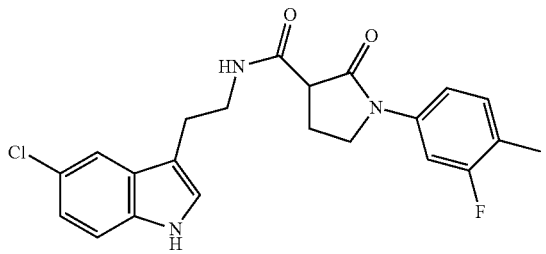 [SMILES: Cc1ccc(N2CCC(C(=O)NCCc3c[nH]c4ccc(Cl)cc34)C2=O)cc1F] |

US 8,618,138 B2
153                                                                                          154
TABLE 1B-continued
| Compound code | STRUCTURE |
|---|---|
| D153 | 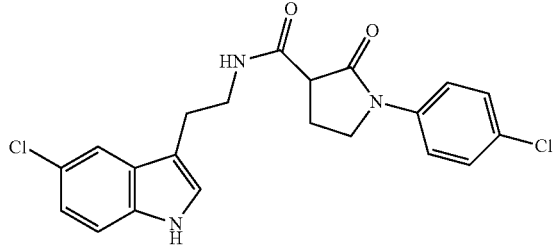 [SMILES: O=C(NCCc1c[nH]c2ccc(Cl)cc12)C1CCN(c2ccc(Cl)cc2)C1=O] |
| D154 | 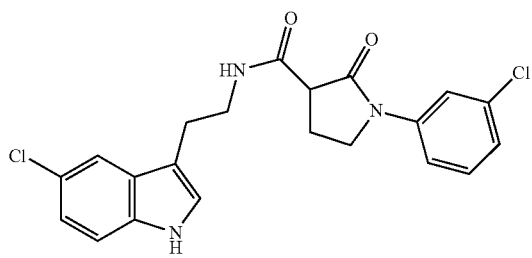 [SMILES: O=C(NCCc1c[nH]c2ccc(Cl)cc12)C1CCN(c2cccc(Cl)c2)C1=O] |
| D155 | 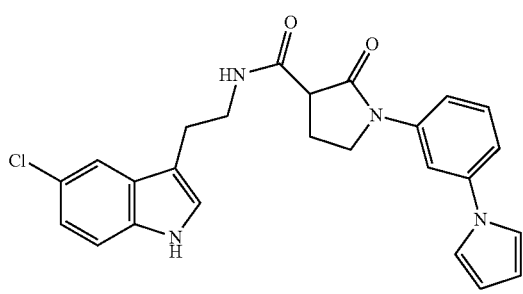 [SMILES: O=C(NCCc1c[nH]c2ccc(Cl)cc12)C1CCN(c2cccc(-n3cccc3)c2)C1=O] |
| D156 | 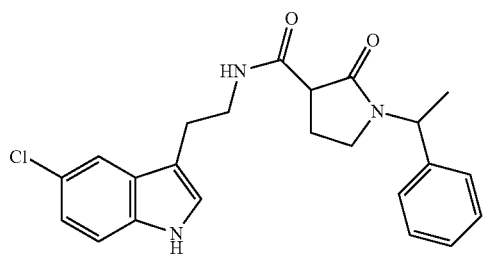 [SMILES: CC(c1ccccc1)N1CCC(C(=O)NCCc2c[nH]c3ccc(Cl)cc23)C1=O] |
| D157 | 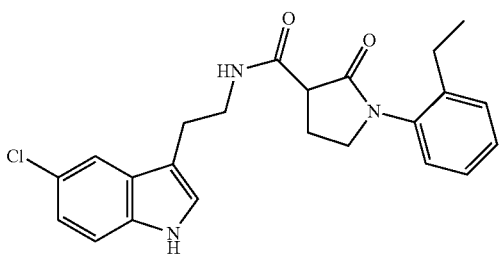 [SMILES: CCc1ccccc1N1CCC(C(=O)NCCc2c[nH]c3ccc(Cl)cc23)C1=O] |
| D158 | 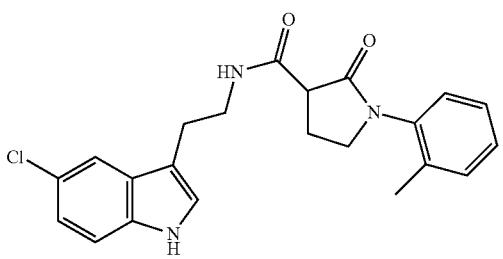 [SMILES: Cc1ccccc1N1CCC(C(=O)NCCc2c[nH]c3ccc(Cl)cc23)C1=O] |

TABLE 1B-continued

| Compound code | STRUCTURE |
|---|---|
| D159 | 5-chloro-tryptamine linked via amide to 3-(2-oxo-1-(3-methylphenyl)pyrrolidin-3-yl) |
| D160 | 5-chloro-tryptamine linked via amide to 3-(2-oxo-1-(1-methyl-1H-pyrazol-3-yl)pyrrolidin-3-yl) |
| D161 | 5-chloro-tryptamine linked via amide to 3-(2-oxo-1-(2-chlorophenyl)pyrrolidin-3-yl) |
| D162 | 5-chloro-tryptamine linked via amide to 3-(2-oxo-1-(3-methoxyphenyl)pyrrolidin-3-yl) |
| D163 | 5-chloro-tryptamine linked via amide to 3-(2-oxo-1-(2-methoxyphenyl)pyrrolidin-3-yl) |
| D164 | 5-chloro-tryptamine linked via amide to 3-(2-oxo-1-(cyclohexylmethyl)pyrrolidin-3-yl) |

TABLE 1B-continued
| Compound code | STRUCTURE |
|---|---|
| D165 | 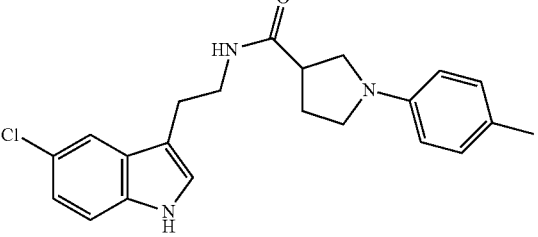 |
| D166 | 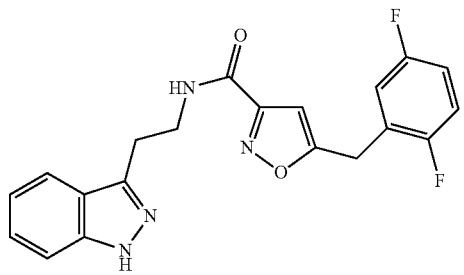 [SMILES: O=C(NCCc1n[nH]c2ccccc12)c1cc(Cc2cc(F)ccc2F)on1] |
| D167 | 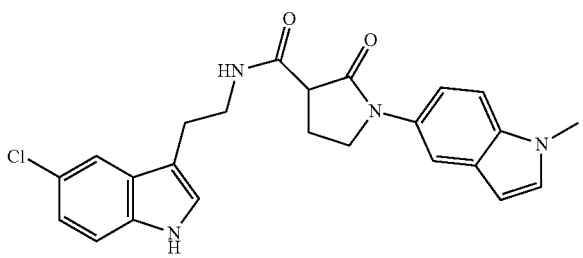 [SMILES: Cn1ccc2cc(N3CCC(C(=O)NCCc4c[nH]c5ccc(Cl)cc45)C3=O)ccc21] |
| D168 | 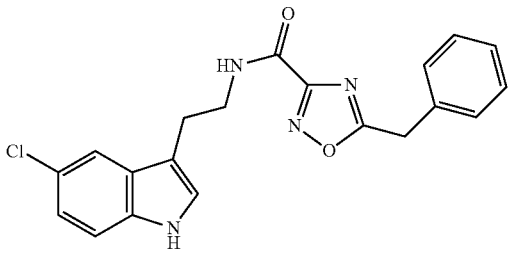 [SMILES: O=C(NCCc1c[nH]c2ccc(Cl)cc12)c1noc(Cc2ccccc2)n1] |
| D169 | 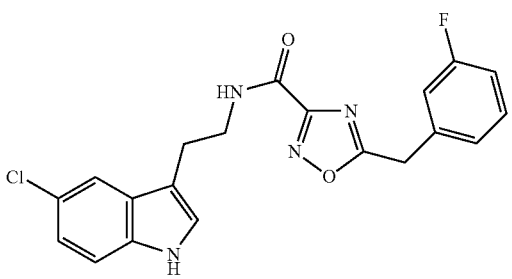 [SMILES: O=C(NCCc1c[nH]c2ccc(Cl)cc12)c1noc(Cc2cccc(F)c2)n1] |
| D170 | 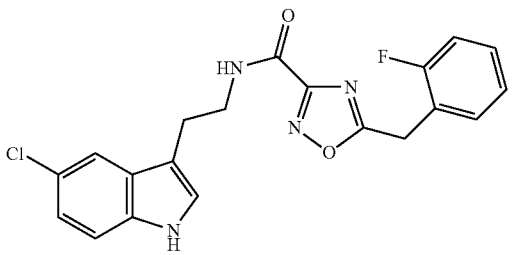 [SMILES: O=C(NCCc1c[nH]c2ccc(Cl)cc12)c1noc(Cc2ccccc2F)n1] |

TABLE 1B-continued
| Compound code | STRUCTURE |
|---|---|
| D171 | 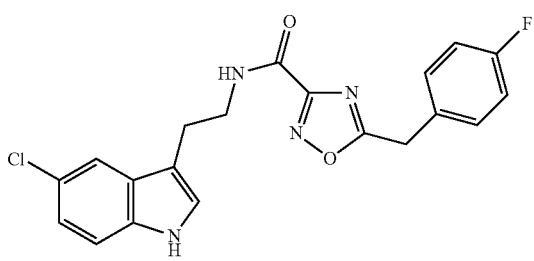 [SMILES: O=C(NCCc1c[nH]c2ccc(Cl)cc12)c1noc(Cc2ccc(F)cc2)n1] |
| D172 | 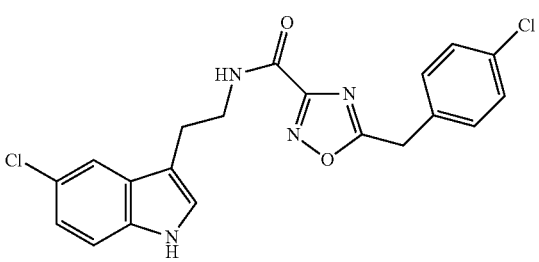 [SMILES: O=C(NCCc1c[nH]c2ccc(Cl)cc12)c1noc(Cc2ccc(Cl)cc2)n1] |
| D173 | 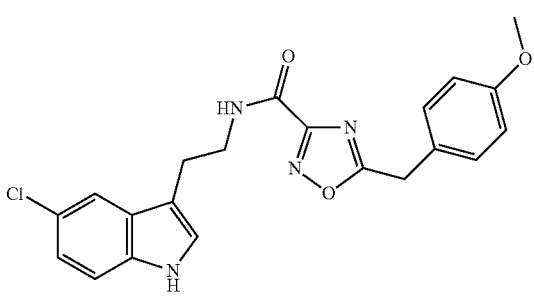 [SMILES: COc1ccc(Cc2nc(C(=O)NCCc3c[nH]c4ccc(Cl)cc34)no2)cc1] |
| D174 | 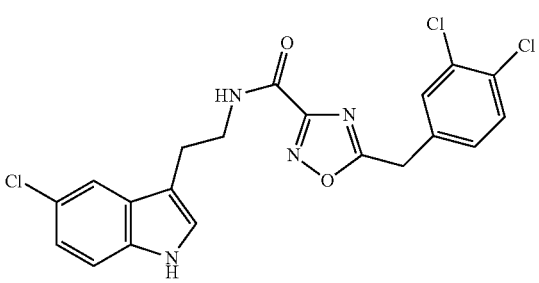 |
| D175 | 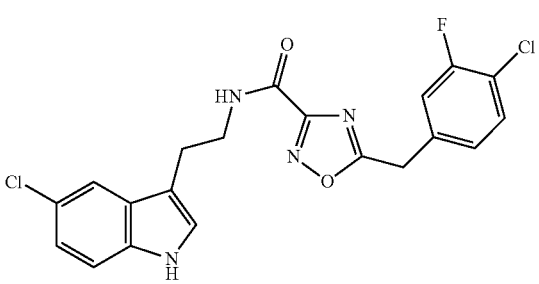 [SMILES: O=C(NCCc1c[nH]c2ccc(Cl)cc12)c1noc(Cc2ccc(Cl)c(Cl)c2)n1] |

TABLE 1B-continued
| Compound code | STRUCTURE |
|---|---|
| D176 | 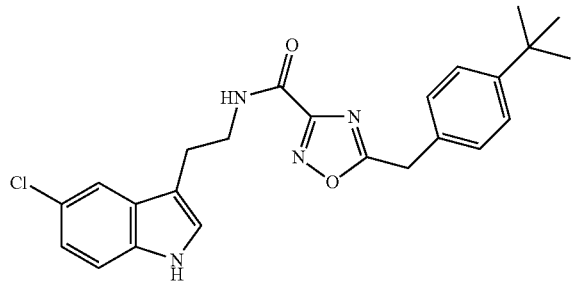 [SMILES: CC(C)(C)c1ccc(Cc2nc(C(=O)NCCc3c[nH]c4ccc(Cl)cc34)no2)cc1] |
| D177 | 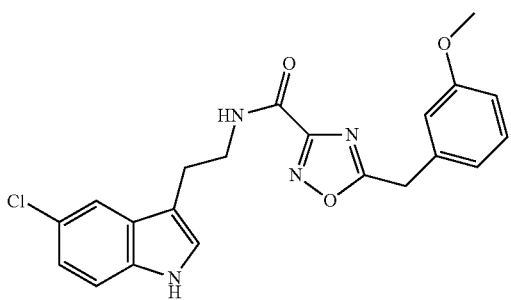 [SMILES: COc1cccc(Cc2nc(C(=O)NCCc3c[nH]c4ccc(Cl)cc34)no2)c1] |
| D178 | 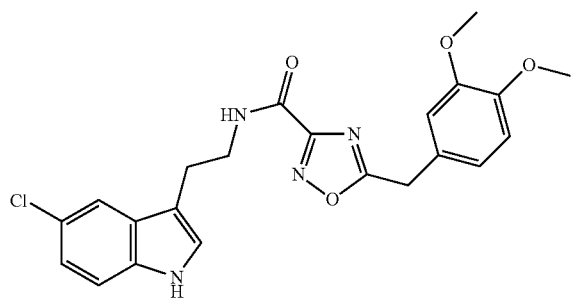 [SMILES: COc1ccc(Cc2nc(C(=O)NCCc3c[nH]c4ccc(Cl)cc34)no2)cc1OC] |
| D179 | 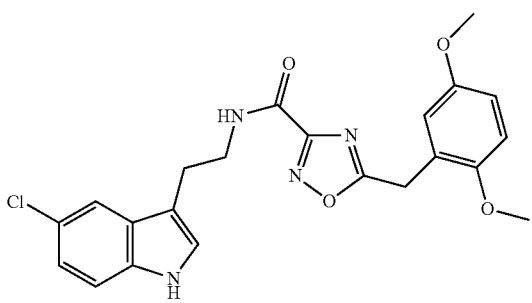 [SMILES: COc1ccc(OC)c(Cc2nc(C(=O)NCCc3c[nH]c4ccc(Cl)cc34)no2)c1] |
| D180 | 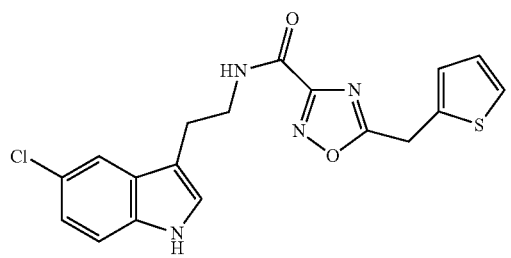 [SMILES: O=C(NCCc1c[nH]c2ccc(Cl)cc12)c1noc(Cc2cccs2)n1] |

TABLE 1B-continued
| Compound code | STRUCTURE |
|---|---|
| D181 | 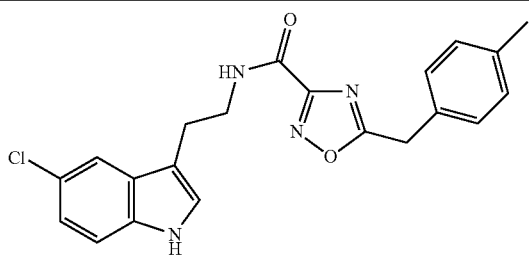 |
| D182 | 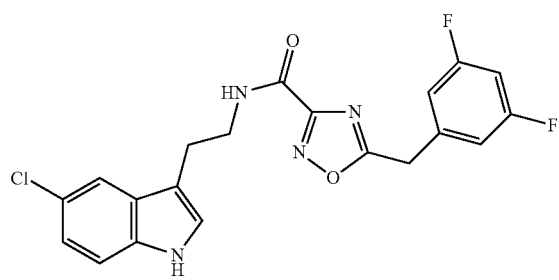 [SMILES: O=C(NCCc1c[nH]c2ccc(Cl)cc12)c1noc(Cc2cc(F)cc(F)c2)n1] |
| D183 | 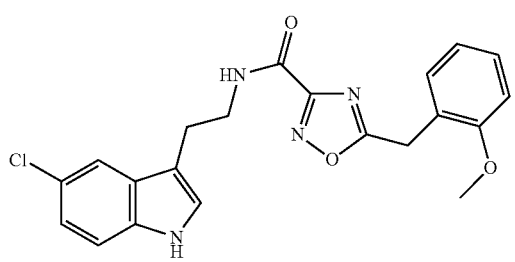 [SMILES: COc1ccccc1Cc1nc(C(=O)NCCc2c[nH]c3ccc(Cl)cc23)no1] |
| D184 | 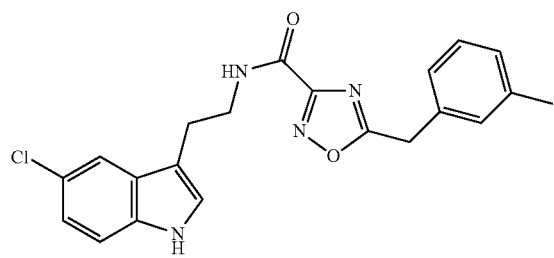 [SMILES: Cc1cccc(Cc2nc(C(=O)NCCc3c[nH]c4ccc(Cl)cc34)no2)c1] |
| D185 | 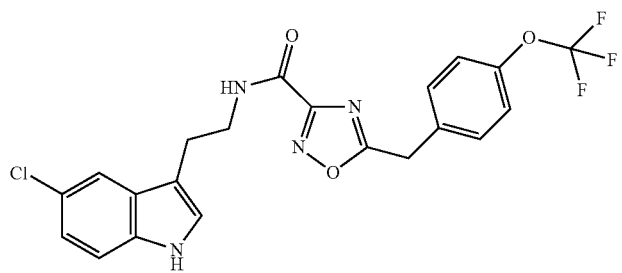 [SMILES: O=C(NCCc1c[nH]c2ccc(Cl)cc12)c1noc(Cc2ccc(OC(F)(F)F)cc2)n1] |
| D186 | 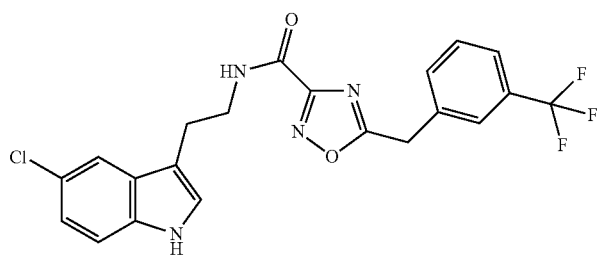 [SMILES: O=C(NCCc1c[nH]c2ccc(Cl)cc12)c1noc(Cc2cccc(C(F)(F)F)c2)n1] |

TABLE 1B-continued
| Compound code | STRUCTURE |
|---|---|
| D187 | 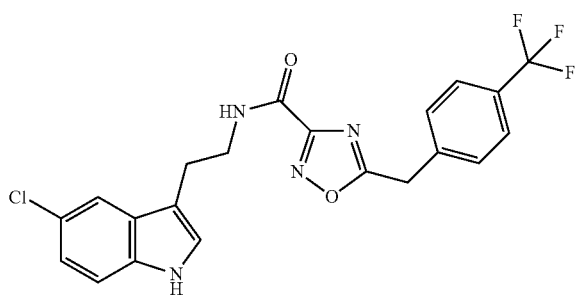 [SMILES: O=C(NCCc1c[nH]c2ccc(Cl)cc12)c1noc(Cc2ccc(C(F)(F)F)cc2)n1] |
| D188 | 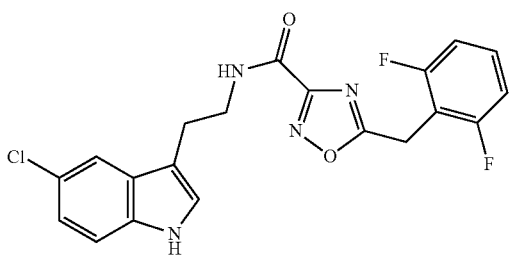 [SMILES: O=C(NCCc1c[nH]c2ccc(Cl)cc12)c1noc(Cc2c(F)cccc2F)n1] |
| D189 | 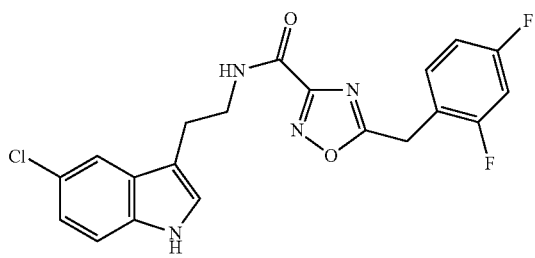 [SMILES: O=C(NCCc1c[nH]c2ccc(Cl)cc12)c1noc(Cc2ccc(F)cc2F)n1] |
| D190 | 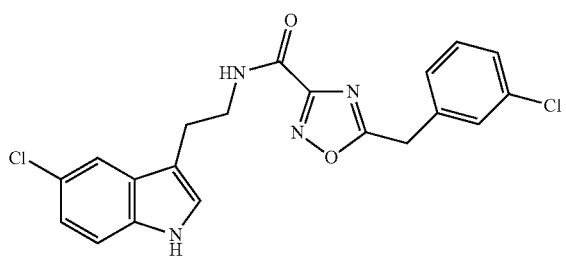 [SMILES: O=C(NCCc1c[nH]c2ccc(Cl)cc12)c1noc(Cc2cccc(Cl)c2)n1] |
| D191 | 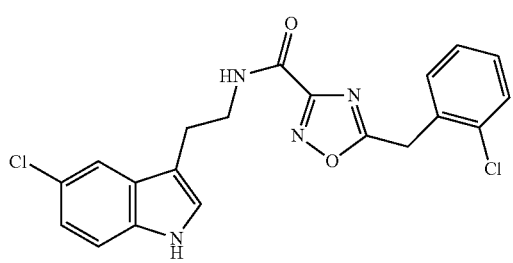 [SMILES: O=C(NCCc1c[nH]c2ccc(Cl)cc12)c1noc(Cc2ccccc2Cl)n1] |

TABLE 1B-continued
| Compound code | STRUCTURE |
|---|---|
| D192 | 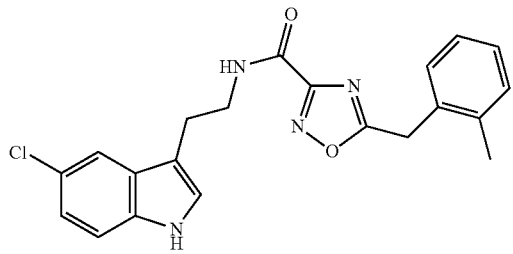 [SMILES: Cc1ccccc1Cc1nc(C(=O)NCCc2c[nH]c3ccc(Cl)cc23)no1] |
| D193 | 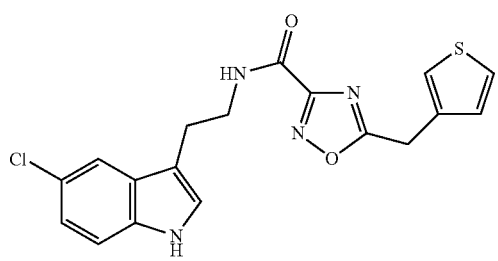 [SMILES: O=C(NCCc1c[nH]c2ccc(Cl)cc12)c1noc(Cc2ccsc2)n1] |
| D194 | 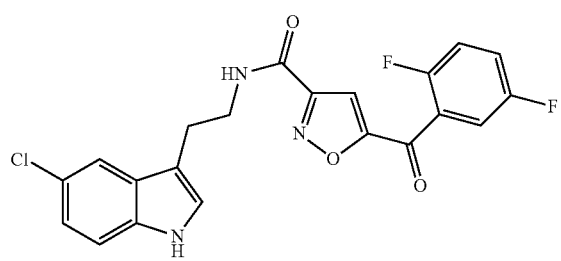 [SMILES: O=C(NCCc1c[nH]c2ccc(Cl)cc12)c1cc(C(=O)c2cc(F)ccc2F)on1] |
| D195 | 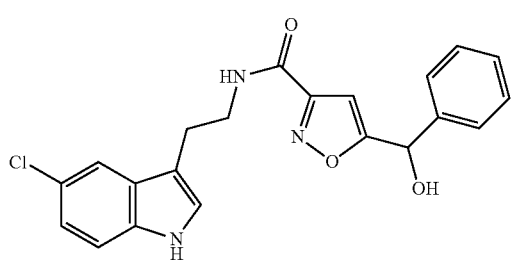 [SMILES: O=C(NCCc1c[nH]c2ccc(Cl)cc12)c1cc(C(O)c2ccccc2)on1] |
| D196 | 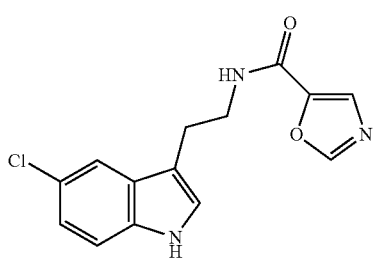 [SMILES: O=C(NCCc1c[nH]c2ccc(Cl)cc12)c1cnco1] |
| D197 | 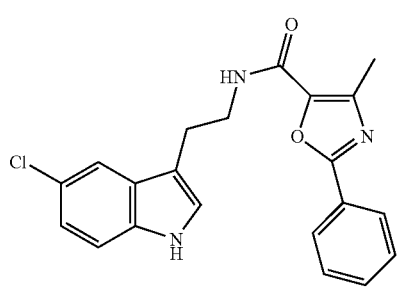 [SMILES: Cc1nc(-c2ccccc2)oc1C(=O)NCCc1c[nH]c2ccc(Cl)cc12] |

TABLE 1B-continued
| Compound code | STRUCTURE |
|---|---|
| D198 | 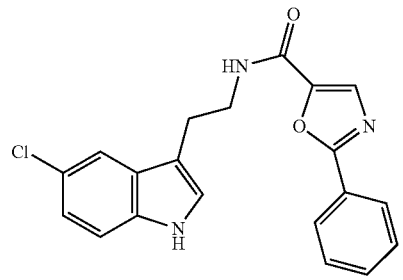 |
| D199 | 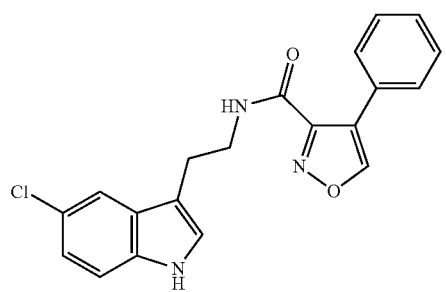 [SMILES: O=C(NCCc1c[nH]c2ccc(Cl)cc12)c1nocc1-c1ccccc1] |
| D200 | 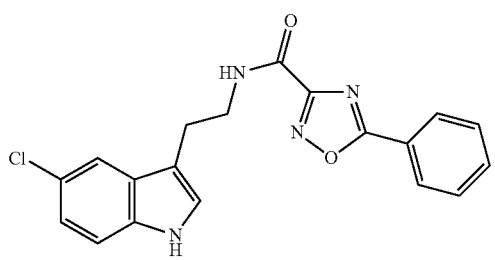 [SMILES: O=C(NCCc1c[nH]c2ccc(Cl)cc12)c1noc(-c2ccccc2)n1] |
| D201 | 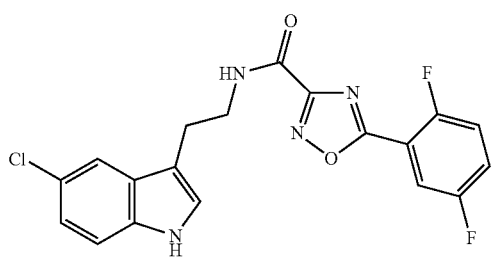 [SMILES: O=C(NCCc1c[nH]c2ccc(Cl)cc12)c1noc(-c2cc(F)ccc2F)n1] |
| D202 | 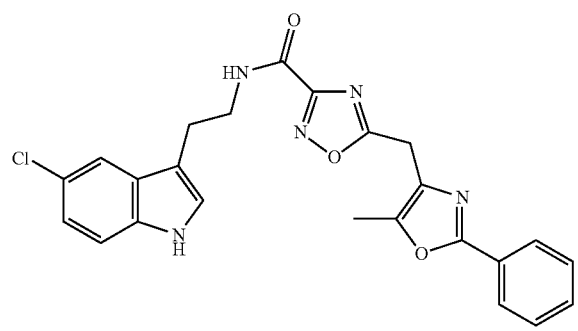 [SMILES: Cc1oc(-c2ccccc2)nc1Cc1nc(C(=O)NCCc2c[nH]c3ccc(Cl)cc23)no1] |

TABLE 1B-continued
| Compound code | STRUCTURE |
|---|---|
| D203 | 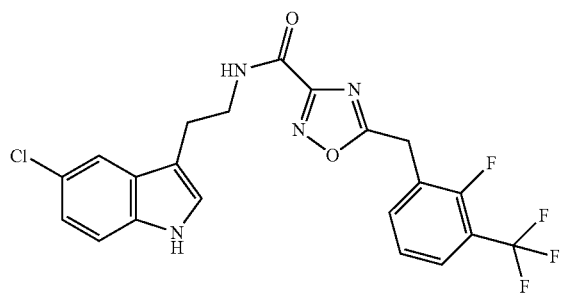 [SMILES: O=C(NCCc1c[nH]c2ccc(Cl)cc12)c1noc(Cc2cccc(C(F)(F)F)c2F)n1] |
| D204 | 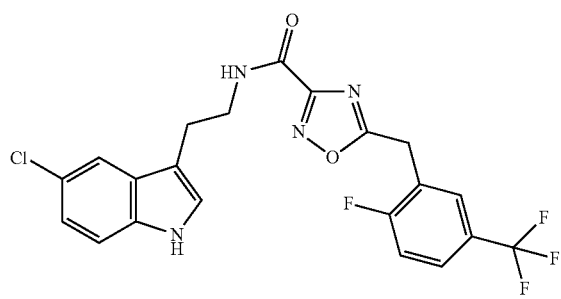 [SMILES: O=C(NCCc1c[nH]c2ccc(Cl)cc12)c1noc(Cc2cc(C(F)(F)F)ccc2F)n1] |
| D205 | 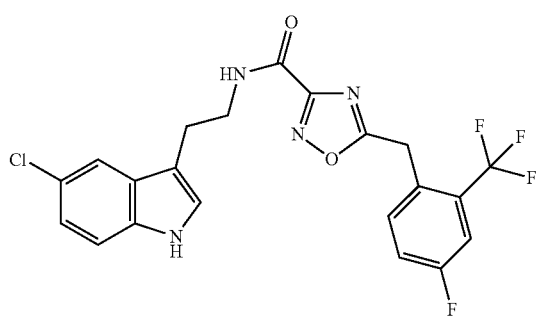 [SMILES: O=C(NCCc1c[nH]c2ccc(Cl)cc12)c1noc(Cc2ccc(F)cc2C(F)(F)F)n1] |
| D206 | 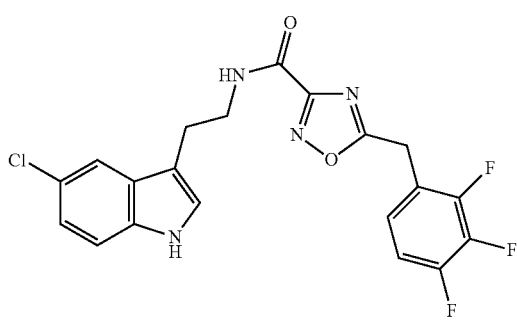 [SMILES: O=C(NCCc1c[nH]c2ccc(Cl)cc12)c1noc(Cc2ccc(F)c(F)c2F)n1] |
| D207 | 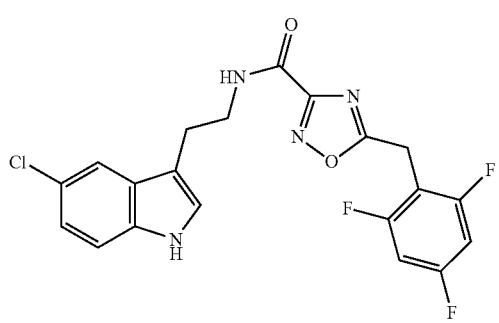 [SMILES: O=C(NCCc1c[nH]c2ccc(Cl)cc12)c1noc(Cc2c(F)cc(F)cc2F)n1] |

TABLE 1B-continued
| Compound code | STRUCTURE |
|---|---|
| D208 | 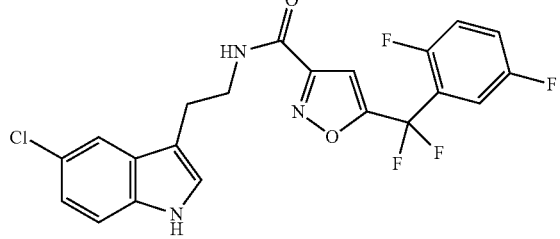 |
| D209 | 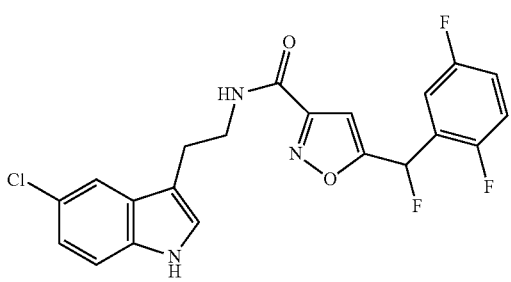 [SMILES: O=C(NCCc1c[nH]c2ccc(Cl)cc12)c1cc(C(F)c2cc(F)ccc2F)on1] |
| D210 | 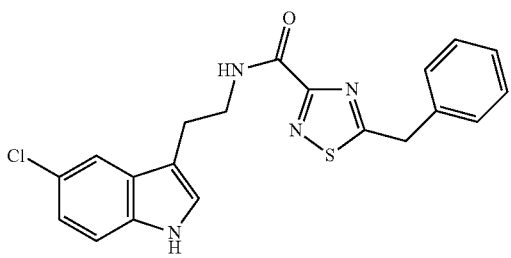 [SMILES: O=C(NCCc1c[nH]c2ccc(Cl)cc12)c1nsc(Cc2ccccc2)n1] |
| D211 | 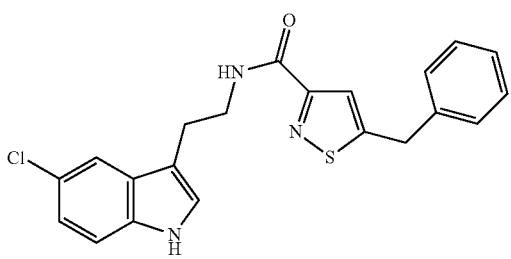 [SMILES: O=C(NCCc1c[nH]c2ccc(Cl)cc12)c1cc(Cc2ccccc2)sn1] |
| D212 | 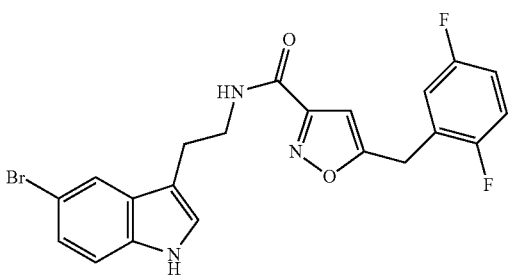 [SMILES: O=C(NCCc1c[nH]c2ccc(Br)cc12)c1cc(Cc2cc(F)ccc2F)on1] |
| D213 | 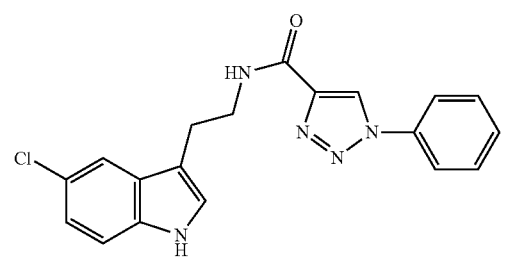 [SMILES: O=C(NCCc1c[nH]c2ccc(Cl)cc12)c1cn(-c2ccccc2)nn1] |

TABLE 1B-continued

| Compound code | STRUCTURE |
|---|---|
| D214 | 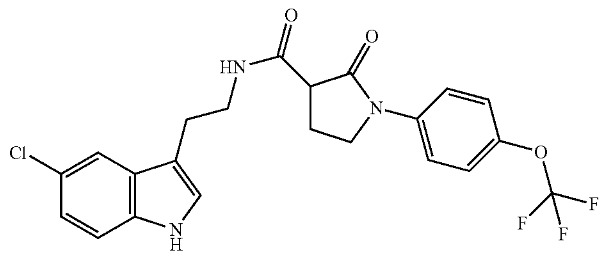 [SMILES: O=C(NCCc1c[nH]c2ccc(Cl)cc12)C1CCN(c2ccc(OC(F)(F)F)cc2)C1=O] |
| D215 | 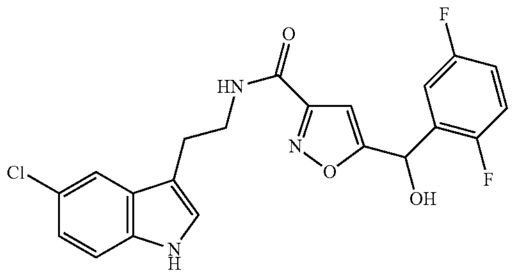 [SMILES: O=C(NCCc1c[nH]c2ccc(Cl)cc12)c1cc(C(O)c2cc(F)ccc2F)on1] |
| D216 | 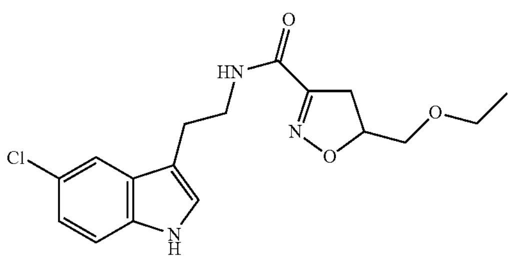 [SMILES: CCOCC1CC(C(=O)NCCc2c[nH]c3ccc(Cl)cc23)=NO1] |

Part A

Intermediate 1

Preparation of ethyl 5-chloroisoxazole-3-carboxylate

A mixture of triethylamine (13.12 mL; 90.73 mmol) in 1,1-dichloroethene (75 mL) was added to ethyl 2-chloro-2-(hydroxyimino)acetate (5.5 g; 36.29 mmol) in 1,1-dichloroethene (50 mL) over a period of 2 h the reaction mixture was stirred at room temperature for 20 min and portioned between water (75 mL) and dichloromethane (75 mL). The aqueous were extracted with dichloromethane, the organic layers rejoined were dried, concentrated under reduced pressure and the crude material was purified by flash chromatography on silica gel (eluent 2 to 20% ethyl acetate in heptane) to afford ethyl 5-chloroisoxazole-3-carboxylate 2.5 g (39%).

ESI/APCI (+): 176 (M+H).
$^1$H NMR (CDCl$_3$) δ 6.61 (s, 1H); 4.46 (q, 2H); 1.42 (t, 3H).

Intermediate 2

Preparation of 5-chloroisoxazole-3-carboxylic acid

Ethyl-5-chloroisoxazole (1.5 g; 8.54 mmol) was added to a mixture of lithium hydroxide (10 mL; 2M in water) and dioxane (10 mL). The reaction mixture was stirred vigorously at room temperature for 1 h and concentrated under reduced pressure. The crude material was reparted between ethyl acetate and HCl 1M; the phases were separated and the aqueous were extracted with ethyl acetate. The organic rejoined were dried, concentrated under reduced pressure and the crude material 1.2 g (95%) was used without further purification.

Intermediate 3

Preparation of 5-chloro-N-(2-(5-chloro-1H-indol-3-yl)ethyl)isoxazole-3-carboxamide A mixture of 2-(5-chloro-1H-indol-3-yl)ethanammonium hydrochloride (1.3 g; 5.62 mmol), 5-chloroisoxazole-3-carboxylic acid (0.912 g; 6.19 mmol), HATU (N,N,N',N'-Tetramethyl-O-(7-azabenzotriazol-1-yl)uronium hexafluorophosphate) (2.35 g; 6.19 mmol) and N,N-diisopropylethylamine (2.6 mL; 14.06 mmol) in DMF (15 mL) was stirred at room temperature overnight and concentrated under reduced pressure. The crude material was dissolved in ethyl acetate, washed with water, dried and concentrated under reduced pressure. The crude material was purified by flash chromatography on silica gel (eluent 2 to 20% ethyl acetate in dichloromethane) to afford 5-chloro-N-(2-(5-chloro-1H-indol-3-yl)ethyl)isoxazole-3-carboxamide (0.204 g; 11%).

ESI/APCI (+): 324 (M+H).

Intermediate 4

Preparation of Ethyl 5-(hydroxymethyl)isoxazole-3-carboxylate

To a mixture of propargyl alcohol (1.0 mL; 16.76 mmol) and ethyl 2-nitroacetate (3.79 mL; 33.52 mmol) in ethanol (23.5 mL) in an Ace pressure tube was added 1,4-diazobicyclo[2.2.2]octane (DABCO, 0.194 g; 1.68 mmol). The tube was heated at 80° C. for 72 h. After cooling, the mixture was evaporated to dryness and the residue was purified by flash chromatography on silica gel (eluent: 0 to 6% methanol in dichloromethane) to yield 2.32 g (81%) of ethyl 5-(hydroxymethyl)isoxazole-3-carboxylate as an oil.

ESI/APCI (+): 172 (M+H).

Intermediate 5

Preparation of 5-(Hydroxymethyl)isoxazole-3-carboxylic acid

The mixture of Ethyl 5-(hydroxymethyl)isoxazole-3-carboxylate (1.5 g; 8.76 mmol) and 1M sodium hydroxide (18 mL; 18 mmol) was stirred at room temperature for 3.5 h. Brine (40 mL) was added and the pH of the solution was adjusted to 2 by addition of 6N hydrochloric acid. The acidic solution was extracted with 8×60 mL of ethyl acetate. Organic extracts were dried over magnesium sulfate. Evaporation of the solvent produced 1.20 g (95%) of 5-(hydroxymethyl)isoxazole-3-carboxylic acid as a white solid which was used without further purification.

Intermediate 6

Preparation of Ethyl 5-(bromomethyl)isoxazole-3-carboxylate

Method 1

Carbon tetrabromide (5.44 g; 16.39 mmol) was added to the solution of triphenylphosphine (4.34 g, 16.39 mmol) in THF (50 mL) and the resulting mixture was stirred at room temperature for 15 min. To this green suspension was added a solution of ethyl 5-(hydroxymethyl)isoxazole-3-carboxylate (1.87 g, 10.93 mmol) in THF (10 mL) and the resulting reaction mixture was stirred overnight at room temperature. The solid material was removed by filtration. The filtrate was concentrated under reduced pressure and the residue was purified by flash chromatography on silica gel (eluent: 15 to 100% dichloromethane in heptane) to afford 1.73 g (68%) of ethyl 5-(bromomethyl)isoxazole-3-carboxylate as a solid.

Method 2

A solution of ethyl 2-chloro-2-(hydroxyimino)acetate (11 g; 70.41 mmol) in ethyl acetate (60 mL) was added dropwise at room temperature to a mixture of 3-bromoprop-1-yne (15.2 mL; 141 mmol), sodium bicarbonate (11.95 g; 141 mmol), ethyl acetate (400 mL), and water (4 mL). The mixture was stirred at room temperature for 24 h and the solid was removed by filtration and washed with ethyl acetate. The filtrate was concentrated under reduced pressure and the residue was purified by flash chromatography on silica gel (eluent: 15 to 100% of dichloromethane in heptane) to give 14.38 g (87%) of ethyl 5-(bromomethyl)isoxazole-3-carboxylate as a white solid.

ESI/APCI (+): 234 (M+H).

$^1$H NMR (CDCl$_3$) 6.74 (s, 1H); 4.50 (s, 2H); 4.45 (q, 2H); 1.42 (t, 3H).

Intermediate 7

Preparation of N-(2-(5-chloro-1H-indol-3-yl)ethyl)-5-(chloromethyl)isoxazole-3-carboxamide Thionyl chloride (0.5 mL; 7.26 mmol) was added to a mixture of 5-(hydroxymethyl)isoxazole-3-carboxylic acid (0.207 g; 7.26 mmol) and stirred at 80° C. for 72 h. The solution was concentrated under reduced pressure and the crude material was dissolved in dichloromethane (5 mL) and added to a mixture of 2-(5-chloro-1H-indol-3-yl)ethanamine hydrochloride (0.370 g; 1.60 mmol) and triethylamine (0.524 mL; 3.62 mmol) in dichloromethane (5 mL). The resulting solution was stirred at room temperature for 20 min, concentrated under reduced pressure and the crude material was purified by flash chromatography on silica gel (eluent 2 to 20% ethyl acetate in dichloromethane) to afford N-(2-(5-chloro-1H-indol-3-yl)ethyl)-5-(chloromethyl)isoxazole-3-carboxamide 0.088 g (22%).

ESI/APCI (+): 338 (M+H).

Intermediate 8

Preparation of 5-(Bromomethyl)-N-(2-(5-chloro-1H-indol-3-yl)ethyl)isoxazole-3-carboxamide Carbon tetrabromide (1.71 g; 5.16 mmol) was added to the solution of triphenylphosphine (1.35 g, 5.16 mmol) in THF (20 mL) and the resulting mixture was stirred at room temperature for 10 min. To this green suspension was added a solution of N-(2-(5-chloro-1H-indol-3-yl)ethyl)-5-hydroxymethyl)isoxazole-3-carboxamide (1.10 g; 3.44 mmol) in THF (10 mL) and the resulting reaction mixture was stirred overnight at room temperature. The reaction mixture was concentrated under reduced pressure and the residue was purified by flash chromatography on silica gel (eluent: 2 to 10% ethyl acetate in dichloromethane) to afford 0.900 g (68%) of 5-(bromomethyl)-N-(2-(5-chloro-1H-indol-3-yl)ethyl)isoxazole-3-carboxamide as a solid.

ESI/APCI (+): 382 (M+H), 404 (M+Na).

Intermediate 9

Preparation of 5-(Ethoxymethyl)isoxazole-3-carboxylic acid

To an oily suspension of ethyl 5-(bromomethyl)isoxazole-3-carboxylate (0.680 g; 2.91 mmol) in aqueous 1M sodium hydroxide (6.4 mL; 6.4 mmol) was added 1 mL of ethanol. The oily suspension immediately transformed to a white solid suspension. The mixture was stirred overnight at room temperature. The pH of the solution was adjusted between 2 and 3 by addition of 6N hydrochloric acid. The solution was extracted with ethyl acetate. Organic extracts were dried over magnesium sulfate and evaporated to afford 0.189 g (38%) of 5-(ethoxymethyl)isoxazole-3-carboxylic acid as a white solid which was directly used in the next step.

Intermediate 10

Preparation of Ethyl 5-(3-fluorobenzyl)isoxazole-3-carboxylate 1,2-Dimethoxyethane (8 mL) and water (2 mL) were added to the mixture of ethyl 5-(bromomethyl)isoxazole-3-carboxylate (0.710 g; 3.03 mmol), 3-fluorophenylboronic acid (0.481 g; 3.34 mmol), tetrakis(triphenylphosphine)palladium (0) (0.176 g; 0.151 mmol) and sodium carbonate (0.646 g, 6.07 mmol). The mixture was irradiated in a microwave oven at 130° C. for 15 min and was evaporated. The residue was partitioned between dichloromethane (30 mL) and brine (20 mL). The organic layer was separated and concentrated. The residue was purified by flash chromatography on silica gel (eluent: 15 to 100% of dichloromethane in heptane) to afford 0.460 g (61%) of ethyl 5-(3-fluorobenzyl)isoxazole-3-carboxylate as a yellow oil.

ESI/APCI (+): 250 (M+H), 272 (M+Na).

Intermediate 11

Preparation of
5-(3-fluorobenzyl)isoxazole-3-carboxylic acid

Ethanol (3 mL) was added to the mixture of ethyl 5-(3-fluorobenzyl)isoxazole-3-carboxylate (0.688 g; 2.82 mmol) and 1M sodium hydroxide (10.5 mL; 10.5 mmol). The mixture was stirred overnight at room temperature and was concentrated under reduced pressure to remove ethanol. The aqueous solution was acidified by addition of 6N hydrochloric acid to pH 0-1. The formed precipitate was collected by filtration and was dried. 0.5026 g (82%) of 5-(3-fluorobenzyl)isoxazole-3-carboxylic acid was obtained as a white solid which was directly used in the next step.

Intermediate 12

Preparation of
3-(Ethoxycarbonyl)isoxazole-5-carboxylic acid

A 2M solution of the Jone's reagent was prepared by addition of 6 g of chromium (VI) oxide to a solution of $H_2SO_4$ (8.1 g) in water (25.5 mL). To a solution of ethyl 5-(hydroxymethyl)isoxazole-3-carboxylate (4.00 g; 23.37 mmol) in acetone in an ice bath was added dropwise during a period of 20 min the Jone's reagent (27.71 mL; 51.42 mmol). The reaction mixture was then stirred at room temperature for additional 3.5 hours. 5 mL of 2-propanol were added and the stirring continued for further 1 hour. The solution became green. Brine (60 mL) and ethyl acetate (150 mL) were added to the reaction mixture and after separation, the organic layer was washed with an aqueous solution of sodium bisulphite (15 g in 100 mL of $H_2O$) and with brine (100 mL). The organic layer was dried over magnesium sulfate. The evaporation of the solution furnished 3.03 g (70%) of 3-(ethoxycarbonyl)isoxazole-5-carboxylic acid as a white solid.

ESI/APCI (+): 142 (M+H—$CO_2$).
ESI/APCI (−): 184 (M−H).

Intermediate 13

Preparation of Ethyl 5-(tert-butoxycarbonylamino)
isoxazole-3-carboxylate

To a solution of 3-(ethoxycarbonyl)isoxazole-5-carboxylic acid (2.00 g; 10.80 mmol), triethylamine (1.74 mL; 12.42 mmol) and tert-butanol (2.58 mL; 27.01 mmol) in toluene (25 mL) was added at room temperature diphenylphosphoryl azide (2.74 mL; 12.42 mmol). The solution was stirred at room temperature for 10 min and was heated at 100° C. for 4 h. After evaporation, the residue was purified by flash chromatography on silica gel (eluent: 1 to 6% of ethyl acetate in dichloromethane) to afford 1.47 g (53%) of ethyl 5-(tert-butoxycarbonylamino)isoxazole-3-carboxylate as a white solid.

ESI/APCI (+): 257 (M+H), 279 (M+Na).
ESI/APCI (−): 255 (M−H).

Intermediate 14

Preparation of
5-(tert-Butoxycarbonylamino)isoxazole-3-carboxylic acid

Sodium hydroxide 1M (14.05 mL; 14.05 mmol) was added to ethyl 5-(tert-butoxycarbonylamino)isoxazole-3-carboxylate (1.44 g; 5.62 mmol) and the mixture was stirred at room temperature for 2 h. The solution was acidified to pH 0-2 by addition of 6N hydrochloric acid. There was formation of a white precipitate. The suspension was cooled in an ice bath for 5 min and the precipitate was collected by filtration and dried to afford 1.03 g of a white solid. The filtrate was extracted with (3×50 mL) of ethyl acetate. Organic extracts were dried over magnesium sulfate and evaporated to afford 0.191 g of a white solid. A total of 1.22 g (95%) of 5-(tert-butoxycarbonylamino)isoxazole-3-carboxylic acid was obtained as a white solid which was directly used in the next step Intermediate 15

Preparation of Ethyl
5-cyclopropylisoxazole-3-carboxylate

A solution of ethynylcyclopropane (0.40 mL; 4.58 mmol), ethyl 2-nitroacetate (1.30 mL; 11.46 mmol), and 1,4-diazobicyclo[2.2.2]octane (DABCO, 0.053 g; 0.458 mmol) in ethanol (3 mL) was irradiated in a microwave oven at 150° C. for 20 min and was then evaporated. The residue was dissolved in ethyl acetate and the solution was washed with water. The organic layer was evaporated and the residue was purified by flash chromatography on silica gel (eluent: 20 to 100% of dichloromethane in heptane) to afford 0.765 g (92%) of ethyl 5-cyclopropylisoxazole-3-carboxylate as a yellow oil.

ESI/APCI (+): 182 (M+H).

Intermediate 16

Preparation of 5-Cyclopropylisoxazole-3-carboxylic acid

The mixture of ethyl 5-cyclopropylisoxazole-3-carboxylate (0.550 g; 3.04 mmol) and 1M aqueous sodium hydroxide (9.11 mL; 9.11 mmol) was stirred at room temperature during the weekend (72 h). The pH of the solution was adjusted to 1 by addition of 6N hydrochloric acid and extracted with ethyl acetate. The ethyl acetate layer was dried over magnesium sulfate and was evaporated to furnish 0.446 g (96%) of 5-cyclopropylisoxazole-3-carboxylic acid as a solid.

ESI/APCI (+): 154 (M+H), 176 (M+Na).
ESI/APCI (−): 152 (M−H).

Intermediate 17

Preparation of Ethyl
5-cyclopentylisoxazole-3-carboxylate

To a mixture of ethynylcyclopentane (0.74 mL; 6.05 mmol) and ethyl 2-nitroacetate (1.37 mL; 12.11 mmol) in ethanol (9 mL) in an Ace pressure tube was added 1,4-diazobicyclo[2.2.2]octane (DABCO, 0.070 g; 0.60 mmol). The

181 tube was heated at 80° C. for 96 h. The mixture was evaporated. The flash chromatography on silica gel (eluent: 20 to 80% dichloromethane in heptane) of the residue provided 1.21 g (96%) of ethyl 5-(hydroxymethyl)isoxazole-3-carboxylate as an oil.
ESI/APCI (+): 210 (M+H), 232 (M+Na).

Intermediate 18

Preparation of 5-Cyclopentylisoxazole-3-carboxylic acid

The mixture of ethyl 5-cyclopentylisoxazole-3-carboxylate (1.10 g; 5.26 mmol) and 1M sodium hydroxide (13.14 mL; 13.14 mmol) was stirred at room temperature overnight. The solution was acidified to pH 1-2 by addition of 6N hydrochloric acid. The formed precipitate was collected by filtration, washed with water and dried. 0.827 g (87%) of 5-cyclopentylisoxazole-3-carboxylic was isolated as a white solid which was directly used in the next step.

Intermediate 19

Preparation of Ethyl 5-cyclohexylisoxazole-3-carboxylate

To a mixture of ethynylcyclohexane (0.600 g; 5.44 mmol) and ethyl 2-nitroacetate (1.23 mL; 10.87 mmol) in ethanol (9 mL) in an Ace pressure tube was added 1,4-diazobicyclo[2.2.2]octane (DABCO, 0.070 g; 0.60 mmol). The tube was heated at 80° C. for 96 h. The mixture was evaporated. The flash chromatography on silica gel (eluent: 20 to 80% dichloromethane in heptane) of the residue provided 1.18 g (97%) of ethyl 5-cyclohexylisoxazole-3-carboxylate as an oil.
ESI/APCI (+): 224 (M+H), 246 (M+Na).

Intermediate 20

Preparation of 5-cyclohexylisoxazole-3-carboxylic acid

The mixture of ethyl 5-cyclohexylisoxazole-3-carboxylate (1.13 g; 5.06 mmol) and 1M sodium hydroxide (12.65 mL; 12.65 mmol) was stirred at room temperature overnight. The solution was acidified to pH 1-2 by addition of 6N hydrochloric acid. The formed precipitate was collected by filtration, washed with water and dried. 0.944 g (96%) of 5-cyclohexylisoxazole-3-carboxylic was isolated as a white solid which was directly used in the next step.

Intermediate 21

Preparation of ethyl 5-phenyl-4,5-dihydroisoxazole-3-carboxylate

A mixture of ethyl 2-nitroacetate (0.96 mL; 8.70 mmol), styrene (0.5 mL; 4.35 mmol) and 1,4-diazabicyclo[2.2.2]octane (DABCO) (0.050 mg, 0.438 mmol) in ethanol (2 mL) was stirred at 80° C. for 60 hrs. The reaction mixture was concentrated under reduced pressure and purified by flash chromatography on silica gel (eluent 2 to 20% ethyl acetate in heptane) to afford ethyl 5-phenyl-4,5-dihydroisoxazole-3-carboxylate 0.234 g (25%)
ESI/APCI (+): 220 (M+H), and 242 (M+Na). .

182

Intermediate 22

Preparation of 5-phenyl-4,5-dihydroisoxazole-3-carboxylic acid

Ethyl 5-phenyl-4,5-dihydroisoxazole-3-carboxylate (0.1 g; 0.4 mmol) was dissolved in a mixture of sodium hydroxide (5 mL, 1M, water) and dioxane (2 mL). The reaction mixture was stirred vigorously at room temperature overnight and concentrated under reduced pressure. The resulting solution was acidified and extracted with ethyl acetate, dried and concentrated under reduced pressure, the crude material was used without further purification.

Intermediate 23

Preparation of ethyl 5-cyclohexyl-4,5-dihydroisoxazole-3-carboxylate

A mixture of ethyl 2-nitroacetate (0.96 mL; 8.70 mmol), vinylcyclohexane (0.6 mL; 4.35 mmol), 1,4-diazabicyclo[2.2.2]octane (DABCO) (0.050 mg, 0.438 mmol) and ethanol (2 mL) was stirred at 80° C. for 60 hrs. The reaction mixture was concentrated under reduced pressure and purified by flash chromatography on silica gel (eluent 2 to 20% ethyl acetate in heptane) to afford ethyl 5-phenyl-4,5-dihydroisoxazole-3-carboxylate 0.690 g (63%).
ESI/APCI (+): 226 (M+H), 248 (M+Na).

Intermediate 24

Preparation of 5-cyclohexyl-4,5-dihydroisoxazole-3-carboxylic acid

Ethyl 5-cyclohexyl-4,5-dihydroisoxazole-3-carboxylate (0.1 g; 0.44 mmol) was dissolved in a mixture of sodium hydroxide (5 mL, 1M in water) and dioxane (2 mL). The reaction mixture was stirred vigorously at room temperature overnight and concentrated under reduced pressure. The resulting solution was acidified and extracted with ethyl acetate, dried and concentrated under reduced pressure, the crude material was used without further purification.

Intermediate 25

Preparation of Ethyl 5-(hydroxymethyl)-4,5-dihydroisoxazole-3-carboxylate

To a mixture of allylic alcohol (0.650 mL; 9.35 mmol) and ethyl 2-nitroacetate (2.65 mL; 23.37 mmol) in ethanol (12 mL) in an Ace pressure tube was added 1,4-diazobicyclo[2.2.2]octane (DABCO, 0.189 g; 1.64 mmol). The tube was heated at 80° C. for 48 h. The mixture was evaporated. The flash chromatography on silica gel (eluent: 0 to 6% of methanol in dichloromethane) of the residue provided 1.51 g (93%) of ethyl 5-(hydroxymethyl)-4,5-dihydroisoxazole-3-carboxylate as an oil.
ESI/APCI (+): 174 (M+H), 196 (M+Na).

Intermediate 26

Preparation of Ethyl 5-(ethoxymethyl)-4,5-dihydroisoxazole-3-carboxylate

Sodium hydride (0.141 g; 3.51 mmol) was added to a solution of ethyl 5-(hydroxymethyl)-4,5-dihydroisoxazole- 3-carboxylate (0.338 g; 1.76 mmol) in DMF (3 mL) in an ice bath. The mixture was stirred for 10 min before addition of iodoethane (0.430 mL; 5.27 mmol). The ice bath was removed and the mixture was stirred at room temperature for 2 h. After evaporation, the residue was partitioned between brine and dichloromethane and the solution extracted with dichloromethane. Organic extracts were evaporated and the residue was purified by flash chromatography on silica gel (eluent: 1-6% ethyl acetate in dichloromethane) to afford 0.142 g (40%) of ethyl 5-(ethoxymethyl)-4,5-dihydroisoxazole-3-carboxylate.

ESI/APCI (+): 224 (M+Na).

$^1$H NMR (CDCl$_3$) δ 4.95 (m, 1H); 4.35 (q, 2H); 3.57 (m, 4H); 3.24 (dd, 1H); 3.12 (dd, 1H), 1.37 (t, 3H); 1.20 (t, 3H).

Intermediate 27

Preparation of 5-(Ethoxymethyl)-4,5-dihydroisoxazole-3-carboxylic acid

A 1M solution of sodium hydroxide (5 mL; 5 mmol) was added to the solution of ethyl 5-(ethoxymethyl)-4,5-dihydroisoxazole-3-carboxylate (0.135 g, 0.67 mmol) in ethanol (1 mL). The reaction mixture was stirred at room temperature overnight. The solution was acidified to pH 0-1 by addition of 6N hydrochloric acid and was extracted with ethyl acetate. Combined ethyl acetate extracts were dried over magnesium sulfate and evaporated to provide 0.109 g (94%) of 5-(ethoxymethyl)-4,5-dihydroisoxazole-3-carboxylic acid as a white solid which was directly used in the next step.

Intermediate 28

Preparation of Ethyl 5-benzyl-4,5-dihydroisoxazole-3-carboxylate

To a mixture of allylbenzene (0.73 mL; 5.39 mmol) and ethyl 2-nitroacetate (1.53 mL; 13.48 mmol) in ethanol (12 mL) in an Ace pressure tube was added 1,4-diazobicyclo[2.2.2]octane (DABCO, 0.106 g; 0.92 mmol). The tube was heated at 80° C. for 60 h. The mixture was evaporated. The flash chromatography on silica gel (eluent: 15 to 100% of dichloromethane in heptane) of the residue provided 1.06 g (85%) of ethyl 5-benzyl-4,5-dihydroisoxazole-3-carboxylate as an oil.

ESI/APCI (+): 234 (M+H), 256 (M+Na).

Intermediate 29

Preparation of Methyl 3-phenyl-4,5-dihydroisoxazole-5-carboxylate

A solution of N-hydroxybenzimidoyl chloride (0.500 g; 3.21 mmol) in ethyl acetate (4 mL) was added dropwise to the mixture of methyl acrylate (0.58 mL; 6.43 mmol), sodium bicarbonate (0.818 g; 9.64 mmol), water 0.1 mL and ethyl acetate (16 mL) at room temperature and the resulting mixture was stirred for 22 hours. The solid was eliminated by filtration and washed with ethyl acetate. The filtrate was evaporated and the residue purified by flash chromatography on silica gel (eluent: 15 to 100% dichloromethane in heptane) to afford 0.482 g (73%) of methyl 3-phenyl-4,5-dihydroisoxazole-5-carboxylate as a white solid.

ESI/APCI (+): 206 (M+H), 228 (M+Na).

Intermediate 30

Preparation of 1-benzyl-2-oxopyrrolidine-3-carboxylic acid

A mixture of benzylamine (0.962 mL; 8.82 mmol) and 6,6-dimethyl-5,7-dioxaspiro[2.5]octane-4,8-dione (0.5 g; 2.94 mmol) in ethanol (3 mL) was irradiated in a microwave oven for 3 minutes at 100° C. and concentrated under reduced pressure. The crude material was purified by flash chromatography on silica gel (eluent 30 to 100% ethyl acetate in heptane with 5% acetic acid) to afford 0.512 g (79%) of 1-benzyl-2-oxopyrrolidine-3-carboxylic acid.

ESI/APCI (+): 220 (M+H), and 242 (M+Na).

ESI/APCI (−): 218 (M−H).

Intermediate 31

Preparation of 2-oxo-1-phenylpyrrolidine-3-carboxylic acid

A mixture of aniline (0.803 mL; 8.82 mmol) and 6,6-dimethyl-5,7-dioxaspiro[2.5]octane-4,8-dione (0.5 g; 2.94 mmol) in ethanol (3 mL) was irradiated in a microwave oven for 3 minutes at 100° C. and concentrated under reduced pressure. The crude material was purified by flash chromatography on silica gel (eluent 30 to 100% ethyl acetate in heptane with 5% acetic acid) to afford 0.456 g (76%) of 2-oxo-1-phenylpyrrolidine-3-carboxylic acid.

ESI/APCI (+): 206 (M+H).

Intermediate 32

Preparation of 1-cyclohexyl-2-oxopyrrolidine-3-carboxylic acid

A mixture of cyclohexylamine (1.02 mL; 8.82 mmol) and 6,6-dimethyl-5,7-dioxaspiro[2.5]octane-4,8-dione (0.5 g; 2.94 mmol) in ethanol (3 mL) was irradiated in a microwave oven for 3 minutes at 100° C. and concentrated under reduced pressure. The crude material was purified by flash chromatography on silica gel (eluent 30 to 100% ethyl acetate in heptane with 5% acetic acid) to afford 0.228 g (36%) of 1-cyclohexyl-2-oxopyrrolidine-3-carboxylic acid.

ESI/APCI (+): 212 (M+H).

Intermediate 33

Preparation of 1-(4-ethylphenyl)-2-oxopyrrolidine-3-carboxylic acid

A mixture of 4-ethylaniline (1.1 mL; 8.73 mmol) and 6,6-dimethyl-5,7-dioxaspiro[2.5]octane-4,8-dione (0.5 g; 2.94 mmol) in ethanol (3 mL) was irradiated in a microwave oven for 3 minutes at 100° C. and concentrated under reduced pressure. The crude material was purified by flash chromatography on silica gel (eluent 10 to 80% ethyl acetate in heptane with 5% acetic acid) to afford 1-(4-ethylphenyl)-2-oxopyrrolidine-3-carboxylic acid 0.453 g (67%).

ESI/APCI (+): 234 (M+H), 255 (M+Na).

ESI/APCI (−): 232 (M−H).

Intermediate 34

Preparation of Ethyl 4-methyl-2-p-tolylthiazole-5-carboxylate

4-Methylbenzothioamide (0.312 g; 2.00 mmol) and ethyl 2-chloro-3-oxobutanoate (0.323 mL; 2.10 mmol) were dissolved in ethanol (3 mL). The mixture was irradiated in a microwave oven at 170° C. for 10 min. After evaporation, the residue was purified by flash chromatography on silica gel (eluent: 20 to 100% dichloromethane in heptane) to afford 0.359 g (69%) of ethyl 4-methyl-2-p-tolylthiazole-5-carboxylate as a solid.

ESI/APCI (+): 262 (M+H).

Intermediate 35

Preparation of 4-Methyl-2-p-tolylthiazole-5-carboxylic acid

The mixture of ethyl 4-methyl-2-p-tolylthiazole-5-carboxylate (0.200 g; 0.765 mmol) and sodium hydroxide (0.0643 g; 1.61 mmol) in water (4 mL) and ethanol (8 mL) was irradiated in a microwave oven at 130° C. for 5 min. The mixture was concentrated (removal of ethanol), and the pH of the solution was adjusted to 3 by addition of 6N hydrochloric acid. The acidic solution was extracted with (3×10 mL) of ethyl acetate. Combined organic layers were dried over magnesium sulfate, and evaporated to afford 0.157 g (88%) of 4-methyl-2-p-tolylthiazole-5-carboxylic acid as a white solid which was directly used in the next step.

Intermediate 36

Preparation of (5-Chloro-1H-indol-3-yl)methanamine

A solution of 5-chloro-1H-indole-3-carbaldehyde (0.690 g; 3.76 mmol), hydroxylamine hydrochloride (0.366 g; 5.27 mmol) and sodium acetate (0.463 g; 5.65 mmol) in ethanol (10 mL) was stirred at reflux for 3.5 h. The reaction mixture was concentrated under reduced pressure and the residue was partitioned between ethyl acetate and brine and extracted with ethyl acetate. The solvent was evaporated and the resulting residue (crude oxime) was dissolved in glacial acetic acid (30 mL). Zinc dust (1.48 g; 22.59 mmol) was added to the solution, and the mixture was stirred overnight at room temperature. The suspension was filtered through Celite, the cake was washed with ethyl acetate, and the organic solution was concentrated under reduced pressure. An aqueous solution of sodium carbonate was added to the residue and the resulting mixture was extracted with ethyl acetate. The organic extracts were dried over magnesium sulfate, filtered, and concentrated to afford the (5-chloro-1H-indol-3-yl)methanamine as a brown solid, which was used without further purification in the next step.

ESI/APCI (+): 164 (M+H—NH$_3$).
ESI/APCI (−): 179 (M−H).

Intermediate 37

Preparation of 3-(5-Chloro-1H-indol-3-yl)propan-1-ol

A mixture of (4-chlorophenyl)hydrazine hydrochloride (5.26 g; 28.50 mmol) and 3,4-dihydro-2H-pyran (2.63 mL; 28.50 mmol) in a mixture of water (9 mL) and dioxane (36 mL) was stirred at 100° C. for 48 hours. After cooling to room temperature the mixture was diluted with ethyl acetate. The aqueous layer was separated and further extracted with ethyl acetate. The combined organic layers were dried over magnesium sulfate, and concentrated under reduced pressure. The residue was purified by flash chromatography on silica gel (eluent: 0 to 6% methanol in dichloromethane) to afford 3.85 g (64%) of 3-(5-chloro-1H-indol-3-yl)propan-1-ol as an oily residue.

ESI/APCI (+): 210.
ESI/APCI (−): 208 (M−H).

Intermediate 38

Preparation of 3-(3-Bromopropyl)-5-chloro-1H-indole

Carbon tetrabromine (2.37 g; 7.15 mmol) was added to the solution of triphenylphosphine (1.90 g; 7.15 mmol) in tetrahydrofuran (20 mL) and the mixture was stirred at room temperature for 15 min. A solution of intermediate 37 (1 g; 4.77 mmol) in tetrahydrofuran (12 mL) was then added to the green suspension and the resulting reaction mixture was stirred overnight at room temperature. The volatiles were removed under reduced pressure, and the residue was purified by flash chromatography on silica gel (eluent: 2 to 40% ethyl acetate in heptane) to afford 0.791 g, (61%) of 3-(3-bromopropyl)-5-chloro-1H-indole as a dark oily residue.

$^1$H NMR (DMSO-d$_6$) δ 11.04 (s, 1H); 7.56 (d, 1H); 7.35 (d, 1H); 7.24 (d, 1H); 7.06 (dd, 1H, 3.54 (t, 2H); 2.80 (t, 2H); 2.13 (quint, 2H).

Intermediate 39

Preparation of 3-(3-Azidopropyl)-5-chloro-1H-indole

A mixture of intermediate 38 (0.730 g; 2.68 mmol) and sodium azide (0.522 g; 8.03 mmol) was stirred in DMF (5 mL) for 18 h and was then concentrated under reduced pressure. The residue was partitioned between water and dichloromethane. After separation, the organic layer was dried over magnesium sulfate and the volatiles were evaporated under reduced pressure to furnish (0.664 g) of the desired 3-(3-azidopropyl)-5-chloro-1H-indole as an oily residue which was used without purification in the next step.

Intermediate 40

Preparation of 3-(5-Chloro-1H-indol-3-yl)propan-1-amine

To a solution of intermediate 39 (0.299 g; 1.27 mmol) in tetrahydrofuran (9 mL) were added triphenylphosphine (0.354 g; 1.34 mmol) and water (0.6 mL). The reaction mixture was stirred at room temperature for 22 h and was then evaporated to dryness. The residue was dissolved in dichloromethane (10 mL) and 10 mL of 6N hydrochloric acid were added. After separation, the aqueous layer was further extracted with dichloromethane (2×10 mL) and the pH was adjusted to 14 with a solution of sodium hydroxide 6N. This basic solution was extracted dichloromethane (3×20 mL) and the combined organic layer was dried over magnesium sulfate, and evaporated to afford 0.089 g (34%) of 3-(5-chloro-1H-indol-3-yl)propan-1-amine as a white solid.

ESI/APCI (+): 209 (M+H).
ESI/APCI (−): 207 (M−H).

Intermediate 41

Preparation of 5-Benzyl-4,5-dihydroisoxazole-3-carboxylic acid

Sodium hydroxide 1M (7.1 mL; 7.1 mmol) was added to intermediate 28 (0.55 g; 2.36 mmol) and the mixture was stirred at room temperature for 40 hours. The solution was acidified to pH 0-1 by addition of 6N hydrochloric acid. The resulting white precipitate was collected by filtration and was dried to afford 0.277 g (57%) of 5-benzyl-4,5-dihydroisoxazole-3-carboxylic acid as a white solid which was used without further purification.

Intermediate 42

Preparation of
5-Benzyl-4,5-dihydroisoxazole-3-carboxylic acid

Sodium hydroxide 1M (6.2 mL; 6.2 mmol) was added to intermediate 29 (0.421 g; 2.05 mmol) and the mixture was stirred at room temperature for 40 hours. The solution was acidified to pH 0-1 by addition of 6N hydrochloric acid. The resulting white precipitate was collected by filtration and was dried to afford (0.313 g (80%) of 5-benzyl-4,5-dihydroisoxazole-3-carboxylic acid as a white solid.
ESI/APCI (+): 214 (M+Na).
ESI/APCI (−): 190 (M−H).

Intermediate 43

Preparation of (S)-methyl 2-(1-cyclohexyl-2-hydroxyethylamino)-2-oxoacetate

Triethylamine (1.24 mL; 8.85 mmol) was added to the mixture of (L)-2-Cyclohexylglycinol (1.05 g; 6.81 mmol) and methyl 2-chloro-2-oxoacetate (0.666 mL; 7.01 mmol) in dichloromethane (10 mL) at 0° C. The mixture was stirred at room temperature for 30 minutes and diluted with dichloromethane (40 mL) and the organic layer was washed successively with a saturated aqueous solution of sodium carbonate, and water. The volatiles were removed under reduced pressure and the residue was purified by flash chromatography (eluent: 1 to 20% methanol in dichloromethane) to furnish 0.667 g (43%) of (S)-methyl 2-(1-cyclohexyl-2-hydroxyethylamino)-2-oxoacetate as an oil.
ESI/APCI (+): 230 (M+H), 252 (M+Na).
ESI/APCI (−): 228 (M−H).

Intermediate 44

Preparation of (S)-2-(1-cyclohexyl-2-hydroxyethylamino)-2-oxoacetic acid

Sodium hydroxide 1M (8.7 mL; 8.7 mmol) was added to (S)-methyl 2-(1-cyclohexyl-2-hydroxyethylamino)-2-oxoacetate (0.660 g; 2.88 mmol) and the mixture was stirred at room temperature for 2 hours. The solution was acidified to pH 0-1 by addition of concentrated hydrochloric acid and the resulting precipitate was collected by filtration, washed with water, and dried to afford 0.350 g (56%) of (S)-2-(1-cyclohexyl-2-hydroxyethylamino)-2-oxoacetic acid as a white solid.
ESI/APCI (+): 216 (M+H).
ESI/APCI (−): 214 (M−H).

Intermediate 45

Preparation of (S)—N$^1$-(2-(5-Chloro-1H-indol-3-yl)ethyl)-N$^2$-(1-cyclohexyl-2-hydroxyethyl)oxalamide A mixture of 2-(5-chloro-1H-indol-3-yl)ethanaminium chloride (0.250 g; 1.08 mmol), intermediate 44 (0.244 g; 1.14 mmol), HATU (0.452 g; 1.19 mmol) and N,N-diisopropylethylamine (0.463 mL; 2.70 mmol) in DMF (5 mL) was stirred at room temperature overnight and concentrated under reduced pressure. The residue was dissolved in ethyl acetate and the organic layer was washed with water, and concentrated under reduced pressure. The crude material was purified by flash chromatography on silica gel (eluent: 1 to 10% methanol in dichloromethane) to yield 0.301 g of (S)—N$^1$-(2-(5-chloro-1H-indol-3-yl)ethyl)-N$^2$-(1-cyclohexyl-2-hydroxyethyl)oxalamide as a white solid.
ESI/APCI (+): 414 (M+Na).
ESI/APCI (−): 390 (M−H).

Intermediate 46

Preparation of (R)-methyl 2-(1-cyclohexyl-2-hydroxyethylamino)-2-oxoacetate

Triethylamine (1.22 mL; 8.67 mmol) was added to the mixture of (D)-2-Cyclohexylglycinol (1.04 g; 6.67 mmol) and methyl 2-chloro-2-oxoacetate (0.653 mL; 6.87 mmol) in dichloromethane (10 mL) at 0° C. The mixture was stirred at room temperature for 30 minutes and diluted with dichloromethane (40 mL) and the organic layer was washed successively with a saturated aqueous solution of sodium carbonate, and water. The volatiles were removed under reduced pressure and the residue was purified by flash chromatography (eluent: 1 to 20% methanol in dichloromethane) to afford 0.550 g (36%) of (R)-methyl 2-(1-cyclohexyl-2-hydroxyethylamino)-2-oxoacetate as an oil.
ESI/APCI (+): 230 (M+H), 252 (M+Na).
ESI/APCI (−): 228 (M−H).

Intermediate 47

Preparation of (R)-2-(1-cyclohexyl-2-hydroxyethylamino)-2-oxoacetic acid

Sodium hydroxide 1M (7.2 mL; 7.2 mmol) was added to intermediate 46 (0.545 g; 2.38 mmol) and the mixture was stirred at room temperature for 2 hours. The solution was acidified to pH 0-1 by addition of concentrated hydrochloric acid and the resulting precipitate was collected by filtration, washed with water, and dried to furnish 0.321 g (63%) of (R)-2-(1-cyclohexyl-2-hydroxyethylamino)-2-oxoacetic acid as a white solid.
ESI/APCI (+): 216 (M+H).
ESI/APCI (−): 214 (M−H).

Intermediate 48

Preparation of (R)—N$^1$-(2-(5-Chloro-1H-indol-3-yl)ethyl)-N$^2$-(1-cyclohexyl-2-hydroxyethyl)oxalamide A mixture of 2-(5-chloro-1H-indol-3-yl)ethanaminium chloride (0.250 g; 1.08 mmol), intermediate 47 ((R)-2-(1-cyclohexyl-2-hydroxyethylamino)-2-oxoacetic acid) (0.244 g; 1.14 mmol), HATU (0.452 g: 1.19 mmol) and N,N-diisopropylethylamine (0.463 mL; 2.70 mmol) in DMF (5 mL) was stirred at room temperature overnight and concentrated under reduced pressure. The residue was dissolved in ethyl acetate and the organic layer was washed with water, and concentrated under reduced pressure. The crude material was purified by flash chromatography on silica gel (eluent: 1 to 10% methanol in dichloromethane) to yield 0.351 of (R)—N$^1$-(2-(5-Chloro-1H-indol-3-yl)ethyl)-N$^2$-(1-cyclohexyl-2-hydroxyethyl)oxalamide as a white solid.
ESI/APCI (+): 414 (M+Na).
ESI/APCI (−): 390 (M−H).

Intermediate 49

Preparation of 5-oxo-1-phenylpyrrolidine-3-carboxylic acid

A mixture of aniline (3.26 g; 34.68 mmol) and 2-methylenesuccinic acid (5.47 g; 41.62 mmol) in water (10 ml) was heated in a sealed tube at 110° C. for 30 hours. After cooling to room temperature, 6N NaOH (13 mL) was added and the resulting precipitate was filtered off. The filtrate was acidified with 6N hydrochloric acid to pH 1 and the resulting precipitate was filtered, washed with water, and dried to yield 6.92 g (97%) of 5-oxo-1-phenypyrrolidine-3-carboxylic acid as a white solid.
ESI/APCI (+): 206 (M+H), 228 (M+Na).
ESI/APCI (−): 204 (M−H).

Intermediate 50

Preparation of 1-Cyclohexyl-5-oxopyrrolidine-3-carboxylic acid

A mixture of cyclohexanamine (3.70 mL; 31.94 mmol) and 2-methylenesuccinic acid (5.04 g; 41.62 mmol) in water (10 ml) was heated in a sealed tube at 110° C. for 21 hours. After cooling to room temperature, 6N NaOH (10 mL) was added and the resulting precipitate was filtered off. The filtrate was acidified with 6N hydrochloric acid to pH 1 and the resulting precipitate was filtered, washed with water, and dried to yield 3.92 g (58%) of 1-cyclohexyl-5-oxopyrrolidine-3-carboxylic acid as a white solid.
ESI/APCI (+): 212 (M+H), 234 (M+Na).
ESI/APCI (−): 210 (M−H).

Intermediate 51

Preparation of Ethyl 5-phenyloxazole-2-carboxylate

Triethylamine (1.08 mL; 7.69 mmol) was added to a mixture of 2-amino-1-phenylethanone hydrochloride (0.550 g; 3.08 mmol) and ethyl 2-chloro-2-oxoacetate (0.369 mL; 3.23 mmol) in dichloromethane (10 mL) at 0° C. The reaction mixture was then stirred at room temperature for 22 hand diluted with dichloromethane (40 mL). The organic layer was washed successively with a saturated aqueous solution of sodium carbonate, and water. The organic layer was dried over magnesium sulfate and was concentrated under reduced pressure. The crude residue was dissolved in phosphorus (V) oxychloride (10 ml) and the solution was refluxed for 4 hours. After cooling, the volatiles were removed under reduced pressure and the residue was dissolved in dichloromethane. The organic layer was then carefully washed with a saturated aqueous solution of sodium carbonate, dried over magnesium sulfate and concentrated under reduced pressure. The residue was purified by flash chromatography on silica gel (eluent 15 to 100% dichloromethane in heptane) to afford 0.146 g (22% overall yield) of ethyl 5-phenyloxazole-2-carboxylate as a solid.
ESI/APCI (+): 218 (M+H), 240 (M+Na).

Intermediate 52

Preparation of 5-Phenyloxazole-2-carboxylic acid

Sodium hydroxide 2M (1 mL; 2 mmol) was added to a solution of intermediate 51 (0.140 g; 0.644 mmol) in ethanol (1 mL) and the mixture was stirred at room temperature for 2 h. The solution was acidified to pH 0-1 by addition of a solution of hydrochloric acid 6N and the resulting precipitate was collected by filtration, washed with water, and dried to furnish 0.092 g (75%) of 5-phenyloxazole-2-carboxylic acid as a white solid.
ESI/APCI (+): 190 (M+H).
ESI/APCI (−): 188 (M−H).

Intermediate 53

Preparation of ethyl 1-cyclohexyl-1H-1,2,3-triazole-4-carboxylate

A mixture of ethyl propriolate (0.280 2.24 mmol) and cyclohexyl azido (0.227 mL, 2.24 mmol) in ethanol was heated at 90° C. in a sealed tube overnight. The volatiles were removed under reduced pressure and the residue was crystallized from a mixture of dichloromethane-heptane to yield 0.213 g (43%) ethyl 1-cyclohexyl-1H-1,2,3-triazole-4-carboxylate as white crystals.

Intermediate 54

Preparation of ethyl 3-phenylisoxazole-5-carboxylate

A mixture of ethyl propriolate (0.657 mL; 6.43 mmol), (E)-N-hydroxybenzimidoyl chloride (0.500 g; 3.21 mmol) and sodium bicarbonate (0.818 g; 9.64 mmol) in a mixture of ethyl acetate (16 mL) and water (1 mL) was stirred at room temperature. overnight. The reaction mixture was filtered and the filtrate was concentrated under reduced pressure. The crude material was purified by flash chromatography on silica gel (eluent 5 to 80% dichloromethane in heptane) to furnish 0.295 g (42%) of ethyl 3-phenylisoxazole-5-carboxylate.
ESI/APCI (+): 218 (M+H).

Intermediate 55

Preparation of phenyl 2-(5-chloro-1H-indol-3-yl)ethylcarbamate

N,N-diisopropylethylamine (0.745; 4.33 mmol) was added to a mixture of 2-(5-chloro-1H-indol-3-yl)ethanamine hydrochloride (0.500 g; 2.16 mmol), and phenyl chloroformate (0.406 mL; 3.25 mmol) in dichloromethane (20 mL). The solution was stirred at room temperature. for 20 minutes, diluted in dichloromethane, washed with sodium hydrogen sulfate (1M, water), sodium carbonate (1M, water) and brine. The organic layer was dried and concentrated under reduced pressure to furnish 0.60 g (88%) of phenyl 2-(5-chloro-1H-indol-3-yl)ethylcarbamate as a yellow oil.
ESI/APCI (+): 315 (M+H) 337 (M+Na).

Intermediate 56

Preparation of ethyl 1-benzyl-1H-1,2,3-triazole-4-carboxylate

A solution of benzyl azide (0.200 mL; 1.61 mmol), ethyl propriolate (0.163 mL; 1.61 mmol), copper sulfate pentahydrate (0.016 mL, 1M solution in water), sodium ascorbate (0.161 mL; solution 1M in water) in a mixture of tert-butanol (3 mL) and water (3 mL) was stirred at room temperature overnight. The reaction mixture was diluted in water and the product crystallized out to furnish 0.090 g (24%) of ethyl 1-benzyl-1H-1,2,3-triazole-4-carboxylate as white crystals.

ESI/APCI (+): 232 (M+H) 254 (M+Na).
$^1$H NMR (DMSO-d6) δ 7.97 (s, 1H), 7.40 (m, 3H), 7.27 (m, 2H), 5.58 (s, 2H), 4.40 (q, 2H), 1.40 (t, 3H).

Intermediate 57

Preparation of methyl 5-oxo-1-phenylpyrrolidine-3-carboxylate

Iodomethane (0.333 mL; 5.36 mmol) was added to a mixture of the intermediate 49 (5-oxo-1-phenylpyrrolidine-3-carboxylic acid) (1.00 g; 4.87 mmol) and sodium hydrogen carbonate (0.818 g; 9.75 mmol) in DMF (10 mL). The resulting solution was stirred at room temperature for one week. The solution was concentrated under reduced pressure and the residue was partitioned between water and ethyl acetate. The organic layer was washed with a solution of sodium carbonate, a solution of sodium hydrogen sulfate and a solution of sodium thiosulfate, dried and concentrated under reduced pressure to afford 0.682 g (64%) of methyl 5-oxo-1-phenylpyrrolidine-3-carboxylate as a white solid.
ESI/APCI (+): 220 (M+H), 242 (M+Na).

Intermediate 58

Preparation of methyl 1-phenylpyrrolidine-3-carboxylate

9-BBN (4.01 mL, 0.5M solution in THF) was added to a solution of intermediate 57 (0.20 g; 0.912 mmol) in THF (2 mL). The reaction mixture was stirred at 65° C. for 2 h under a protective atmosphere of argon. The reaction mixture was cooled to room temperature and ethanolamine (0.121 mL; 2.01 mmol) was added. The reaction mixture was concentrated under reduced pressure and the residue was triturated with pentane, kept at +4° C. overnight and filtered on a celite pad. The filtrate was concentrated under reduced pressure to afford 0.20 g (quantitative yield) of methyl 1-phenylpyrrolidine-3-carboxylate as a pale yellow oil which was used without further purification.
ESI/APCI (+): 206 (M+H).

Intermediate 59

Preparation of 1-phenylpyrrolidine-3-carboxylic acid

The intermediate 58 (0.15 g; 0.709 mmol) was dissolved in a solution of sodium hydroxide
2M (5 mL). The resulting mixture was stirred at room temperature for 1.5 h and acidified with sodium hydrogen sulfate. The resulting solution was extracted with ethyl acetate, dried and concentrated under reduced pressure to afford 0.156 g (84%) of 1-phenylpyrrolidine-3-carboxylic acid as a pale rose solid which was used without further purification.

Intermediate 60

Preparation of 1-(4-cyanophenyl)-2-oxopyrrolidine-3-carboxylic acid

A mixture of 6,6-dimethyl-5,7-dioxaspiro[2.5]octane-4,8-dione (0.500 g, 2.94 mmol) and 4-aminobenzonitrile (1.04 g, 8.82 mmol) in ethanol (3 mL) was irradiated in a microwave oven for 3 minutes at 100° C. The solution was concentrated under reduced pressure and the residue was dissolved in a solution of sodium hydroxide 6N, washed with dichloromethane, acidified with a solution of sodium hydrogen phosphate (1M) to pH=2, extracted with ethyl acetate dried and concentrated under reduced pressure to yield 0.240 g (36%) of a brown solid which was used in the next step without further purification.
ESI/APCI (+): 246 (M+CH$_3$+H) spectrum recorded in methanol.

Intermediate 61

Preparation of 1-(3-fluorophenyl)-2-oxopyrrolidine-3-carboxylic acid

A mixture of 6,6-dimethyl-5,7-dioxaspiro[2.5]octane-4,8-dione (0.500 g; 2.94 mmol) and 3-fluoroaniline (0.847 mL; 8.82 mmol) in ethanol (3 mL) was irradiated in a microwave oven for 3 minutes at 100° C. The mixture was concentrated under reduced pressure and the residue was dissolved in a solution of sodium hydroxide 6N, washed with dichloromethane, acidified with a solution of hydrochloric acid 6N to pH=2, extracted with ethyl acetate dried and concentrated under reduced pressure to yield 0.560 g (85%) of a dark orange solid which was used in the next step without further purification.
ESI/APCI (+): 224 (M+H), 246 (M+Na).
ESI/APCI (−): 222 (M−H).

Intermediate 62

Preparation of 1-(4-methoxyphenyl)-2-oxopyrrolidine-3-carboxylic acid

A mixture of 6,6-dimethyl-5,7-dioxaspiro[2.5]octane-4,8-dione (0.500 g; 2.94 mmol) and 4-methoxyaniline (1.09 g; 8.82 mmol) in ethanol (3 mL) was irradiated in a microwave oven for 3 minutes at 100° C. The mixture was concentrated under reduced pressure and the residue was dissolved in a solution of sodium hydroxide 6N, washed with dichloromethane, acidified with a solution of hydrochloric acid 6N to pH=2, extracted with ethyl acetate dried and concentrated under reduced pressure to yield 0.11 g (16%) of a pale pink solid which was used in the next step without further purification.
ESI/APCI (+): 236 (M+H), 258 (M+Na).
ESI/APCI (−): 234 (M−H).

Intermediate 63

Preparation of 1-(4-isopropylphenyl)-2-oxopyrrolidine-3-carboxylic acid

A mixture of 6,6-dimethyl-5,7-dioxaspiro[2.5]octane-4,8-dione (0.500 g; 2.94 mmol) and 4-isopropylaniline (1.21 mL; 8.82 mmol) in ethanol (3 mL) was irradiated in a microwave oven for 3 minutes at 100° C. The mixture was concentrated under reduced pressure and the residue was dissolved in a solution of sodium hydroxide 6N, washed with dichloromethane, acidified with a solution of hydrochloric acid 6N to pH=2, extracted with ethyl acetate dried and concentrated under reduced pressure to yield 0.036 g (5%) of a pale green solid which was used in the next step without further purification.
ESI/APCI (+): 248 (M+H), 270 (M+Na).
ESI/APCI (−): 246 (M−H).

Intermediate 64

Preparation of
1-(2-fluorophenyl)-2-oxopyrrolidine-3-carboxylic
acid

A mixture of 6,6-dimethyl-5,7-dioxaspiro[2.5]octane-4,8-dione (0.500 g; 2.94 mmol) and 2-fluoroaniline (0.851 mL; 8.82 mmol) in ethanol (3 mL) was irradiated in a microwave oven for 3 minutes at 100° C. The mixture was concentrated under reduced pressure and the residue was dissolved in a solution of sodium hydroxide 6N, washed with dichloromethane, acidified with a solution of hydrochloric acid 6N to pH=2, extracted with ethyl acetate dried and concentrated under reduced pressure to yield 0.511 g (78%) of a yellow solid which was used in the next step without further purification.

ESI/APCI (+): 246 (M+Na).
ESI/APCI (−): 222 (M−H).

Intermediate 65

Preparation of
1-(3-ethylphenyl)-2-oxopyrrolidine-3-carboxylic
acid

A mixture of 6,6-dimethyl-5,7-dioxaspiro[2.5]octane-4,8-dione (0.500 g; 2.94 mmol) and 3-ethylaniline (1.1 mL; 8.82 mmol) in ethanol (3 mL) was irradiated in a microwave oven for 3 minutes at 100° C. The mixture was concentrated under reduced pressure and the residue was dissolved in a solution of sodium hydroxide 6N, washed with dichloromethane, acidified with a solution of hydrochloric acid 6N to pH=2, extracted with ethyl acetate dried and concentrated under reduced pressure to yield 0.240 g (35%) of a yellow oil which was used in the next step without further purification.

ESI/APCI (+): 234 (M+H).
ESI/APCI (−): 232 (M−H).

Intermediate 66

Preparation of 2-(2-(5-Chloro-1H-indol-3-yl)ethylamino)-2-oxoacetic acid

Triethylamine (2.28 mL; 16.22 mmol) was added to the mixture of 2-(5-chloro-1H-indol-3-yl)ethanamine hydrochloride (1.53 g; 6.49 mmol) and ethyl 2-chloro-2-oxoacetate (0.815 mL; 7.14 mmol) in dichloromethane (50 mL) at 0° C. After addition, the mixture was stirred at room temperature for 30 minutes and washed with an aqueous solution of sodium carbonate, dried over magnesium sulfate, and concentrated under reduced pressure. Ethanol (2 mL) and water (7.5 mL) were added to the resulting residue, followed by a 2M solution of sodium hydroxide (9.5 mL, 19 mmol). The mixture was stirred at room temperature for 20 minutes and the pH of the solution was adjusted to 1 by addition of a 6N hydrochloric acid. The precipitate was collected, and was dissolved in ethyl acetate. The ethyl acetate layer was dried over magnesium sulfate and was evaporated to dryness to give 1.36 g (81%) of 2-(2-(5-chloro-1H-indol-3-yl)ethylamino)-2-oxoacetic acid as a yellowish solid.

ESI/APCI (−): 265 (M−H).

Intermediate 67

Preparation of
2-(2-Hydroxy-1-phenylethylamino)-2-oxoacetic acid

Triethylamine (0.775 mL; 5.52 mmol) was added to the mixture of (DL)-2-amino-2-phenylethanol (0.515 g; 3.68 mmol) and ethyl 2-chloro-2-oxoacetate (0.441 mL; 3.86 mmol) in dichloromethane (15 mL) at 0° C. After addition, the mixture was stirred at room temperature for 30 minutes, diluted with 40 mL of dichloromethane, and washed successively with an aqueous solution of sodium carbonate, and water. The organic layer was dried over magnesium sulfate and was concentrated under reduced pressure. Water (5.5 mL) and a 2M solution of sodium hydroxide (5.5 mL; 11 mmol) were added to the resulting residue and the mixture was stirred at room temperature for 10 minutes. Water (10 mL) was added and the pH of the solution was adjusted to 1 by addition of a 6N hydrochloric acid. The formed precipitate was filtered off, and the filtrate was extracted with ethyl acetate (5×20 mL). The combined organic layers were dried over magnesium sulfate and evaporated to dryness to give 0.567 g (74%) of 2-(2-hydroxy-1-phenylethylamino)-2-oxoacetic acid as a white solid.

ESI/APCI (−): 208 (M−H).

Intermediate 68

Preparation of $N^1$-(2-(5-Chloro-1H-indol-3-yl)
ethyl)-$N^2$-(2-hydroxy-1-phenylethyl)oxalamide The mixture of 2-(5-chloro-1H-indol-3-yl)ethanamine hydrochloride (0.256 g; 1.09 mmol), 2-(2-hydroxy-1-phenylethylamino)-2-oxoacetic acid (0.250 g; 1.19 mmol), HATU (0.413 g: 1.09 mmol) and N,N-diisopropylethylamine (0.474 mL; 2.71 mmol) in DMF (5 mL) was stirred at room temperature overnight and was concentrated under reduced pressure. The residue was dissolved in dichloromethane, the organic layer was washed with water and was concentrated under reduced pressure. The crude material was purified by flash chromatography on silica gel (eluent 1 to 10% methanol in dichloromethane) to yield 0.440 g of $N^1$-(2-(5-chloro-1H-indol-3-yl)ethyl)-$N^2$-(2-hydroxy-1-phenylethyl)oxalamide as a white solid.

ESI/APCI (+): 386 (M+H), 408 (M+Na);
ESI/APCI (−): 384 (M−H).

Intermediate 69

Preparation of (S)-2-(1-hydroxy-3-phenylpropan-2-ylamino)-2-oxoacetic acid

Triethylamine (0.703 mL; 5.01 mmol) was added to the mixture of (S)-2-amino-3-phenylpropan-1-ol (0.515 g; 3.34 mmol) and ethyl 2-chloro-2-oxoacetate (0.400 mL; 3.50 mmol) in dichloromethane (15 mL) at 0° C. After addition, the mixture was stirred at room temperature for 30 minutes, diluted with 40 mL of dichloromethane, and washed successively with an aqueous solution of sodium carbonate, and water. The organic layer was dried over magnesium sulfate and concentrated under reduced pressure. Water (5 mL) and a 2M solution of sodium hydroxide (5 mL; 10 mmol) were added to the resulting residue and the mixture was stirred at room temperature for 10 minutes. Water (10 mL) was added and the pH of the solution was adjusted to 1 by addition of a 6N hydrochloric acid. The formed solid was filtered off, and the filtrate was extracted with ethyl acetate (5×20 mL). The combined organic layers were dried over magnesium sulfate and evaporated to dryness to give 0.692 g (94%) of (S)-2-(1-hydroxy-3-phenylpropan-2-ylamino)-2-oxoacetic acid as a white solid.

ESI/APCI (−): 222 (M−H).

Intermediate 70

Preparation of (S)—N$^1$-(2-(5-Chloro-1H-indol-3-yl)ethyl)-N$^2$-(1-hydroxy-3-phenylpropan-2-yl)oxalamide The mixture of 2-(5-chloro-1H-indol-3-yl)ethanamine hydrochloride (0.256 g; 1.09 mmol), (S)-2-(1-hydroxy-3-phenylpropan-2-ylamino)-2-oxoacetic acid (0.267 g; 1.19 mmol), HATU (0.413 g: 1.09 mmol) and N,N-diisopropylethylamine (0.474 mL; 2.71 mmol) in DMF (5 mL) was stirred at room temperature overnight and concentrated under reduced pressure. The residue was dissolved in dichloromethane, the organic layer was washed with water, and was concentrated under reduced pressure. The crude material was purified by flash chromatography on silica gel (eluent 1 to 10% methanol in dichloromethane) to yield 0.251 g (58%) of (S)—N$^1$-(2-(5-chloro-1H-indol-3-yl)ethyl)-N$^2$-(1-hydroxy-3-phenylpropan-2-yl)oxalamide as a white solid.

ESI/APCI (+): 400 (M+H), 422 (M+Na).
ESI/APCI (−): 398 (M−H).

Intermediate 71

Preparation of (R)-2-(1-hydroxy-3-phenylpropan-2-ylamino)-2-oxoacetic acid

Triethylamine (0.703 mL; 5.01 mmol) was added to the mixture of (R)-2-amino-3-phenylpropan-1-ol (0.515 g; 3.34 mmol) and ethyl 2-chloro-2-oxoacetate (0.400 mL; 3.50 mmol) in dichloromethane (15 mL) at 0° C. After addition, the mixture was stirred at room temperature for 30 minutes, diluted with 40 mL of dichloromethane, and washed successively with an aqueous solution of sodium carbonate, and water. The organic layer was dried over magnesium sulfate and concentrated under reduced pressure. Water (5 mL) and a 2M solution of sodium hydroxide (5 mL; 10 mmol) were added to the resulting residue and the mixture was stirred at room temperature for 10 minutes. Water (10 mL) was added and the pH of the solution was adjusted to 1 by addition of a 6N hydrochloric acid. The formed precipitate was filtered off, and the filtrate was extracted with ethyl acetate (5×20 mL). The combined organic layers were dried over magnesium sulfate and evaporated to dryness to give 0.671 g (91%) of (R)-2-(1-hydroxy-3-phenylpropan-2-ylamino)-2-oxoacetic acid as a white solid.

ESI/APCI (−): 222 (M−H).

Intermediate 72

Preparation of (R)—N$^1$-(2-(5-Chloro-1H-indol-3-yl)ethyl)-N$^2$-(1-hydroxy-3-phenylpropan-2-yl)oxalamide The mixture of 2-(5-chloro-1H-indol-3-yl)ethanamine hydrochloride (0.210 g; 0.890 mmol), (R)-2-(1-hydroxy-3-phenylpropan-2-ylamino)-2-oxoacetic acid (0.219 g; 0.979 mmol), HATU (0.339 g: 0.890 mmol) and N,N-diisopropylethylamine (0.389 mL; 2.23 mmol) in DMF (5 mL) was stirred at room temperature overnight and concentrated under reduced pressure. The residue was dissolved in dichloromethane, the organic layer was washed with water, and was concentrated under reduced pressure. The crude material was purified by flash chromatography on silica gel (eluent 1 to 10% methanol in dichloromethane) to yield 0.226 g (63%) of (R)—N$^1$-(2-(5-chloro-1H-indol-3-yl)ethyl)-N$^2$-(1-hydroxy-3-phenylpropan-2-yl)oxalamide as a white solid.

ESI/APCI (+): 400 (M+H), 422 (M+Na).
ESI/APCI (−): 398 (M−H).

Intermediate 73

Preparation of Ethyl 5-(2,5-difluorobenzyl)isoxazole-3-carboxylate 1,2-Dimethoxyethane (8 mL) and water (2 mL) were added to the mixture of ethyl 5-(bromomethyl)isoxazole-3-carboxylate (1.00 g; 4.27 mmol), 2,5-difluorophenylboronic acid (0.773 g; 4.70 mmol), tetrakis(triphenylphosphine)palladium(0) (0.248 g; 0.640 mmol) and sodium carbonate (0.911 g; 8.55 mmol). The mixture was irradiated in a microwave oven at 130° C. for 20 minutes. After cooling, the reaction mixture was extracted with ethyl acetate and water. The organic layer was concentrated under reduced pressure and the residue was purified by flash chromatography on silica gel (eluent: 5 to 40% of ethyl acetate in heptane) to give 0.67 g (59%) of ethyl 5-(2,5-difluorobenzyl)isoxazole-3-carboxylate as a yellow oil.

ESI/APCI (+): 268 (M+H); 290 (M+Na).
ESI/APCI (−): 266 (M−H).

Intermediate 74

Preparation of 5-(2,5-Difluorobenzyl)isoxazole-3-carboxylic acid

A solution of sodium hydroxide 1M (28 mL; 28 mmol) was added to a solution of ethyl 5-(2,5-difluorobenzyl)isoxazole-3-carboxylate (2.50 g; 9.36 mmol) in ethanol (3 mL). The mixture was stirred at room temperature. After 1 hour, a precipitation occurred and The reaction mixture was allowed to stir for 30 minutes. The solution was acidified to pH 1 by addition of a solution of hydrochloric acid 6N. The precipitate was collected by filtration and dried under reduced pressure to give 1.90 g (84%) of 5-(2,5-difluorobenzyl)isoxazole-3-carboxylic acid as a white solid.

ESI/APCI (−): 194 (M−H—CO$_2$).

Intermediate 75

Preparation of (Z)-Ethyl 2-amino-2-(2-(2,5-difluorophenyl)acetoxyimino)acetate 2-(2,5-difluorophenyl)acetyl chloride was prepared by heating overnight a suspension of 2,5-difluorophenylacetic acid (0.865 g; 3.67 mmol) and thionyl chloride (1.34 mL; 18.15 mmol) in chloroform (30 mL) at 80° C. After evaporation of the solvent and the excess of the thionyl chloride under reduced pressure, the residue was dissolved in dried dichloromethane (10 mL). This solution was added to a suspension of (Z)-ethyl 2-amino-2-(hydroxyimino)acetate (0.500 g; 3.67 mmol) and N,N-diisopropylethylamine (1.03 mL; 5.87 mmol) in dry dichloromethane (20 mL) cooled at −10° C. and stirred for 10 minutes. The mixture was stirred at room temperature for 23 h and poured into a mixture of ice/water. The white precipitate is filtered off and washed with dichloromethane and dried under reduced pressure to afford 0.469 g (45%) of (Z)-ethyl 2-amino-2-(2-(2,5-difluorophenyl)acetoxyimino)acetate as a white solid.
ESI/APCI (+): 287 (M+H), 309 (M+Na).
ESIAPCI (−): 285 (M−H).

Intermediate 76

Preparation of ethyl 5-(2,5-difluorobenzyl)-1,2,4-oxadiazole-3-carboxylate (Z)-ethyl 2-amino-2-(2-(2,5-difluorophenyl)acetoxyimino)acetate (0.455 g; 1.59 mmol) was dissolved in pyridine (10 mL). The solution was heated at 120° C. for 2 h and was evaporated to dryness. The residue was purified by flash chromatography on silica gel (eluent: 0 to 20% of ethyl acetate in dichloromethane) to give 0.301 g (71%) of ethyl 5-(2,5-difluorobenzyl)-1,2,4-oxadiazole-3-carboxylate as a white solid.
ESI/APCI (+): 269 (M+H), 291 (M+Na).
ESI/APCI (−): 267 (M−H).

Intermediate 77

Preparation of 5-(2,5-difluorobenzyl)-1,2,4-oxadiazole-3-carboxylic acid

A solution of sodium hydroxide 1M (2 ml, 2 mmol) was added to a mixture of ethyl 5-(2,5-difluorobenzyl)-1,2,4-oxadiazole-3-carboxylate (0.150 g; 0.559 mmol) in ethanol (1 mL) and the reaction was stirred at room temperature for 1 hour. The pH of the solution was adjusted to 1 by addition of a solution of hydrochloric acid 6N. The precipitate was collected by filtration and dried under reduced pressure to afford 0.124 g (92%) of 5-(2,5-difluorobenzyl)-1,2,4-oxadiazole-3-carboxylic acid as a white solid.
ESI/APCI (+): 241 (M+H).

General Method 1

Preparation of 1-N-substituted-2oxopyrrolidine-3-carboxylic acid

A mixture of 6,6-dimethyl-5,7-dioxaspiro[2.5]octane-4,8-dione (1.47 mmol) and an amine (4.41 mmol) in ethanol (3 mL) was irradiated in the microwave oven for 5 minutes at 100° C. The mixture was concentrated under reduced pressure and the residue was dissolved in a solution of sodium hydroxide (2N in water), washed with DCM, acidified with a solution of hydrochloric acid 6N in water to pH=2, extracted with ethyl acetate dried and concentrated under reduced pressure to yield the desired compound which was used without any further purification.

Intermediate 78

Preparation of 2-oxo-1-(4-(trifluoromethoxy)phenyl) pyrrolidine-3-carboxylic acid This compound was prepared according to general method 1 starting from 6,6-dimethyl-5,7-dioxaspiro[2.5]octane-4,8-dione (0.250 g, 1.47 mmol) and 4-(trifluoromethoxy)aniline (0.595 mL; 4.41 mmol) in ethanol (3 mL). 2-oxo-1-(4-(trifluoromethoxy)phenyl)pyrrolidine-3-carboxylic acid 0.350 g (82%) was obtained as a yellow solid.
ESI/APCI (+): 290 (M+H).

Intermediate 79

Preparation of 1-(cyclohexylmethyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and cyclohexylmethanamine (0.574 mL; 4.41 mmol) in ethanol (3 mL). 1-(cyclohexylmethyl)-2-oxopyrrolidine-3-carboxylic acid 0.286 g (86%) was obtained as a yellow solid.
ESI/APCI (+): 226 (M+H).

Intermediate 80

Preparation of 1-(2-methoxyphenyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 2-methoxyaniline (0.495 mL; 4.41 mmol) in ethanol (3 mL). 1-(2-methoxyphenyl)-2-oxopyrrolidine-3-carboxylic acid 0.350 g (quantitative) was obtained as a grey solid.
ESI/APCI (+): 236 (M+H).

Intermediate 81

Preparation of 1-(3-methoxyphenyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 3-methoxyaniline (0.495 mL; 4.41 mmol) in ethanol (3 mL 1-(3-methoxyphenyl)-2-oxopyrrolidine-3-carboxylic acid 0.350 g (quantitative) was obtained as a brown oil.
ESI/APCI (+): 236 (M+H).

Intermediate 82

Preparation of 1-(2-chlorophenyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 2-chloroaniline (0.464 mL; 4.41 mmol) in ethanol (3 mL). 1-(2-chlorophenyl)-2-oxopyrrolidine-3-carboxylic acid 0.253 g (72%) was obtained as a yellow solid.
ESI/APCI (+): 240 (M+H).

Intermediate 83

Preparation of 2-oxo-1-m-tolylpyrrolidine-3-carboxylic acid

This compound was prepared according to general method 1 starting from 6,6-dimethyl-5,7-dioxaspiro[2.5]octane-4,8-dione (0.250 g, 1.47 mmol) and m-toluidine (0.470 mL; 4.41 mmol) in ethanol (3 mL). 2-oxo-1-m-tolylpyrrolidine-3-carboxylic acid 0.270 g (84%) was obtained as a pink film.
ESI/APCI (+): 220 (M+H).

Intermediate 84

Preparation of
2-oxo-1-o-tolylpyrrolidine-3-carboxylic acid

This compound was prepared according to general method 1 starting from 6,6-dimethyl-5,7-dioxaspiro[2.5]octane-4,8-dione (0.250 g, 1.47 mmol) and o-toluidine (0.470 mL; 4.41 mmol) in ethanol (3 mL). 2-oxo-1-o-tolylpyrrolidine-3-carboxylic acid 0.292 g (91%) was obtained as a white film.
ESI/APCI (+): 220 (M+H).

Intermediate 85

Preparation of 1-(1-methyl-1H-pyrazol-3-yl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 1-methyl-1H-pyrazol-3-amine (0.428 g; 4.41 mmol) in ethanol (3 mL). 1-(1-methyl-1H-pyrazol-3-yl)-2-oxopyrrolidine-3-carboxylic acid 0.063 g (21%) was obtained as a yellow oil.
ESI/APCI (+): 210 (M+H).

Intermediate 86

Preparation of 1-(3-(1H-pyrrol-1-yl)phenyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 3-(1H-pyrrol-1-yl)aniline (0.697 g; 4.41 mmol) in ethanol (3 mL). 1-(3-(1H-pyrrol-1-yl)phenyl)-2-oxopyrrolidine-3-carboxylic acid 0.313 g (80%) was obtained as a brown oil.
ESI/APCI (+): 271 (M+H).

Intermediate 87

Preparation of
1-(2-ethylphenyl)-2-oxopyrrolidine-3-carboxylic acid

This compound was prepared according to general method 1 starting from 6,6-dimethyl-5,7-dioxaspiro[2.5]octane-4,8-dione (0.250 g, 1.47 mmol) and 2-ethylaniline (0.543 mL; 4.41 mmol) in ethanol (3 mL). 1-(2-ethylphenyl)-2-oxopyrrolidine-3-carboxylic acid 0.327 g (95%) was obtained as a pale pink solid.
ESI/APCI (+): 234 (M+H).

Intermediate 88

Preparation of
2-oxo-1-(1-phenylethyl)pyrrolidine-3-carboxylic acid

This compound was prepared according to general method 1 starting from 6,6-dimethyl-5,7-dioxaspiro[2.5]octane-4,8-dione (0.250 g, 1.47 mmol) and 1-phenylethanamine (0.568 mL; 4.41 mmol) in ethanol (3 mL). 2-oxo-1-(1-phenylethyl)pyrrolidine-3-carboxylic acid 0.306 g (89%) was obtained as a white solid.
ESI/APCI (+): 234 (M+H).

Intermediate 89

Preparation of
1-(4-acetylphenyl)-2-oxopyrrolidine-3-carboxylic acid

This compound was prepared according to general method 1 starting from 6,6-dimethyl-5,7-dioxaspiro[2.5]octane-4,8-dione (0.500 g, 2.94 mmol) and 1-(4-aminophenyl)ethanone (1.19 g, 1.19 mmol) in ethanol (3 mL). 1-(4-acetylphenyl)-2-oxopyrrolidine-3-carboxylic acid 0.307 g (42%) was obtained as a bright yellow solid.

Intermediate 90

Preparation of
2-oxo-1-p-tolylpyrrolidine-3-carboxylic acid

This compound was prepared according to general method 1 starting from 6,6-dimethyl-5,7-dioxaspiro[2.5]octane-4,8-dione (0.500 g, 2.94 mmol) and 1-(4-aminophenyl)ethanone (1.19 g, 1.19 mmol) in ethanol (3 mL). 2-oxo-1-p-tolylpyrrolidine-3-carboxylic acid 0.644 g (quantitative) was obtained as a bright yellow solid.
ESI/APCI (−): 218 (M−H).

Intermediate 91

Preparation of 2-oxo-1-(4-(trifluoromethyl)phenyl)pyrrolidine-3-carboxylic acid

This compound was prepared according to general method 1 starting from 6,6-dimethyl-5,7-dioxaspiro[2.5]octane-4,8-dione (0.500 g, 2.94 mmol) and 4-trifluoromethyl aniline (1.28 mL, 8.82 mmol) in ethanol (3 mL). 2-oxo-1-(4-(trifluoromethyl)phenyl)pyrrolidine-3-carboxylic acid 0.343 g (43%) was obtained as a bright yellow solid.

Intermediate 92

Preparation of
1-(3-chlorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 3-chloroaniline (0.469 mL; 4.36 mmol) in ethanol (3 mL). 1-(3-chlorophenyl)-2-oxopyrrolidine-3-carboxylic acid 0.282 g (81%) was obtained as a solid.
ESI/APCI (+): 240 (M+H), 196 (M+H—$CO_2$).

Intermediate 93

Preparation of
1-(4-chlorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 4-chloroaniline (0.568 g;

4.36 mmol) in ethanol (3 mL). 1-(4-chlorophenyl)-2-oxopyrrolidine-3-carboxylic acid 0.234 g (67%) was obtained as a white solid.

ESI/APCI (+): 240 (M+H), 196 (M+H—$CO_2$).

Intermediate 94

Preparation of 1-(2,6-difluorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 2,6-difluoroaniline (0.575 g; 4.36 mmol) in ethanol (3 mL). 1-(2,6-difluorophenyl)-2-oxopyrrolidine-3-carboxylic acid 0.161 g (46%) was obtained as a solid.

ESI/APCI (+): 242 (M+H), 198 (M+H—$CO_2$).

Intermediate 95

Preparation of 1-(3-fluoro-4-(trifluoromethyl)phenyl)-2-oxopyrrolidine-3-carboxylic acid This compound was prepared according to general method 1 starting from 6,6-dimethyl-5,7-dioxaspiro[2.5]octane-4,8-dione (0.250 g; 1.45 mmol) and 3-fluoro-4-(trifluoromethyl)aniline (0.806 g; 4.36 mmol) in ethanol (3 mL). 1-(3-fluoro-4-(trifluoromethyl)phenyl)-2-oxopyrrolidine-3-carboxylic acid 0.147 g (35%) was obtained as a solid.

Intermediate 96

Preparation of 1-cyclopropyl-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and cyclopropanamine (0.309 mL; 4.36 mmol) in ethanol (3 mL). 1-cyclopropyl-2-oxopyrrolidine-3-carboxylic acid 0.172 g (70%) was obtained as a white solid.

ESI/APCI (+): 170 (M+H), 192 (M+Na), 126 (M+H—$CO_2$).
ESI/APCI (−): 168 (M−H).

Intermediate 97

Preparation of 1-(3,4-difluorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 3,4-difluoroaniline (0.442 mL; 4.36 mmol) in ethanol (3 mL). 1-(3,4-difluorophenyl)-2-oxopyrrolidine-3-carboxylic acid 0.172 g (70%) was obtained as a white solid.

ESI/APCI (+): 242 (M+H), 264 (M+Na), 198 (M+H—$CO_2$).
ESI/APCI (−): 240 (M−H).

Intermediate 98

Preparation of 1-(3-fluoro-4-methoxyphenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) 3-fluoro-4-methoxyaniline (0.628 g; 4.36 mmol) in ethanol (3 mL). 1-(3-fluoro-4-methoxyphenyl)-2-oxopyrrolidine-3-carboxylic acid 0.336 g (91%) was obtained as a white solid.

ESI/APCI (+): 254 (M+H), 276 (M+Na), 210 (M+H—$CO_2$).
ESI/APCI (−): 252 (M−H).

Intermediate 99

Preparation of 1-(1,3-dihydroisobenzofuran-5-yl)-2-oxopyrrolidine-3-carboxylic acid This compound was prepared according to general method 1 starting from 6,6-dimethyl-5,7-dioxaspiro[2.5]octane-4,8-dione (0.250 g; 1.45 mmol) and 1,3-dihydroisobenzofuran-5-amine (0.608 g; 4.36 mmol) in ethanol (3 mL). 1-(1,3-dihydroisobenzofuran-5-yl)-2-oxopyrrolidine-3-carboxylic acid 0.300 g (84%) was obtained as a white solid.

ESI/APCI (+): 248 (M+H), 270 (M+Na), 204 (M+H—$CO_2$).
ESI/APCI (−): 246 (M−H).

Intermediate 100

Preparation of 1-(2,3-dihydro-1H-inden-5-yl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 2,3-dihydro-1H-inden-5-amine (0.593 g; 4.36 mmol) in ethanol (3 mL). 1-(2,3-dihydro-1H-inden-5-yl)-2-oxopyrrolidine-3-carboxylic acid 0.255 g (71%) was obtained as a white solid.

ESI/APCI (+): 246 (M+H), 268 (M+Na), 202 (M+H—$CO_2$)
ESI/APCI (−): 244 (M−H).

Intermediate 101

Preparation of 1-(3,5-difluorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 3,5-difluoroaniline (0.575 g; 4.36 mmol) in ethanol (3 mL). 1-(3,5-difluorophenyl)-2-oxopyrrolidine-3-carboxylic acid 0.167 g (48%) was obtained as a white solid.

ESI/APCI (+): 242 (M+H), 264 (M+Na), 198 (M+H—$CO_2$).
ESI/APCI (−): 240 (M−H).

Intermediate 102

Preparation of 1-(3,4-dimethylphenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 3,4-dimethylaniline (0.540 g; 4.36 mmol) in ethanol (3 mL). 1-(3,4-dimethylphenyl)-2-oxopyrrolidine-3-carboxylic acid 0.292 g (86%) was obtained as a white solid.

ESI/APCI (+): 234 (M+H), 256 (M+Na), 190 (M+H—$CO_2$)
ESI/APCI (−): 232 (M−H). .

Intermediate 103

Preparation of 1-(4-chloro-3-fluorophenyl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 4-chloro-3-fluoroaniline (0.642 g; 4.36 mmol) in ethanol (3 mL). 1-(3,5-difluorophenyl)-2-oxopyrrolidine-3-carboxylic acid 0.150 g (40%) was obtained as a white solid.
ESI/APCI (+): 258 (M+H), 280 (M+Na), 214 (M+H—$CO_2$).

Intermediate 104

Preparation of 1-(1-methyl-1H-indol-5-yl)-2-oxopyrrolidine-3-carboxylic acid

This compound was prepared according to general method 1 starting from 6,6-dimethyl-5,7-dioxaspiro[2.5]octane-4,8-dione (0.250 g; 1.45 mmol) and 1-methyl-1H-indol-5-amine (0.400 g; 2.74 mmol) in ethanol (3 mL). 11-(1-methyl-1H-indol-5-yl)-2-oxopyrrolidine-3-carboxylic acid 0.065 g (17%) was prepared as a solid.
ESI/APCI (+): 258 (M+H), 280 (M+Na), 214 (M+H—$CO_2$).

General Method 2

Preparation of ethyl-5-substituted-1,2,4-oxadiazole-3-carboxylate

Step I
A mixture of a 2-aryl acetic acid (3.78 mmol; 1 equivalent) and oxalyl chloride (4.16 mmol, 1.1 equivalents) in dichloromethane (12 mL) with few drops of DMF was stirred at room temperature for 3 h.
Step II
The resulting solution from step I was added to a mixture of ethyl 2-amino-2-(hydroxyimino)acetate (3.78 mmol 1 equivalent) and N,N diisopropylethylamine (6.06 mmol, 1.60 equivalents) in dichloromethane (6 mL) at −15° C. The reaction mixture was then stirred at room temperature for 12 to 36 h and poured into a mixture of ice and water. The formed precipitate was filtered off. When a precipitate was not formed, the organic layer was separated, dried over magnesium sulphate, filtered and evaporated to dryness.
Step III
The precipitate or the residue from step II was refluxed in a sealed tube with pyridine (18 mL) for 20 h and concentrated under reduced pressure. The crude material was purified by flash chromatography on silica to yield the desired compound.

Intermediate 105

Preparation of ethyl 5-(thiophen-3-ylmethyl)-1,2,4-oxadiazole-3-carboxylate

This compound was prepared according to general method 2 with (step I) 2-(thiophen-3-yl)acetic acid (0.568 g; 3.78 mmol), oxalyl chloride (0.352 mL; 4.16 mmol) in dichloromethane (12 mL) with few drops of DMF; (step II) ethyl 2-amino-2-(hydroxyimino)acetate (0.5 g; 3.78 mmol); N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.343 g (38%) of ethyl 5-(thiophen-3-ylmethyl)-1,2,4-oxadiazole-3-carboxylate as a yellow solid.
ESI/APCI (+): 239 (M+H).

Intermediate 106

Preparation of ethyl 5-(2-methylbenzyl)-1,2,4-oxadiazole-3-carboxylate

This compound was prepared according to general method 2 with (step I) 2-o-tolylacetic acid (0.568 g; 3.78 mmol); oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.165 g (18%) of ethyl 5-(2-methylbenzyl)-1,2,4-oxadiazole-3-carboxylate as a white solid.
ESI/APCI (+): 248 (M+H).
ESI/APCI (−): 247 (M−H).

Intermediate 107

Preparation of ethyl 5-(2-chlorobenzyl)-1,2,4-oxadiazole-3-carboxylate

This compound was prepared according to general method 2 with (step I) 2-(2-chlorophenyl)acetic acid (0.646 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.387 g (38%) of ethyl 5-(2-chlorobenzyl)-1,2,4-oxadiazole-3-carboxylate as a white solid.
ESI/APCI (+): 267 (M+H).

Intermediate 108

Preparation of ethyl 5-(3-chlorobenzyl)-1,2,4-oxadiazole-3-carboxylate

This compound was prepared according to general method 2 with (step I) 2-(3-chlorophenyl)acetic acid (0.646 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.283 g (28%) of ethyl 5-(3-chlorobenzyl)-1,2,4-oxadiazole-3-carboxylate as a white solid.
ESI/APCI (+): 267 (M+H).

Intermediate 109

Preparation of ethyl 5-(2,4-difluorobenzyl)-1,2,4-oxadiazole-3-carboxylate

This compound was prepared according to general method 2 with (step I) 2-(2,4-difluorophenyl)acetic acid (0.651 g;

3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.372 g (37%) of the title compound as a white solid.

ESI/APCI (+): 269 (M+H).

Intermediate 110

Preparation of ethyl 5-(2,6-difluorobenzyl)-1,2,4-oxadiazole-3-carboxylate

This compound was prepared according to general method 2 with (step I) 2-(2,6-difluorophenyl)acetic acid (0.651 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.345 g (34%) of ethyl 5-(2,6-difluorobenzyl)-1,2,4-oxadiazole-3-carboxylate as a white solid.

ESI/APCI (+): 269 (M+H).

Intermediate 111

Preparation of ethyl 5-(2,3-difluorobenzyl)-1,2,4-oxadiazole-3-carboxylate

This compound was prepared according to general method 2 with (step I) 2-(2,3-difluorophenyl)acetic acid (0.651 g; 3.78 mmol) and oxalyl chloride (0.352 mL; 4.16 mmol) in dichloromethane (12 mL) and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.079 g (8%) of ethyl 5-(2,3-difluorobenzyl)-1,2,4-oxadiazole-3-carboxylate as a white solid.

ESI/APCI (+): 269 (M+H), 291 (M+Na).
ESI/APCI (−): 267 (M−H).

Intermediate 112

Preparation of ethyl 5-(4-(trifluoromethyl)benzyl)-1,2,4-oxadiazole-3-carboxylate This compound was prepared according to general method 2 with (step I) 2-(4-(trifluoromethyl)phenyl)acetic acid (0.773 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL), and (step III) pyridine (18 mL). The crude material was purified by flash chromatography on silica (eluent 20 to 100% ethyl acetate in heptane) to yield 0.345 g (34%) of the title compound as a white solid.

ESI/APCI (+): 269 (M+H).

Intermediate 113

Preparation of ethyl 5-(3-(trifluoromethyl)benzyl)-1,2,4-oxadiazole-3-carboxylate This compound was prepared according to general method 2 with (step I) 2-(3-(trifluoromethyl)phenyl)acetic acid (0.773 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.040 g (4%) of ethyl 5-(3-(trifluoromethyl)benzyl)-1,2,4-oxadiazole-3-carboxylate as a white solid.

ESI/APCI (+): 301 (M+H).
ESI/APCI (−): 299 (M−H).

Intermediate 114

Preparation of ethyl 5-(4-(trifluoromethoxy)benzyl)-1,2,4-oxadiazole-3-carboxylate This compound was prepared according to general method 2 with (step I) 2-(4-(trifluoromethoxy)phenyl)acetic acid (0.833 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL); (step III) pyridine (18 mL). The crude material was purified by flash chromatography on silica (eluent 20 to 100% ethyl acetate in heptane) to yield 0.124 g (10%) of ethyl 5-(4-(trifluoromethoxy)benzyl)-1,2,4-oxadiazole-3-carboxylate as a white solid.

ESI/APCI (+): 317 (M+H).
ESI/APCI (−): 315 (M−H).

Intermediate 115

Preparation of ethyl 5-(3-methylbenzyl)-1,2,4-oxadiazole-3-carboxylate

This compound was prepared according to general method 2 with (step I) 2-m-tolylacetic acid (0.568 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL), and (step III) pyridine (18 mL). The crude material was purified by flash chromatography on silica (eluent 20 to 100% ethyl acetate in heptane) to yield 0.216 g (23%) of ethyl 5-(3-methylbenzyl)-1,2,4-oxadiazole-3-carboxylate as a colorless oil.

ESI/APCI (+): 247 (M+H).

Intermediate 116

Preparation of ethyl 5-(2-methoxybenzyl)-1,2,4-oxadiazole-3-carboxylate

This compound was prepared according to general method 2 with (step I) 2-(2-methoxyphenyl)acetic acid (0.629 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.346 g (12%) of ethyl 5-(2-methoxybenzyl)-1,2,4-oxadiazole-3-carboxylate as a white solid.
ESI/APCI (+): 263 (M+H).

Intermediate 117

Preparation of ethyl 5-(3,5-difluorobenzyl)-1,2,4-oxadiazole-3-carboxylate

This compound was prepared according to general method 2 with (step I) 2-(3,5-difluorophenyl)acetic acid (0.651 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (18 mL). The crude material was purified by flash chromatography on silica (eluent 20 to 100% ethyl acetate in heptane) to yield 0.349 g (34%) of thyl 5-(3,5-difluorobenzyl)-1,2,4-oxadiazole-3-carboxylate as a white solid.
ESI/APCI (+): 269 (M+H).
ESI/APCI (−): 267 (M−H).

Intermediate 118

Preparation of ethyl 5-(4-methylbenzyl)-1,2,4-oxadiazole-3-carboxylate

This compound was prepared according to general method 2 with (step I) 2-p-tolylacetic acid (0.568 g; 3.78 mmol) and oxalyl chloride (0.352 mL; 4.16 mmol) in dichloromethane (12 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (6 mL) and (step III) pyridine (12 mL). The crude material was purified by flash chromatography on silica (eluent 20 to 100% ethyl acetate in heptane) to yield 0.2118 g (23%) of ethyl 5-(4-methylbenzyl)-1,2,4-oxadiazole-3-carboxylate as a yellow solid.
ESI/APCI (+): 247 (M+H).

Intermediate 119

Preparation of ethyl 5-(2,5-dimethoxybenzyl)-1,2,4-oxadiazole-3-carboxylate 2-(2,5-dimethoxyphenyl)acetyl chloride (0.662 mL; 3.78 mmol) was added to a mixture of ethyl 2-amino-2-(hydroxyimino)acetate (0.500 g; 3.78 mmol) and N,N diisopropylethylamine (1.05 mL; 6.06 mmol) in dichloromethane (18 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.414 g (37%) of ethyl 5-(2,5-dimethoxybenzyl)-1,2,4-oxadiazole-3-carboxylate as a yellow oil.
SI/APCI (−): 291 (M−H)
SI/APCI (−): 291 (M−H).

Intermediate 120

Preparation of ethyl 5-(3,4-dimethoxybenzyl)-1,2,4-oxadiazole-3-carboxylate 2-(3,4-dimethoxyphenyl)acetyl chloride (0.650 mL; 3.78 mmol) was added to a mixture of ethyl 2-amino-2-(hydroxyimino)acetate (0.500 g; 3.78 mmol) and N,N diisopropylethylamine (1.05 mL; 6.06 mmol) in dichloromethane (18 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.395 g (36%) of ethyl 5-(3,4-dimethoxybenzyl)-1,2,4-oxadiazole-3-carboxylate as a yellow solid.
ESI/APCI (+): 293 (M+H).
ESI/APCI (−): 292 (M−H).

Intermediate 121

Preparation of ethyl 5-(3-methoxybenzyl)-1,2,4-oxadiazole-3-carboxylate 2-(3-methoxyphenyl)acetyl chloride (1.18 mL; 7.57 mmol) was added to a mixture of ethyl 2-amino-2-(hydroxyimino)acetate (0.500 g; 3.78 mmol) and N,N diisopropylethylamine (1.05 mL; 6.06 mmol) in dichloromethane (18 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.146 g (15%) of ethyl 5-(3-methoxybenzyl)-1,2,4-oxadiazole-3-carboxylate as a yellow oil.
ESI/APCI (+): 263 (M+H).
ESI/APCI (−): 261 (M−H).

Intermediate 122

Preparation of ethyl 5-(4-tert-butylbenzyl)-1,2,4-oxadiazole-3-carboxylate

A mixture of 2-(3-tert-butylphenyl)acetic acid (0.728 g; 3.78 mmol) and oxalyl chloride (0.352 mL; 4.16 mmol) in dichloromethane (8 mL) with few drops of DMF was stirred at room temperature for 3 hours and added to a mixture of ethyl 2-amino-2-(hydroxyimino)acetate (0.500 g; 3.78 mmol) and N,N diisopropylethylamine (1.05 mL; 6.06 mmol) in dichloromethane (10 mL) at −15° C. The reaction mixture was stirred at room temperature for 60 h and poured into a mixture of ice and water. The organic layer was separated, dried over $MgSO_4$ and concentrated under reduced pressure. The residue was refluxed in a sealed tube with pyridine (18 mL) for 20 h and concentrated under reduced pressure. The crude material was purified by flash chromatography on silica (eluent 20 to 100% ethyl acetate in heptane) to yield 0.422 g (30%) of the title compound as a yellow solid
ESI/APCI (+): 289 (M+H)
ESI/APCI (−): 287 (M−H). .

Intermediate 123

Preparation of ethyl 5-(4-chloro-3-fluorobenzyl)-1,2,4-oxadiazole-3-carboxylate This compound was prepared according to general method 2 with (step I) 2-(4-chloro-3-fluorophenyl)acetic acid (0.714 g; 3.78 mmol) and oxalyl chloride (0.352 mL; 4.16 mmol) in dichloromethane (8 mL) with few drops of DMF and (step II) ethyl 2-amino-2-(hydroxyimino)acetate (0.500 g; 3.78 mmol) and N,N diisopropylethylamine (1.05 mL; 6.06 mmol) in dichloromethane (10 mL) and (step III) pyridine (18 mL). The crude material was purified by flash chromatography on silica (eluent 20 to 100% ethyl acetate in heptane) to yield 0.252 g (23%) of ethyl 5-(4-chloro-3-fluorobenzyl)-1,2,4-oxadiazole-3-carboxylate as a yellow solid.
ESI/APCI (+): 285 (M+H).
ESI/APCI (−): 283 (M−H).

Intermediate 124

Preparation of ethyl 5-(3,4-dichlorobenzyl)-1,2,4-oxadiazole-3-carboxylate

This compound was prepared according to general method 2 with (step I) 2-(3,4-dichlorophenyl)acetic acid (0.775 g; 3.78 mmol) and oxalyl chloride (0.352 mL; 4.16 mmol) in dichloromethane (8 mL) with few drops of DMF and (step II) ethyl 2-amino-2-(hydroxyimino)acetate (0.500 g; 3.78 mmol) and N,N diisopropylethylamine (1.05 mL; 6.06 mmol) in dichloromethane (10 mL) and (step III) pyridine (18 mL). The crude material was purified by flash chromatography on silica (eluent 20 to 100% ethyl acetate in heptane) to yield 0.2004 g (18%) of ethyl 5-(3,4-dichlorobenzyl)-1,2,4-oxadiazole-3-carboxylate as a white solid.
ESI/APCI (+): 301 (M+H).
ESI/APCI (−): 299 (M−H).

Intermediate 125

Preparation of ethyl 5-(3,4-difluorobenzyl)-1,2,4-oxadiazole-3-carboxylate

This compound was prepared according to general method 2 with (step I) 2-(3,4-difluorophenyl)acetic acid (0.651 g; 3.78 mmol) and oxalyl chloride (0.352 mL; 4.16 mmol) in dichloromethane (8 mL) with few drops of DMF and (step II) ethyl 2-amino-2-(hydroxyimino)acetate (0.5 g; 3.78 mmol) and N,N diisopropylethylamine (1.05 mL; 6.06 mmol) in dichloromethane (10 mL), and (step III) pyridine (18 mL). The crude material was purified by flash chromatography on silica (eluent 20 to 100% ethyl acetate in heptane) to yield 0.346 g (34%) of ethyl 5-(3,4-difluorobenzyl)-1,2,4-oxadiazole-3-carboxylate as a yellow solid.
ESI/APCI (+): 269 (M+H).
ESI/APCI (−): 267 (M−H).

Intermediate 126

Preparation of ethyl 5-(4-chlorobenzyl)-1,2,4-oxadiazole-3-carboxylate 2-(4-chlorophenyl)acetyl chloride (0.554 mL; 3.78 mmol) was added to a mixture of ethyl 2-amino-2-(hydroxyimino)acetate (0.5 g; 3.78 mmol) and N,N diisopropylethylamine (1.05 mL; 6.06 mmol) in dichloromethane (15 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.506 g (50%) of ethyl 5-(4-chlorobenzyl)-1,2,4-oxadiazole-3-carboxylate as a white solid.
ESI/APCI (+): 267 (M+H), 289 (M+Na).
ESI/APCI (−): 265 (M−H).

Intermediate 127

Preparation of ethyl 5-(4-fluorobenzyl)-1,2,4-oxadiazole-3-carboxylate 2-(4-fluorophenyl)acetyl chloride (0.518 mL; 3.78 mmol) was added to a mixture of ethyl 2-amino-2-(hydroxyimino)acetate (0.5 g; 3.78 mmol) and N,N diisopropylethylamine (1.05 mL; 6.06 mmol) in dichloromethane (15 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.315 g (33%) of ethyl 5-(4-fluorobenzyl)-1,2,4-oxadiazole-3-carboxylate as a white solid.
ESI/APCI (+): 251 (M+H), 273 (M+Na).
ESI/APCI (−): 249 (M−H).

Intermediate 128

Preparation of ethyl 5-(2-fluorobenzyl)-1,2,4-oxadiazole-3-carboxylate

This compound was prepared according to general method 2 with 2-(2-fluorophenyl)acetic acid (1.19 g; 7.57 mmol) and oxalyl chloride (0.704 mL; 8.33 mmol) in dichloromethane (5 mL) with a few drops of DMF; and ethyl 2-amino-2-(hydroxyimino)acetate (1.0 g; 7.57 mmol) and N,N diisopropylethylamine (2.11 mL; 12.11 mmol) in dichloromethane (10 mL). The crude material was purified by flash chromatography on silica (eluent 20 to 100% ethyl acetate in heptane) to yield 0.249 g (14%) of ethyl 5-(2-fluorobenzyl)-1,2,4-oxadiazole-3-carboxylate as a white solid.
ESI/APCI (+): 251 (M+H), 273 (M+Na).

Intermediate 129

Preparation of ethyl 5-(3-fluorobenzyl)-1,2,4-oxadiazole-3-carboxylate

This compound was prepared according to general method 2 with (step I) 2-(3-fluorophenyl)acetic acid (1.03 g; 7.57 mmol) and oxalyl chloride (0.704 mL; 8.33 mmol) in dichloromethane (5 mL) and a few drops of DMF and (step II) ethyl 2-amino-2-(hydroxyimino)acetate (1.0 g; 7.57 mmol) and N,N diisopropylethylamine (2.11 mL; 12.11 mmol) in dichloromethane (10 mL) and (step 110 pyridine (18 mL). The crude material was purified by flash chromatography on silica (eluent 20 to 100% ethyl acetate in heptane) to yield 0.555 g (30%) of the title compound as a white solid.
ESI/APCI (+): 251 (M+H).

Intermediate 130

Preparation of ethyl 5-benzyl-1,2,4-oxadiazole-3-carboxylate 2-phenyl acetyl chloride (1.0 mL; 7.57 mmol) was added to a mixture of ethyl 2-amino-2-(hydroxyimino)acetate (0.5 g; 3.78 mmol) and N,N diisopropylethylamine (1.05 mL; 6.06 mmol) in dichloromethane (15 mL) at −15° C. The reaction mixture was stirred at room temperature overnight and poured into a mixture of ice and water. The formed precipitate was filtered off, suspended in pyridine (18 mL) and refluxed in a sealed tube for 20 h and concentrated under reduced pressure. The crude material was purified by flash chromatography on silica (eluent 20 to 100% ethyl acetate in heptane) to yield 0.308 g (35%) of the title compound as a white solid.
ESI/APCI (+): 233 (M+H), 255 (M+Na).

Intermediate 131

Preparation of ethyl 5-(hydroxy(phenyl)methyl)isoxazole-3-carboxylate 1-phenylprop-2-yn-1-ol (0.802 mL, 6.60 mmol) was added to a mixture of (Z)-ethyl 2-chloro-2-(hydroxyimino)acetate (0.50 g; 3.30 mmol) and sodium hydrogen carbonate (0.554 g; 6.60 mmol) in ethyl acetate (15 mL) and water (0.2 mL) and stirred at room temperature for 24 hours. The resulting mixture was filtered and concentrated under reduced pressure. The crude mixture was purified by flash chromatography on silica (eluent 2 to 40% ethyl acetate in heptane) to yield 0.571 g (70%) of ethyl 5-(hydroxy(phenyl)methyl)isoxazole-3-carboxylate as a colorless oil.
ESI/APCI (+): 248 (M+H).

Intermediate 132

Preparation of 2-iodo-4-(trifluoromethyl)aniline

Iodine (1.58 g; 6.21 mmol) was added to a stirred mixture of silver sulphate (1.94 g; 6.21 mmol) and 4-(trifluoromethyl)aniline (0.8 mL; 6.21 mmol) in ethanol (40 mL). The reaction mixture was then stirred at room temperature for 18 hours and filtered through celite. The volatiles were removed under reduced pressure and the residue was partitioned between ethyl acetate and a saturated aqueous solution of sodium thiosulphate. The organic layer was washed with brine, dried and concentrated under reduced pressure. The crude residue was purified by flash chromatography on silica gel (eluent 2 to 40% ethyl acetate in heptane) to afford 1.08 g (61%) of 2-iodo-4-(trifluoromethyl)aniline as a red oil.
$^1$H NMR (DMSO-$d_6$) δ 7.80 (s, 1H), 7.38 (d, 1H), 6.82 (d, 2H), 5.93 (s, 2H)

Intermediate 133

Preparation of 2-(2-(triethylsilyl)-5-(trifluoromethyl)-1H-indol-3-yl)ethanol 2-iodo-4-(trifluoromethyl)aniline (1.0 g; 3.48 mmol), 4-(triethylsilyl)but-3-yn-1-ol (0.807 mL; 3.83 mmol), Bis(diphenylphosphino)ferrocene]palladium(II) chloride (0.142 g; 0.174 mmol), lithium chloride (0.147 g; 3.48 mmol) and sodium carbonate (0.738 g; 6.97 mmol) were suspended in DMF (10 mL) and the mixture was stirred at 100° C. for 15 hours. The solution was concentrated under reduced pressure and diluted in ethyl acetate. The organic layer was successively washed with brine, sodium thiosulphate, dried and concentrated under reduced pressure. The crude material was purified by flash chromatography on silica gel (eluent 2 to 40% ethyl acetate in heptane) to afford 0.733 g (61%) of the title compound as a yellow oil.
ESI/APCI (+): 344 (M+H).
ESI/APCI (−): 343 (M−H).

Intermediate 134

Preparation of 3-(2-bromoethyl)-2-(triethylsilyl)-5-(trifluoromethyl)-1H-indole A solution 2-(2-(triethylsilyl)-5-(trifluoromethyl)-1H-indol-3-yl)ethanol (0.730 g; 2.13 mmol) in THF (6 mL) was added to a solution of triphenyl phosphine (0.836 g; 3.19 mmol) and perbromomethane (1.06 g; 3.19 mmol) in THF (12 mL) pre-stirred for 1 hour. The resulting mixture was stirred at room temperature for 18 hours. The reaction mixture was then filtered and concentrated under reduced pressure. The crude material was purified by flash chromatography on silica gel (eluent 5 to 40% ethyl acetate in heptane) to afford 0.449 g (52%) of the title compound as a yellow oil.

Intermediate 135

Preparation of 3-(2-azidoethyl)-2-(triethylsilyl)-5-(trifluoromethyl)-1H-indole A mixture of 3-(2-bromoethyl)-2-(triethylsilyl)-5-(trifluoromethyl)-1H-indole (0.448 g; 1.10 mmol) and sodium azide (0.215 g; 3.31 mmol) in DMF (10 mL) was stirred at 70° C. for 4 hours and concentrated under reduced pressure. The residue was diluted in ethyl acetate, washed with brine, dried and concentrated under reduced pressure to give 0.402 g (99%) of the title compound as a brown oil.
ESI/APCI (+): 391 (M+Na).
ESI/APCI (−): 367 (M−H).

Intermediate 136

Preparation of 2-(5-(trifluoromethyl)-1H-indol-3-yl)ethanamine

A mixture of 3-(2-azidoethyl)-2-(triethylsilyl)-5-(trifluoromethyl)-1H-indole (0.400 g; 1.09 mmol) and triphenyl phosphine (0.427 g; 1.63 mmol) in methanol (5 mL) stirred at 70° C. for 2 hours. The reaction mixture was concentrated under reduced pressure. The residue was dissolved in a solution of tetrabutylamonium fluoride (3.26 mL, 1M) in THF and stirred at room temperature for 36 hours and concentrated under reduced pressure to yield 2-(5-(trifluoromethyl)-1H-indol-3-yl)ethanamine which was used without any further purification.

Intermediate 137

Preparation of 5-chloro-2-iodo-4-methylaniline

A solution of iodine (9.86 g; 38.84 mmol) and potassium iodide (6.45 g; 38.84 mmol) in water was added dropwise to a mixture of 3-chloro-4-methylaniline (5.00 g; 35.31 g), sodium bicarbonate (4.75 g; 56.50 mmol) in water. The resulting mixture was stirred 72 hours at room temperature filtrated and the solid dissolved in dichloromethane, washed with a saturated solution of sodium thiosulphate dried and concentrated under reduced pressure. The crude residue was purified by flash chromatography on silica gel (eluent 2 to 20% ethyl acetate in heptane) to yield 2.30 g (24%) of the title compound as a brown solid.

ESI/APCI (+): 268 (M+H).

Intermediate 138

Preparation of 2-(6-chloro-5-methyl-2-(triethylsilyl)-1H-indol-3-yl)ethanol 5-chloro-2-iodo-4-methylaniline (1.50 g; 5.61 mmol), 4-(triethylsilyl)but-3-yn-1-ol (2.36 mL; 11.22 mmol), Bis(diphenylphosphino)ferrocene]palladium(II) chloride (0.229 g; 0.280 mmol), lithium chloride (0.237 g; 5.61 mmol) and sodium carbonate (1.19 g; 11.22 mmol) were suspended in DMF (14 mL) and the mixture was stirred at 100° C. for 15 hours. The mixture was concentrated under reduced pressure and diluted in ethyl acetate. The organic layer was successively washed with brine, sodium thiosulphate, dried and concentrated under reduced pressure. The crude mixture was purified by flash chromatography on silica gel (eluent 2 to 20% ethyl acetate in heptane) to afford 1.44 g (79%) of the title compound as a brown oil.

ESI/APCI (+): 324 (M+H).
ESI/APCI (−): 322 (M−H).

Intermediate 139

Preparation of 3-(2-bromoethyl)-6-chloro-5-methyl-2-(triethylsilyl)-1H-indole

A solution 2-(6-chloro-5-methyl-2-(triethylsilyl)-1H-indol-3-yl)ethanol (1.44 g; 4.45 mmol) in THF (6 mL) was added to a solution of triphenyl phosphine (1.75 g; 6.67 mmol) and perbromomethane (2.21 g; 6.67 mmol) in THF (40 mL) pre-stirred for 30 minutes. The resulting mixture was stirred at room temperature for 18 hours. The reaction mixture was then filtered and concentrated under reduced pressure. The crude residue was purified by flash chromatography on silica gel (eluent 2 to 20% ethyl acetate in heptane) to afford 0.725 g (42%) of the title compound as a brown oil.

Intermediate 140

Preparation of 3-(2-azidoethyl)-6-chloro-5-methyl-2-(triethylsilyl)-1H-indole

A mixture of 3-(2-bromoethyl)-6-chloro-5-methyl-2-(triethylsilyl)-1H-indole (0.725 g; 1.87 mmol) and sodium azide (0.365 g; 5.62 mmol) in DMF (8 mL) was stirred at 70° C. for 4 hours and concentrated under reduced pressure. The residue was diluted in ethyl acetate, washed with brine, dried and concentrated under reduced pressure to afford 0.690 g (quantitative yield) of the title compound as a brown oil.

Intermediate 141

Preparation of 2-(6-chloro-5-methyl-1H-indol-3-yl)ethanamine

A mixture of 3-(2-azidoethyl)-6-chloro-5-methyl-2-(triethylsilyl)-1H-indole (0.654 g; 1.87 mmol) and triphenylphosphine (0.737 g; 2.81 mmol) in methanol (10 mL) was stirred at 70° C. for 2 hours. The reaction mixture was concentrated under reduced pressure and the residue was dissolved in a solution of tetrabutylamonium fluoride (5.62 mL 1M) in THF and stirred at room temperature for 36 hours and concentrated under reduced pressure to yield 2-(6-chloro-5-methyl-1H-indol-3-yl)ethanamine which was used without any further purification.

Intermediate 142

Preparation of 4-amino-3-iodobenzonitrile

Iodine (0.645 g; 2.54 mmol) was added to a stirred mixture of silver sulphate (0.791 g; 2.54 mmol) and 4-aminobenzonitrile (0.300 g; 2.54 mmol) in ethanol (10 mL). The reaction mixture was stirred at room temperature for 18 hours and filtered over celite. The volatiles were removed under reduced pressure and the residue was partitioned between ethyl acetate and a saturated aqueous solution of sodium thiosulphate. The organic layer was washed with brine, dried and concentrated under reduced pressure. The crude residue was purified by flash chromatography on silica gel (eluent 2 to 40% ethyl acetate in heptane) to afford 0.222 g (36%) of the title compound as a white solid.

$^1$H NMR (DMSO-d$_6$) δ 7.96 (d, 1H), 7.45 (dd, 1H), 6.76 (d, 1H), 6.22 (s, 2H).

Intermediate 143

Preparation of 3-(2-hydroxyethyl)-2-(triethylsilyl)-1H-indole-5-carbonitrile 4-amino-3-iodobenzonitrile (1.65 g; 5.61 mmol), 4-(triethylsilyl)but-3-yn-1-ol (1.57 mL; 7.44 mmol), Bis(diphenylphosphino)ferrocene]palladium(II) chloride (0.276 g; 0.338 mmol), lithium chloride (0.287 g; 6.76 mmol), sodium carbonate (1.43 g; 13.52 mmol) in DMF (14 mL) was stirred at 100° C. for 15 hours. The solution was filtered through celite, diluted in ethyl acetate, washed with brine and sodium thiosulphate, dried and concentrated under reduced pressure. The crude mixture was purified by flash chromatography on silica (eluent 2 to 20% ethyl acetate in heptane) to yield 0.873 g (43%) of the title compound as a yellow solid.

ESI/APCI (+): 301 (M+H); ESI/APCI (−): 299 (M−H).

Intermediate 144

Preparation of 3-(2-bromoethyl)-2-(triethylsilyl)-1H-indole-5-carbonitrile

A solution 3-(2-hydroxyethyl)-2-(triethylsilyl)-1H-indole-5-carbonitrile (0.873 g; 2.91 mmol) in THF (6 mL) was added to a solution of triphenylphosphine (1.52 g; 5.81 mmol) and perbromomethane (1.93 g; 5.81 mmol) in THF (30 mL) pre-stirred for 30 minutes. The resulting mixture was stirred at room temperature overnight, filtered and concentrated under reduced pressure. The crude mixture was purified by flash chromatography on silica (eluent 2 to 40% ethyl acetate in heptane) to yield 0.906 g (86%) of the title compound as a white solid.

$^1$H NMR (DMSO-d$_6$) δ 11.19 (s, 1H); 8.21 (s, 1H); 7.53 (d, 1H); 7.41 (d, 1H); 3.65 (t, 2H), 3.33 (t, 2H, hidden by water); 0.96 (m, 15H)

Intermediate 145

Preparation of 3-(2-azidoethyl)-2-(triethylsilyl)-1H-indole-5-carbonitrile

A mixture of 3-(2-bromoethyl)-2-(triethylsilyl)-1H-indole-5-carbonitrile (0.906 g; 2.49 mmol) and sodium azide (0.486 g; 7.48 mmol) in DMF (7 mL) was stirred at 70° C. for 4 hours and concentrated under reduced pressure. The residue was diluted in ethyl acetate, washed with brine, dried and concentrated under reduced pressure to yield 0.900 g (quantitative) of the title compound as a brown oil.
ESI/APCI (−): 324 (M−H).

Intermediate 146

Preparation of N-(2-(5-cyano-2-(triethylsilyl)-1H-indol-3-yl)ethyl)-5-(2,5-difluorobenzyl)isoxazole-3-carboxamide A mixture of 3-(2-azidoethyl)-2-(triethylsilyl)-1H-indole-5-carbonitrile (0.400 g; 1.23 mmol) and triphenylphosphine (0.523 g; 2.00 mmol) in methanol (10 mL) was stirred at 70° C. for 2 hours. The reaction mixture was concentrated under reduced pressure and the crude material was dissolved in a mixture of 5-(2,5-difluorobenzyl)isoxazole-3-carboxylic acid intermediate 74 (0.318 g, 1.33 mmol), HATU (0.506 g; 1.33 mmol) and N,N diisopropylethylamine (0.614 mL; 3.33 mmol) in DMF (10 mL), was stirred at room temperature for 72 hours. The reaction mixture was partitioned between ethyl acetate and sodium hydrogen sulphate; the organic layer was washed with sodium carbonate, brine, dried and concentrated under reduced pressure. The crude mixture was purified by flash chromatography on silica (eluent 2 to 60% ethyl acetate in heptane) to yield 0.338 g (48%) of N-(2-(5-cyano-2-(triethylsilyl)-1H-indol-3-yl)ethyl)-5-(2,5-difluorobenzyl)isoxazole-3-carboxamide as a solid.
ESI/APCI (+): 521 (M+H), 543 (M+Na); ESI/APCI (−): 519 (M−H).

Intermediate 147

Preparation of 4-(triethylsilyl)but-3-ynyl 4-methylbenzenesulfonate

A solution of 4-(triethylsilyl)but-3-yn-1-ol (2 mL; 9.22 mmol), p-toluensulfonyl chloride (3.52 g; 18.44 mmol) and pyridine (1.49 mL; 18.44 mmol) in dichloromethane (30 mL) was stirred at room temperature for 3 days. The reaction mixture was then washed with a saturated solution of sodium hydrogen sulphate and brine. The organic layer was dried, concentrated under reduced pressure and the crude material was purified by flash chromatography on silica gel (eluent 2 to 20% ethyl acetate in heptane) to yield 3.20 g (quantitative yield) of 4-(triethylsilyl)but-3-ynyl 4-methylbenzenesulfonate as a yellow oil.
ESI/APCI (+): 361 (M+Na).

Intermediate 148

Preparation of (4-azidobut-1-ynyl)triethylsilane

Sodium azide (1.80 g; 27.65 mmol) was added to a solution of 4-(triethylsilyl)but-3-ynyl 4-methylbenzenesulfonate (3.12 g; 9.22 mmol) in DMF (15 mL) and stirred at 60° C. for 3 hours. After cooling, the volatiles were removed under reduced pressure and the residue was partitioned between saturated ammonium chloride and ethyl acetate. The organic layer was dried and concentrated under reduced pressure to afford 2.0 g (quantitative yield) of (4-azidobut-1-ynyl)triethylsilane as a colorless oil.
ESI/APCI (+): 419 (2M+H).

Intermediate 149

Preparation of 5-(2,5-difluorobenzyl)-N-(4-(triethylsilyl)but-3-ynyl)isoxazole-3-carboxamide A mixture of (4-azidobut-1-ynyl)triethylsilane (1.00; 4.78 mmol) and triphenylphosphine (1.88 g; 7.16 mmol) in methanol (10 mL) was stirred at 60° C. for two hours. HCl (4N in dioxane was added to resulting solution and the mixture was concentrated under reduced pressure. The residue was dissolved in dichloromethane. HATU (2.18 g; 5.73 mmol), N,N-diisopropylethylamine (2.06 mL; 4.78 mmol) and 5-(2,5-difluorobenzyl)isoxazole-3-carboxylic acid intermediate 74 (1.26 g; 5.25 mmol) were added and the resulting mixture was stirred at room temperature overnight and diluted in dichloromethane, washed with sodium hydrogen sulphate, sodium carbonate and brine and concentrated under reduced pressure. The crude mixture was purified by flash chromatography on silica (eluent 1 to 60% ethyl acetate in heptane) to yield 0.901 g (47%) of 5-(2,5-difluorobenzyl)-N-(4-(triethylsilyl)but-3-ynyl)isoxazole-3-carboxamide as a yellow oil.
ESI/APCI (+): 405 (M+H), 427 (M+Na); ESI/APCI (−): 403 (M−H).

Intermediate 150

Preparation of N-(2-(5-chloro-7-fluoro-2-(triethylsilyl)-1H-indol-3-yl)ethyl)-5-(2,5-difluorobenzyl)isoxazole-3-carboxamide A mixture of 4-chloro-2-fluoro-6-iodoaniline (0.100 g; 0.368 mmol), 5-(2,5-difluorobenzyl)-N-(4-(triethylsilyl)but-3-ynyl)isoxazole-3-carboxamide (0.150 g; 0.347 mmol), Bis (diphenylphosphino)ferrocene]palladium(II) chloride (0.015 g; 0.018 mmol), lithium chloride (0.016 mg; 0.368 mmol), sodium carbonate (0.078 g; 0.737 mmol) in DMF (5 mL) was stirred at 100° C. overnight. The solution was reparted between ethyl acetate and brine, washed with sodium thiosulphate, dried and concentrated under reduced pressure. The crude mixture was purified by flash chromatography on silica (eluent 2 to 60% ethyl acetate in heptane) to yield 0.05 g (25%) of N-(2-(5-chloro-7-fluoro-2-(triethylsilyl)-1H-indol-3-yl)ethyl)-5-(2,5-difluorobenzyl)isoxazole-3-carboxamide as a yellow oil.
ESI/APCI (+): 549 (M+H).

Intermediate 151

Preparation of ethyl 5-phenyl-1,2,4-oxadiazole-3-carboxylate

Benzoyl chloride (0.219 mL; 1.89 mmol) was added to a mixture of ethyl 2-amino-2-(hydroxyimino)acetate (0.250 g; 1.89 mmol) and N,N diisopropylethylamine (0.527 mL; 3.03 mmol) in dichloromethane (18 mL) at −15° C. The reaction mixture was stirred at room temperature overnight and poured into a mixture of ice and water. The aqueous layer was extracted with dichloromethane, and the combined organic extracts were dried and concentrated under reduced pressure. The residue was refluxed in a sealed tube with pyridine (6 mL) for 20 hours and concentrated under reduced pressure. The crude material was purified by flash chromatography on silica (eluent 20 to 100% ethyl acetate in heptane) to yield 0.239 (60%) of ethyl 5-phenyl-1,2,4-oxadiazole-3-carboxylate as a yellow solid.
ESI/APCI (+): 219 (M+H).

Intermediate 152

Preparation of ethyl 5-(2,5-difluorophenyl)-1,2,4-oxadiazole-3-carboxylate

This compound was prepared according to general method 2 with (step I) 2,5-difluorobenzoic acid (0.299 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.172 g (36%) of ethyl 5-(2,5-difluorophenyl)-1,2,4-oxadiazole-3-carboxylate as a white solid.
ESI/APCI (+): 255 (M+H).

Intermediate 153

Preparation of ethyl 5-((5-methyl-2-phenyloxazol-4-yl)methyl)-1,2,4-oxadiazole-3-carboxylate This compound was prepared according to general method 2 with (step I) 2-(5-methyl-2-phenyloxazol-4-yl)acetic acid (0.411 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.076 g (13%) of ethyl 5-((5-methyl-2-phenyloxazol-4-yl)methyl)-1,2,4-oxadiazole-3-carboxylate as a white solid.
ESI/APCI (+): 314 (M+H), 336 (M+Na).

Intermediate 154

Preparation of ethyl 5-(2-fluoro-3-(trifluoromethyl)benzyl)-1,2,4-oxadiazole-3-carboxylate This compound was prepared according to general method 2 with (step I) 2-(2-fluoro-3-(trifluoromethyl)phenyl)acetic acid (0.420 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.085 g (14%) of ethyl 5-(2-fluoro-3-(trifluoromethyl)benzyl)-1,2,4-oxadiazole-3-carboxylate as a white solid.
ESI/APCI (+): 319 (M+H).
ESI/APCI (−): 317 (M−H).

Intermediate 155

Preparation of ethyl 5-(2-fluoro-5-(trifluoromethyl)benzyl)-1,2,4-oxadiazole-3-carboxylate This compound was prepared according to general method 2 with (step I) 2-(2-fluoro-5-(trifluoromethyl)phenyl)acetic acid (0.420 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.116 g (20%) of ethyl 5-(2-fluoro-5-(trifluoromethyl)benzyl)-1,2,4-oxadiazole-3-carboxylate as a white solid.
ESI/APCI (+): 319 (M+H).
ESI/APCI (−): 317 (M−H).

Intermediate 156

Preparation of ethyl 5-(4-fluoro-2-(trifluoromethyl)benzyl)-1,2,4-oxadiazole-3-carboxylate This compound was prepared according to general method 2 with (step I) 2-(4-fluoro-2-(trifluoromethyl)phenyl)acetic acid (0.420 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.063 g (10%) of ethyl 5-(4-fluoro-2-(trifluoromethyl)benzyl)-1,2,4-oxadiazole-3-carboxylate as a white solid.
ESI/APCI (+): 319 (M+H).
ESI/APCI (−): 317 (M−H).

Intermediate 157

Preparation of ethyl 5-(2,3,4-trifluorobenzyl)-1,2,4-oxadiazole-3-carboxylate

This compound was prepared according to general method 2 with (step I) 2-(2,3,4-trifluorophenyl)acetic acid (0.360 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.065 g (12%) of ethyl 5-(2,3,4-trifluorobenzyl)-1,2,4-oxadiazole-3-carboxylate as a white solid.
ESI/APCI (+): 287 (M+H).
ESI/APCI (−): 286 (M−H).

Intermediate 158

Preparation of ethyl 5-(2,4,6-trifluorobenzyl)-1,2,4-oxadiazole-3-carboxylate

This compound was prepared according to General method 2 with (step I) 2-(2,4,6-trifluorophenyl)acetic acid (0.360 g; 1.89 mmol) and oxalyl chloride (0.176 mL; 2.08 mmol) in dichloromethane (12 mL) with few drops of DMF and (step II) ethyl 2-amino-2-(hydroxyimino)acetate (0.250 g; 1.89 mmol) and N,N diisopropylethylamine (0.527 mL; 3.03 mmol) in dichloromethane (10 mL) and (step III) pyridine (18 mL). The crude material was purified by flash chromatography on silica (eluent 20 to 100% ethyl acetate in heptane) to yield 0.1002 g (19%) of ethyl 5-(2,4,6-trifluorobenzyl)-1,2,4-oxadiazole-3-carboxylate as a white solid.
ESI/APCI (+): 287 (M+H).

Intermediate 159

Preparation of 5-chloro-3-iodopyridin-2-amine

Iodine (7.55 g; 29.73 mmol) was added to a mixture of 5-chloropyridin-2-amine (3.00 g; 22.87 mmol) and silver sulphate (9.36 g; 29.73 mmol) in ethanol (150 mL) and the mixture was stirred overnight at room temperature. The mixture was filtered over celite, washed with ethanol, and the filtrate concentrated under reduced pressure. The residue was dissolved in dichloromethane, and the solution was washed with a saturated aqueous solution of sodium thiosulphate. The organic layer was dried over magnesium sulphate, concentrated under reduced pressure and the crude material purified by flash chromatography on silica gel (eluent: 0 to 30% of ethyl acetate in heptane) to give 3.71 g (64%) of 5-chloro-3-iodopyridin-2-amine as a beige solid.

ESI/APCI (+): 255 (M+Na).
$^1$H NMR (CDCl$_3$) δ 7.99 (d, 1H); 7.84 (d, 1H), 4.96 (s, 2H).

Intermediate 160

Preparation of 2-(5-chloro-2-(triethylsilyl)-1H-pyrrolo[2,3-b]pyridin-3-yl)ethanol A mixture of 5-chloro-3-iodopyridin-2-amine (2 g; 7.86 mmol), 4-(triethylsilyl)but-3-yn-1-ol (4.35 g; 23.58 mmol); (1,1'-bis(diphenylphosphino)ferrocene)-dichloromethane (0.321 g; 0.393 mmol), lithium chloride (0.333 g; 7.86 mmol) and sodium carbonate (1.67 g; 15.72 mmol) in DMF (15 mL) was heated at 100° C. for approximately 20 hours. After cooling, the mixture was concentrated under reduced pressure and the residue was partitioned between brine and ethyl acetate. After separation the organic layer was evaporated and the residue was purified by flash chromatography on silica gel (eluent 7 to 80% of ethyl acetate in heptane) to give 2.15 g (88%) of 2-(5-chloro-2-(triethylsilyl)-1H-pyrrolo[2,3-b]pyridin-3-yl)ethanol as a white solid.

ESI/APCI (+): 311 (M+H); ESI/APCI (−): 309 (M−H).

Intermediate 161

Preparation of 3-(2-bromoethyl)-5-chloro-2-(triethylsilyl)-1H-pyrrolo[2,3-b]pyridine Carbon tetrabromide (3.27 g, 9.65 mmol) was added to the solution of triphenylphosphine (2.56 g; 9.65 mmol) in THF (30 ml). The mixture was stirred at room temperature for 30 min. To this green suspension was added a solution of 2-(5-chloro-2-(triethylsilyl)-1H-pyrrolo[2,3-b]pyridin-3-yl)ethanol (2.00 g; 6.43 mmol) in THF (20 mL) and the resulting reaction mixture was stirred for 20 hours. The precipitate was eliminated by filtration and the filtrate was concentrated under reduced pressure. The crude material was purified by flash chromatography (eluent: 5 to 40% of ethyl acetate in heptanes) to give 1.08 g (45%) of 3-(2-bromoethyl)-5-chloro-2-(triethylsilyl)-1H-pyrrolo[2,3-b]pyridine as a white solid.

$^1$H NMR (CDCl$_3$) δ 8.72 (s, 1H); 8.24 (d, 1H); 7.87 (d, 1H); 3.50 (t, 2H), 3.31 (t, 2H) 1.01 (m, 9H); 0.93 (m, 6H).

Intermediate 162

Preparation of 3-(2-azidoethyl)-5-chloro-2-(triethylsilyl)-1H-pyrrolo[2,3-b]pyridine A mixture of 3-(2-bromoethyl)-5-chloro-2-(triethylsilyl)-1H-pyrrolo[2,3-b]pyridine (1.05 g; 2.81 mmol) and sodium azide (0.547 g; 8.43 mmol) in DMF (8 mL) was stirred for 18 hours at 80° C. and was concentrated under reduced pressure. The residue was partitioned between water and dichloromethane. After separation, the dichloromethane solution was dried over MgSO$_4$ and was evaporated to give 0.943 g (100%) of 3-(2-azidoethyl)-5-chloro-2-(triethylsilyl)-1H-pyrrolo[2,3-b]pyridine as a solid.

ESI/APCI (+): 336 (M+H).
ESI/APCI (−): 334 (M−H).

Intermediate 163

Preparation of 2-(5-chloro-2-(triethylsilyl)-1H-pyrrolo[2,3-b]pyridin-3-yl)ethanamine A mixture of 3-(2-azidoethyl)-5-chloro-2-(triethylsilyl)-1H-pyrrolo[2,3-b]pyridine (0.900 g; 2.68 mmol) and triphenylphosphine 1.05 g; 4.02 mmol) in methanol (25 ml) was stirred at 80° C. for 1 hour and was concentrated under reduced pressure. The residue was dissolved in toluene (15 mL). Hydrochloric acid (2 mL) and water 15 mL were added. After separation of the two layers, the aqueous solution was extracted with 3×15 mL of toluene and was made alkaline by addition of a solution of sodium hydroxide 2N. The formed precipitate for filtered off. The filtrate was extracted with dichloromethane (5×15 mL). Combined dichloromethane extracts were dried over magnesium sulphate and was concentrated under reduced pressure to give 0.515 g (62%) of 2-(5-chloro-2-(triethylsilyl)-1H-pyrrolo[2,3-b]pyridin-3-yl) ethanamine as an oily residue.

ESI/APCI (+): 310 (M+H); 293 (M+H—NH$_3$).
ESI/APCI (−): 308 (M−H).

Intermediate 164

Preparation of N-(2-(5-chloro-2-(triethylsilyl)-1H-pyrrolo[2,3-b]pyridin-3-yl)ethyl)-5-(2,5-difluorobenzyl)isoxazole-3-carboxamide A mixture of 2-(5-chloro-2-(triethylsilyl)-1H-pyrrolo[2,3-b]pyridin-3-yl)ethanamine (0.128 g; 0.413 mmol), 5-(2,5-difluorobenzyl)isoxazole-3-carboxylic acid intermediate 74 (0.104 g; 0.434 mmol), HATU (N,N,N',N'-Tetramethyl-O-(7-azabenzotriazol-1-yl)uronium hexafluorophosphate) (0.165 g: 0.434 mmol) and N,N-diisopropylethylamine (0.108 mL; 0.619 mmol) in DMF (3 mL) was stirred overnight at room temperature and concentrated under reduced pressure. The crude material was dissolved in dichloromethane and the organic layer was washed with water and concentrated under reduced pressure. The crude material was purified by flash chromatography on silica gel (eluent: 1 to 10% of ethyl acetate in dichloromethane) to give 0.108 g (49%) of N-(2-(5-chloro-2-(triethylsilyl)-1H-pyrrolo[2,3-b]pyridin-3-yl) ethyl)-5-(2,5-difluorobenzyl)isoxazole-3-carboxamide as a solid.

ESI/APCI (+): 531 (M+H).
ESI/APCI (−): 529 (M−H).

Intermediate 165

Preparation of 2-(5-chloro-1H-pyrrolo[2,3-b]pyridin-3-yl)ethanamine hydrochloride 2-(5-chloro-2-(triethylsilyl)-1H-pyrrolo[2,3-b]pyridin-3-yl)ethanamine (0.360 g; 1.16 mmol) was dissolved in a 1M solution of tetrabutylammonium fluoride in THF (4 mL; 4 mmol). The mixture was stirred overnight at room temperature and was concentrated under reduced pressure. The residue was dissolved in dichloromethane. A 2M solution of hydrogen chloride was added and the formed precipitate collected by filtration and dried under reduced pressure to give 0.239 g (89%) of 2-(5-chloro-1H-pyrrolo[2,3-b]pyridin-3-yl)ethanamine hydrochloride as a beige solid.
ESI/APCI (+): 196 (M+H), 179 (M+H—NH$_3$).

Intermediate 166

Preparation of 3-(5-chloro-1H-indol-3-yl)propanoic acid

A mixture of 5-chloro-1H-indole (2.5 g; 16.49 mmol), acrylic acid (2.49 mL; 36.28 mmol) and acetic anhydride (3.09 mL; 32.98 mmol) in acetic acid was stirred at 100° C. for 48 hours, concentrated under reduced pressure and diluted in NaOH 3N (water), the precipitate was filtered off and the solution acidified to pH 2 and extracted with dichloromethane. The organic phase was dried and concentrated under reduced pressure and the crude material was purified by flash chromatography on silica gel (eluent: 2 to 20% of ethyl acetate in dichloromethane) and (eluent: 15 to 60% of ethyl acetate in heptane) to give 0.900 g (24%) of 3-(5-chloro-1H-indol-3-yl)propanoic acid as a brown solid.
ESI/APCI (+): 224 (M+H)
ESI/APCI (−): 222 (M−H), Intermediate 167

Preparation of tert-butyl 3-benzylimidazolidine-1-carboxylate

N1-benzylethane-1,2-diamine (2.00 mL; 13.31 mmol) was added to a suspension of paraformaldehyde (0.400 g; 13.31 mmol), sodium bicarbonate (3.69 mL; 43.94 mmol) and magnesium sulphate (6.41 g; 53.25 mmol) and stirred at room temperature overnight. Di-tert-butyl dicarbonate (2.91 g; 13.31 mmol) was added and the resulting suspension was stirred for further 18 hours. The suspension was filtered, concentrated under reduced pressure, treated with brine and extracted with dichloromethane dried and concentrated under reduced pressure. The crude material was purified by flash chromatography on silica gel (eluent: 15 to 60% of ethyl acetate in heptane) to yield 2.92 g (83%) of tert-butyl 3-benzylimidazolidine-1-carboxylate.
ESI/APCI (+): 263 (M+H).

Intermediate 168

Preparation of tert-butyl 4-(5-chloro-1H-indol-3-yl)-5,6-dihydropyridine-1(2H)-carboxylate 5-chloro-1H-indole (2.15 g; 13.90 mmol), tert-butyl 4-oxopiperidine-1-carboxylate (3.08 g; 15.29 mmol) and potassium hydroxide (3.67 g; 55.6 mmol) were added in MeOH (50 mL) and heated to reflux for 24 hours. The reaction mixture was cooled to room temperature and poured into ice water (70 mL). The reaction mixture was extracted with dichloromethane. The combined organic extracts were dried over magnesium sulphate and concentrated to give 4.52 g (98%) of tert-butyl 4-(5-chloro-1H-indol-3-yl)-5,6-dihydropyridine-1(2H)-carboxylate as a yellow solid.
ESI/APCI (+): 277 (M+H-isobutene);
ESI/APCI (−): 331 (M−H).

Intermediate 169

Preparation of tert-butyl 4-(5-chloro-1H-indol-3-yl)piperidine-1-carboxylate

Platinum(IV) oxide (0.107 g) was added to the suspension of tert-butyl 4-(5-chloro-1H-indol-3-yl)-5,6-dihydropyridine-1(2H)-carboxylate (1.05 g; 3.15 mmol) in the mixture of ethanol (20 mL) and acetic acid (10 mL). After degassing, the mixture was subjected to hydrogenation for 20 hours and was filtered through celite. The filtrate was concentrated under reduced pressure to give 1.03 g (98%) of tert-butyl 4-(5-chloro-1H-indol-3-yl)piperidine-1-carboxylate as a solid.
ESI/APCI (−): 333 (M−H).

Intermediate 170

Preparation of 5-chloro-3-(piperidin-4-yl)-1H-indole hydrochloride tert-butyl 4-(5-chloro-1H-indol-3-yl)piperidine-1-carboxylate (1 g; 2.99 mmol) was dissolved in 7.5 mL of a 4M solution of HCl in dioxane. The mixture was stirred at room temperature for 2 hours and was concentrated under reduced pressure to give quantitatively 5-chloro-3-(piperidin-4-yl)-1H-indole hydrochloride as a solid.
ESI/APCI (+): 235 (M+H).
ESI/APCI (−): 233 (M−H).

Intermediate 171

Preparation of ethyl oxazole-5-carboxylate 1,8-Diazabicyclo[5.4.0]undec-7-ene (0.574 mL; 3.84 mmol) was added simultaneously with ethyl glyoxalate (50% in toluene, 0.659 mL; 3.33 mmol) to a mixture of tosylmethyl isocyanide (0.500 g; 2.560 mmol) in dichloromethane (10 mL) at 0° C. The resulting mixture was stirred at room temperature for 3 hours, diluted in dichloromethane and washed with sodium hydrogen sulphate, sodium carbonate, dried over magnesium sulphate and concentrated under reduced pressure. The crude mixture was purified by flash chromatography on silica (eluent 5 to 60% ethyl acetate in heptane) to yield 0.194 g (54%) of ethyl oxazole-5-carboxylate as a colorless oil.
ESI/APCI (+): 142 (M+H).

Intermediate 172

Preparation of ethyl 4-phenylisoxazole-3-carboxylate

Ethynylbenzene (0.300 mL; 2.73 mmol) and ethyl 2-chloro-2-(hydroxyimino)acetate (0.455 g; 3.00 mmol) were dissolved in degassed dichloroethane (15 mL), chloro (1,5-cyclooctadiene)(pentamethylcyclopentadienyl)ruthenium (II) (0.052 g; 0.136 mmol) and triethyl amine (0.476 mL; 3.41 mmol) were added and the resulting mixture was stirred at room temperature for 18 hours. The reaction mixture was then filtered through a pad of silica gel and the filtrate was concentrated under reduced pressure. The crude material was purified by flash chromatography on silica (eluent 2 to 20% ethyl acetate in heptane) and by preparative HPLC method 3 to yield 0.030 g (5%) of the title compound as a solid.
ESI/APCI (+): 218 (M+H), 240 (M+Na).

¹H NMR (CDCl₃): δ8.49 (s, 1H), 7.35 (m, 5H), 4.33 (q, 2H), 1.28 (t, 3H).

Intermediate 173

Preparation of tert-butyl 4-(1H-indol-3-yl)piperidine-1-carboxylate

Pd/C 10% (0.25 g) was added to the suspension of tert-butyl 4-(5-chloro-1H-indol-3-yl)-5,6-dihydropyridine-1 (2H)-carboxylate (1.10 g; 3.31 mmol) in a mixture of methanol (100 mL) and ammonium formate (2/1 g; 42.97 mmol). The mixture was refluxed for 20 hours and was filtered through celite. The filtrate was concentrated under reduced pressure and the crude material was purified by flash chromatography on silica gel (eluent: 0 to 10% ethyl acetate in dichloromethane) to give 0.65 g (61%) of the title compound as a pink solid.

ESI/APCI (+): 301 (M+H).
ESI/APCI (−): 299 (M−H).

Intermediate 174

Preparation of 3-(piperidin-4-yl)-1H-indole hydrochloride tert-butyl 4-(1H-indol-3-yl)piperidine-1-carboxylate (0.6 g; 2.0 mmol) was dissolved in 6 mL of a 4M solution of HCl in dioxane. The mixture was stirred at room temperature for 2 hours and was concentrated under reduced pressure to give 0.46 g (97%) of the desired compound as a solid.

ESI/APCI (+): 201 (M+H).
ESI/APCI (−): 199 (M−H).

General Methods for the Preparation of the Compounds of the Invention

Method A:

A mixture of 2-(1H-indol-3-yl)alkylamine (0.346 mmol, 1 equivalent), carboxylic acid (0.380 mmol, 1.1 equivalent), HATU (0.449 mmol, 1.3 equivalent) and N,N-diisopropylethylamine (0.865 mmol, 2.5 equivalent) in DMF (5 mL) was stirred at room temperature overnight and concentrated under reduced pressure. The residue was dissolved in ethyl acetate and the organic layer was washed with water, dried over magnesium sulfate and concentrated under reduced pressure. The crude material was purified by flash chromatography on silica gel to yield the desired compound.

Method B:

Triethylamine (0.811 mmol, 2.5 equivalent) was added to a mixture of 2-(1H-indol-3-yl)alkylamonium chloride (0.324 mmol, 1 equivalent) and acid chloride (0.340 mmol, 1.05 equivalent) in dichloromethane (2 mL) at 0° C. The reaction mixture was allowed to warm at room temperature and stirred until consumption of the amine (0.5 to 24 hours). The reaction mixture was concentrated under reduced pressure and the crude material was purified by flash chromatography on silica gel to yield the desired compound.

Method C:

A mixture of the intermediate 8 (5-(Bromomethyl)-N-(2-(5-chloro-1H-indol-3-yl)ethyl)isoxazole-3-carboxamide) (0.209 mmol, 1 equivalent), a boronic acid (0.219 mmol, 1.05 equivalent), sodium carbonate (0.418 mmol, 2 equivalent) and tetrakis(triphenylphosphine)palladium (0.010 mmol, 0.05 equivalent) or [1,1'-Bis(diphenylphosphino)ferrocene]palladium(II) chloride, complex with dichloromethane (0.01 mmol, 0.05 equivalent) in a mixture of water (1 mL) and dimethoxyethane (3 mL) was irradiated in a microwave oven at 130° C. for 15 min. After cooling, the reaction mixture was partitioned between water and ethyl acetate and the layers were separated. The organic layer was washed with water and concentrated under reduced pressure. The crude material was purified by flash chromatography on silica gel to yield the desired compound.

Method D:

A mixture of the intermediate 8 (5-(Bromomethyl)-N-(2-(5-chloro-1H-indol-3-yl)ethyl)isoxazole-3-carboxamide) (0.260 mmol, 1 equivalent) and an amine (2.6 mmol, 10 equivalent) in THF (2 mL) was irradiated in a microwave oven at 130° C. for 10 min. The mixture was concentrated under reduced pressure and the crude material was purified by flash chromatography on silica gel to yield the desired compound.

Method E:

A mixture of 2-(5-chloro-1H-indol-3-yl)ethanamine hydrochloride (0.433 mmol; 1 equivalent), PyBOP (0.433 mmol; 1 equivalent), N,N diisopropylethylamine (1.08 mmol, 2.5 equivalents) and a 1-(substituted)-2-oxopyrrolidine-3-carboxylic acid (0.433 mmol, 1 equivalent) was stirred in DMF (3 mL) overnight. The reaction mixture was partitioned between ethyl acetate and sodium hydrogen sulphate, the organic layer was washed with sodium carbonate, brine, dried and concentrated under reduced pressure. The crude material was purified flash chromatography on silica to yield the title compound.

Method F

A mixture of an ethyl 5-substituted-1,2,4-oxadiazole-3-carboxylate (0.433 mmol, 1 equivalent) in methanol or THF (1 mL) and sodium hydroxide in water (2M, 5 equivalents) was stirred at room temperature until completion. The reaction mixture is the diluted with water and extracted with dichloromethane. The aqueous layer was acidified with HCl 6N until pH 2 and extracted with ethyl acetate. The combined organic extracts were dried over sodium sulphate and concentrated under reduced pressure. The residue was then added to a mixture of 2-(5-chloro-1H-indol-3-yl)ethanamine hydrochloride (0.433 mmol, 1 equivalent), HATU (0.432 mmol, 1 equivalent) and N,N diisopropylethylamine (0.433 mmol-1.08 mmol, 1-2.5 equivalents) in DMF (4 mL) and was stirred at room temperature overnight. The reaction mixture was diluted in ethyl acetate, washed with sodium disulphate, sodium carbonate and brine, dried and concentrated under reduced pressure. The crude material was purified by flash chromatography on silica to yield the desired compounds.

Example 1

Preparation of N-(2-(5-chloro-1H-indol-3-yl)ethyl)-1-methyl-5-(thiophen-2-yl)-1H-pyrazole-3-carboxamide N-(2-(5-chloro-1H-indol-3-yl)ethyl)-1-methyl-5-(thiophen-2-yl)-1H-pyrazole-3-carboxamide was prepared according to method B with 1-methyl-5-thien-2-yl-1H-pyrazole-3-carbonyl chloride (0.077 g; 0.340 mmol), 2-(5-chloro-1H-indol-3-yl)ethanammonium chloride (0.075 g; 0.324 mmol), triethylamine (0.117 mL; 0.811 mmol) in dichloromethane (2 mL). The crude material was purified by flash chromatography on silica gel (eluent 2 to 10% ethyl acetate in dichloromethane) to afford N-(2-(5-chloro-1H-indol-3-yl)ethyl)-1-methyl-5-(thiophen-2-yl)-1H-pyrazole-3-carboxamide 0.0388 g (31%).

ESI/APCI (+): 385 (M+H), 407 (M+Na).

¹H NMR (DMSO-d₆) δ 11.03 (1H, s), 8.31 (2H, t), 7.77 (1H, dd), 7.66 (1H, d), 7.47 (1H, dd), 7.35 (1H, d), 7.27 (1H, d) 7.24 (1H, dd), 7.06 (1H, dd), 6.84 (1H, s), 4.00 (3H, s), 3.49 (2H, m), 2.90 (2H, t).

Example 2

Preparation of N-(2-(5-chloro-1H-indol-3-yl)ethyl)-5-(4-chlorophenyl)-2-(trifluoromethyl)furan-3-carboxamide N-(2-(5-chloro-1H-indol-3-yl)ethyl)-5-(4-chlorophenyl)-2-(trifluoromethyl)furan-3-carboxamide was prepared according to method B with 5-(4-chlorophenyl)-2-(trifluoromethyl)furan-3-carbonyl chloride (0.105 g; 0.340 mmol), 2-(5-chloro-1H-indol-3-yl)ethanammonium chloride (0.075 g; 0.324 mmol), triethylamine (0.117 mL; 0.811 mmol) in dichloromethane (2 mL). The crude was purified by flash chromatography on silica gel (eluent 2 to 10% ethyl acetate in dichloromethane) to afford N-(2-(5-chloro-1H-indol-3-yl)ethyl)-5-(4-chlorophenyl)-2-(trifluoromethyl)furan-3-carboxamide 0.117 g (77%).

ESI/APCI (+): 467 (M+H), 489 (M+Na).
¹H NMR (DMSO-d₆) 11.08 (1H, s), 8.75 (1H, t), 7.78 (2H, d) 7.60 (3H, m), 7.41 (1H, s), 7.38 (1H, d), 7.30 (1H, d), 7.07 (1H, dd), 3.50 (2H, m), 2.93 (2H, t).

Example 3

Preparation of N-(2-(5-chloro-1H-indol-3-yl)ethyl)-5-(4-chlorophenyl)-2-methylfuran-3-carboxamide N-(2-(5-chloro-1H-indol-3-yl)ethyl)-5-(4-chlorophenyl)-2-methylfuran-3-carboxamide was prepared according to method B with 5-(4-chlorophenyl)-2-methylfuran-3-carbonyl chloride (0.869 g; 0.340 mmol), 2-(5-chloro-1H-indol-3-yl)ethanammonium chloride (0.075 g; 0.324 mmol), triethylamine (0.117 mL; 0.811 mmol) in dichloromethane (2 mL). The crude was purified by flash chromatography on silica gel (eluent 2 to 10% ethyl acetate in dichloromethane) to afford N-(2-(5-chloro-1H-indol-3-yl)ethyl)-5-(4-chlorophenyl)-2-methylfuran-3-carboxamide 0.021 g (16%).

ESI/APCI (+): 413 (M+H), 435 (M+Na).
¹H NMR (DMSO-d₆) 11.05 (1H, s), 8.20 (1H, t), 7.63 (2H, d), 7.62 (1H, s), 7.50 (2H, d), 7.36 (1H, d), 7.28 (1H, d), 7.25 (1H, s), 7.06 (1H, dd), 3.46 (2H, m), 2.9 (2H, t).

Example 4

Preparation of N-(2-(5-chloro-1H-indol-3-yl)ethyl)-5-(furan-2-yl)isoxazole-3-carboxamide N-(2-(5-chloro-1H-indol-3-yl)ethyl)-5-(furan-2-yl)isoxazole-3-carboxamide was prepared according to method B with 5-(2furyl)isoxazole-3-carbonyl chloride (0.0897 g; 0.454 mmol), 2-(5-chloro-1H-indol-3-yl)ethanammonium chloride (0.100 g; 0.432 mmol), triethylamine (0.156 mL; 1.08 mmol) in dichloromethane (2 mL). The crude was purified by flash chromatography on silica gel (eluent 2 to 10% ethyl acetate in dichloromethane) to afford N-(2-(5-chloro-1H-indol-3-yl)ethyl)-5-(furan-2-yl)isoxazole-3-carboxamide 0.063 g (40%).

ESI/APCI (+): 478 (M+Na).

Example 5

Preparation of N-(2-(5-chloro-1H-indol-3-yl)ethyl)-5-(thiophen-2-yl)isoxazole-3-carboxamide N-(2-(5-chloro-1H-indol-3-yl)ethyl)-5-(thiophen-2-yl)isoxazole-3-carboxamide was prepared according to method B with 5-(2-thienyl)-3-isoxazolecarbonyl chloride (0.097 g; 0.454 mmol), 2-(5-chloro-1H-indol-3-yl)ethanammonium chloride (0.100 g; 0.432 mmol), triethylamine (0.156 mL; 1.08 mmol) in dichloromethane (2 mL). The crude was purified by flash chromatography on silica gel (eluent 2 to 10% ethyl acetate in dichloromethane) to afford N-(2-(5-chloro-1H-indol-3-yl)ethyl)-5-(thiophen-2-yl)isoxazole-3-carboxamide
0.0476 g (30%).
ESI/APCI (+): 394 (M+Na).

Example 6

Preparation of N-(2-(5-chloro-1H-indol-3-yl)ethyl)-1-methyl-5-phenyl-1H-pyrazole-3-carboxamide N-(2-(5-chloro-1H-indol-3-yl)ethyl)-1-methyl-5-phenyl-1H-pyrazole-3-carboxamide was prepared according to method B with 1-methyl-5-phenyl-1h-pyrazole-3-carbonyl chloride (0.100 g; 0.454 mmol), 2-(5-chloro-1H-indol-3-yl)ethanammonium chloride (0.100 g; 0.432 mmol), triethylamine (0.156 mL; 1.08 mmol) in dichloromethane (2 mL). The crude was purified by flash chromatography on silica gel (eluent 2 to 10% ethyl acetate in dichloromethane) to afford N-(2-(5-chloro-1H-indol-3-yl)ethyl)-1-methyl-5-phenyl-1H-pyrazole-3-carboxamide 0.121 g (76%).

ESI/APCI (+): 369 (M+H), 391 (M+Na).

Example 7

Preparation of N-(2-(5-chloro-1H-indol-3-yl)ethyl)-4-methyl-2-p-tolylthiazole-5-carboxamide This compound was prepared following Method A starting from 2-(5-chloro-1H-indol-3-yl)ethanamine hydrochloride (0.080 g; 0.339 mmol), INTERMEDIATE 35—4-methyl-2-p-tolylthiazole-5-carboxylic acid (0.087 g; 0.373 mmol), HATU (0.142 g; 0.373 mmol) and N,N-diisopropylethylamine (0.148 mL; 0.848 mmol) in DMF (3 mL). Flash chromatography on silica gel eluting with 1 to 10% of ethyl acetate in dichloromethane gave 0.053 g (38%) of N-(2-(5-chloro-1H-indol-3-yl)ethyl)-4-methyl-2-p-tolylthiazole-5-carboxamide as a solid.

ESI/APCI (+): 410 (M+H), 432 (M+Na).
¹H NMR (DMSO-d₆) δ 11.05 (s, 1H); 8.33 (br s, 1H); 7.82 (d, 2H), 7.62 (s, 1H); 7.32 (m, 4H); 7.06 (d, 1H); 3.47 (m, 2H); 2.92 (t, 2H); 2.55 (s, 3H); 2.36 (s, 3H).

Example 8

Preparation of N-(2-(5-Chloro-1H-indol-3-yl)ethyl)-4-methyl-2-phenylthiazole-5-carboxamide This compound was obtained following Method B starting from 2-(5-chloro-1H-indol-3-yl)ethanamine hydrochloride (0.0452 g, 0.192 mmol), 4-methyl-2-phenylthiazole-5-carbonyl chloride (0.047 g; 0.192 mmol), and triethylamine (0.067 mL; 0.479 mmol) in dichloromethane (3 mL). Flash chromatography on silica gel eluting with 3 to 30% of ethyl acetate in dichloromethane gave 0.0571 g (75%) of N-(2-(5-chloro-1H-indol-3-yl)ethyl)-4-methyl-2-phenylthiazole-5-carboxamide as a solid.

ESI/APCI (+): 396 (M+H); ESI/APCI (−): 394 (M−H).

$^1$H NMR (DMSO-d$_6$) δ 11.06 (s, 1H); 8.37 (t, 1H); 7.93 (m, 2H), 7.63 (s, 1H); 7.53 (m, 3H); 7.36 (d, 1H); 7.29 (s, 1H); 7.07 (d, 1H); 3.49 (q, 2H); 2.93 (t, 2H); 2.57 (s, 3H).

Example 9

Preparation of N-(2-(5-Chloro-1H-indol-3-yl)ethyl)-2-phenylthiazole-4-carboxamide This compound was obtained following Method B starting from 2-(5-chloro-1H-indol-3-yl)ethanamine hydrochloride (0.0441 g, 0.187 mmol), 2-phenylthiazole-4-carbonyl chloride (0.044 g; 0.187 mmol), and triethylamine (0.066 mL; 0.467 mmol) in dichloromethane (3 mL). Flash chromatography on silica gel eluting with 3 to 30% of ethyl acetate in dichloromethane gave 0.047 g (66%) of N-(2-(5-chloro-1H-indol-3-yl)ethyl)-2-phenylthiazole-4-carboxamide as a solid.

ESI/APCI (+): 382 (M+H); ESI/APCI (−): 380 (M−H).

$^1$H NMR (DMSO-d$_6$) δ 11.06 (s, 1H); 8.64 (t, 1H); 8.30 (s, 1H); 8.04 (d, 2H); 7.69 (s, 1H); 7.54 (m, 3H); 7.36 (d, 1H); 7.31 (s, 1H); 7.06 (d, 1H); 3.56 (q, 2H); 2.96 (t, 2H).

Example 10

Preparation of N-(2-(5-Chloro-1H-indol-3-yl)ethyl)-4-methyl-2-(pyrazin-2-yl)thiazole-5-carboxamide This compound was obtained following Method B starting from 2-(5-chloro-1H-indol-3-yl)ethanamine hydrochloride (0.0486 g, 0.190 mmol), 4-methyl-2-(pyrazin-2-yl)thiazole-5-carbonyl chloride (0.047 g; 0.190 mmol), and triethylamine (0.067 mL; 0.475 mmol) in dichloromethane (3 mL). Flash chromatography on silica gel eluting with 3 to 30% of ethyl acetate in dichloromethane gave 0.0427 g (56%) of N-(2-(5-chloro-1H-indol-3-yl)ethyl)-4-methyl-2-(pyrazin-2-yl)thiazole-5-carboxamide as a solid.

ESI/APCI (+): 398 (M+H)

ESI/APCI (−): 396 (M−H).

$^1$H NMR (DMSO-d$_6$) δ 11.07 (s, 1H); 9.31 (s, 1H); 8.77 (d, 2H); 8.50 (t, 1H); 7.62 (s, 1H); 7.36 (d, 1H); 7.29 (s, 1H); 7.07 (d, 1H); 3.50 (m, 2H); 2.94 (t, 2H), 2.61 (s, 3H).

Example 11

Preparation of N-(2-(5-Chloro-1H-indol-3-yl)ethyl)-5-methyl-3-phenylisoxazole-4-carboxamide This compound was obtained following Method B starting from 2-(5-chloro-1H-indol-3-yl)ethanamine hydrochloride (0.0421 g, 0.179 mmol), 5-methyl-3-phenylisoxazole-4-carbonyl chloride (0.044 g; 0.179 mmol), and triethylamine (0.063 mL; 0.447 mmol) in dichloromethane (3 mL). Flash chromatography on silica gel eluting with 2 to 20% of ethyl acetate in dichloromethane gave 0.016 g (24%) of N-(2-(5-chloro-1H-indol-3-yl)ethyl)-5-methyl-3-phenylisoxazole-4-carboxamide as a solid.

ESI/APCI (+): 380 (M+H).

ESI/APCI (−): 378 (M−H).

Example 12

Preparation of N-(2-(5-Chloro-1H-indol-3-yl)ethyl)-4-methyloxazole-5-carboxamide This compound was obtained following Method B starting from 2-(5-chloro-1H-indol-3-yl)ethanamine hydrochloride (0.0456 g, 0.193 mmol), 4-methyloxazole-5-carbonyl chloride (0.029 g; 0.193 mmol), and triethylamine (0.068 mL; 0.483 mmol) in dichloromethane (3 mL). Flash chromatography on silica gel eluting with 4 to 30% of ethyl acetate in dichloromethane gave 0.0458 g (78%) of N-(2-(5-Chloro-1H-indol-3-yl)ethyl)-4-methyloxazole-5-carboxamide as a solid.

ESI/APCI (+): 304 (M+H).

ESI/APCI (−): 302 (M−H).

$^1$H NMR (DMSO-d$_6$) δ 11.04 (s, 1H); 8.52 (t, 1H); 8.42 (s, 1H); 7.61 (s, 1H); 7.35 (d, 1H); 7.27 (s, 1H); 7.06 (d, 1H); 3.46 (m, 2H); 2.90 (t, 2H); 2.39 (s, 3H).

Example 13

Preparation of N-(2-(5-Chloro-1H-indol-3-yl)ethyl)-5-phenyloxazole-4-carboxamide This compound was obtained following Method B starting from 2-(5-chloro-1H-indol-3-yl)ethanamine hydrochloride (0.0452 g, 0.192 mmol), 5-phenyl-1,3-oxazole-4-carbonyl chloride (0.041 g; 0.192 mmol), and triethylamine (0.0672 mL; 0.479 mmol) in dichloromethane (3 mL). Flash chromatography on silica gel eluting with 2 to 16% of ethyl acetate in dichloromethane gave 0.028 g (40%) of N-(2-(5-chloro-1H-indol-3-yl)ethyl)-5-phenyloxazole-4-carboxamide as a solid.

ESI/APCI (+): 366 (M+H).

ESI/APCI (−): 364 (M−H).

Example 14

Preparation of N-(2-(5-chloro-1H-indol-3-yl)ethyl)-3-methyl-5-phenylisoxazole-4-carboxamide This compound was obtained following Method B starting from 2-(5-chloro-1H-indol-3-yl)ethanamine hydrochloride (0.0454 g, 0.193 mmol), 3-methyl-5-phenyl-4-isoxazolecarbonyl chloride (0.044 g; 0.193 mmol), and triethylamine (0.068 mL; 0.481 mmol) in dichloromethane (3 mL). Flash chromatography on silica gel eluting with 2 to 20% of ethyl acetate in dichloromethane gave 0.0614 g (84%) of N-(2-(5-chloro-1H-indol-3-yl)ethyl)-3-methyl-5-phenylisoxazole-4-carboxamide as a solid.

ESI/APCI (+): 380 (M+H).

ESI/APCI (−): 378 (M−H).

Example 15

Preparation of N-(2-(5-Chloro-1H-indol-3-yl)ethyl)-2,5-dimethyloxazole-4-carboxamide This compound was obtained following Method B starting from 2-(5-chloro-1H-indol-3-yl)ethanamine hydrochloride (0.0459 g, 0.195 mmol), 2,5-dimethyl-1,3-oxazole-4-carbonyl chloride (0.032 g; 0.195 mmol), and triethylamine (0.0683 mL; 0.486 mmol) in dichloromethane (3 mL). Flash chromatography on silica gel eluting with 2 to 20% of ethyl acetate in dichloromethane gave 0.0414 g (67%) of N-(2-(5-Chloro-1H-indol-3-yl)ethyl)-2,5-dimethyloxazole-4-carboxamide as a solid.
ESI/APCI (+): 318 (M+H).
ESI/APCI (−): 316 (M−H).

Example 16

Preparation of N-(2-(5-Chloro-1H-indol-3-yl)ethyl)-5-methyl-2-phenyloxazole-4-carboxamide This compound was obtained following Method B starting from 2-(5-chloro-1H-indol-3-yl)ethanamine hydrochloride (0.0454 g, 0.193 mmol), 5-methyl-2-phenyl-1,3-oxazole-4-carbonyl chloride (0.044 g; 0.193 mmol), and triethylamine (0.0676 mL; 0.481 mmol) in dichloromethane (3 mL). Flash chromatography on silica gel eluting with 2 to 20% of ethyl acetate in dichloromethane gave 0.0555 g (76%) of N-(2-(5-chloro-1H-indol-3-yl)ethyl)-5-methyl-2-phenyloxazole-4-carboxamide as a solid.
ESI/APCI (+): 380 (M+H).
ESI/APCI (−): 378 (M−H).

Example 17

Preparation of N-(2-(5-Chloro-1H-indol-3-yl)ethyl)-5-phenylisoxazole-3-carboxamide This compound was obtained following Method B starting from 2-(5-chloro-1H-indol-3-yl)ethanamine hydrochloride (0.0419 g, 0.178 mmol), 5-phenylisoxazole-3-carbonyl chloride (0.041 g; 0.178 mmol), and triethylamine (0.0624 mL; 0.444 mmol) in dichloromethane (3 mL). Flash chromatography on silica gel eluting with 2 to 16% of ethyl acetate in dichloromethane gave 0.022 g (34%) of N-(2-(5-chloro-1H-indol-3-yl)ethyl)-5-phenylisoxazole-3-carboxamide as a solid.
ESI/APCI (+): 366 (M+H).
ESI/APCI (−): 364 (M−H).

Example 18

Preparation of N-(2-(5-Chloro-1H-indol-3-yl)ethyl)-5-phenyl-1,3,4-oxadiazole-2-carboxamide This compound was obtained following Method B starting from 2-(5-chloro-1H-indol-3-yl)ethanamine hydrochloride (0.0417 g, 0.177 mmol), 5-phenyl-1,3,4-oxadiazole-2-carbonyl chloride (0.041 g; 0.177 mmol), and triethylamine (0.0621 mL; 0.442 mmol) in dichloromethane (3 mL). Flash chromatography on silica gel eluting with 2 to 16% of ethyl acetate in dichloromethane gave 0.0223 g (34%) of N-(2-(5-chloro-1H-indol-3-yl)ethyl)-5-phenyl-1,3,4-oxadiazole-2-carboxamide as a solid.
ESI/APCI (+): 367 (M+H).
ESI/APCI (−): 365 (M−H).

Example 19

Preparation of N-(2-(5-Chloro-1H-indol-3-yl)ethyl)-1-phenyl-1H-pyrazole-5-carboxamide This compound was obtained following Method B starting from 2-(5-chloro-1H-indol-3-yl)ethanamine hydrochloride (0.0454 g, 0.192 mmol), 1-phenyl-1H-pyrazole-5-carbonyl chloride (0.041 g; 0.192 mmol), and triethylamine (0.068 mL; 0.481 mmol) in dichloromethane (3 mL). Flash chromatography on silica gel eluting with 4 to 30% of ethyl acetate in dichloromethane gave 0.044 g (63%) of N-(2-(5-chloro-1H-indol-3-yl)ethyl)-1-phenyl-1H-pyrazole-5-carboxamide as a solid.
ESI/APCI (+): 365 (M+H); ESI/APCI (−): 364 (M−H).
$^1$H NMR (DMSO-d$_6$) δ 11.06 (s, 1H); 8.74 (t, 1H); 7.71 (s, 1H); 7.57 (s, 1H); 7.38 (m, 4H); 7.28 (m, 3H); 7.06 (d, 1H); 6.79 (s, 1H); 3.44 (q, 2H), 2.88 (t, 2H).

Example 20

Preparation of N-(2-(5-Chloro-1H-indol-3-yl)ethyl)-1-methyl-1H-pyrazole-3-carboxamide This compound was obtained following Method B starting from 2-(5-chloro-1H-indol-3-yl)ethanamine hydrochloride (0.0443 g, 0.188 mmol), 1-methyl-1H-pyrazole-3-carbonyl chloride (0.028 g; 0.188 mmol), and triethylamine (0.066 mL; 0.470 mmol) in dichloromethane (3 mL). Flash chromatography on silica gel eluting with 2 to 16% of ethyl acetate in dichloromethane gave 0.0367 g (65%) of N-(2-(5-chloro-1H-indol-3-yl)ethyl)-1-methyl-1H-pyrazole-3-carboxamide as a solid.
ESI/APCI (+): 303 (M+H).
ESI/APCI (−): 301 (M−H).
$^1$H NMR (DMSO-d$_6$) δ 11.03 (s, 1H); 8.20 (s, 1H); 7.76 (s, 1H); 7.66 (s, 1H), 7.35 (d, 1H); 7.26 (s, 1H); 7.06 (d, 1H); 6.61 (s, 1H); 3.89 (s, 3H); 3.47 (m, 2H); 2.89 (t, 2H).

Example 21

Preparation of N-(2-(5-Chloro-1H-indol-3-yl)ethyl)-1-methyl-1H-pyrazole-5-carboxamide This compound was obtained following Method B starting from 2-(5-chloro-1H-indol-3-yl)ethanamine hydrochloride (0.0443 g, 0.188 mmol), 1-methyl-1H-pyrazole-5-carbonyl chloride (0.028 g; 0.188 mmol), and triethylamine (0.066 mL; 0.470 mmol) in dichloromethane (3 mL). Flash chromatography on silica gel eluting with 2 to 16% of ethyl acetate in dichloromethane gave 0.0487 g (86%) of N-(2-(5-chloro-1H-indol-3-yl)ethyl)-1-methyl-1H-pyrazole-5-carboxamide as a solid.
ESI/APCI (+): 303 (M+H).
ESI/APCI (−): 301 (M−H).
$^1$H NMR (DMSO-d$_6$) δ 11.05 (s, 1H), 8.59 (s, 1H); 7.61 (1, 1H); 7.45 (s, 1H); 7.36 (d, 1H); 7.27 (s, 1H); 7.06 (d, 1H); 6.79 (s, 1H); 4.05 (s, 3H); 3.47 (m, 2H); 2.92 (t, 2H).

Example 22

Preparation of 1-Benzyl-3-tert-butyl-N-(2-(5-chloro-1H-indol-3-yl)ethyl)-1H-pyrazole-5-carboxamide This compound was obtained following Method B starting from 2-(5-chloro-1H-indol-3-yl)ethanamine hydrochloride (0.0445 g, 0.189 mmol), 1-benzyl-3-(tert-butyl)-1H-pyrazole-5-carbonyl chloride (0.055 g; 0.189 mmol), and triethylamine (0.0663 mL; 0.472 mmol) in dichloromethane (3 mL). Flash chromatography on silica gel eluting with 2 to 16% of ethyl acetate in dichloromethane gave 0.0485 g (59%) of 1-benzyl-3-tert-butyl-N-(2-(5-chloro-1H-indol-3-yl)ethyl)-1H-pyrazole-5-carboxamide as a solid.
ESI/APCI (+): 435 (M+H).
ESI/APCI (−): 433 (M−H).

¹H NMR (DMSO-d₆) δ 11.03 (s, 1H); 8.53 (t, 1H), 7.58 (s, 1H); 7.31 (m, 5H); 7.08 (m, 3H); 5.67 (s, 2H); 3.44 (q, 2H); 2.86 (t, 2H); 1.25 (s, 9H).

Example 23

Preparation of N-(2-(5-Chloro-1H-indol-3-yl)ethyl)-5-methyl-2-phenyl-2H-1,2,3-triazole-4-carboxamide This compound was obtained following Method B starting from 2-(5-chloro-1H-indol-3-yl)ethanamine hydrochloride (0.0454 g, 0.193 mmol), 5-methyl-2-phenyl-2H-1,2,3-triazole-4-carbonyl chloride (0.044 g; 0.193 mmol), and triethylamine (0.0676 mL; 0.481 mmol) in dichloromethane (3 mL). Flash chromatography on silica gel eluting with 2 to 16% of ethyl acetate in dichloromethane gave 0.0453 g (62%) of N-(2-(5-chloro-1H-indol-3-yl)ethyl)-5-methyl-2-phenyl-2H-1,2,3-triazole-4-carboxamide as a solid.

ESI/APCI (+): 380 (M+H).
ESI/APCI (−): 378 (M−H).
$^1$H NMR (DMSO-d$_6$) δ 11.06 (s, 1H), 8.66 (s, 1H); 8.04 (d, 2H); 7.63 (m, 3H); 7.37 (m, 3H); 7.08 (d, 1H); 3.53 (br s, 2H); 2.96 (br s, 2H); 2.53 (s, 3H).

Example 24

Preparation of N-(2-(5-Chloro-1H-indol-3-yl)ethyl)-5-methylisoxazole-3-carboxamide This compound was obtained following Method B starting from 2-(5-chloro-1H-indol-3-yl)ethanamine hydrochloride (0.046 g, 0.193 mmol), 5-methylisoxazole-3-carbonyl chloride (0.029 g; 0.193 mmol), and triethylamine (0.068 mL; 0.483 mmol) in dichloromethane (3 mL). Flash chromatography on silica gel eluting with 2 to 20% of ethyl acetate in dichloromethane gave 0.040 g (68%) of N-(2-(5-Chloro-1H-indol-3-yl)ethyl)-5-methylisoxazole-3-carboxamide as a solid.

ESI/APCI (+): 304 (M+H).
ESI/APCI (−): 302 (M−H).

Example 25

Preparation of N-(2-(5-chloro-1H-indol-3-yl)ethyl)-5-(hydroxymethyl)isoxazole-3-carboxamide This compound was prepared following Method A starting from 2-(5-chloro-1H-indol-3-yl)ethanamine hydrochloride (0.500 g; 2.12 mmol), intermediate 5 (0.303 g; 2.12 mmol), HATU (0.887 g; 2.33 mmol) and N,N-diisopropylethylamine (0.699 g; 5.30 mmol) in DMF (5 mL). Flash chromatography on silica gel eluting with 1 to 15% of methanol in dichloromethane gave 0.528 g (78%) of N-(2-(5-chloro-1H-indol-3-yl)ethyl)-5-(hydroxymethyl)isoxazole-3-carboxamide as a solid.

ESI/APCI (+): 320 (M+H), 342 (M+Na).
$^1$H NMR (DMSO-d$_6$) δ 11.04 (s, 1H); 8.86 (t, 1H); 7.62 (d, 1H); 7.35 (d, 1H); 7.26 (d, 1H); 7.06 (dd, 1H); 6.64 (s, 1H); 5.75 (t, 1H); 4.60 (d, 2H); 3.48 (q, 2H); 2.91 (t, 2H).

Example 26

Preparation of N-(2-(5-chloro-1H-indol-3-yl)ethyl)-5-(4-cyanobenzyl)isoxazole-3-carboxamide N-(2-(5-chloro-1H-indol-3-yl)ethyl)-5-(4-cyanobenzyl)isoxazole-3-carboxamide was prepared according to method C with the Intermediate 8 (5-(Bromomethyl)-N-(2-(5-chloro-1H-indol-3-yl)ethyl)isoxazole-3-carboxamide) (0.070 g; 0.183 mmol), 4-cyanophenylboronic acid (0.028 g; 0.192 mmol), sodium carbonate (0.039 g; 0.365 mmol), tetrakis (triphenylphosphine)palladium (0.011 g; 0.009 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(4-cyanobenzyl)isoxazole-3-carboxamide 0.016 g (22%).

ESI/APCI (+): 405 (M+H) 427 (M+Na).
$^1$H NMR (DMSO-d$_6$) 11.03 (1H, s), 8.83 (1H, t), 7.84 (2H, d), 7.60 (1H, d), 7.52 (2H, d), 7.35 (1H, d), 7.26 (1H, d), 7.05 (1H, dd), 6.57 (1Hs), 4.35 (2H, s), 3.47 (2H, m), 2.90 (2H, t).

Example 27

Preparation of N-(2-(5-chloro-1H-indol-3-yl)ethyl)-5-(3-cyanobenzyl)isoxazole-3-carboxamide N-(2-(5-chloro-1H-indol-3-yl)ethyl)-5-(3-cyanobenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.060 g; 0.152 mmol), 3-cyanophenylboronic acid (0.024 g; 0.160 mmol), sodium carbonate (0.033 g; 0.305 mmol), tetrakis (triphenylphosphine)palladium (0.0088 g; 0.008 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3-cyanobenzyl)isoxazole-3-carboxamide 0.004 g (7%).

ESI/APCI (+): 405 (M+H).
$^1$H NMR (DMSO-d$_6$) 11.03 (1H, s), 8.83 (1H, t), 7.82 (1H, s), 7.78 (1H, d), 7.67 (1H, d), 7.60 (3H, m), 7.34 (1H, d), 7.26 (1H, d), 7.05 (1H, dd), 4.30 (2H, s), 3.47 (2H, m), 2.90 (2H, t).

Example 28

Preparation of N-(2-(5-chloro-1H-indol-3-yl)ethyl)-5-(2-methoxybenzyl)isoxazole-3-carboxamide N-(2-(5-chloro-1H-indol-3-yl)ethyl)-5-(2-methoxybenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.070 g; 0.182 mmol), 2-methoxyphenylboronic acid (0.030 g; 0.192 mmol), sodium carbonate (0.040 g; 0.365 mmol), tetrakis(triphenylphosphine)palladium (0.0106 g; 0.001 mmol) in water (1 mL) and dimethoxyethane (3 mL). The crude material was purified by flash chromatography on silica gel (eluent 2 to 10% ethyl acetate in dichloromethane) to N-(2-(5-chloro-1H-indol-3-yl)ethyl)-5-(2-methoxybenzyl)isoxazole-3-carboxamide 0.015 g (21%).

ESI/APCI (+): 410 (M+H), 432 (M+Na).
ESI/APCI (−): 408 (M−H).

Example 29

Preparation of N-(2-(5-chloro-1H-indol-3-yl)ethyl)-5-(3-methoxybenzyl)isoxazole-3-carboxamide N-(2-(5-chloro-1H-indol-3-yl)ethyl)-5-(3-methoxybenzyl)isoxazole-3-carboxamide was prepared according to method C with the intermediate 8 (5-(Bromomethyl)-N-(2-(5-chloro-1H-indol-3-yl)ethyl)isoxazole-3-carboxamide)

(0.070 g; 0.182 mmol), 3-methoxyphenylboronic acid (0.029 g; 0.192 mmol), sodium carbonate (0.040 g; 0.366 mmol), tetrakis(triphenylphosphine)palladium (0.0106 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3-methoxybenzyl)isoxazole-3-carboxamide 0.010 g (13%).

ESI/APCI (+): 410 (M+H), 432 (M+Na).
ESI/APCI (−): 408 (M−H).

Example 30

Preparation of N-(2-(5-chloro-1H-indol-3-yl)ethyl)-5-(4-methylbenzyl)isoxazole-3-carboxamide N-(2-(5-chloro-1H-indol-3-yl)ethyl)-5-(4-methylbenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), p-tolylboronic acid (0.030 g; 0.220 mmol), sodium carbonate (0.044 g; 0.418 mmol), tetrakis(triphenylphosphine)palladium (0.012 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(4-methylbenzyl)isoxazole-3-carboxamide 0.049 g (60%).

ESI/APCI (+): 394 (M+H), 416 (M+Na).
ESI/APCI (−): 392 (M−H).

Example 31

Preparation of N-(2-(5-chloro-1H-indol-3-yl)ethyl)-5-(3-methylbenzyl)isoxazole-3-carboxamide N-(2-(5-chloro-1H-indol-3-yl)ethyl)-5-(3-methylbenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), m-tolylboronic acid (0.030 g; 0.220 mmol), sodium carbonate (0.044 g; 0.418 mmol), tetrakis(triphenylphosphine)palladium (0.012 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3-methylbenzyl)isoxazole-3-carboxamide (0.055 g, 68%).

ESI/APCI (+): 394 (M+H), 416 (M+Na).
ESI/APCI (−): 392 (M−H).

Example 32

Preparation of N-(2-(5-chloro-1H-indol-3-yl)ethyl)-5-(4-(trifluoromethyl)benzyl)isoxazole-3-carboxamide N-(2-(5-chloro-1H-indol-3-yl)ethyl)-5-(4-(trifluoromethyl)benzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), 4-(trifluoromethyl)phenylboronic acid (0.042 g; 0.220 mmol), sodium carbonate (0.044 g; 0.418 mmol), tetrakis(triphenylphosphine)palladium (0.012 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(4-(trifluoromethyl)benzyl)isoxazole-3-carboxamide (0.083 g, 88%).

ESI/APCI (+): 448 (M+H), 470 (M+Na).
ESI/APCI (−): 446 (M−H).

Example 33

Preparation of N-(2-(5-chloro-1H-indol-3-yl)ethyl)-5-(3-(trifluoromethyl)benzyl)isoxazole-3-carboxamide N-(2-(5-chloro-1H-indol-3-yl)ethyl)-5-(3-(trifluoromethyl)benzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), 3-(trifluoromethyl)phenylboronic acid (0.042 g; 0.220 mmol), sodium carbonate (0.044 g; 0.418 mmol), tetrakis(triphenylphosphine)palladium (0.012 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3-(trifluoromethyl)benzyl)isoxazole-3-carboxamide (0.067 g, 71%).

ESI/APCI (+): 448 (M+H), 470 (M+Na).
ESI/APCI (−): 446 (M−H).

Example 34

Preparation of N-(2-(5-chloro-1H-indol-3-yl)ethyl)-5-(3-fluorobenzyl)isoxazole-3-carboxamide N-(2-(5-chloro-1H-indol-3-yl)ethyl)-5-(3-fluorobenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), 3-(fluoro)phenylboronic acid (0.030 g; 0.220 mmol), sodium carbonate (0.044 g; 0.418 mmol), [1,1'-Bis(diphenylphosphino)ferrocene]palladium(II) chloride, complex with dichloromethane (0.085 g; 0.001 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3-fluorobenzyl)isoxazole-3-carboxamide (0.041 g, 50%).

ESI/APCI (+): 398 (M+H).
ESI/APCI (−): 396 (M−H).

Example 35

Preparation of N-(2-(5-chloro-1H-indol-3-yl)ethyl)-5-(2-fluoro-3-methoxybenzyl)isoxazole-3-carboxamide N-(2-(5-chloro-1H-indol-3-yl)ethyl)-5-(2-fluoro-3-methoxybenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.070 g; 0.182 mmol), 2-fluoro-3-methoxyphenylboronic acid (0.033 g; 0.192 mmol), sodium carbonate (0.038 g; 0.365 mmol), [1,1'-Bis(diphenylphosphino)ferrocene]palladium(II) chloride, complex with dichloromethane (0.015 g; 0.018 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(2-fluoro-3-methoxybenzyl)isoxazole-3-carboxamide (0.026 g, 33%).

ESI/APCI (+): 428 (M+H).
ESI/APCI (−): 426 (M−H).

Example 36

Preparation of N-(2-(5-chloro-1H-indol-3-yl)ethyl)-5-(2,5-difluorobenzyl)isoxazole-3-carboxamide Method 1.

N-(2-(5-chloro-1H-indol-3-yl)ethyl)-5-(2,5-difluorobenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.070 g; 0.182 mmol), 2,5-difluorophenylboronic acid (0.030 g; 0.192 mmol), sodium carbonate (0.038 g; 0.365 mmol), [1,1'-Bis(diphenylphosphino)ferrocene]palladium (II) chloride, complex with dichloromethane (0.015 g; 0.018 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(2,5-difluorobenzyl)isoxazole-3-carboxamide (0.023 g, 30%).

Method 2.

Thionyl chloride (0.508 mL; 6.98 mmol) was added to the suspension of (2,5-difluorobenzyl)isoxazole-3-carboxylic acid (0.200 g; 0.838 mmol) in chloroform (12 mL). The mixture was heated overnight at 80° C. and the solution was evaporated under reduced pressure. 2-(5-chloro-1H-indol-3-yl)ethanamine hydrochloride (0.183 g; 0.776 mmol) followed by a solution of triethylamine (0.480 mL; 3.41 mmol) in dichloromethane (8 mL) were added to the resulting residue. The mixture was stirred at room temperature for 30 minutes and was washed with a solution of sodium carbonate. The organic layer was concentrated under reduced pressure and the residue was purified by flash column chromatography on silica gel (eluent: 2 to 10% of ethyl acetate in dichloromethane) to give 0.201 g (62%) of N-(2-(5-chloro-1H-indol-3-yl)ethyl)-5-(2,5-difluorobenzyl)isoxazole-3-carboxamide as a white solid.

ESI/APCI (+): 416 (M+H).
ESI/APCI (−): 415 (M−H).
$^1$H NMR (DMSO-$d_6$) 11.04 (1H, s); 8.82 (1H, t), 7.61 (1H, d), 7.33 (1H, d), 7.31 (2H, m), 7.24 (1H, d), 7.22 (1H, m), 7.04 (1H, dd), 6.52 (1H, s), 4.25 (2H, s), 3.57 (2H, m), 2.88 (2H, t).

Example 37

Preparation of N-(2-(5-chloro-1H-indol-3-yl)ethyl)-5-(3,5-difluorobenzyl)isoxazole-3-carboxamide N-(2-(5-chloro-1H-indol-3-yl)ethyl)-5-(3,5-difluorobenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), 3,5-difluorophenylboronic acid (0.037 g; 0.219 mmol), sodium carbonate (0.044 g; 0.418 mmol), [1,1'-Bis(diphenylphosphino)ferrocene]palladium (II) chloride, complex with dichloromethane (0.015 g; 0.018 mmol) in water (1 mL) and dimethoxyethane (3 mL). The crude material was purified by flash chromatography on silica gel (eluent 2 to 10% ethyl acetate in dichloromethane) to afford N-(2-(5-chloro-1H-indol-3-yl)ethyl)-5-(3,5-difluorobenzyl)isoxazole-3-carboxamide (0.014 g, 17%).

ESI/APCI (+): 416 (M+H)
ESI/APCI (−): 414 (M−H). .

Example 38

Preparation of 5-Benzyl-N-(2-(5-chloro-1H-indol-3-yl)ethyl)isoxazole-3-carboxamide 5-Benzyl-N-(2-(5-chloro-1H-indol-3-yl)ethyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.056 mg; 0.146 mmol), phenylboronic acid (0.0186 g; 0.149 mmol); tetrakis(triphenylphosphine)palladium(0) (0.0086 g; 0.0073 mmol), sodium carbonate (0.0312 g; 0.293 mmol), in dimethoxyethane (3 mL) and water (1 mL). The crude material was purified by flash chromatography on silica gel (eluent 1 to 10% ethyl acetate in dichloromethane) to afford 0.0128 g (23%) of 5-benzyl-N-(2-(5-chloro-1H-indol-3-yl)ethyl)isoxazole-3-carboxamide as a solid.

ESI/APCI (+): 380 (M+H), 402 (M+Na).
$^1$H NMR (DMSO-$d_6$) δ 11.03 (s, 1H); 8.82 (t, 1H); 7.60 (d, 1H); 7.32 (m, 6H); 7.25 (d, 1H); 7.05 (dd, 1H); 6.51 (s, 1H); 4.21 (s, 2H); 3.47 (q, 2H); 2.89 (t, 2H).

Example 39

Preparation of N-(2-(5-Chloro-1H-indol-3-yl)ethyl)-5-(4-methoxybenzyl)isoxazole-3-carboxamide N-(2-(5-Chloro-1H-indol-3-yl)ethyl)-5-(4-methoxybenzyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.0545 mg; 0.142 mmol), 4-methoxyphenylboronic acid (0.0228 g; 0.145 mmol), tetrakis(triphenylphosphine)palladium(0) (0.0083 g; 0.0071 mmol), sodium carbonate (0.0303 g; 0.285 mmol), in 1,2-dimethoxyethane (3 mL) and water (1 mL). The crude material was purified by flash chromatography on silica gel (eluent 1 to 10% ethyl acetate in dichloromethane) to afford 0.0127 g (22%) of N-(2-(5-chloro-1H-indol-3-yl)ethyl)-5-(4-methoxybenzyl)isoxazole-3-carboxamide as a solid.

ESI/APCI (+): 410 (M+H), 432 (M+Na).
$^1$H NMR (DMSO-$d_6$) δ 11.03 (s, 1H); 8.80 (t, 1H); 7.60 (d, 1H); 7.34 (d, 1H); 7.23 (m, 3H); 7.05 (dd, 1H); 6.91 (d, 2H); 6.46 (s, 1H); 4.12 (s, 2H); 3.74 (s, 3H); 3.46 (m, 2H); 2.89 (t, 2H).

Example 40

Preparation of N-((5-chloro-1H-indol-3-yl)methyl)-5-(3-fluorobenzyl)isoxazole-3-carboxamide This compound was prepared following Method A starting from (5-chloro-1H-indol-3-yl)methanamine (0.060 g; 0.332 mmol), the intermediate 11 (0.081 g; 0.365 mmol), HATU (0.139 g; 0.365 mmol) and N,N-diisopropylethylamine (0.075 mL; 0.432 mmol) in DMF (5 mL). Flash chromatography on silica gel eluting with 2 to 10% of ethyl acetate in dichloromethane afforded 0.028 g (22%) of N-((5-chloro-1H-indol-3-yl)methyl)-5-(3-fluorobenzyl)isoxazole-3-carboxamide as a solid.

ESI/APCI (+): 384 (M+H).
$^1$H NMR (DMSO-$d_6$) δ 11.15 (s, 1H); 9.13 (t, 1H); 7.34 (s, 1H); 7.38 (m, 3H); 7.12 (m, 4H); 6.57 (s, 1H); 4.52 (d, 2H); 4.23 (s, 2H).

Example 41

Preparation of tert-butyl 3-(2-(5-chloro-1H-indol-3-yl)ethylcarbamoyl)isoxazol-5-ylcarbamate This compound was prepared following Method A starting from 2-(5-chloro-1H-indol-3-yl)ethanamine hydrochloride (0.505 g; 2.14 mmol), the INTERMEDIATE 14: 5-(tert-butoxycarbonylamino)isoxazole-3-carboxylic acid (0.513 g; 2.25 mmol), HATU (0.896 g; 2.36 mmol) and N,N-diisopropylethylamine (0.935 mL; 5.35 mmol) in DMF (5 mL). Flash chromatography on silica gel eluting with 2 to 20% of ethyl acetate in dichloromethane afforded 0.819 g (94%) of tert-butyl 3-(2-(5-chloro-1H-indol-3-yl)ethylcarbamoyl)isoxazol-5-ylcarbamate as a white solid.

ESI/APCI (+): 405 (M+H).

Example 42

Preparation of 5-amino-N-(2-(5-Chloro-1H-indol-3-yl)ethyl)isoxazole-3-carboxamide To a solution of tert-butyl 3-(2-(5-chloro-1H-indol-3-yl)ethylcarbamoyl)isoxazol-5-ylcarbamate (0.400 g; 0.988 mmol) in dichloromethane (8 mL) was added trifluoroacetic acid (2 mL). The mixture was stirred at room temperature for 4 h and was then evaporated to dryness to remove the excess of TFA. The residue was dissolved in dichloromethane and the solution was washed with an aqueous solution of sodium carbonate. The organic layer was evaporated and the crude material was purified by flash chromatography on silica gel (eluent: 1 to 10% methanol in dichloromethane) to afford 0.207 g (69%) of 5-amino-N-(2-(5-chloro-1H-indol-3-yl)ethyl)isoxazole-3-carboxamide as a solid.

ESI/APCI (+): 305 (M+H).

$^1$H NMR (DMSO-$d_6$) δ 11.03 (s, 1H); 8.48 (t, 1H); 7.61 (d, 1H); 7.35 (d, 1H); 7.25 (d, 1H); 7.05 (dd; 1H); 6.93 (s, 2H); 5.18 (s, 1H); 3.47 (m, 2H); 2.87 (t, 2H).

Example 43

Preparation of N-(2-(5-chloro-1H-indol-3-yl)ethyl)-5-(ethoxymethyl)isoxazole-3-carboxamide N-(2-(5-chloro-1H-indol-3-yl)ethyl)-5-(ethoxymethyl)isoxazole-3-carboxamide was prepared following 2 different procedures:

According to method A with the intermediate 9 (5-(Ethoxymethyl)isoxazole-3-carboxylic acid) (0.091 g; 0.530 mmol), 2-(5-chloro-1H-indol-3-yl)ethanammonium chloride (0.125 g; 0.530 mmol), N,N-Diisopropylethylamine (0.296 mL; 1.7 mmol) and HATU (0.221 g; 0.583 mmol) in DMF (5 mL). The crude material was purified by flash chromatography on silica gel (eluent 2 to 16% ethyl acetate in dichloromethane) to afford N-(2-(5-chloro-1H-indol-3-yl)ethyl)-5-(ethoxymethyl)isoxazole-3-carboxamide 0.061 g (33%).

A mixture of sodium hydroxide (1M, 10 mL) in water was added to a suspension of the intermediate 8 (5-(Bromomethyl)-N-(2-(5-chloro-1H-indol-3-yl)ethyl)isoxazole-3-carboxamide) (0.600 g; 1.57 mmol) in EtOH (20 mL), the resulting mixture was stirred at room temperature overnight, concentrated under reduced pressure, dissolved in dichloromethane and washed with brine, dried and evaporated to dryness under reduced pressure. The crude material was purified by flash chromatography on silica gel (eluent 2 to 16% ethyl acetate in dichloromethane) to afford the N-(2-(5-chloro-1H-indol-3-yl)ethyl)-5-cyclohexyl-4,5-dihydroisoxazole-3-carboxamide 0.396 g (73%)

ESI/APCI (+): 348 (M+H).

$^1$H NMR (DMSO-$d_6$) 11.04 (1H, s), 8.89 (1H, t), 7.62 (1H, d), 7.35 (1H, d), 7.27 (1H, d), 7.06 (1H, dd), 6.77 (1H, s), 4.63 (2H, s), 3.55-3.50 (4H, m), 2.91 (2H, t), 1.14 (3H, t).

Example 44

Preparation of N-(2-(5-chloro-1H-indol-3-yl)ethyl)-5-(dimethylamino)isoxazole-3-carboxamide A mixture of the intermediate 3 (5-chloro-N-(2-(5-chloro-1H-indol-3-yl)ethyl)isoxazole-3-carboxamide) (0.05 g; 0.154 mmol), dimethylamine (1.3 mL, 2M in THF) in THF (1 mL) was irradiated in a microwave oven at 150° C. for 30 min and concentrated under reduced pressure. The crude material was purified by flash chromatography on silica gel (eluent 0 to 10% MeOH in dichloromethane) to afford N-(2-(5-chloro-1H-indol-3-yl)ethyl)-5-(dimethylamino)isoxazole-3-carboxamide 0.0089 g (17%).

ESI/APCI (+): 333 (M+H).

Example 45

Preparation of N-(2-(5-chloro-1H-indol-3-yl)ethyl)-5-cyclopropylisoxazole-3-carboxamide This compound was prepared following Method A starting from 2-(5-chloro-1H-indol-3-yl)ethanamine hydrochloride (0.080 g; 0.339 mmol), intermediate 16 (5-cyclopropylisoxazole-3-carboxylic acid) (0.062 g; 0.407 mmol), HATU (0.155 g; 0.407 mmol) and N,N-diisopropylethylamine (0.112 g; 0.848 mmol) in DMF (3 mL). Flash chromatography on silica gel eluting with 1 to 10% of ethyl acetate in dichloromethane furnished 0.092 g (82%) of N-(2-(5-chloro-1H-indol-3-yl)ethyl)-5-cyclopropylisoxazole-3-carboxamide as a solid.

ESI/APCI (+): 330 (M+H), 352 (M+Na).

$^1$H NMR (DMSO-$d_6$) δ 11.03 (s, 1H); 8.75 (br s, 1H); 7.61 (s, 1H); 7.35 (d, 1H); 7.26 (s, 1H); 7.05 (d, 1H); 6.47 (s, 1H); 3.47 (m, 2H); 2.90 (t, 2H); 2.18 (m, 1H); 1.07 (m, 2H); 0.92 (s, 2H).

Example 46

Preparation of N-(2-(5-chloro-1H-indol-3-yl)ethyl)-5-cyclopentylisoxazole-3-carboxamide This compound was prepared following Method A starting from 2-(5-chloro-1H-indol-3-yl)ethanamine hydrochloride (0.100 g; 0.424 mmol), intermediate 18 (5-cyclopentylisoxazole-3-carboxylic acid) (0.081 g; 0.445 mmol), HATU (0.177 g; 0.466 mmol) and N,N-diisopropylethylamine (0.185 mL; 1.06 mmol) in DMF (3 mL). Flash chromatography on silica gel eluting with 7 to 60% of ethyl acetate in heptane gave 0.111 g (73%) of N-(2-(5-chloro-1H-indol-3-yl)ethyl)-5-cyclopentylisoxazole-3-carboxamide as a solid.

ESI/APCI (+): 358 (M+H).

$^1$H NMR (CDCl$_3$) δ 8.32 (s, 1H); 7.56 (s, 1H); 7.02 (m, 4H); 6.40 (s, 1H); 3.73 (m, 2H); 3.20 (m, 1H); 3.01 (t, 2H); 2.07 (br s, 2H); 1.74 (m, 6H).

Example 47

Preparation of N-(2-(5-Chloro-1H-indol-3-yl)ethyl)-5-cyclohexylisoxazole-3-carboxamide This compound was prepared following Method A starting from 2-(5-chloro-1H-indol-3-yl)ethanamine hydrochloride (0.100 g; 0.424 mmol), intermediate 20 (5-cyclohexylisoxazole-3-carboxylic acid) (0.087 g; 0.445 mmol), HATU (0.177 g; 0.466 mmol) and N,N-diisopropylethylamine (0.185 mL; 1.06 mmol) in DMF (3 mL). Flash chromatography on silica gel eluting with 7 to 60% of ethyl acetate in heptane gave 0.079 g (50%) of N-(2-(5-chloro-1H-indol-3-yl)ethyl)-5-cyclohexylisoxazole-3-carboxamide as a solid.

ESI/APCI (+): 372 (M+H).

$^1$H NMR (CDCl$_3$) δ 8.19 (s, 1H); 7.57 (s, 1H); 7.29 (d, 1H); 7.14 (d, 1H); 7.08 (s, 1H); 6.92 (br s, 1H); 6.40 (s, 1H); 3.74 (m, 2H); 3.02 (t, 2H); 2.79 (m, 1H); 2.03 (m, 2H); 1.80 (m, 4H); 1.38 (m, 4H).

Example 48

Preparation of N-(2-(5-chloro-1H-indol-3-yl)ethyl)-5-(4-chlorophenyl)isoxazole-3-carboxamide N-(2-(5-chloro-1H-indol-3-yl)ethyl)-5-(4-chlorophenyl) isoxazole-3-carboxamide was prepared according to method A with 5-(4-chlorophenyl)isoxazole-3 carboxylic acid (0.085 g; 0.380 mmol), 2-(5-chloro-1H-indol-3-yl)ethanammonium chloride (0.080 g; 0.346 mmol), N,N-diisopropylethylamine (0.160 mL; 0.865 mmol), HATU (0.171 g; 0.449 mmol) in DMF (5 mL). The crude material was purified by flash chromatography on silica gel (eluent 2 to 10% ethyl acetate in dichloromethane) to afford N-(2-(5-chloro-1H-indol-3-yl) ethyl)-5-(4-chlorophenyl)isoxazole-3-carboxamide 0.023 g (17%).

ESI/APCI (+): 400 (M+H).

Example 49

Preparation of N-(2-(5-chloro-1H-indol-3-yl)ethyl)-5-p-tolylisoxazole-3-carboxamide N-(2-(5-chloro-1H-indol-3-yl)ethyl)-5-p-tolylisoxazole-3-carboxamide was prepared according to method A with 5-p-tolylisoxazole-3-carboxylic acid (0.077 g; 0.380 mmol), 2-(5-chloro-1H-indol-3-yl)ethanammonium chloride (0.080 g; 0.346 mmol), N,N-diisopropylethylamine (0.160 mL; 0.865 mmol), HATU (0.171 g; 0.449 mmol) in DMF (5 mL). The crude material was purified by flash chromatography on silica gel (eluent 2 to 10% ethyl acetate in dichloromethane) to afford N-(2-(5-chloro-1H-indol-3-yl)ethyl)-5-p-tolylisoxazole-3-carboxamide 0.035 g (27%).

ESI/APCI (+): 380 (M+H).

Example 50

Preparation of N-(2-(5-chloro-1H-indol-3-yl)ethyl)-5-(4-methoxyphenyl)isoxazole-3-carboxamide N-(2-(5-chloro-1H-indol-3-yl)ethyl)-5-(4-methoxyphenyl)isoxazole-3-carboxamide was prepared according to method A with 5-(4-methoxyphenyl)isoxazole-3-carboxylic acid (0.083 g; 0.380 mmol), 2-(5-chloro-1H-indol-3-yl)ethanammonium chloride (0.080 g; 0.346 mmol), N,N-Diisopropylethylamine (0.160 mL; 0.865 mmol), HATU (0.171 g; 0.449 mmol) in DMF (5 mL). The crude material was purified by flash chromatography on silica gel (eluent 2 to 10% ethyl acetate in dichloromethane) to afford N-(2-(5-chloro-1H-indol-3-yl)ethyl)-5-(4-methoxyphenyl)isoxazole-3-carboxamide 0.030 g (22%).

ESI/APCI (+): 396 (M+H).

Example 51

Preparation of N-(2-(5-chloro-1H-indol-3-yl)ethyl)-5-(2,3-dihydrobenzo[b][1,4]dioxin-5-yl)isoxazole-3-carboxamide N-(2-(5-chloro-1H-indol-3-yl)ethyl)-5-(2,3-dihydrobenzo[b][1,4]dioxin-5-yl)isoxazole-3-carboxamide was prepared according to method A with 5-(2,3 dihydro-1,4-benzodioxin-6-yl)-3-isoxazole carboxylic acid (0.094 g; 0.380 mmol), 2-(5-chloro-1H-indol-3-yl)ethanammonium chloride (0.080 g; 0.346 mmol), N,N-diisopropylethylamine (0.160 mL; 0.865 mmol), HATU (0.171 g; 0.449 mmol) in DMF (5 mL). The crude material was purified by flash chromatography on silica gel (eluent 2 to 10% ethyl acetate in dichloromethane) to afford N-(2-(5-chloro-1H-indol-3-yl) ethyl)-5-(2,3-dihydrobenzo[b][1,4]dioxin-5-yl)isoxazole-3-carboxamide 0.046 g (31%).

ESI/APCI (+): 424 (M+H).

Example 52

Preparation of 5-((1H-Pyrazol-1-yl)methyl)-N-(2-(5-chloro-1H-indol-3-yl)ethyl)isoxazole-3-carboxamide A mixture of the intermediate 8 (5-(Bromomethyl)-N-(2-(5-chloro-1H-indol-3-yl)ethyl)isoxazole-3-carboxamide) (0.0545 mg; 0.142 mmol), pyrazole (0.0445 g; 0.641 mmol) and sodium iodide (0.0647 g; 0.427 mmol) in THF (3 mL) was irradiated in a microwave oven at 150° C. for 20 min and was diluted with ethyl acetate (20 mL). Brine was added and the organic layer was separated and concentrated. The residue was purified by flash chromatography on silica gel (eluent: 7 to 60% ethyl acetate in dichloromethane to afford 0.027 g (52%) of 5-((1H-pyrazol-1-yl)methyl)-N-(2-(5-chloro-1H-indol-3-yl)ethyl)isoxazole-3-carboxamide as a white solid.

ESI/APCI (+): 370 (M+H), 392 (M+Na).

$^1$H NMR (DMSO-d$_6$) δ 11.03 (s, 1H); 8.88 (t, 1H); 7.88 (d, 1H); 7.60 (d, 1H); 7.51 (d, 1H); 7.34 (d, 1H); 7.24 (d, 1H), 7.05 (dd, 1H); 6.64 (s, 1H); 6.32 (t, 1H); 5.63 (s, 2H); 3.47 (q, 2H); 2.89 (t, 2H).

Example 53

Preparation of N-(2-(5-chloro-1H-indol-3-yl)ethyl)-5-((ethylamino)methyl)isoxazole-3-carboxamide A mixture of the intermediate 7: N-(2-(5-chloro-1H-indol-3-yl)ethyl)-5-(chloromethyl)isoxazole-3-carboxamide (0.088 g; 0.260 mmol) NaI (0.078 g; 0.520 mmol) and ethylamine (1.30 mL; 2M in THF) in THF (1 mL) was irradiated in a microwave oven at 130° C. for 10 min and concentrated under reduced pressure. The crude material was purified by flash chromatography (eluent 2 to 10% MeOH in dichloromethane) to afford N-(2-(5-chloro-1H-indol-3-yl)ethyl)-5-((ethylamino)methyl)isoxazole-3-carboxamide 0.044 g (50%).

ESI/APCI (+): 347 (M+H).

Example 54

Preparation of N-(2-(5-chloro-1H-indol-3-yl)ethyl)-5-((diethylamino)methyl)isoxazole-3-carboxamide N-(2-(5-chloro-1H-indol-3-yl)ethyl)-5-((diethylamino) methyl)isoxazole-3-carboxamide was prepared according to method D with intermediate 8 (5-(Bromomethyl)-N-(2-(5- chloro-1H-indol-3-yl)ethyl)isoxazole-3-carboxamide) (0.080 g; 0.209 mmol), diethylamine (0.21 mL; 2.09 mmol) in THF (2 mL). The crude material was purified by flash chromatography on silica gel (eluent 2 to 10% MeOH in dichloromethane) to afford N-(2-(5-chloro-1H-indol-3-yl) ethyl)-5-((diethylamino)methyl)isoxazole-3-carboxamide 0.065 g (83%).
ESI/APCI (+): 375 (M+H).
ESI/APCI (−): 373 (M−H).

Example 55

Preparation of N-(2-(5-chloro-1H-indol-3-yl)ethyl)-5-(pyrrolidin-1-ylmethyl)isoxazole-3-carboxamide N-(2-(5-chloro-1H-indol-3-yl)ethyl)-5-(pyrrolidin-1-ylmethyl)isoxazole-3-carboxamide was prepared according to method D with intermediate 8 (5-(Bromomethyl)-N-(2-(5-chloro-1H-indol-3-yl)ethyl)isoxazole-3-carboxamide) (0.080 g; 0.209 mmol) and pyrrolidine (0.0.290 mL; 2.91 mmol) in THF (2 mL). The crude material was purified by flash chromatography on silica gel (eluent 2 to 10% MeOH in dichloromethane) to afford N-(2-(5-chloro-1H-indol-3-yl) ethyl)-5-(pyrrolidin-1-ylmethyl)isoxazole-3-carboxamide 0.070 g (90%).
ESI/APCI (+): 375 (M+H).
ESI/APCI (−): 373 (M−H).

Example 56

Preparation of 1-benzyl-N-(2-(5-chloro-1H-indol-3-yl)ethyl)-2-oxopyrrolidine-3-carboxamide A mixture of 2-(5-chloro-1H-indol-3-yl)ethanammonium chloride (0.105 g; 0.456 mmol), PyBOP (0.356 g; 0.684), N,N-diisopropylethylamine (0.235 mL; 1.37 mmol) and the intermediate 30 (1-benzyl-2-oxopyrrolidine-3-carboxylic acid) (0.100; 0.456) in DMF (3 mL) was stirred at room temperature overnight. The solvent was evaporated under reduced pressure and the residue was dissolved in dichloromethane and washed with water, dried and concentrated under reduced pressure. The crude material was purified by flash chromatography on silica gel (eluent 2 to 10% methanol in dichloromethane) to afford 1-benzyl-N-(2-(5-chloro-1H-indol-3-yl)ethyl)-2-oxopyrrolidine-3-carboxamide 0.055 g (31%).
ESI/APCI (+): 396 (M+H).
ESI/APCI (−): 394 (M−H).

Example 57

Preparation of N-(2-(5-chloro-1H-indol-3-yl)ethyl)-2-oxo-1-phenylpyrrolidine-3-carboxamide A mixture of 2-(5-chloro-1H-indol-3-yl)ethanammonium chloride (0.124 g; 0.539 mmol), PyBOP (0.421 g; 0.809 mmol), N,N diisopropylethylamine (0.280 mL; 1.62 mmol) and the intermediate 31 (2-oxo-1-phenylpyrrolidine-3-carboxylic acid) (0.100; 0.539) in DMF (3 mL) was stirred at room temperature overnight. The solvent was evaporated under reduced pressure and the residue was dissolved in dichloromethane and washed with water, dried and concentrated under reduced pressure. The crude material was purified by preparative HPLC (method 1) to afford N-(2-(5-chloro-1H-indol-3-yl)ethyl)-2-oxo-1-phenylpyrrolidine-3-carboxamide 0.028 g (14%).
ESI/APCI (+): 382 (M+H)
ESI/APCI (−): 380 (M−H). .

Example 58

Preparation of N-(2-(5-chloro-1H-indol-3-yl)ethyl)-1-cyclohexyl-2-oxopyrrolidine-3-carboxamide A mixture of 2-(5-chloro-1H-indol-3-yl)ethanammonium chloride (0.125 g; 0.540 mmol), PyBOP (0.421 g; 0.809 mmol), N,N diisopropylethylamine (0.280 mL; 1.62 mmol) and the intermediate 32 (1-cyclohexyl-2-oxopyrrolidine-3-carboxylic acid) (0.100; 0.539) in DMF (3 mL) was stirred at room temperature overnight. The solvent was evaporated under reduced pressure and the residue was dissolved in dichloromethane and washed with water, dried and concentrated under reduced pressure. The crude material was purified twice by flash chromatography on silica gel (eluent 2 to 10% methanol in dichloromethane and 80 to 100% ethyl acetate in heptane) to afford N-(2-(5-chloro-1H-indol-3-yl) ethyl)-1-cyclohexyl-2-oxopyrrolidine-3-carboxamide 0.061 g (30%).
ESI/APCI (+): 388 (M+H).
ESI/APCI (−): 386 (M−H).

Example 59

Preparation of N-(2-(5-chloro-1H-indol-3-yl)ethyl)-1-(4-ethylphenyl)-2-oxopyrrolidine-3-carboxamide N-(2-(5-chloro-1H-indol-3-yl)ethyl)-1-(4-ethylphenyl)-2-oxopyrrolidine-3-carboxamide was prepared according to method A with the intermediate 33 (1-(4-ethylphenyl)-2-oxopyrrolidine-3-carboxylic acid) (0.083 g; 0.356 mmol), 2-(5-chloro-1H-indol-3-yl)ethanammonium chloride (0.070 g; 0.296 mmol), N,N-Diisopropylethylamine (0.125 mL; 0.742 mmol), HATU (0.135 g; 0.356 mmol). The crude material was purified by flash chromatography on silica gel (eluent 2 to 20% ethyl acetate in dichloromethane) to afford N-(2-(5-chloro-1H-indol-3-yl)ethyl)-1-(4-ethylphenyl)-2-oxopyrrolidine-3-carboxamide
0.0078 g (7%).
ESI/APCI (+): 410 (M+H), 432 (M+Na).
ESI/APCI (−): 408 (M−H).

Example 60

Preparation of N-(2-(5-chloro-1H-indol-3-yl)ethyl)-5-phenyl-4,5-dihydroisoxazole-3-carboxamide N-(2-(5-chloro-1H-indol-3-yl)ethyl)-5-phenyl-4,5-dihydroisoxazole-3-carboxamide was prepared according to method A with the intermediate 22 (5-phenyl-4,5-dihydroisoxazole-3-carboxylic acid) (0.073 g; 0.380 mmol), 2-(5-chloro-1H-indol-3-yl)ethanammonium chloride (0.080 g; 0.346 mmol), N,N-Diisopropylethylamine (0.150 mL; 0.865 mmol), HATU (0.157 g; 0.415 mmol). The crude material was purified by preparative HPLC (method 1) to afford N-(2-(5-chloro-1H-indol-3-yl)ethyl)-5-phenyl-4,5-dihydroisoxazole-3-carboxamide 0.059 g (46%).
ESI/APCI (+): 368 (M+H).
ESI/APCI (−): 366 (M−H).

Example 61

Preparation of N-(2-(5-chloro-1H-indol-3-yl)ethyl)-5-cyclohexyl-4,5-dihydroisoxazole-3-carboxamide N-(2-(5-chloro-1H-indol-3-yl)ethyl)-5-cyclohexyl-4,5-dihydroisoxazole-3-carboxamide was prepared according to method A with the intermediate 23 (ethyl 5-cyclohexyl-4,5-dihydroisoxazole-3-carboxylate) (0.075 g; 0.380 mmol), 2-(5-chloro-1H-indol-3-yl)ethanammonium chloride (0.080 g; 0.346 mmol), N,N-Diisopropylethylamine (0.150 mL; 0.865 mmol), HATU (0.157 g; 0.415 mmol). The crude material was purified by flash chromatography on silica gel (eluent 2 to 10% ethyl acetate in dichloromethane) to afford N-(2-(5-chloro-1H-indol-3-yl)ethyl)-5-cyclohexyl-4,5-dihydroisoxazole-3-carboxamide 0.056 g (43%).

ESI/APCI (+): 374 (M+H).
ESI/APCI (−): 372 (M−H).

Example 62

Preparation of N-(2-(5-chloro-1H-indol-3-yl)ethyl)-1-phenyl-1H-1,2,3-triazole-4-carboxamide N-(2-(5-chloro-1H-indol-3-yl)ethyl)-1-phenyl-1H-1,2,3-triazole-4-carboxamide was prepared according to method A with 1-phenyl-1H-1,2,3-triazole-4-carboxylic acid (0.072 g; 0.380 mmol), 2-(5-chloro-1H-indol-3-yl)ethanammonium chloride (0.080 g; 0.346 mmol), N,N-Diisopropylethylamine (0.150 mL; 0.865 mmol) and HATU (0.157 g; 0.415 mmol) in DMF (5 mL). The crude material was purified by flash chromatography on silica gel (eluent 20 to 100% ethyl acetate in heptane) to afford N-(2-(5-chloro-1H-indol-3-yl)ethyl)-1-phenyl-1H-1,2,3-triazole-4-carboxamide 0.008 g (7%).

ESI/APCI (+): 366 (M+H).
ESI/APCI (−): 364 (M−H).

Example 63

Preparation of N-(2-(5-chloro-1H-indol-3-yl)ethyl)-1-cyclohexyl-1H-1,2,3-triazole-4-carboxamide A solution of NaOH 1 M in water (2 mL) was added to a mixture of the intermediate 53 (0.110 g; 0.493 mmol). The mixture was stirred vigorously at room temperature overnight and concentrated under reduced pressure. The pH was adjusted to 1 with HCl 6N, and the aqueous layer was extracted with ethyl acetate. The organic layer was dried over magnesium sulfate, filtered and evaporated to dryness under reduced pressure to afford the desired crude carboxylic acid which was directly engaged in the next step.

A solution of the crude acid, 2-(5-chloro-1H-indol-3-yl)ethanamine hydrochloride (0.125 g; 0.541 mmol), HATU (0.225 g; 0.591 mmol) and N,N-Diisopropylethylamine (0.212 mL; 1.23 mmol) in DMF (2 mL), was stirred at room temperature overnight. The reaction mixture was concentrated under reduced pressure, diluted in ethyl acetate, successively washed with sodium hydrogen sulfate (1M), sodium carbonate (1M) and brine. The organic layer was dried over magnesium sulfate, filtered and concentrated under reduced pressure. The crude material was purified by flash chromatography on silica gel (eluent 3 to 20% ethyl acetate in dichloromethane) to afford N-(2-(5-chloro-1H-indol-3-yl)ethyl)-1-cyclohexyl-1H-1,2,3-triazole-4-carboxamide 0.034 g (20%).

ESI/APCI (+): 372 (M+H), 394 (M+Na).
ESI/APCI (−): 370 (M−H).

Example 64

Preparation of N-(2-(5-fluoro-1H-indol-3-yl)ethyl)-5-(3-fluorobenzyl)isoxazole-3-carboxamide N-(2-(5-fluoro-1H-indol-3-yl)ethyl)-5-(3-fluorobenzyl)isoxazole-3-carboxamide was prepared according to method A with the intermediate 11 (5-(3-fluorobenzyl)isoxazole-3-carboxylic acid) (0.068 g; 0.307 mmol), 2-(5-fluoro-1H-indol-3-yl)ethanamine (0.060 g; 0.279 mmol), N,N-Diisopropylethylamine (0.120 mL; 0.698 mmol) and HATU (0.128 g; 0.335 mmol) in DMF (2 mL). The crude material was purified by flash chromatography on silica gel (eluent 3 to 20% ethyl acetate in dichloromethane) to afford N-(2-(5-fluoro-1H-indol-3-yl)ethyl)-5-(3-fluorobenzyl)isoxazole-3-carboxamide 0.056 g (52%).

ESI/APCI (+): 382 (M+H), 404 (M+Na).
ESI/APCI (−): 380 (M−H).

Example 65

Preparation of N-(2-(1H-indol-3-yl)ethyl)-5-(3-fluorobenzyl)isoxazole-3-carboxamide N-(2-(1H-indol-3-yl)ethyl)-5-(3-fluorobenzyl)isoxazole-3-carboxamide was prepared according to method A the intermediate 11 (5-(3-fluorobenzyl)isoxazole-3-carboxylic acid) (0.106 g; 0.480 mmol), 2-(1H-indol-3-yl)ethanamine (0.070 g; 0.436 mmol), N,N-Diisopropylethylamine (0.188 mL; 1.09 mmol) and HATU (0.199 g; 0.524 mmol) in DMF (2 mL). The crude material was purified by flash chromatography on silica gel (eluent 3 to 20% ethyl acetate in dichloromethane) to afford N-(2-(1H-indol-3-yl)ethyl)-5-(3-fluorobenzyl)isoxazole-3-carboxamide 0.050 g (31%).

ESI/APCI (+): 364 (M+H).
ESI/APCI (−): 363 (M−H).

Example 66

Preparation of 5-(3-fluorobenzyl)-N-(2-(5-methoxy-1H-indol-3-yl)ethyl)isoxazole-3-carboxamide 5-(3-fluorobenzyl)-N-(2-(5-methoxy-1H-indol-3-yl)ethyl)isoxazole-3-carboxamide was prepared according to method A with the intermediate 11 (5-(3-fluorobenzyl)isoxazole-3-carboxylic acid) (0.077 g; 0.347 mmol), 2-(5-methoxy-1H-indol-3-yl)ethanamine (0.060 g; 0.315 mol), N,N-Diisopropylethylamine (0.136 mL; 0.789 mmol) and HATU (0.199 g; 0.524 mmol) in DMF (2 mL). The crude material was purified by flash chromatography on silica gel (eluent 1 to 20% ethyl acetate in dichloromethane) to afford 0.037 g (30%) of 5-(3-fluorobenzyl)-N-(2-(5-methoxy-1H-indol-3-yl)ethyl)isoxazole-3-carboxamide.

ESI/APCI (+): 394 (M+H).
ESI/APCI (−): 392 (M−H).

Example 67

Preparation of 5-(3-fluorobenzyl)-N-(2-(5-methyl-1H-indol-3-yl)ethyl)isoxazole-3-carboxamide 5-(3-fluorobenzyl)-N-(2-(5-methyl-1H-indol-3-yl)ethyl)isoxazole-3-carboxamide was prepared according to method A with the intermediate 11 (5-(3-fluorobenzyl)isoxazole-3-carboxylic acid) (0.076 g; 0.341 mmol), 2-(5-methyl-1H-indol-3-yl)ethanamine hydrochloride (0.060 g; 0.284 mmol), N,N-Diisopropylethylamine (0.123 mL; 0.711 mmol) and HATU (0.141 g; 0.370 mmol) in DMF (5 mL). The crude material was purified by flash chromatography on silica gel (eluent 20 to 100% ethyl acetate in heptane) to afford 0.034 g (32%) of 5-(3-fluorobenzyl)-N-(2-(5-methyl-1H-indol-3-yl)ethyl)isoxazole-3-carboxamide as a white solid.

ESI/APCI (+): 378 (M+H).
ESI/APCI (−): 377 (M−H).

Example 68

Preparation of (S)-1-Benzyl-N-(2-(5-chloro-1H-indol-3-yl)ethyl)pyrrolidine-3-carboxamide This compound was prepared according to method A starting from 2-(5-chloro-1H-indol-3-yl)ethanamine hydrochloride (0.100 g; 0.433 mmol), HATU (0.181 g; 0.476 mmol), (S)-1-benzylpyrrolidine-3-carboxylic acid hydrochloride (0.119 g; 0.476 mmol), and N,N-diisopropylethylamine (0.189 mL; 1.08 mmol) in DMF (5 mL). The crude material was purified by flash chromatography on silica gel (eluent: 1 to 10% of a solution of 5% ammonium hydroxide in methanol, in dichloromethane) to afford 0.036 g (22%) of (S)-1-benzyl-N-(2-(5-chloro-1H-indol-3-yl)ethyl)pyrrolidine-3-carboxamide as a white solid.

ESI/APCI (+): 382 (M+H).
ESI/APCI (−): 380 (M−H).

Example 69

Preparation of (R)-1-Benzyl-N-(2-(5-chloro-1H-indol-3-yl)ethyl)pyrrolidine-3-carboxamide This compound was prepared according to method A starting from 2-(5-chloro-1H-indol-3-yl)ethanamine hydrochloride (0.100 g; 0.433 mmol), HATU (0.181 g; 0.476 mmol), (R)-1-benzylpyrrolidine-3-carboxylic acid hydrochloride (0.119 g; 0.476 mmol), and N,N-diisopropylethylamine (0.189 mL; 1.08 mmol) in DMF (5 mL). The crude material was purified by flash chromatography on silica gel (eluent: 1 to 10% of a solution of 5% ammonium hydroxide in methanol, in dichloromethane) to afford 0.056 g (34%) of (R)-1-benzyl-N-(2-(5-chloro-1H-indol-3-yl)ethyl)pyrrolidine-3-carboxamide as a white solid.

ESI/APCI (+): 382 (M+H).
ESI/APCI (−): 380 (M−H).

Example 70

Preparation of 5-Benzyl-N-(2-(5-chloro-1H-indol-3-yl)ethyl)-4,5-dihydroisoxazole-3-carboxamide This compound was prepared according to method A starting from 2-(5-chloro-1H-indol-3-yl)ethanamine hydrochloride (0.100 g; 0.433 mmol), HATU (0.181 g; 0.476 mmol), the intermediate 41 (0.098 g; 0.476 mmol), and N,N-diisopropylethylamine (0.98 mL; 0.562 mmol) in DMF (5 mL). The purification by flash chromatography on silica gel (eluent: 1 to 10% ethyl acetate in dichloromethane) yielded 0.083 g (50%) of 5-benzyl-N-(2-(5-chloro-1H-indol-3-yl)ethyl)-4,5-dihydroisoxazole-3-carboxamide as a white solid.

ESI/APCI (+): 382 (M+H).
ESI/APCI (−): 380 (M−H).

Example 71

Preparation of N-(2-(5-Chloro-1H-indol-3-yl)ethyl)-3-phenyl-4,5-dihydroisoxazole-5-carboxamide This compound was prepared according to method A starting from 2-(5-chloro-1H-indol-3-yl)ethanamine hydrochloride (0.100 g; 0.433 mmol), HATU (0.181 g; 0.476 mmol), the intermediate 42 (0.091 g; 0.476 mmol), and N,N-diisopropylethylamine (0.98 mL; 0.562 mmol) in DMF (5 mL). The purification by flash chromatography on silica gel (eluent: 1 to 16% ethyl acetate in dichloromethane) yielded 0.033 g (21%) of N-(2-(5-chloro-1H-indol-3-yl)ethyl)-3-phenyl-4,5-dihydroisoxazole-5-carboxamide as a white solid.

ESI/APCI (+): 368 (M+H).
ESI/APCI (−): 366 (M−H).

Example 72

Preparation of N-(3-(5-chloro-1H-indol-3-yl)propyl)-5-(3-fluorobenzyl)isoxazole-3-carboxamide This compound was prepared according to method A starting from the intermediate 39 (0.043 g; 0.206 mmol), the intermediate 11 (5-(3-fluorobenzyl)isoxazole-3-carboxylic acid) (0.048 g; 0.216 mmol), HATU (0.086 g: 0.227 mmol) and N,N-diisopropylethylamine (0.053 mL; 0.309 mmol) in DMF (3 mL). The purification by flash chromatography on silica gel (eluent: 0 to 8% ethyl acetate in dichloromethane) yielded 0.052 g (61%) of N-(3-(5-chloro-1H-indol-3-yl)propyl)-5-(3-fluorobenzyl)isoxazole-3-carboxamide as a white solid.

ESI/APCI (+): 412 (M+H); ESI/APCI (−): 410 (M−H).
$^1$H NMR (DMSO-$d_6$) 10.97 (s, 1H); 8.75 (br t, 1H); 7.52 (s, 1H); 7.35 (m, 2H); 7.12 (m, 5H); 6.55 (s, 1H); 4.24 (s, 2H); 3.27 (m, 2H); 2.67 (t, 2H); 1.84 (m, 2H).

Example 73

Preparation of (S)—N-(2-(5-Chloro-1H-indol-3-yl)ethyl)-4-cyclohexyl-4,5-dihydrooxazole-2-carboxamide A sealed tube containing the intermediate 45 (0.290 g, 0.740 mmol) and the Burgess reagent [(methoxycarbonylsulfamoyl)triethylammonium hydroxide inner salt (0.218 g; 0.888 mmol)] in dry THF (12 mL) was stirred at 80° C. for 20 hours. The solution was evaporated to dryness and the residue was purified by flash chromatography (eluent: 7 to 60% ethyl acetate in dichloromethane) to afford 0.011 g (4%) of (S)—N-(2-(5-chloro-1H-indol-3-yl)ethyl)-4-cyclohexyl-4,5-dihydrooxazole-2-carboxamide as a white solid.

ESI/APCI (+): 374 (M+H), 396 (M+Na).
ESI/APCI (−): 372 (M−H).
$^1$H NMR (DMSO-$d_6$) 11.02 (s, 1H); 8.64 (br t, 1H); 7.60's, 1H); 7.34 (d, 1H); 7.24 (s, 1H); 7.05 (d, 1H); 4.37 (t, 1H); 4.11 (t, 1H); 4.03 (m, 1H); 3.37 (m, 2H); 2.85 (br t, 2H); 1.85-0.95 (m, 11H).

Example 74

Preparation of (R)—N-(2-(5-Chloro-1H-indol-3-yl)ethyl)-4-cyclohexyl-4,5-dihydrooxazole-2-carboxamide A sealed tube containing the intermediate 48 ((R)—N$^1$-(2-(5-Chloro-1H-indol-3-yl)ethyl)-N$^2$-(1-cyclohexyl-2-hydroxyethyl)oxalamide) (0.340 g, 0.867 mmol) and the Burgess reagent [(methoxycarbonylsulfamoyl)triethylammonium hydroxide inner salt (0.256 g; 1.04 mmol)] in dry THF (12 mL) was stirred at 80° C. for 20 hours. The solution was evaporated to dryness and the residue was purified by flash chromatography (eluent: 7 to 60% ethyl acetate in dichloromethane) to afford 0.006 g (2%) of (R)—N-(2-(5-chloro-1H-indol-3-yl)ethyl)-4-cyclohexyl-4,5-dihydrooxazole-2-carboxamide as white solid.

ESI/APCI (+): 374 (M+H), 396 (M+Na).
ESI/APCI (−): 372 (M−H).

Example 75

Preparation of N-(2-(5-chloro-1H-indol-3-yl)ethyl)-5-oxo-1-phenylpyrrolidine-3-carboxamide This compound was prepared according to method A starting from 2-(5-chloro-1H-indol-3-yl)ethanaminium chloride (0.100 g; 0.432 mmol), the intermediate 49 (5-oxo-1-phenylpyrrolidine-3-carboxylic acid) (0.093 g; 0.454 mmol), HATU (0.181 g: 0.476 mmol) and N,N-diisopropylethylamine (0.185 mL; 1.08 mmol) in DMF (5 mL). The purification by flash chromatography on silica gel (eluent: 1 to 10% methanol in dichloromethane) yielded 0.110 g (67%) of N-(2-(5-chloro-1H-indol-3-yl)ethyl)-5-oxo-1-phenylpyrrolidine-3-carboxamide as a white solid.
ESI/APCI (+): 382 (M+H).
ESI/APCI (−): 380 (M−H).

Example 76

Preparation of N-(2-(5-chloro-1H-indol-3-yl)ethyl)-1-cyclohexyl-5-oxopyrrolidine-3-carboxamide This compound was prepared according to method A starting from of 2-(5-chloro-1H-indol-3-yl)ethanaminium chloride (0.100 g; 0.432 mmol), the intermediate 50 (1-Cyclohexyl-5-oxopyrrolidine-3-carboxylic acid) (0.096 g; 0.454 mmol), HATU (0.181 g: 0.476 mmol) and N,N-diisopropylethylamine (0.185 mL; 1.08 mmol) in DMF (5 mL). The purification by flash chromatography on silica gel (eluent: 1 to 10% methanol in dichloromethane) yielded 0.100 g (59%) of N-(2-(5-chloro-1H-indol-3-yl)ethyl)-1-cyclohexyl-5-oxopyrrolidine-3-carboxamide as a white solid.
ESI/APCI (+): 388 (M+H); 410 (M+Na).
ESI/APCI (−): 386 (M−H).

Example 77

Preparation of N-(2-(5-chloro-1H-indol-3-yl)ethyl)-5-phenyloxazole-2-carboxamide This compound was prepared according to method A starting from 2-(5-chloro-1H-indol-3-yl)ethanaminium chloride (0.090 g; 0.381 mmol), the intermediate 52 (5-Phenyloxazole-2-carboxylic acid) (0.076 g; 0.400 mmol), HATU (0.152 g: 0.400 mmol) and N,N-diisopropylethylamine (0.163 mL; 0.954 mmol) in DMF (3 mL). The purification by flash chromatography on silica gel (eluent: 1 to 10% ethyl acetate in dichloromethane) yielded 0.058 g (42%) of N-(2-(5-chloro-1H-indol-3-yl)ethyl)-5-phenyloxazole-2-carboxamide as a white solid.
ESI/APCI (+): 366 (M+H); 388 (M+Na).
ESI/APCI (−): 364 (M−H).

Example 78

Preparation of N-(2-(5-chloro-1H-indol-3-yl)ethyl)-3-phenylisoxazole-5-carboxamide A solution of lithium hydroxide 2 M in water (3 mL) was added to a mixture of the intermediate 54 (ethyl 3-phenylisoxazole-5-carboxylate) (0.200 g; 1.18 mmol) in ethanol (2 mL). The mixture was stirred vigorously at room temperature overnight and concentrated under reduced pressure. The pH was adjusted to 1 with HCl 6N, and the aqueous layer was extracted with ethyl acetate. The organic layer was dried over magnesium sulfate, filtered and evaporated to dryness under reduced pressure to afford the desired crude carboxylic acid which was directly engaged in the next step.

A solution of the crude acid, 2-(5-chloro-1H-indol-3-yl)ethanamine hydrochloride (0.298 g; 1.29 mmol), HATU (0.536 g; 1.41 mmol) and N,N-Diisopropylethylamine (0.506 mL; 2.94 mmol) in DMF (5 mL), was stirred at room temperature for 72 hours. The reaction mixture was concentrated under reduced pressure, diluted in ethyl acetate, and washed with water. The organic layer was dried over magnesium sulfate, filtered and concentrated under reduced pressure. The crude material was purified by flash chromatography on silica gel (eluent 20 to 80% ethyl acetate in heptane) to afford 0.0146 g (3%) of N-(2-(5-chloro-1H-indol-3-yl)ethyl)-3-phenylisoxazole-5-carboxamide.
ESI/APCI (+): 379 (M+H).
ESI/APCI (−): 377 (M−H).

Example 79

Preparation of N-(2-(5-chloro-1H-indol-3-yl)ethyl)-5-(furan-3-ylmethyl)isoxazole-3-carboxamide N-(2-(5-chloro-1H-indol-3-yl)ethyl)-5-(furan-3-ylmethyl)isoxazole-3-carboxamide was prepared according to method C with the intermediate 8 (5-(Bromomethyl)-N-(2-(5-chloro-1H-indol-3-yl)ethyl)isoxazole-3-carboxamide) (0.080 g; 0.209 mmol), furan-3-ylboronic acid (0.025 g; 0.220 mmol), [1,1'-Bis(diphenylphosphino)ferrocene]palladium(II) chloride, complex with dichloromethane (0.017; 0.021 mmol) and sodium carbonate (0.044 g; 0.418 mmol) in DME (3 mL) and water (1 mL). The crude material was purified by flash chromatography on silica gel (eluent 20 to 80% ethyl acetate in heptane) to afford 0.009 g (12%) of N-(2-(5-chloro-1H-indol-3-yl)ethyl)-5-(furan-3-ylmethyl)isoxazole-3-carboxamide as a white solid.
ESI/APCI (+): 370 (M+H).
ESI/APCI (−): 368 (M−H).

Example 80

Preparation of N-(2-(5-chloro-1H-indol-3-yl)ethyl)-5-(furan-2-ylmethyl)isoxazole-3-carboxamide N-(2-(5-chloro-1H-indol-3-yl)ethyl)-5-(furan-2-ylmethyl)isoxazole-3-carboxamide was prepared according to method C with furan-2-ylboronic acid (0.025 g; 0.220 mmol), the intermediate 8 (5-(Bromomethyl)-N-(2-(5-chloro-1H-indol-3-yl)ethyl)isoxazole-3-carboxamide) (0.080 g; 0.209 mmol), tetrakis(triphenylphosphine)palladium (0.017; 0.021 mmol) and sodium carbonate (0.044 g; 0.418 mmol) in DME (3 mL) and water (1 mL). The crude mixture was purified by flash chromatography on silica (eluent 20 to 80% ethyl acetate in heptane) to afford 0.011 g (14%) of N-(2-(5-chloro-1H-indol-3-yl)ethyl)-5-(furan-2-ylmethyl)isoxazole-3-carboxamide as a pale yellow solid.
ESI/APCI (+): 370 (M+H).
ESI/APCI (−): 368 (M−H).

Example 81

Preparation of N-(2-(5-chloro-1H-indol-3-yl)ethyl)-5-(thiophen-2-ylmethyl)isoxazole-3-carboxamide N-(2-(5-chloro-1H-indol-3-yl)ethyl)-5-(thiophen-2-ylmethyl)isoxazole-3-carboxamide was prepared according to

249 method C with thiophen-2-ylboronic acid (0.028 g; 0.220 mmol), the intermediate 8 (5-(Bromomethyl)-N-(2-(5-chloro-1H-indol-3-yl)ethyl)isoxazole-3-carboxamide) (0.080 g; 0.209 mmol), tetrakis(triphenylphosphine)palladium (0.017; 0.021 mmol) and sodium carbonate (0.044 g; 0.418 mmol) in DME (3 mL) and water (1 mL). The crude mixture was purified by flash chromatography on silica (eluent 20 to 80% ethyl acetate in heptane) to afford 0.018 g (22%) of N-(2-(5-chloro-1H-indol-3-yl)ethyl)-5-(thiophen-2-ylmethyl)isoxazole-3-carboxamide as a pale yellow solid.

ESI/APCI (+): 386 (M+H).
ESI/APCI (−): 384 (M−H).

Example 82

Preparation of N-(2-(5-chloro-1H-indol-3-yl)ethyl)-5-(thiophen-3-ylmethyl)isoxazole-3-carboxamide N-(2-(5-chloro-1H-indol-3-yl)ethyl)-5-(thiophen-3-ylmethyl)isoxazole-3-carboxamide was prepared according to method C with thiophen-3-ylboronic acid (0.028 g; 0.220 mmol), the intermediate 8 (5-(Bromomethyl)-N-(2-(5-chloro-1H-indol-3-yl)ethyl)isoxazole-3-carboxamide) (0.080 g; 0.209 mmol), tetrakis(triphenylphosphine)palladium (0.017; 0.021 mmol) and sodium carbonate (0.044 g; 0.418 mmol) in DME (3 mL) and water (1 mL). The crude mixture was purified by flash chromatography on silica (eluent 20 to 80% ethyl acetate in heptane) to afford 0.019 g (23%) of N-(2-(5-chloro-1H-indol-3-yl)ethyl)-5-(thiophen-3-ylmethyl)isoxazole-3-carboxamide as a pale yellow solid.

ESI/APCI (+): 386 (M+H).
ESI/APCI (−): 384 (M−H).

Example 83

Preparation of N-(2-(5-chloro-1H-indol-3-yl)ethyl)-5-(pyridin-4-ylmethyl)isoxazole-3-carboxamide N-(2-(5-chloro-1H-indol-3-yl)ethyl)-5-(pyridin-4-ylmethyl)isoxazole-3-carboxamide was prepared according to method C with pyridin-4-ylboronic acid (0.027 g; 0.220 mmol), the intermediate 8 (5-(Bromomethyl)-N-(2-(5-chloro-1H-indol-3-yl)ethyl)isoxazole-3-carboxamide) (0.080 g; 0.209 mmol), tetrakis(triphenylphosphine)palladium (0.017; 0.021 mmol) and sodium carbonate (0.044 g; 0.418 mmol) in DME (3 mL) and water (1 mL). The crude mixture was purified by flash chromatography on silica (eluent 75 to 100% ethyl acetate in heptane) to afford 0.013 g (16%) of N-(2-(5-chloro-1H-indol-3-yl)ethyl)-5-(pyridin-4-ylmethyl)isoxazole-3-carboxamide as a pale yellow solid.

ESI/APCI (+): 381 (M+H).
ESI/APCI (−): 379 (M−H).

Example 84

Preparation of N-(2-(5-chloro-1H-indol-3-yl)ethyl)-3-phenylpyrrolidine-1-carboxamide Sodium hydride (60% in mineral oil) (12.20 mg; 0.304 mmol) was added to a mixture of 3-phenylpyrrolidine (0.075 g; 0.508 mmol) in dry THF (3 mL) and stirred at room temperature for 5 minutes. The Intermediate 55 (phenyl 2-(5-chloro-1H-indol-3-yl)ethylcarbamate) (0.080 g; 0.245 mmol) in solution in dry THF (4 mL) was then added to the reaction mixture and stirred at room temperature overnight. The crude material was purified by preparative HPLC (method 1) to yield 0.033 g (35%) of N-(2-(5-chloro-1H-indol-3-yl)ethyl)-3-phenylpyrrolidine-1-carboxamide as a pale yellow solid.

ESI/APCI (+): 368 (M+H).
ESI/APCI (−): 366 (M−H).

Example 85

Preparation of 1-benzyl-N-(2-(5-chloro-1H-indol-3-yl)ethyl)-1H-1,2,3-triazole-4-carboxamide The intermediate 56 (ethyl 1-benzyl-1H-1,2,3-triazole-4-carboxylate) (0.080 g; 0.779 mmol) was dissolved in a solution of 2M NaOH (1 mL) and stirred vigorously at room temperature for 1 hour. The reaction mixture was acidified with a solution of sodium hydrogen sulfate 1M and the resulting precipitate was collected by filtration and used without further purification in the next step.

A solution of the carboxylic acid, 2-(5-chloro-1H-indol-3-yl)ethanamine hydrochloride (0.060 g; 0.260 mmol), HATU (0.108 g; 0.285 mmol) and N,N-diisopropylethylamine (0.112 mL; 0.649 mmol) in DMF (3 mL), was stirred at room temperature overnight. The reaction mixture was concentrated under reduced pressure and dissolved in ethyl acetate, washed with water and evaporated to dryness. The residue was purified flash chromatography on silica (eluent 80 to 100% ethyl acetate in heptane) to afford 0.016 g (16%) of the desired compound as a white solid.

ESI/APCI (+): 380 M+H, 402 (M+Na).
ESI/APCI (−): 379 M−H, 424 (M−H+ formic acid).

Example 86

Preparation of N-(2-(5-chloro-1H-indol-3-yl)ethyl)-1-phenylpyrrolidine-3-carboxamide A mixture of the intermediate 60 (1-(4-cyanophenyl)-2-oxopyrrolidine-3-carboxylic acid) (0.124 g, 0.649 mmol), 2-(5-chloro-1H-indol-3-yl)ethanamine hydrochloride (0.150 g; 0.649 mmol), HATU (0.271 g; 0.713 mmol) and N,N-diisoprpylethylamine (0.280 mL; 1.62 mmol) in DMF (3 mL), was stirred at room temperature overnight. The reaction mixture was partitioned between ethyl acetate and sodium hydrogen sulphate and the organic layer was successively washed with sodium carbonate, brine, dried and evaporated to dryness. The crude mixture was purified by crystallization from a mixture of dichloromethane and methanol to afford 0.044 g (18%) of the desired compound as a white solid.

ESI/APCI (+): 368 (M+H).

Example 87

Preparation of 3-benzyl-N-(2-(5-chloro-1H-indol-3-yl)ethyl)pyrrolidine-1-carboxamide NaH in mineral oil (60%) (12.20 mg) was added to a mixture of 3-benzylpyrrolidine (0.085 g; 0.508 mmol) in THF (2 mL) and stirred at room temperature for 10 minutes. Phenyl 2-(5-chloro-1H-indol-3-yl)ethylcarbamate (0.080 g; 0.245 mmol) in THF (2 mL) was added to the above mixture and stirred at room temperature overnight. The crude material was purified by preparative HPLC (method 2) to yield 0.03 g (31%) of 3-benzyl-N-(2-(5-chloro-1H-indol-3-yl)ethyl)pyrrolidine-1-carboxamide as a white solid.

ESI/APCI (+): 382 (M+H).
ESI/APCI (−): 380 (M−H).

Similarly, the compound 3-benzyl-N-(2-(5-chloro-1H-indol-3-yl)ethyl)imidazolidine-1-carboxamide can be obtained following the procedure described hereabove starting from the 1-benzylimidazolidine and phenyl 2-(5-chloro-1H-indol-3-yl)ethylcarbamate.

Example 88

Preparation of N-(2-(6-fluoro-1H-indol-3-yl)ethyl)-5-(3-fluorobenzyl)isoxazole-3-carboxamide A mixture of the 5-(3-fluorobenzyl)isoxazole-3-carboxylic acid (0.057 g; 0.257 mmol), 2-(6-fluoro-1H-indol-3-yl)ethanamine (0.051 g; 0.284 mmol), HATU (0.108 g; 0.284 mmol) and N,N-diisoprpylethylamine (0.112 mL; 0.649 mmol) in DMF (3 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 20 to 100% ethyl acetate in heptane) to yield 0.040 g (41%) of the title compound as a white solid.

ESI/APCI (+): 382 (M+H).
ESI/APCI (−): 380 (M−H).

Example 89

Preparation of N-(2-(5-chloro-1-methyl-1H-indol-3-yl)ethyl)-5-(3-fluorobenzyl)isoxazole-3-carboxamide A solution of 5-(3-fluorobenzyl)isoxazole-3-carboxylic acid (0.057 g; 0.257 mmol), 2-(5-chloro-1-methyl-1H-indol-3-yl)ethanamine (0.060 g; 0.284 mmol), HATU (0.108 g; 0.284 mmol) and N,N-diisoprpylethylamine (0.112 mL; 0.649 mmol) in DMF (3 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 20 to 100% ethyl acetate in heptane) to yield 0.039 g (36%) of the title compound as a yellow solid.

ESI/APCI (+): 412 (M+H).

Example 90

Preparation of 5-(3-fluorobenzyl)-N-(2-(6-methoxy-1H-indol-3-yl)ethyl)isoxazole-3-carboxamide A solution of the 5-(3-fluorobenzyl)isoxazole-3-carboxylic acid (0.057 g; 0.257 mmol), 2-(6-methoxy-1H-indol-3-yl)ethanamine (0.054 g; 0.284 mmol), HATU (0.108 g; 0.284 mmol) and N,N-diisoprpylethylamine (0.112 mL; 0.649 mmol) in DMF (3 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 20 to 100% ethyl acetate in heptane) to yield 0.035 g (38%) of the title compound as a white solid.

ESI/APCI (+): 394 (M+H).
ESI/APCI (−): 392 (M−H).

Example 91

Preparation of N-(2-(benzofuran-3-yl)ethyl)-5-(3-fluorobenzyl)isoxazole-3-carboxamide A solution of the 5-(3-fluorobenzyl)isoxazole-3-carboxylic acid (0.057 g, 0.257 mmol), 2-(benzofuran-3-yl)ethanamine (0.042 g; 0.260 mmol), HATU (0.108 g; 0.285 mmol) and N,N-diisoprpylethylamine (0.112 mL; 0.649 mmol) in DMF (3 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by preparative HPLC (method 2) to yield 0.008 g (9%) of the title compound as a white solid.

ESI/APCI (+): 365 (M+H).
ESI/APCI (+): 363 (M−H).

Example 92

Preparation of N-(2-(5-chloro-1H-indol-3-yl)ethyl)-1-(4-cyanophenyl)-2-oxopyrrolidine-3-carboxamide A mixture of 2-(5-chloro-1H-indol-3-yl)ethanamine hydrochloride (0.100 g; 0.434 mmol), PyBOP (0.340 g; 0.651 mmol), N,N-diisoprpylethylamine (0.224 mL; 1.30 mmol) and 1-(4-cyanophenyl)-2-oxopyrrolidine-3-carboxylic acid (0.100 g; 0.434 mmol) was stirred in DMF (3 mL) overnight. The reaction mixture was partitioned between ethyl acetate and sodium hydrogen sulfate, the organic layer was washed with sodium carbonate, brine, dried and concentrated under reduced pressure. The crude mixture was purified preparative HPLC (method 1) to yield 0.006 g (3%) of the title compound as a white solid.

ESI/APCI (+): 407 (M+H).
ESI/APCI (+): 405 (M−H).

Example 93

Preparation of N-(2-(5-chloro-1H-indol-3-yl)ethyl)-1-(4-methoxyphenyl)-2-oxopyrrolidine-3-carboxamide A mixture of 2-(5-chloro-1H-indol-3-yl)ethanamine hydrochloride (0.098 g; 0.425 mmol), PyBOP (0.332 g; 0.638 mmol), N,N-diisoprpylethylamine (0.220 mL; 1.28 mmol) and 1-(4-methoxyphenyl)-2-oxopyrrolidine-3-carboxylic acid (0.100 g; 0.425 mmol) was stirred in DMF (3 mL) overnight. The reaction mixture was partitioned between ethyl acetate and sodium hydrogen sulfate, the organic layer was washed with sodium carbonate, brine, dried and concentrated under reduced pressure. The crude mixture was purified flash chromatography on silica (eluent 20 to 100% ethyl acetate in heptane) to yield 0.074 g (42%) of the title compound as a solid.

ESI/APCI (+): 412 (M+H), 434 (M+Na).
ESI/APCI (−): 410 (M−H).
$^1$H NMR (DMSO-d6) δ 11.04 (s, 1H), 8.26 (t, 1H), 7.59-7.53 (m, 3H), 7.34 (d, 1H), 7.29 (s, 1H), 7.06 (d, 1H), 6.95 (d,

2H), 3.84-3.75 (m, 2H), 3.75 (s, 3H), 3.47 (t, 1H), 3.47 (m, 2H, hidden by the water signal), 2.83 (t, 2H), 2.3-2.2 (m, 2H).

Example 94

Preparation of N-(2-(5-chloro-1H-indol-3-yl)ethyl)-1-(3-fluorophenyl)-2-oxopyrrolidine-3-carboxamide A mixture of 2-(5-chloro-1H-indol-3-yl)ethanamine hydrochloride (0.104 g; 0.448 mmol), PyBOP (0.350 g; 0.672 mmol), N,N-diisoprpylethylamine (0.232 mL; 1.34 mmol) and 1-(3-fluorophenyl)-2-oxopyrrolidine-3-carboxylic acid (0.100 g; 0.448 mmol) was stirred in DMF (3 mL) overnight. The reaction mixture was partitioned between ethyl acetate and sodium hydrogen sulphate, the organic layer was washed with sodium carbonate, brine, dried and concentrated under reduced pressure. The crude mixture was purified flash chromatography on silica (eluent 20 to 100% ethyl acetate in heptane) to yield 0.074 g (41%) of the title compound as a white solid.

ESI/APCI (+): 400 (M+H), 422 (M+Na).
ESI/APCI (−): 398 (M−H).

Example 95

Preparation of N-(2-(5-chloro-1H-indol-3-yl)ethyl)-1-(4-isopropylphenyl)-2-oxopyrrolidine-3-carboxamide A mixture of 2-(5-chloro-1H-indol-3-yl)ethanamine hydrochloride (0.036 g; 0.146 mmol), PyBOP (0.113 g; 0.219 mmol), N,N-diisoprpylethylamine (0.075 mL; 0.437 mmol) and 1-(4-isopropylphenyl)-2-oxopyrrolidine-3-carboxylic acid (0.100 g; 0.425 mmol) was stirred in DMF (3 mL) overnight. The reaction mixture was partitioned between ethyl acetate and sodium hydrogen sulfate, the organic layer was washed with sodium carbonate, brine, dried and concentrated under reduced pressure. The crude mixture was purified flash chromatography on silica (eluent 20 to 100% ethyl acetate in heptane) to yield 0.020 g (32%) of the title compound as a white solid.

ESI/APCI (+): 424 (M+H).
ESI/APCI (−): 422 (M−H).

Example 96

Preparation of N-(2-(5-chloro-1H-indol-3-yl)ethyl)-1-(2-fluorophenyl)-2-oxopyrrolidine-3-carboxamide A mixture of 2-(5-chloro-1H-indol-3-yl)ethanamine hydrochloride (0.104 g; 0.448 mmol), PyBOP (0.349 g; 0.672 mmol), N,N-diisoprpylethylamine (0.232 mL; 1.34 mmol) and 1-(2-fluorophenyl)-2-oxopyrrolidine-3-carboxylic acid (0.100 g; 0.448 mmol) was stirred in DMF (3 mL) overnight. The reaction mixture was partitioned between ethyl acetate and sodium hydrogen sulfate, the organic layer was washed with sodium carbonate, brine, dried and concentrated under reduced pressure. The crude mixture was purified flash chromatography on silica (eluent 20 to 100% ethyl acetate in heptane) to yield 0.078 g (44%) of the title compound as a white solid.

ESI/APCI (+): 422 (M+Na).
ESI/APCI (−): 398 (M−H).

Example 97

Preparation of N-(2-(5-chloro-1H-indol-3-yl)ethyl)-1-(3-ethylphenyl)-2-oxopyrrolidine-3-carboxamide A mixture of 2-(5-chloro-1H-indol-3-yl)ethanamine hydrochloride (0.099 g; 0.428 mmol), PyBOP (0.335 g; 0.643 mmol), N,N-diisoprpylethylamine (0.222 mL; 1.29 mmol) and 1-(3-ethylphenyl)-2-oxopyrrolidine-3-carboxylic acid (0.100 g; 0.428 mmol) was stirred in DMF (3 mL) overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 20 to 100% ethyl acetate in heptane) to yield 0.059 g (33%) of the title compound as a white solid.

ESI/APCI (+): 410 (M+H).
ESI/APCI (−): 408 (M−H).

Example 98

Preparation of 5-Benzyl-N-(2-(5-chloro-1H-indol-3-yl)ethyl)-1,3,4-oxadiazole-2-carboxamide To a suspension of 2-(2-(5-chloro-1H-indol-3-yl)ethylamino)-2-oxoacetic acid (0.350 mg; 1.31 mmol) in chloroform (20 mL) was added thionyl chloride (0.955 mL; 13.12 mmol) and the mixture was stirred at 80° C. for 3 h and was then evaporated to dryness. The resulting 2-(2-(5-chloro-1H-indol-3-yl)ethylamino)-2-oxoacetyl chloride (0.180 g, 0.631 mmol) was dissolved in dichloromethane (12 mL) and a mixture of triethylamine (0.355 mL; 2.53 mmol) and 2-phenylacetic acid hydrazide (0.092 g; 0.600 mmol) in dichloromethane (2 mL) was added at 0° C. The mixture was stirred at room temperature for 3 days and p-toluenesulfonyl chloride (0.122 g, 0.631 mmol) was added. The resulting mixture was stirred 18 h at room temperature, diluted with dichloromethane, washed with an aqueous solution of sodium carbonate, and concentrated under reduced pressure. The residue was purified by flash column chromatography on silica gel (eluent 12 to 100% ethyl acetate in heptane) to give 0.006 g (2.5%) of 5-benzyl-N-(2-(5-chloro-1H-indol-3-yl)ethyl)-1,3,4-oxadiazole-2-carboxamide as a white solid.

ESI/APCI (+): 381 (M+H), 403 (M+Na).
ESI/APCI (−): 379 (M−H).

Example 99

Preparation of N-(2-(5-Chloro-1H-indol-3-yl)ethyl)-5-cyclohexyl-1,3,4-oxadiazole-2-carboxamide To a suspension of 2-(2-(5-chloro-1H-indol-3-yl)ethylamino)-2-oxoacetic acid (0.920 mg; 3.45 mmol) in chloroform (50 mL) was added thionyl chloride (2.51 mL; 34.50 mmol) and the mixture was stirred at 80° C. for 3 h and was then evaporated to dryness. The resulting 2-(2-(5-chloro-1H-indol-3-yl)ethylamino)-2-oxoacetyl chloride (0.480 g; 1.68 mmol) was dissolved in dichloromethane (12 mL) and a mixture of triethylamine (0.945 mL; 6.73 mmol) and cyclohexanecarboxylic acid hydrazide (0.232 g; 1.60 mmol) in dichloromethane (8 mL) was added at 0° C. The mixture was stirred at room temperature for 2 h and p-toluenesulfonyl chloride (0.324 g, 1.68 mmol) was added. The resulting mixture was stirred overnight at room temperature, diluted with dichloromethane, washed with an aqueous solution of sodium carbonate, and concentrated under reduced pressure. The residue was purified by flash column chromatography on silica gel (eluent: 12 to 100% ethyl acetate in heptane) to give 0.0088 g (1.40%) of N-(2-(5-chloro-1H-indol-3-yl)ethyl)-5-cyclohexyl-1,3,4-oxadiazole-2-carboxamide as a white solid.

ESI/APCI (+): 373 (M+H), 395 (M+Na).

ESI/APCI (−): 371 (M−H).

Example 100

Preparation of N-(2-(5-chloro-1H-indol-3-yl)ethyl)-4-phenyl-4,5-dihydrooxazole-2-carboxamide A sealed tube containing (N$^1$-(2-(5-chloro-1H-indol-3-yl)ethyl)-N$^2$-(2-hydroxy-1-phenylethyl)oxalamide (0.211 g, 0.546 mmol) and Burgess reagent [(methoxycarbonylsulfamoyl)triethylammonium hydroxide inner salt (0.161 g; 0.656 mmol)] in dry THF (6 mL) was stirred at 80° C. for 20 hours. The solution was evaporated and the resulting residue was purified by flash chromatography on silica gel (eluent 7 to 60% ethyl acetate in dichloromethane) to give 0.007 g (4%) of N-(2-(5-chloro-1H-indol-3-yl)ethyl)-4-phenyl-4,5-dihydrooxazole-2-carboxamide as a white solid.

ESI/APCI (+): 368 (M+H), 390 (M+Na).

ESI/APCI (−): 366 (M−H).

Example 101

Preparation of (S)-4-benzyl-N-(2-(5-chloro-1H-indol-3-yl)ethyl)-4,5-dihydrooxazole-2-carboxamide A sealed tube containing (S)—N$^1$-(2-(5-chloro-1H-indol-3-yl)ethyl)-N$^2$-(1-hydroxy-3-phenylpropan-2-yl)oxalamide (0.117 g, 0.293 mmol) and Burgess reagent [(methoxycarbonylsulfamoyl)triethylammonium hydroxide inner salt (0.115 g; 0.468 mmol)] in dry THF (6 mL) was stirred at 80° C. for 20 hours. The solution was evaporated and the resulting residue was purified by flash chromatography on silica gel (eluent 7 to 60% ethyl acetate in dichloromethane) to give 0.005 g (4%) of (S)-4-benzyl-N-(2-(5-chloro-1H-indol-3-yl)ethyl)-4,5-dihydrooxazole-2-carboxamide as a white solid.

ESI/APCI (+): 382 (M+H), 404 (M+Na).

ESI/APCI (−): 380 (M−H).

Example 102

Preparation of (R)-4-benzyl-N-(2-(5-chloro-1H-indol-3-yl)ethyl)-4,5-dihydrooxazole-2-carboxamide A sealed tube containing (R)—N$^1$-(2-(5-chloro-1H-indol-3-yl)ethyl)-N$^2$-(1-hydroxy-3-phenylpropan-2-yl)oxalamide (0.104 g, 0.260 mmol) and Burgess reagent [(methoxycarbonylsulfamoyl)triethylammonium hydroxide inner salt (0.102 g; 0.416 mmol)] in dry THF (6 mL) was stirred at 80° C. for 20 hours. The solution was evaporated and the resulting residue was purified by flash chromatography on silica gel (eluent 7 to 60% ethyl acetate in dichloromethane) to give 0.003 g (3%) of (R)-4-benzyl-N-(2-(5-chloro-1H-indol-3-yl)ethyl)-4,5-dihydrooxazole-2-carboxamide as a white solid.

ESI/APCI (+): 382 (M+H), 404 (M+Na)

ESI/APCI (−): 380 (M−H). .

Example 103

Preparation of N-(2-(5-chloro-2-methyl-1H-indol-3-yl)ethyl)-5-(2,5-difluorobenzyl)isoxazole-3-carboxamide A solution of 5-(2,5-difluorobenzyl)isoxazole-3-carboxylic acid (0.080 g, 0.334 mmol), 2-(5-chloro-2-methyl-1H-indol-3-yl)ethanamine hydrochloride (0.090 g; 0.368 mmol), HATU (0.127 g; 0.334 mmol) and N,N-diisopropylethylamine (0.144 mL; 0.836 mmol) in DMF (5 mL), was stirred at room temperature for 18 hours. The reaction mixture was partitioned between ethyl acetate and a solution of sodium hydrogen sulfate. The organic layer was washed with sodium carbonate, brine, dried and concentrated under reduced pressure. The residue was purified by flash chromatography on silica gel (eluent 20 to 100% ethyl acetate in heptane) to afford 0.090 g (62%) of the title compound as a pink solid.

ESI/APCI (+): 430 (M+H).

ESI/APCI (−): 428 (M−H).

Example 104

Preparation of N-(2-(5-chloro-1H-indol-3-yl)ethyl)-5-(2,5-difluorobenzyl)-1,2,4-oxadiazole-3-carboxamide This compound was prepared following Method A starting from 2-(5-chloro-1H-indol-3-yl)ethanamine hydrochloride (0.100 g; 0.424 mmol), 5-(2,5-difluorobenzyl)-1,2,4-oxadiazole-3-carboxylic acid (0.102 g; 0.424 mmol), HATU (0.161 g: 0.424 mmol) and N,N-diisopropylethylamine (0.222 mL; 1.27 mmol) in DMF (3 mL). The purification by flash chromatography on silica gel (eluent: 1 to 10% of ethyl acetate in dichloromethane) gave 0.022 g (12%) of N-(2-(5-chloro-1H-indol-3-yl)ethyl)-5-(2,5-difluorobenzyl)-1,2,4-oxadiazole-3-carboxamide as a solid.

ESI/APCI (+): 417 (M+H).

ESI/APCI (−): 415 (M+H).

Example 105

Preparation of N-(2-(5-chloro-1H-indol-3-yl)ethyl)-5-(3,4-difluorobenzyl)isoxazole-3-carboxamide N-(2-(5-chloro-1H-indol-3-yl)ethyl)-5-(3,4-difluorobenzyl)isoxazole-3-carboxamide was prepared according to method C with the Intermediate 8 (5-(Bromomethyl)-N-(2-(5-chloro-1H-indol-3-yl)ethyl)isoxazole-3-carboxamide) (0.080 g; 0.209 mmol), 3,4-difluorophenylboronic acid (0.035 g; 0.219 mmol), sodium carbonate (0.044 g; 0.418 mmol), Bis(diphenylphosphino)ferrocene]palladium(II) chloride, complex with dichloromethane (0.017; 0.021 mmol) in water (1 mL) and dimethoxyethane (3 mL). The crude material was purified by flash chromatography on silica (eluent 20 to 80% ethyl acetate in heptane) and by preparative HPLC (method 2) to yield 0.006 g (7%) of N-(2-(5-chloro-1H-indol-3-yl)ethyl)-5-(3,4-difluorobenzyl)isoxazole-3-carboxamide as a white solid.

ESI/APCI (+): 416 (M+H)

ESI/APCI (−): 414 (M−H). .

Example 106

Preparation of N-(2-(5-chloro-1H-indol-3-yl)ethyl)-5-(2,3-difluorobenzyl)isoxazole-3-carboxamide N-(2-(5-chloro-1H-indol-3-yl)ethyl)-5-(2,3-difluorobenzyl)isoxazole-3-carboxamide was prepared according to method C with the Intermediate 8 (5-(Bromomethyl)-N-(2-(5-chloro-1H-indol-3-yl)ethyl)isoxazole-3-carboxamide) (0.080 g; 0.209 mmol), 2,3-difluorophenylboronic acid (0.035 g; 0.220 mmol), sodium carbonate (0.044 g; 0.418 mmol), Bis(diphenylphosphino)ferrocene]palladium(II) chloride, complex with dichloromethane (0.017; 0.021 mmol) in water (1 mL) and dimethoxyethane (3 mL). The crude material was purified by flash chromatography on silica (eluent 20 to 80% ethyl acetate in heptane) and by preparative HPLC (method 2) to yield 0.006 g (7%) of N-(2-(5-chloro-1H-indol-3-yl)ethyl)-5-(2,3-difluorobenzyl)isoxazole-3-carboxamide as a white solid.

ESI/APCI (+): 416 (M+H).
ESI/APCI (−): 414 (M−H).

Example 107

Preparation of N-(2-(5-chloro-1H-indol-3-yl)ethyl)-2-oxo-1-(4-(trifluoromethoxy)phenyl)pyrrolidine-3-carboxamide This compound was prepared according to method E with 2-(5-chloro-1H-indol-3-yl)ethanamine hydrochloride (0.100 g; 0.433 mmol), 2-oxo-1-(4-(trifluoromethoxy)phenyl)pyrrolidine-3-carboxylic acid (0.125; 0.433 mmol), PyBOP (0.225 g; 0.433 mmol), N,N diisopropylethylamine (0.186 mL; 1.08 mmol) in DMF (3 mL). The crude mixture was purified by flash chromatography on silica (eluent 20 to 100% ethyl acetate in heptane) to yield 0.075 g (37%) of N-(2-(5-chloro-1H-indol-3-yl)ethyl)-2-oxo-1-(4-(trifluoromethoxy)phenyl)pyrrolidine-3-carboxamide as a solid.

ESI/APCI (+): 466 (M+H).
ESI/APCI (−): 464 (M−H).

Example 108

Preparation of N-(2-(5-chloro-1H-indol-3-yl)ethyl)-1-(cyclohexylmethyl)-2-oxopyrrolidine-3-carboxamide This compound was prepared according to method E with 2-(5-chloro-1H-indol-3-yl)ethanamine hydrochloride (0.100 g; 0.433 mmol), 1-(cyclohexylmethyl)-2-oxopyrrolidine-3-carboxylic acid (0.097; 0.433 mmol), PyBOP (0.225 g; 0.433 mmol), N,N diisopropylethylamine (0.186 mL; 1.08 mmol) in dichloromethane (2 mL) and DMF (3 mL). The crude mixture was purified flash chromatography on silica (eluent 20 to 100% ethyl acetate in heptane) to yield 0.0668 g (38%) of N-(2-(5-chloro-1H-indol-3-yl)ethyl)-1-(cyclohexylmethyl)-2-oxopyrrolidine-3-carboxamide as a white solid.

ESI/APCI (+): 402 (M+H), (M+Na).
ESI/APCI (−): 400 (M−H).
$^1$H NMR (DMSO-d$_6$): δ 11.00 (s, 1H); 8.16 (t, 1H); 7.57 (d, 1H); 7.34 (d, 1H); 7.27 (d, 1H); 7.05 (dd, 1H); 3.25-3.21 (m, 5H+water); 3.02 (m, 2H); 2.80 (m, 2H); 2.15-2.09 (m, 2H); 1.65-1.58 (m, 6H); 1.20-1.13 (m, 3H); 0.84 (m, 2H).

Example 109

Preparation of N-(2-(5-chloro-1H-indol-3-yl)ethyl)-1-(2-methoxyphenyl)-2-oxopyrrolidine-3-carboxamide This compound was prepared according to method E with 2-(5-chloro-1H-indol-3-yl)ethanamine hydrochloride (0.100 g; 0.433 mmol), 1-(2-methoxyphenyl)-2-oxopyrrolidine-3-carboxylic acid (0.102; 0.433 mmol), PyBOP (0.225 g; 0.433 mmol), N,N diisopropylethylamine (0.186 mL; 1.08 mmol) in dichloromethane (2 mL) and DMF (3 mL). The crude mixture was purified flash chromatography on silica (eluent 20 to 100% ethyl acetate in heptane) to yield 0.121 g (68%) of N-(2-(5-chloro-1H-indol-3-yl)ethyl)-1-(2-methoxyphenyl)-2-oxopyrrolidine-3-carboxamide as a white solid.

ESI/APCI (+): 412 (M+H).
ESI/APCI (−): 410 (M−H).

Example 110

Preparation of N-(2-(5-chloro-1H-indol-3-yl)ethyl)-1-(3-methoxyphenyl)-2-oxopyrrolidine-3-carboxamide This compound was prepared according to method E with 2-(5-chloro-1H-indol-3-yl)ethanamine hydrochloride (0.100 g; 0.433 mmol), 1-(3-methoxyphenyl)-2-oxopyrrolidine-3-carboxylic acid 1-(3-methoxyphenyl)-2-oxopyrrolidine-3-carboxylic acid (0.102; 0.433 mmol), PyBOP (0.225 g; 0.433 mmol), N,N diisopropylethylamine (0.186 mL; 1.08 mmol) in dichloromethane (2 mL) and DMF (3 mL). The crude mixture was purified flash chromatography on silica (eluent 20 to 100% ethyl acetate in heptane) to yield 0.075 g (42%) of N-(2-(5-chloro-1H-indol-3-yl)ethyl)-1-(3-methoxyphenyl)-2-oxopyrrolidine-3-carboxamide as a white solid.

ESI/APCI (+): 412 (M+H), (M+Na).
ESI/APCI (−): 410 (M−H).

Example 111

Preparation of N-(2-(5-chloro-1H-indol-3-yl)ethyl)-1-(2-chlorophenyl)-2-oxopyrrolidine-3-carboxamide This compound was prepared according to method E with 2-(5-chloro-1H-indol-3-yl)ethanamine hydrochloride (0.100 g; 0.433 mmol), 1-(2-chlorophenyl)-2-oxopyrrolidine-3-carboxylic acid 1-(2-chlorophenyl)-2-oxopyrrolidine-3-carboxylic acid (0.104; 0.433 mmol), PyBOP (0.225 g; 0.433 mmol), N,N diisopropylethylamine (0.186 mL; 1.08 mmol) in dichloromethane (2 mL) and DMF (3 mL). The crude mixture was purified flash chromatography on silica (eluent 20 to 100% ethyl acetate in heptane) to yield 0.098 g (54%) of the N-(2-(5-chloro-1H-indol-3-yl)ethyl)-1-(2-chlorophenyl)-2-oxopyrrolidine-3-carboxamide as a white solid.

ESI/APCI (+): 416 (M+H).
ESI/APCI (−): 415 (M−H).

Example 112

Preparation of N-(2-(5-chloro-1H-indol-3-yl)ethyl)-2-oxo-1-m-tolylpyrrolidine-3-carboxamide This compound was prepared according to method E with 2-(5-chloro-1H-indol-3-yl)ethanamine hydrochloride (0.100 g; 0.433 mmol), 2-oxo-1-m-tolylpyrrolidine-3-carboxylic acid 2-oxo-1-m-tolylpyrrolidine-3-carboxylic acid (0.095;

0.433 mmol), PyBOP (0.225 g; 0.433 mmol), N,N diisopropylethylamine (0.186 mL; 1.08 mmol) in DMF (3 mL). The crude mixture was purified flash chromatography on silica (eluent 20 to 100% ethyl acetate in heptane) to yield 0.075 g (44%) of N-(2-(5-chloro-1H-indol-3-yl)ethyl)-2-oxo-1-m-tolylpyrrolidine-3-carboxamide as a white solid.
ESI/APCI (+): 396 (M+H), (M+Na).
ESI/APCI (−): 394 (M−H).
$^1$H NMR (DMSO-d$_6$): δ 11.06 (s, 1H); 8.31 (t, 1H); 7.61 (d; 1H); 7.47-7.24 (m, 5H); 7.07 (dd, 1H); 6.97 (d, 1H); 3.82 (m, 2H); 3.51 (t, 1H); 3.37 (m, 2H under the water's signal); 2.85 (t, 2H); 2.31-2.27 (m, 5H).

Example 113

Preparation of N-(2-(5-chloro-1H-indol-3-yl)ethyl)-2-oxo-1-O— tolylpyrrolidine-3-carboxamide This compound was prepared according to method E with 2-(5-chloro-1H-indol-3-yl)ethanamine hydrochloride (0.100 g; 0.433 mmol), 2-oxo-1-o-tolylpyrrolidine-3-carboxylic acid 2-oxo-1-o-tolylpyrrolidine-3-carboxylic acid (0.095; 0.433 mmol), PyBOP (0.225 g; 0.433 mmol), N,N diisopropylethylamine (0.186 mL; 1.08 mmol) in DMF (3 mL). The crude mixture was purified flash chromatography on silica (eluent 20 to 100% ethyl acetate in heptane) to yield 0.076 g (44%) of N-(2-(5-chloro-1H-indol-3-yl)ethyl)-2-oxo-1-o-tolylpyrrolidine-3-carboxamide as a white solid.
ESI/APCI (+): 396 (M+H).
ESI/APCI (−): 394 (M−H).

Example 114

Preparation of N-(2-(5-chloro-1H-indol-3-yl)ethyl)-1-(1-methyl-1H-pyrazol-3-yl)-2-oxopyrrolidine-3-carboxamide This compound was prepared according to method E with 2-(5-chloro-1H-indol-3-yl)ethanamine hydrochloride (0.070 g; 0.303 mmol), 1-(1-methyl-1H-pyrazol-3-yl)-2-oxopyrrolidine-3-carboxylic acid 1-(1-methyl-1H-pyrazol-3-yl)-2-oxopyrrolidine-3-carboxylic acid (0.060; 0.303 mmol), PyBOP (0.158 g; 0.303 mmol), N,N diisopropylethylamine (0.130 mL; 0.757 mmol) in DMF (3 mL). The crude mixture was purified flash chromatography on silica (eluent 20 to 100% ethyl acetate in heptane) to yield 0.015 g (13%) of N-(2-(5-chloro-1H-indol-3-yl)ethyl)-1-(1-methyl-1H-pyrazol-3-yl)-2-oxopyrrolidine-3-carboxamide as a white solid.
ESI/APCI (+): 386 (M+H).
ESI/APCI (−): 385 (M−H).

Example 115

Preparation of 1-(3-(1H-pyrrol-1-yl)phenyl)-N-(2-(5-chloro-1H-indol-3-yl)ethyl)-2-oxopyrrolidine-3-carboxamide This compound was prepared according to method E with 2-(5-chloro-1H-indol-3-yl)ethanamine hydrochloride (0.100 g; 0.433 mmol), 1-(3-(1H-pyrrol-1-yl)phenyl)-2-oxopyrrolidine-3-carboxylic acid 1-(3-(1H-pyrrol-1-yl)phenyl)-2-oxopyrrolidine-3-carboxylic acid (0.117 g; 0.433 mmol), PyBOP (0.225 g; 0.433 mmol), N,N diisopropylethylamine (0.186 mL; 1.08 mmol) in DMF (3 mL). The crude mixture was purified flash chromatography on silica (eluent 20 to 100% ethyl acetate in heptane and 2 to 20% ethyl acetate in dichloromethane) to yield 0.058 g (30%) of 1-(3-(1H-pyrrol-1-yl)phenyl)-N-(2-(5-chloro-1H-indol-3-yl)ethyl)-2-oxopyrrolidine-3-carboxamide as a white solid.
ESI/APCI (+): 447 (M+H).
ESI/APCI (−): 446 (M−H).

Example 116

Preparation of N-(2-(5-chloro-1H-indol-3-yl)ethyl)-1-(2-ethylphenyl)-2-oxopyrrolidine-3-carboxamide This compound was prepared according to method E with 2-(5-chloro-1H-indol-3-yl)ethanamine hydrochloride (0.100 g; 0.433 mmol), 1-(2-ethylphenyl)-2-oxopyrrolidine-3-carboxylic acid (0.101 g; 0.433 mmol), PyBOP (0.225 g; 0.433 mmol), N,N diisopropylethylamine (0.186 mL; 1.08 mmol) in DMF (3 mL). The crude mixture was purified flash chromatography on silica (eluent 20 to 100% ethyl acetate in heptane) to yield 0.094 g (53%) of N-(2-(5-chloro-1H-indol-3-yl)ethyl)-1-(2-ethylphenyl)-2-oxopyrrolidine-3-carboxamide as a white solid.
ESI/APCI (+): 410 (M+H).
ESI/APCI (−): 408 (M−H).

Example 117

Preparation of N-(2-(5-chloro-1H-indol-3-yl)ethyl)-2-oxo-1-(1-phenylethyl)pyrrolidine-3-carboxamide This compound was prepared according to method E with 2-(5-chloro-1H-indol-3-yl)ethanamine hydrochloride (0.100 g; 0.433 mmol), 2-oxo-1-(1-phenylethyl)pyrrolidine-3-carboxylic acid (0.101 g; 0.433 mmol), PyBOP (0.225 g; 0.433 mmol), N,N diisopropylethylamine (0.186 mL; 1.08 mmol) in DFM (3 mL). The crude mixture was purified flash chromatography on silica (eluent 20 to 100% ethyl acetate in heptane) to yield N-(2-(5-chloro-1H-indol-3-yl)ethyl)-2-oxo-1-(1-phenylethyl)pyrrolidine-3-carboxamide in two fractions (two sets of diastereoisomers) A 0.041 g (less polar fraction) and B 0.047 g (more polar fraction) (50% overall) as white solids.
Fraction A:
ESI/APCI (+): 410 (M+H).
ESI/APCI (−): 409 (M−H).
Fraction B:
ESI/APCI (+): 410 (M+H).
ESI/APCI (−): 409 (M−H).

Example 118

Preparation of 1-(4-acetylphenyl)-N-(2-(5-chloro-1H-indol-3-yl)ethyl)-2-oxopyrrolidine-3-carboxamide This compound was prepared according to method E with 2-(5-chloro-1H-indol-3-yl)ethanamine hydrochloride (0.200 g; 0.865 mmol), PyBOP (0.450 g; 0.865 mmol), N,N diisopropylethylamine (0.373 mL; 2.16 mmol) and 1-(4-acetylphenyl)-2-oxopyrrolidine-3-carboxylic acid (0.213 g; 0.865 mmol) in DMF (3 mL). Dichloromethane was added to the crude mixture to precipitate 1-(4-acetylphenyl)-N-(2-(5-chloro-1H-indol-3-yl)ethyl)-2-oxopyrrolidine-3-carboxamide 0.105 g (29%) as a solid.
ESI/APCI (+): 424 (M+H)
ESI/APCI (−): 422 (M−H)

Example 119

Preparation of N-(2-(5-chloro-1H-indol-3-yl)ethyl)-2-oxo-1-p-tolylpyrrolidine-3-carboxamide This compound was prepared according to method E with 2-(5-chloro-1H-indol-3-yl)ethanamine hydrochloride (0200 g; 0.865 mmol), PyBOP (0.450 g; 0.865 mmol), N,N diisopropylethylamine (0.373 mL; 2.16 mmol) and 2-oxo-1-p-tolylpyrrolidine-3-carboxylic acid (0.189 g; 0.865 mmol) in DMF (3 mL). The crude mixture was purified flash chromatography on silica (eluent 20 to 100% ethyl acetate in heptane) to yield 0.144 g (42%) of N-(2-(5-chloro-1H-indol-3-yl)ethyl)-2-oxo-1-p-tolylpyrrolidine-3-carboxamide as a white solid.
ESI/APCI (+): 396 (M+H).
ESI/APCI (−): 394 (M−H)

Example 120

Preparation of N-(2-(5-chloro-1H-indol-3-yl)ethyl)-2-oxo-1-(4-(trifluoromethyl)phenyl)pyrrolidine-3-carboxamide This compound was prepared according to method E with 2-(5-chloro-1H-indol-3-yl)ethanamine hydrochloride (0.200 g; 0.865 mmol), PyBOP (0.450 g; 0.865 mmol), N,N diisopropylethylamine (0.373 mL; 2.16 mmol) and 2-oxo-1-(4-(trifluoromethyl)phenyl)pyrrolidine-3-carboxylic acid (0.236 g; 0.865 mmol) in DMF (3 mL). The crude mixture was purified flash chromatography on silica (eluent 20 to 100% ethyl acetate in heptane and 1 to 7% methanol in dichloromethane) to yield 0.025 g (7%) of N-(2-(5-chloro-1H-indol-3-yl)ethyl)-2-oxo-1-(4-(trifluoromethyl)phenyl)pyrrolidine-3-carboxamide as a white solid.
ESI/APCI (+): 449 (M+H).
ESI/APCI (−): 448 (M−H)

Example 121

Preparation of N-(2-(5-chloro-1H-indol-3-yl)ethyl)-1-(3-chlorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(3-chlorophenyl)-2-oxopyrrolidine-3-carboxylic acid (0.107 g; 0.445 mmol), HATU (0.166 g; 0.437 mmol) and N,N-diisopropylethylamine (0.186 mL; 1.06 mmol) in DMF (5 mL).
The crude material was purified by flash chromatography on silica gel (eluent: 2 to 20% of ethyl acetate in dichloromethane) to give 0.101 g (57%) of N-(2-(5-chloro-1H-indol-3-yl)ethyl)-1-(3-chlorophenyl)-2-oxopyrrolidine-3-carboxamide as a white solid.
ESI/APCI (+): 416 (M+H).
ESI/APCI (−): 414 (M−H).

Example 122

Preparation of N-(2-(5-chloro-1H-indol-3-yl)ethyl)-1-(4-chlorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(4-chlorophenyl)-2-oxopyrrolidine-3-carboxylic acid (0.107 g; 0.445 mmol), HATU (0.166 g; 0.437 mmol) and N,N-diisopropylethylamine (0.186 mL; 1.06 mmol) in DMF (5 mL).
The crude material was purified by flash chromatography on silica gel (eluent: 2 to 20% of ethyl acetate in dichloromethane) to give 0.0929 g (53%) of N-(2-(5-chloro-1H-indol-3-yl)ethyl)-1-(4-chlorophenyl)-2-oxopyrrolidine-3-carboxamide as a white solid.
ESI/APCI (+): 416 (M+H).
ESI/APCI (−): 414 (M−H).

Example 123

Preparation of N-(2-(5-chloro-1H-indol-3-yl)ethyl)-1-(2,6-difluorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(2,6-difluorophenyl)-2-oxopyrrolidine-3-carboxylic acid (0.107 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.033 g (20%) of N-(2-(5-chloro-1H-indol-3-yl)ethyl)-1-(2,6-difluorophenyl)-2-oxopyrrolidine-3-carboxamide as a white solid.
ESI/APCI (+): 418 (M+H).
ESI/APCI (−): 416 (M−H).

Example 124

Preparation of N-(2-(5-chloro-1H-indol-3-yl)ethyl)-1-(4-fluoro-3-(trifluoromethyl)phenyl)-2-oxopyrrolidine-3-carboxamide This compound was prepared according to method A with 2-(5-chloro-1H-indol-3-yl)ethanamine hydrochloride (0.100 g; 0.424 mmol), 1-(3-fluoro-4-(trifluoromethyl)phenyl)-2-oxopyrrolidine-3-carboxylic acid (0.130 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.0389 g (20%) of N-(2-(5-chloro-1H-indol-3-yl)ethyl)-1-(3-fluoro-4-(trifluoromethyl)phenyl)-2-oxopyrrolidine-3-carboxamide as a white solid.
ESI/APCI (+): 468 (M+H).
ESI/APCI (−): 466 (M−H).

Example 125

Preparation of N-(2-(5-chloro-1H-indol-3-yl)ethyl)-1-cyclopropyl-2-oxopyrrolidine-3-carboxamide This compound was prepared according to method A with 2-(5-chloro-1H-indol-3-yl)ethanamine hydrochloride (0.100 g; 0.424 mmol), 1-cyclopropyl-2-oxopyrrolidine-3-carboxylic acid (0.075 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 7 to 60% of ethyl acetate in dichloromethane) to give 0.0995 g (68%) of N-(2-(5-chloro-1H-indol-3-yl)ethyl)-1-cyclopropyl-2-oxopyrrolidine-3-carboxamide as a white solid.
ESI/APCI (+): 346 (M+H), 368 (M+Na).
ESI/APCI (−): 344 (M−H).

Example 126

Preparation of N-(2-(5-chloro-1H-indol-3-yl)ethyl)-1-(3,4-difluorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(3,4-difluorophenyl)-2-oxopyrrolidine-3-carboxylic acid (0.108 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.0446 g (25%) of N-(2-(5-chloro-1H-indol-3-yl)ethyl)-1-(3,4-difluorophenyl)-2-oxopyrrolidine-3-carboxamide as a white solid.

ESI/APCI (+): 418 (M+H), 440 (M+Na).
ESI/APCI (−): 416 (M−H).

Example 127

Preparation of N-(2-(5-chloro-1H-indol-3-yl)ethyl)-1-(3-fluoro-4-methoxyphenyl)-2-oxopyrrolidine-3-carboxamide This compound was prepared according to method A with 2-(5-chloro-1H-indol-3-yl)ethanamine hydrochloride (0.100 g; 0.424 mmol), 1-(3-fluoro-4-methoxyphenyl)-2-oxopyrrolidine-3-carboxylic acid (0.113 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 25% of ethyl acetate in dichloromethane) to give 0.072 g (40%) of N-(2-(5-chloro-1H-indol-3-yl)ethyl)-1-(3-fluoro-4-methoxyphenyl)-2-oxopyrrolidine-3-carboxamide as a white solid.

ESI/APCI (+): 430 (M+H), 452 (M+Na).
ESI/APCI (−): 428 (M−H).

Example 128

Preparation of N-(2-(5-chloro-1H-indol-3-yl)ethyl)-1-(1,3-dihydroisobenzofuran-5-yl)-2-oxopyrrolidine-3-carboxamide This compound was prepared according to method A with 2-(5-chloro-1H-indol-3-yl)ethanamine hydrochloride (0.100 g; 0.424 mmol), 1-(1,3-dihydroisobenzofuran-5-yl)-2-oxopyrrolidine-3-carboxylic acid (0.111 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent 7 to 60% of ethyl acetate in dichloromethane) to give 0.064 g (36%) of N-(2-(5-chloro-1H-indol-3-yl)ethyl)-1-(1,3-dihydroisobenzofuran-5-yl)-2-oxopyrrolidine-3-carboxamide a white solid.

ESI/APCI (+): 424 (M+H), 446 (M+Na).
ESI/APCI (−): 422 (M−H).

Example 129

Preparation of N-(2-(5-chloro-1H-indol-3-yl)ethyl)-1-(2,3-dihydro-1H-inden-5-yl)-2-oxopyrrolidine-3-carboxamide This compound was prepared according to method A with 2-(5-chloro-1H-indol-3-yl)ethanamine hydrochloride (0.100 g; 0.424 mmol), 1-(2,3-dihydro-1H-inden-5-yl)-2-oxopyrrolidine-3-carboxylic acid (0.111 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.077 g (43%) of N-(2-(5-chloro-1H-indol-3-yl)ethyl)-1-(2,3-dihydro-1H-inden-5-yl)-2-oxopyrrolidine-3-carboxamide as a white solid.

ESI/APCI (+): 422 (M+H), 444 (M+Na).
ESI/APCI (−): 420 (M−H).

Example 130

Preparation of N-(2-(5-chloro-1H-indol-3-yl)ethyl)-1-(3,5-difluorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(3,5-difluorophenyl)-2-oxopyrrolidine-3-carboxylic acid (0.110 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.046 g (26%) of N-(2-(5-chloro-1H-indol-3-yl)ethyl)-1-(3,5-difluorophenyl)-2-oxopyrrolidine-3-carboxamide as a white solid.

ESI/APCI (+): 418 (M+H), 440 (M+Na).
ESI/APCI (−): 416 (M−H).

Example 131

Preparation of N-(2-(5-chloro-1H-indol-3-yl)ethyl)-1-(3,4-dimethylphenyl)-2-oxopyrrolidine-3-carboxamide This compound was prepared according to method A with 2-(5-chloro-1H-indol-3-yl)ethanamine hydrochloride (0.100 g; 0.424 mmol), 1-(3,4-dimethylphenyl)-2-oxopyrrolidine-3-carboxylic acid (0.105 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.090 g (52%) of N-(2-(5-chloro-1H-indol-3-yl)ethyl)-1-(3,4-dimethylphenyl)-2-oxopyrrolidine-3-carboxamide as a white solid.

ESI/APCI (+): 410 (M+H), 432 (M+Na).
ESI/APCI (−): 408 (M−H).

Example 132

Preparation of N-(2-(5-chloro-1H-indol-3-yl)ethyl)-1-(4-chloro-3-fluorophenyl)-2-oxopyrrolidine-3-carboxamide This compound was prepared according to method A with 2-(5-chloro-1H-indol-3-yl)ethanamine hydrochloride (0.100 g; 0.424 mmol), 1-(4-chloro-3-fluorophenyl)-2-oxopyrrolidine-3-carboxylic acid (0.115 g; 0.445 mmol), HATU (0.166 g; 0.437 mmol) and N,N-diisopropylethylamine (0.186 mL; 1.06 mmol) in DMF (5 mL). The crude material was purified by flash chromatography on silica gel (eluent: 2 to 20% of ethyl acetate in dichloromethane) to give 0.077 g (42%) of N-(2-(5-chloro-1H-indol-3-yl)ethyl)-1-(4-chloro-3-fluorophenyl)-2-oxopyrrolidine-3-carboxamide as a white solid.

ESI/APCI (+): 434 (M+H), 456 (M+Na)
ESI/APCI (−): 432 (M−H). .

Example 133

Preparation of N-(2-(5-chloro-1H-indol-3-yl)ethyl)-1-(1-methyl-1H-indol-5-yl)-2-oxopyrrolidine-3-carboxamide This compound was prepared according to method A with 2-(5-chloro-1H-indol-3-yl)ethanamine hydrochloride (0.055 g; 0.233 mmol), 1-(1-methylindolin-6-yl)-2-oxopyrrolidine-3-carboxylic acid (0.064 g; 0.245 mmol), HATU (0.091 g; 0.240 mmol) and N,N-diisopropylethylamine (0.101 mL; 0.583 mmol) in DMF (3 mL). The crude material was purified by flash chromatography on silica gel (eluent: 2 to 20% of ethyl acetate in dichloromethane) to give 0.021 g (21%) of N-(2-(5-chloro-1H-indol-3-yl)ethyl)-1-(1-methyl-1H-indol-5-yl)-2-oxopyrrolidine-3-carboxamide as a white solid.

ESI/APCI (+): 435 (M+H), 457 (M+Na).
ESI/APCI (−): 433 (M−H).
$^1$H NMR (d6-DMSO): δ. 11.07 (s, 1H); 8.31 (s, 1H); 7.67 (br s; 1H); 7.61 (br s, 1H); 7.53 (d, 1H); 7.32 (m, 4H); 7.06 (d, 1H); 6.40 (s, 1H); 3.92 (br s, 2H); 3.77 (s, 3H); 3.53 (br s, 1H); 2.85 (br s, 2H); 2.30 (br s, 2H).

Example 134

Preparation of N-(2-(5-chloro-1H-indol-3-yl)ethyl)-5-(thiophen-3-ylmethyl)-1,2,4-oxadiazole-3-carboxamide This compound was prepared according to method F with ethyl 5-(thiophen-3-ylmethyl)-1,2,4-oxadiazole-3-carboxylate (0.103 g; 0.433 mmol) in THF (1 mL) and sodium hydroxide in water (2M, 1 mL); 2-(5-chloro-1H-indol-3-yl)ethanamine hydrochloride (0.100 g; 0.433 mmol), HATU (0.164 g; 0.432 mmol), N,N diisopropylethylamine (0.186 mL; 1.08 mmol), in DMF (4 mL). The crude mixture was purified by flash chromatography on silica (eluent 20 to 100% ethyl acetate in heptane) and preparative HPLC method 2 to yield 0.0487 g (29%) of N-(2-(5-chloro-1H-indol-3-yl)ethyl)-5-(thiophen-3-ylmethyl)-1,2,4-oxadiazole-3-carboxamide as a white solid.

ESI/APCI (+): 387 (M+H), (M+Na).
ESI/APCI (−): 385 (M−H).

Example 135

Preparation of N-(2-(5-chloro-1H-indol-3-yl)ethyl)-5-(2-methylbenzyl)-1,2,4-oxadiazole-3-carboxamide This compound was prepared according to method F with ethyl 5-(2-methylbenzyl)-1,2,4-oxadiazole-3-carboxylate (0.106 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.186 mL; 1.08 mmol), in DMF (4 mL). The crude mixture was purified by flash chromatography on silica (eluent 20 to 100% ethyl acetate in heptane) to yield 0.060 g (35%) of N-(2-(5-chloro-1H-indol-3-yl)ethyl)-5-(2-methylbenzyl)-1,2,4-oxadiazole-3-carboxamide as a white solid.

ESI/APCI (+): 395 (M+H).
ESI/APCI (−): 394 (M−H).

Example 136

Preparation of N-(2-(5-chloro-1H-indol-3-yl)ethyl)-5-(2-chlorobenzyl)-1,2,4-oxadiazole-3-carboxamide This compound was prepared according to method F with ethyl 5-(2-chlorobenzyl)-1,2,4-oxadiazole-3-carboxylate (0.115 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) and preparative HPLC method 2 to yield 0.042 g (24%) of N-(2-(5-chloro-1H-indol-3-yl)ethyl)-5-(2-chlorobenzyl)-1,2,4-oxadiazole-3-carboxamide as a white solid.

ESI/APCI (+): 415 (M+H).
ESI/APCI (−): 413 (M−H).

Example 137

Preparation of N-(2-(5-chloro-1H-indol-3-yl)ethyl)-5-(3-chlorobenzyl)-1,2,4-oxadiazole-3-carboxamide This compound was prepared according to method F with ethyl 5-(3-chlorobenzyl)-1,2,4-oxadiazole-3-carboxylate (0.115 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) and preparative HPLC method 2 to yield 0.0377 g (21%) of N-(2-(5-chloro-1H-indol-3-yl)ethyl)-5-(3-chlorobenzyl)-1,2,4-oxadiazole-3-carboxamide as a white solid.

ESI/APCI (+): 415 (M+H).
ESI/APCI (−): 413 (M−H).

Example 138

Preparation of N-(2-(5-chloro-1H-indol-3-yl)ethyl)-5-(2,4-difluorobenzyl)-1,2,4-oxadiazole-3-carboxamide This compound was prepared according to method F with ethyl 5-(2,4-difluorobenzyl)-1,2,4-oxadiazole-3-carboxylate (0.116 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) to yield 0.084 g (47%) of N-(2-(5-chloro-1H-indol-3-yl)ethyl)-5-(2,4-difluorobenzyl)-1,2,4-oxadiazole-3-carboxamide as a white solid.

ESI/APCI (+): 417 (M+H)

Example 139

Preparation of N-(2-(5-chloro-1H-indol-3-yl)ethyl)-5-(2,6-difluorobenzyl)-1,2,4-oxadiazole-3-carboxamide This compound was prepared according to method F with ethyl 5-(2,6-difluorobenzyl)-1,2,4-oxadiazole-3-carboxylate (0.116 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) and preparative HPLC method 2 to yield 0.083 g (44%) of N-(2-(5-chloro-1H-indol-3-yl)ethyl)-5-(2,6-difluorobenzyl)-1,2,4-oxadiazole-3-carboxamide as a white solid.

ESI/APCI (+): 417 (M+H)

Example 140

Preparation of N-(2-(5-chloro-1H-indol-3-yl)ethyl)-5-(2,3-difluorobenzyl)-1,2,4-oxadiazole-3-carboxamide This compound was prepared according to method F with ethyl 5-(2,3-difluorobenzyl)-1,2,4-oxadiazole-3-carboxylate (0.081 g; 0.303 mmol) in THF (1 mL) and sodium hydroxide in water (2M, 1 mL) and 2-(5-chloro-1H-indol-3-yl)ethanamine hydrochloride (0.070 g; 0.303 mmol), HATU (0.131 g; 0.346 mmol), N,N diisopropylethylamine (0.149 mL; 0.865 mmol), in DMF (4 mL). The crude mixture was purified by flash chromatography on silica (eluent 20 to 100% ethyl acetate in heptane) and preparative HPLC method 2 to yield 0.032 g (25%) of N-(2-(5-chloro-1H-indol-3-yl)ethyl)-5-(2,3-difluorobenzyl)-1,2,4-oxadiazole-3-carboxamide as a white solid.

ESI/APCI (+): 417 (M+H).
ESI/APCI (−): 415 (M−H).

Example 141

Preparation of N-(2-(5-chloro-1H-indol-3-yl)ethyl)-5-(4-(trifluoromethyl)benzyl)-1,2,4-oxadiazole-3-carboxamide This compound was prepared according to method F with 5-(4-(trifluoromethyl)benzyl)-1,2,4-oxadiazole-3-carboxylate (0.104 g; 0.346 mmol) in THF (1 mL) and sodium hydroxide in water (2M, 1 mL) and 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (4 mL). The crude mixture was purified by flash chromatography on silica (eluent 20 to 100% ethyl acetate in heptane) and preparative HPLC method 2 to yield 0.033 g (21%) of N-(2-(5-chloro-1H-indol-3-yl)ethyl)-5-(4-(trifluoromethyl)benzyl)-1,2,4-oxadiazole-3-carboxamide as a white solid.

Example 142

Preparation of N-(2-(5-chloro-1H-indol-3-yl)ethyl)-5-(3-(trifluoromethyl)benzyl)-1,2,4-oxadiazole-3-carboxamide This compound was prepared according to method F with 5-(3-(trifluoromethyl)benzyl)-1,2,4-oxadiazole-3-carboxylate (0.039 g; 0.130 mmol) in THF (1 mL) and sodium hydroxide in water (2M, 1 mL); and 2-(5-chloro-1H-indol-3-yl)ethanamine hydrochloride (0.030 g; 0.130 mmol), HATU (0.050 g; 0.130 mmol), N,N diisopropylethylamine (0.056 mL; 0.324 mmol) in DMF (4 mL). The crude mixture was purified by flash chromatography on silica (eluent 20 to 100% ethyl acetate in heptane) an by preparative HPLC method 2 to yield 0.022 g (38%) of N-(2-(5-chloro-1H-indol-3-yl)ethyl)-5-(3-(trifluoromethyl)benzyl)-1,2,4-oxadiazole-3-carboxamide as a white solid.

ESI/APCI (+): 449 (M+H).
ESI/APCI (−): 447 (M−H).

Example 143

Preparation of N-(2-(5-chloro-1H-indol-3-yl)ethyl)-5-(4-(trifluoromethoxy)benzyl)-1,2,4-oxadiazole-3-carboxamide This compound was prepared according to method F with ethyl 5-(4-(trifluoromethoxy)benzyl)-1,2,4-oxadiazole-3-carboxylate (0.109 g; 0.346 mmol) in THF (1 mL) and sodium hydroxide in water (2M, 1 mL); and 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (4 mL). The crude mixture was purified by flash chromatography on silica (eluent 20 to 100% ethyl acetate in heptane) to yield 0.0587 g (36%) of N-(2-(5-chloro-1H-indol-3-yl)ethyl)-5-(4-(trifluoromethoxy)benzyl)-1,2,4-oxadiazole-3-carboxamide as a white solid.

ESI/APCI (+): 465 (M+H).
ESI/APCI (−): 464 (M−H).

Example 144

Preparation of N-(2-(5-chloro-1H-indol-3-yl)ethyl)-5-(3-methylbenzyl)-1,2,4-oxadiazole-3-carboxamide This compound was prepared according to method F with ethyl 5-(3-methylbenzyl)-1,2,4-oxadiazole-3-carboxylate (0.107 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.114 g (67%) of the title compound as a white solid.

ESI/APCI (+): 395 (M+H).
ESI/APCI (−): 393 (M−H).

Example 145

Preparation of N-(2-(5-chloro-1H-indol-3-yl)ethyl)-5-(2-methoxybenzyl)-1,2,4-oxadiazole-3-carboxamide This compound was prepared according to method F with ethyl 5-(2-methoxybenzyl)-1,2,4-oxadiazole-3-carboxylate (0.113 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.078 g (44%) of N-(2-(5-chloro-1H-indol-3-yl)ethyl)-5-(2-methoxybenzyl)-1,2,4-oxadiazole-3-carboxamide as a white solid.

ESI/APCI (+): 411 (M+H).
ESI/APCI (−): 410 (M−H).

Example 146

Preparation of N-(2-(5-chloro-1H-indol-3-yl)ethyl)-5-(3,5-difluorobenzyl)-1,2,4-oxadiazole-3-carboxamide This compound was prepared according to method F with ethyl 5-(3,5-difluorobenzyl)-1,2,4-oxadiazole-3-carboxylate (0.116 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) and by preparative HPLC method 2 to yield 0.0535 g (30%) of N-(2-(5-chloro-1H-indol-3-yl)ethyl)-5-(3,5-difluorobenzyl)-1,2,4-oxadiazole-3-carboxamide as a white solid.
ESI/APCI (+): 417 (M+H), (M+Na).
ESI/APCI (−): 415 (M−H).

Example 147

Preparation of N-(2-(5-chloro-1H-indol-3-yl)ethyl)-5-(4-methylbenzyl)-1,2,4-oxadiazole-3-carboxamide This compound was prepared according to method F with ethyl 5-(4-methylbenzyl)-1,2,4-oxadiazole-3-carboxylate (0.107 g; 0.433 mmol) in THF (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) to yield 0.062 g (36%) of the title compound as a white solid.
ESI/APCI (+): 395 (M+H).
ESI/APCI (−): 393 (M−H).

Example 148

Preparation of N-(2-(5-chloro-1H-indol-3-yl)ethyl)-5-(2,5-dimethoxybenzyl)-1,2,4-oxadiazole-3-carboxamide This compound was prepared according to method F with ethyl 5-(2,5-dimethoxybenzyl)-1,2,4-oxadiazole-3-carboxylate (0.126 g; 0.433 mmol) in methanol (1 mL) and sodium hydroxide in water (2M, 1 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol), in DMF (4 mL). The crude mixture was purified by flash chromatography on silica (eluent 20 to 100% ethyl acetate in heptane) to yield 0.069 g (36%) of the N-(2-(5-chloro-1H-indol-3-yl)ethyl)-5-(2,5-dimethoxybenzyl)-1,2,4-oxadiazole-3-carboxamide as a white solid.
ESI/APCI (+): 441 (M+H), 463 (M+Na).
ESI/APCI (−): 439 (M−H).

Example 149

Preparation of N-(2-(5-chloro-1H-indol-3-yl)ethyl)-5-(3,4-dimethoxybenzyl)-1,2,4-oxadiazole-3-carboxamide This compound was prepared according to method F with ethyl 5-(3,4-dimethoxybenzyl)-1,2,4-oxadiazole-3-carboxylate (0.126 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.0607 g (32%) of N-(2-(5-chloro-1H-indol-3-yl)ethyl)-5-(3,4-dimethoxybenzyl)-1,2,4-oxadiazole-3-carboxamide as a white solid.
ESI/APCI (+): 441 (M+H).
ESI/APCI (−): 439 (M−H).

Example 150

Preparation of N-(2-(5-chloro-1H-indol-3-yl)ethyl)-5-(3-methoxybenzyl)-1,2,4-oxadiazole-3-carboxamide This compound was prepared according to method F with ethyl 5-(3-methoxybenzyl)-1,2,4-oxadiazole-3-carboxylate (0.113 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to 0.016 g (9%) of N-(2-(5-chloro-1H-indol-3-yl)ethyl)-5-(3-methoxybenzyl)-1,2,4-oxadiazole-3-carboxamide as a white solid.
ESI/APCI (+): 411 (M+H).
ESI/APCI (−): 409 (M−H).

Example 151

Preparation of 5-(4-tert-butylbenzyl)-N-(2-(5-chloro-1H-indol-3-yl)ethyl)-1,2,4-oxadiazole-3-carboxamide This compound was prepared according to method F with ethyl 5-(4-tert-butylbenzyl)-1,2,4-oxadiazole-3-carboxylate (0.125 g; 0.433 mmol) in methanol (2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.042 g (22%) of 5-(4-tert-butylbenzyl)-N-(2-(5-chloro-1H-indol-3-yl)ethyl)-1,2,4-oxadiazole-3-carboxamide as a white solid.
ESI/APCI (+): 0.437 (M+H)

Example 152

Preparation of N-(2-(5-chloro-1H-indol-3-yl)ethyl)-5-(4-chloro-3-fluorobenzyl)-1,2,4-oxadiazole-3-carboxamide This compound was prepared according to method F with ethyl 5-(4-chloro-3-fluorobenzyl)-1,2,4-oxadiazole-3-carboxylate (0.123 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.053 g (28%) of N-(2-(5-chloro-1H-indol-3-yl)ethyl)-5-(4-chloro-3-fluorobenzyl)-1,2,4-oxadiazole-3-carboxamide as a white solid.

ESI/APCI (+): 433 (M+H).
¹H NMR (DMSO-d6): δ. 11.04 (s, 1H), 9.06 (t, 1H), 7.63-7.59 (m, 2H), 7.51 (dd, 1H), 7.35 (d, 1H), 7.28-7.26 (m, 2H), 7.05 (dd, 1H), 4.50 (s, 2H), 3.50 (m, 2H), 2.91 (t, 2H)

Example 153

Preparation of N-(2-(5-chloro-1H-indol-3-yl)ethyl)-5-(3,4-dichlorobenzyl)-1,2,4-oxadiazole-3-carboxamide This compound was prepared according to method F with ethyl 5-(3,4-dichlorobenzyl)-1,2,4-oxadiazole-3-carboxylate (0.130 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.063 g (32%) of N-(2-(5-chloro-1H-indol-3-yl)ethyl)-5-(3,4-dichlorobenzyl)-1,2,4-oxadiazole-3-carboxamide as a white solid.

ESI/APCI (+): 449 (M+H).
¹H NMR (DMSO-d6): δ. 11.04 (s, 1H), 9.05 (t, 1H), 7.72 (d, 1H), 7.65 (d, 1H), 7.61 (d, 1H), 7.40 (dd, 1H), 7.35 (d, 1H), 7.27 (d, 1H), 7.06 (dd, 1H), 4.49 (s, 2H), 3.50 (m, 2H), 2.91 (t, 2H)

Example 154

Preparation of N-(2-(5-chloro-1H-indol-3-yl)ethyl)-5-(3,4-difluorobenzyl)-1,2,4-oxadiazole-3-carboxamide This compound was prepared according to method F with ethyl 5-(3,4-difluorobenzyl)-1,2,4-oxadiazole-3-carboxylate (0.116 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.0806 g (45%) of N-(2-(5-chloro-1H-indol-3-yl)ethyl)-5-(3,4-difluorobenzyl)-1,2,4-oxadiazole-3-carboxamide as a white solid.

ESI/APCI (+): 417 (M+H).
ESI/APCI (−): 416 (M−H).

Example 155

Preparation of N-(2-(5-chloro-1H-indol-3-yl)ethyl)-5-(4-chlorobenzyl)-1,2,4-oxadiazole-3-carboxamide This compound was prepared according to method F with ethyl 5-(4-chlorobenzyl)-1,2,4-oxadiazole-3-carboxylate (0.115 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL). The crude mixture was purified by flash chromatography on silica (eluent 20 to 100% ethyl acetate in heptane) to yield 0.0536 g (30%) of N-(2-(5-chloro-1H-indol-3-yl)ethyl)-5-(4-chlorobenzyl)-1,2,4-oxadiazole-3-carboxamide as a white solid.

ESI/APCI (+): 415 (M+H)
ESI/APCI (−): 414 (M−H).

Example 156

Preparation of N-(2-(5-chloro-1H-indol-3-yl)ethyl)-5-(4-fluorobenzyl)-1,2,4-oxadiazole-3-carboxamide This compound was prepared according to method F with ethyl 5-(4-fluorobenzyl)-1,2,4-oxadiazole-3-carboxylate (0.108 g; 0.433 mmol) in methanol (2 mL) and sodium hydroxide in water (2M, 2 mL); and 2-(5-chloro-1H-indol-3-yl)ethanamine hydrochloride (0.100 g; 0.433 mmol), HATU (0.164 g; 0.432 mmol), N,N diisopropylethylamine (0.075 mL; 0.432 mmol) in DMF (4 mL).

The crude mixture was purified by flash chromatography on silica (eluent 20 to 100% ethyl acetate in heptane and eluent 2 to 30% ethyl acetate in dichloromethane) to yield 0.0603 g (35%) of N-(2-(5-chloro-1H-indol-3-yl)ethyl)-5-(4-fluorobenzyl)-1,2,4-oxadiazole-3-carboxamide as a white solid.

ESI/APCI (+): 399 (M+H), 416 (M+H₂O).
ESI/APCI (−): 397 (M−H).
¹H NMR (DMSO-d6): δ. 11.05 (s, 1H); 9.07 (t, 1H), 7.63 (d, 1H), 7.46-7.41 (m, 2H), 7.35 (d, 1H), 7.28 (d, 1H), 7.22 (t, 2H), 7.06 (dd, 1H), 4.45 (s, 2H), 3.49 (m, 2H), 2.92 (t, 2H).

Example 157

Preparation of N-(2-(5-chloro-1H-indol-3-yl)ethyl)-5-(2-fluorobenzyl)-1,2,4-oxadiazole-3-carboxamide This compound was prepared according to method F with ethyl 5-(2-fluorobenzyl)-1,2,4-oxadiazole-3-carboxylate (0.108 g; 0.432 mmol) in methanol (6 mL) and sodium hydroxide in water (2M, 6 mL); and 2-(5-chloro-1H-indol-3-yl)ethanamine hydrochloride (0.100 g; 0.432 mmol), HATU (0.164 g; 0.432 mmol), N,N diisopropylethylamine (0.075 mL; 0.432 mmol), in DMF (6 mL). The crude mixture was purified by flash chromatography on silica (eluent 20 to 100% ethyl acetate in heptane) to yield 0.045 g (26%) of N-(2-(5-chloro-1H-indol-3-yl)ethyl)-5-(2-fluorobenzyl)-1,2,4-oxadiazole-3-carboxamide as a white solid.

ESI/APCI (+): 399 (M+H).
ESI/APCI (−): 397 (M−H).

Example 158

Preparation of N-(2-(5-chloro-1H-indol-3-yl)ethyl)-5-(3-fluorobenzyl)-1,2,4-oxadiazole-3-carboxamide This compound was prepared according to method F with ethyl 5-(3-fluorobenzyl)-1,2,4-oxadiazole-3-carboxylate (0.108 g; 0.432 mmol) in methanol (6 mL) and sodium hydroxide in water (2M, 6 mL); and 2-(5-chloro-1H-indol-3-yl)ethanamine hydrochloride (0.100 g; 0.432 mmol), HATU (0.164 g; 0.432 mmol), N,N diisopropylethylamine (0.075 mL; 0.432 mmol) in DMF (6 mL). The crude mixture was purified by flash chromatography on silica (eluent 20 to 100% ethyl acetate in heptane) to yield 0.0695 g (40%) of N-(2-(5-chloro-1H-indol-3-yl)ethyl)-5-(3-fluorobenzyl)-1,2,4-oxadiazole-3-carboxamide as a white solid.

ESI/APCI (+): 398 (M+H). ESI/APCI (−): 397 (M−H).

Example 159

Preparation of 5-benzyl-N-(2-(5-chloro-1H-indol-3-yl)ethyl)-1,2,4-oxadiazole-3-carboxamide This compound was prepared according to method F with ethyl 5-benzyl-1,2,4-oxadiazole-3-carboxylate (0.1 g; 0.432 mmol) in methanol (6 mL) and sodium hydroxide in water (2M, 6 mL); and 2-(5-chloro-1H-indol-3-yl)ethanamine hydrochloride (0.100 g; 0.432 mmol), HATU (0.164 g; 0.432 mmol), N,N diisopropylethylamine (0.075 mL; 0.432 mmol), in DMF (6 mL). The crude mixture was purified by flash chromatography on silica (eluent 20 to 100% ethyl acetate in heptane) to yield 0.072 g (44%) of 5-benzyl-N-(2-(5-chloro-1H-indol-3-yl)ethyl)-1,2,4-oxadiazole-3-carboxamide as a white solid.

ESI/APCI (+): 381 (M+H).
ESI/APCI (−): 379 (M−H).

Example 160

Preparation of N-(2-(5-chloro-1H-indol-3-yl)ethyl)-5-(2,5-difluorobenzoyl)isoxazole-3-carboxamide N-(2-(5-chloro-1H-indol-3-yl)ethyl)-5-(2,5-difluorobenzyl)isoxazole-3-carboxamide (0.0641 g; 0.154 mmol) was added to a solution of tetrabutylammonium fluoride in THF (1 M, 0.462 mL). The resulting mixture was stirred at room temperature overnight. As the reaction was not completed, tetrabutylammonium fluoride in THF (1 M, 2 mL) were added, the reaction mixture was stirred for four hours and concentrated under reduced pressure. The crude mixture was purified by flash chromatography on silica (eluent 1 to 20% methanol in dichloromethane) and by preparative HPLC method 2 to yield 0.013 g (19%) of N-(2-(5-chloro-1H-indol-3-yl)ethyl)-5-(2,5-difluorobenzoyl)isoxazole-3-carboxamide as a yellow solid.

ESI/APCI (+): 430 (M+H).
ESI/APCI (−): 428 (M−H).

Example 161

Preparation of N-(2-(5-chloro-1H-indol-3-yl)ethyl)-5-(hydroxy(phenyl)methyl)isoxazole-3-carboxamide A mixture of ethyl 5-(hydroxy(phenyl)methyl)isoxazole-3-carboxylate (0.534 g; 2.16 mmol) in tetrahydrofurane (6 mL) and sodium hydroxide in water (2M, 5.4 mL) was stirred at room temperature for 1 hour and diluted in water, extracted with dichloromethane and the waters acidified with HCl 6N in water to pH 2 extracted with ethyl acetate, the organic layer was dried and concentrated under reduced pressure. The residue was added to a mixture of 2-(5-chloro-1H-indol-3-yl)ethanamine hydrochloride (0.5 g; 2.16 mmol), HATU (0.822 g; 2.16 mmol), N,N diisopropylethylamine (0.932 mL; 5.41 mmol), in DMF (12 mL) and was stirred at room temperature overnight. The reaction mixture was diluted in ethyl acetate, washed with sodium disulphate, sodium carbonate and brine, dried and concentrated under reduced pressure. The crude mixture was purified by flash chromatography on silica (eluent 20 to 100% ethyl acetate in heptane) to yield 0.817 g (95%) of N-(2-(5-chloro-1H-indol-3-yl)ethyl)-5-(hydroxy(phenyl)methyl)isoxazole-3-carboxamide as a white solid.

ESI/APCI (+): 396 (M+H).

Example 162

Preparation of 5-(2,5-difluorobenzyl)-N-(2-(5-(trifluoromethyl)-1H-indol-3-yl)ethyl)isoxazole-3-carboxamide A mixture of 5-(2,5-difluorobenzyl)isoxazole-3-carboxylic acid (0.08 g, 0.334 mmol), 2-(5-(trifluoromethyl)-1H-indol-3-yl)ethanamine (0.080 g; 0.334 mmol), HATU (0.127 g; 0.334 mmol) and N,N diisopropylethylamine (0.144 mL; 0.836 mmol) in DMF (3 mL), was stirred at room temperature overnight. The reaction mixture was partitioned between ethyl acetate and sodium hydrogen sulphate, the organic layer was washed with sodium carbonate, brine, dried and concentrated under reduced pressure. The crude mixture was purified by flash chromatography on silica (eluent 2 to 60% ethyl acetate in heptane) and by preparative HPLC method 2 to yield 0.013 g (9%) of 5-(2,5-difluorobenzyl)-N-(2-(5-(trifluoromethyl)-1H-indol-3-yl)ethyl)isoxazole-3-carboxamide as a white solid.

ESI/APCI (+): 450 (M+H), 472 (M+Na).

Example 163

Preparation of N-(2-(6-chloro-5-methyl-1H-indol-3-yl)ethyl)-5-(2,5-difluorobenzyl)isoxazole-3-carboxamide A mixture of 5-(2,5-difluorobenzyl)isoxazole-3-carboxylic acid (0.180 g, 0.752 mmol), 2-(6-chloro-5-methyl-1H-indol-3-yl)ethanamine intermediate 142 (0.157 g; 0.752 mmol), HATU (0.286 g; 0.753 mmol) and N,N diisopropylethylamine (0.324 mL; 1.88 mmol) in DMF (5 mL), was stirred at room temperature overnight. The reaction mixture was partitioned between ethyl acetate and sodium hydrogen sulphate, the organic layer was washed with sodium carbonate, brine, dried and concentrated under reduced pressure. The crude mixture was purified by flash chromatography on silica (eluent 2 to 60% ethyl acetate in heptane and eluent 1 to 10% ethyl acetate in dichloromethane) and by preparative HPLC method 2 to yield 0.0051 g (2%) of N-(2-(6-chloro-5-methyl-1H-indol-3-yl)ethyl)-5-(2,5-difluorobenzyl)isoxazole-3-carboxamide as a white solid.

ESI/APCI (+): 430 (M+H)
ESI/APCI (−): 428 (M−H).

Example 164

Preparation of N-(2-(5-cyano-1H-indol-3-yl)ethyl)-5-(2,5-difluorobenzyl)isoxazole-3-carboxamide N-(2-(5-cyano-2-(triethylsilyl)-1H-indol-3-yl)ethyl)-5-(2,5-difluorobenzyl)isoxazole-3-carboxamide (0.036 g; 0.069 mmol) was dissolved in trifluoroacetic acid (2 mL) and the resulting mixture was stirred at room temperature for 2 hours. The mixture was concentrated under reduced pressure with toluene. The crude mixture was purified flash chromatography on silica (eluent 20 to 100% ethyl acetate in heptane) to yield 0.012 g (47%) of N-(2-(5-cyano-1H-indol-3-yl)ethyl)-5-(2,5-difluorobenzyl)isoxazole-3-carboxamide as a white solid.

ESI/APCI (+): 407 (M+H); 429 (M+Na).
ESI/APCI (−): 405 (M−H).

Example 165

Preparation of N-(2-(5-bromo-1H-indol-3-yl)ethyl)-5-(2,5-difluorobenzyl)isoxazole-3-carboxamide A solution of 5-(2,5-difluorobenzyl)isoxazole-3-carboxylic acid (0.104 g, 0.435 mmol), 2-(5-bromo-1H-indol-3-yl)ethanamine hydrochloride (0.120 g; 0.435 mmol), HATU (0.166 g; 0.435 mmol) and N,N diisopropylethylamine (0.201 mL; 1.09 mmol) in DMF (5 mL), was stirred at room temperature overnight. The reaction mixture was partitioned between ethyl acetate and sodium hydrogen sulphate, the organic layer was washed with sodium carbonate, brine, dried and concentrated under reduced pressure. The crude mixture was purified by flash chromatography on silica (eluent 20 to 100% ethyl acetate in heptane) to yield 0.120 g (60%) of N-(2-(5-bromo-1H-indol-3-yl)ethyl)-5-(2,5-difluorobenzyl) isoxazole-3-carboxamide as a white solid.

ESI/APCI (+): 460, 462 (M+H); 482,484 (M+Na).
ESI/APCI (−): 460,458 (M−H).

Example 166

Preparation of 5-(2,5-difluorobenzyl)-N-(2-(5-phenyl-1H-indol-3-yl)ethyl)isoxazole-3-carboxamide A mixture of benzene boronic acid (0.023 g; 0.191 mmol), N-(2-(5-bromo-1H-indol-3-yl)ethyl)-5-(2,5-difluorobenzyl) isoxazole-3-carboxamide (0.080 g; 0.174 mmol), tetrakis (triphenylphosphine)palladium(0) (0.020; 0.017 mmol) and sodium carbonate (0.037 g; 0.347 mmol) in DME (3 mL) and water (1 mL) was irradiated in the microwave oven at 130° C. for 20 minutes, the resulting solution was partitioned between water and EA, the organic layer was concentrated under reduced pressure. The crude mixture was purified by flash chromatography on silica (eluent 20 to 100% ethyl acetate in heptane) and by preparative HPLC method 2 to yield 0.0048 g (6%) of 5-(2,5-difluorobenzyl)-N-(2-(5-phenyl-1H-indol-3-yl)ethyl)isoxazole-3-carboxamide as a white solid.

ESI/APCI (+): 458 (M+H).
ESI/APCI (−): 456 (M−H).

Example 167

Preparation of N-(2-(5-chloro-7-fluoro-1H-indol-3-yl)ethyl)-5-(2,5-difluorobenzyl)isoxazole-3-carboxamide N-(2-(5-chloro-7-fluoro-2-(triethylsilyl)-1H-indol-3-yl) ethyl)-5-(2,5-difluorobenzyl)isoxazole-3-carboxamide (0.050 g; 0.092 mmol) was dissolved in trifluoroacetic acid (3 mL) and stirred at room temperature for 3 hours. The solution was concentrated under reduced pressure and the crude mixture was purified by flash chromatography on silica (eluent 20 to 100% ethyl acetate in heptane) to yield 0.005 g (12%) of N-(2-(5-chloro-7-fluoro-1H-indol-3-yl)ethyl)-5-(2,5-difluorobenzyl)isoxazole-3-carboxamide as a white solid.

ESI/APCI (+): 434 (M+H).
ESI/APCI (−): 432 (M−H).

Example 168

Preparation of N-(2-(5-chloro-1H-indol-3-yl)ethyl)-5-phenyl-1,2,4-oxadiazole-3-carboxamide This compound was prepared according to method F with ethyl 5-phenyl-1,2,4-oxadiazole-3-carboxylate (0.075 g; 0.346 mmol) in THF (1 mL) and sodium hydroxide in water (2M, 1 mL); 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (4 mL). The crude mixture was purified by flash chromatography on silica (eluent 20 to 100% ethyl acetate in heptane) and preparative HPLC method 2 to yield 0.034 g (24%) of N-(2-(5-chloro-1H-indol-3-yl)ethyl)-5-phenyl-1,2,4-oxadiazole-3-carboxamide as a white solid.

ESI/APCI (+): 367 (M+H).
ESI/APCI (−): 365 (M−H).

Example 169

Preparation of N-(2-(5-chloro-1H-indol-3-yl)ethyl)-5-(2,5-difluorophenyl)-1,2,4-oxadiazole-3-carboxamide This compound was prepared according to method F with 5-(2,5-difluorophenyl)-1,2,4-oxadiazole-3-carboxylate (0.075 g; 0.346 mmol) in THF (1 mL) and sodium hydroxide in water (2M, 1 mL); 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (4 mL). The crude mixture was purified by flash chromatography on silica (eluent 20 to 100% ethyl acetate in heptane) and preparative HPLC method 2 to yield 0.017 g (12%) of N-(2-(5-chloro-1H-indol-3-yl)ethyl)-5-(2,5-difluorophenyl)-1,2,4-oxadiazole-3-carboxamide as a white solid.

ESI/APCI (+): 403 (M+H).
ESI/APCI (−): 401 (M−H).

Example 170

Preparation of N-(2-(5-chloro-1H-indol-3-yl)ethyl)-5-((5-methyl-2-phenyloxazol-4-yl)methyl)-1,2,4-oxadiazole-3-carboxamide This compound was prepared according to method F with ethyl 5-((5-methyl-2-phenyloxazol-4-yl)methyl)-1,2,4-oxadiazole-3-carboxylate (0.075 g; 0.238 mmol) in THF (1 mL) and sodium hydroxide in water (2M, 1 mL); 2-(5-chloro-1H-indol-3-yl)ethanamine hydrochloride (0.055 g; 0.238 mmol), HATU (0.090 g; 0.238 mmol), N,N diisopropylethylamine (0.102 mL; 0.594 mmol), in DMF (3 mL). The crude mixture was purified by flash column chromatography on silica (eluent 20 to 100% ethyl acetate in heptane) to yield 0.042 (39%) of the title compound as a white solid.

ESI/APCI (+): 462 (M+H).

Example 171

Preparation of N-(2-(5-chloro-1H-indol-3-yl)ethyl)-5-(2-fluoro-3-(trifluoromethyl)benzyl)-1,2,4-oxadiazole-3-carboxamide This compound was prepared according to method F with ethyl 5-(2-fluoro-3-(trifluoromethyl)benzyl)-1,2,4-oxadiazole-3-carboxylate (0.085 g; 0.254 mmol) in THF (1 mL) and sodium hydroxide in water (2M, 1 mL); 2-(5-chloro-1H-indol-3-yl)ethanamine hydrochloride (0.065 g; 0.281 mmol), HATU (0.107 g; 0.281 mmol), N,N diisopropylethylamine (0.094 mL; 0.703 mmol), in DMF (3 mL). The crude mixture was purified by flash column chromatography on silica (eluent 20 to 100% ethyl acetate in heptane) and by preparative HPLC method 2 to yield 0.034 g (26%) of N-(2-(5-chloro-1H-indol-3-yl)ethyl)-5-(2-fluoro-3-(trifluoromethyl)benzyl)-1,2,4-oxadiazole-3-carboxamide as a white solid.

ESI/APCI (+): 467 (M+H).
ESI/APCI (−): 466 (M−H).

Example 172

Preparation of N-(2-(5-chloro-1H-indol-3-yl)ethyl)-5-(2-fluoro-5-(trifluoromethyl)benzyl)-1,2,4-oxadiazole-3-carboxamide This compound was prepared according to method F with ethyl 5-(2-fluoro-5-(trifluoromethyl)benzyl)-1,2,4-oxadiazole-3-carboxylate (0.111 g; 0.346 mmol) in THF (1 mL) and sodium hydroxide in water (2M, 1 mL); 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (3 mL). The crude mixture was purified by flash column chromatography on silica (eluent 20 to 100% ethyl acetate in heptane) and by preparative HPLC method 2 to yield 0.0113 g (7%) of N-(2-(5-chloro-1H-indol-3-yl)ethyl)-5-(2-fluoro-5-(trifluoromethyl)benzyl)-1,2,4-oxadiazole-3-carboxamide as a white solid.

ESI/APCI (+): 467 (M+H).
ESI/APCI (−): 466 (M−H).

Example 173

Preparation of N-(2-(5-chloro-1H-indol-3-yl)ethyl)-5-(4-fluoro-2-(trifluoromethyl)benzyl)-1,2,4-oxadiazole-3-carboxamide This compound was prepared according to method F with ethyl 5-(4-fluoro-2-(trifluoromethyl)benzyl)-1,2,4-oxadiazole-3-carboxylate (0.099 g; 0.311 mmol) in THF (1 mL) and sodium hydroxide in water (2M, 1 mL); 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (3 mL). The crude mixture was purified by flash column chromatography on silica (eluent 20 to 100% ethyl acetate in heptane) and by preparative HPLC method 2 to yield 0.022 (14%) of N-(2-(5-chloro-1H-indol-3-yl)ethyl)-5-(4-fluoro-2-(trifluoromethyl)benzyl)-1,2,4-oxadiazole-3-carboxamide as a white solid.

ESI/APCI (+): 467 (M+H).
ESI/APCI (−): 466 (M−H).

Example 174

Preparation of N-(2-(5-chloro-1H-indol-3-yl)ethyl)-5-(2,3,4-trifluorobenzyl)-1,2,4-oxadiazole-3-carboxamide This compound was prepared according to method F from ethyl 5-(2,3,4-trifluorobenzyl)-1,2,4-oxadiazole-3-carboxylate (0.089 g; 0.311 mmol) in THF (1 mL) and sodium hydroxide in water (2M, 1 mL); 2-(5-chloro-1H-indol-3-yl)ethanamine hydrochloride (0.080 g; 0.346 mmol), HATU (0.131 g; 0.346 mmol), N,N diisopropylethylamine (0.149 mL; 0.865 mmol), in DMF (3 mL). The crude mixture was purified by flash column chromatography on silica (eluent 20 to 100% ethyl acetate in heptane) and by preparative HPLC method 2 to yield 0.013 (9%) of N-(2-(5-chloro-1H-indol-3-yl)ethyl)-5-(2,3,4-trifluorobenzyl)-1,2,4-oxadiazole-3-carboxamide as a white solid.

ESI/APCI (+): 435 (M+H).
ESI/APCI (−): 432 (M−H).

Example 175

Preparation of N-(2-(5-chloro-1H-indol-3-yl)ethyl)-5-(2,4,6-trifluorobenzyl)-1,2,4-oxadiazole-3-carboxamide This compound was prepared according to method F from ethyl 5-(2,4,6-trifluorobenzyl)-1,2,4-oxadiazole-3-carboxylate (0.100 g; 0.350 mmol) in THF (1 mL) and sodium hydroxide in water (2M, 1 mL); 2-(5-chloro-1H-indol-3-yl) ethanamine hydrochloride (0.090 g; 0.389 mmol), HATU (0.148 g; 0.389 mmol), N,N diisopropylethylamine (0.167 mL; 0.973 mmol), in DMF (3 mL). The crude mixture was purified by flash column chromatography on silica (eluent 20 to 100% ethyl acetate in heptane) and by preparative HPLC method 2 to yield 0.020 (12%) of N-(2-(5-chloro-1H-indol-3-yl)ethyl)-5-(2,4,6-trifluorobenzyl)-1,2,4-oxadiazole-3-carboxamide as a white solid.

ESI/APCI (+): 435 (M+H).

Example 176

Preparation of N-(2-(5-chloro-1H-indol-3-yl)ethyl)-5-((2,5-difluorophenyl)difluoromethyl)isoxazole-3-carboxamide diethylaminosulfur trifluoride (0.045 mL; 0.267 mmol) was added to a solution of N-(2-(5-chloro-1H-indol-3-yl) ethyl)-5-(2,5-difluorobenzoyl)isoxazole-3-carboxamide (0.140 g; 0.324 mmol) in dichloromethane (5 mL) and stirred at room temperature overnight. The reaction mixture was diluted in dichloromethane and washed with sodium hydrogen carbonate and brine, dried and concentrated under reduced pressure. The crude material was purified by flash chromatography on silica (eluent 20 to 100% ethyl acetate in heptane) and by preparative HPLC method 2 to yield 0.0071 g (7%) of N-(2-(5-chloro-1H-indol-3-yl)ethyl)-5-((2,5-difluorophenyl)difluoromethyl)isoxazole-3-carboxamide as a white solid.

ESI/APCI (+): 452 (M+H).
ESI/APCI (−): 451 (M−H).

Example 177

Preparation of N-(2-(5-chloro-1H-indol-3-yl)ethyl)-5-((2,5-difluorophenyl)(hydroxy)methyl)isoxazole-3-carboxamide Sodium borohydride (0.02 g; 0.530 mmol) was added to a solution of N-(2-(5-chloro-1H-indol-3-yl)ethyl)-5-(2,5-difluorobenzoyl)isoxazole-3-carboxamide (0.167 g; 0.388 mmol) in methanol (3 mL) and stirred at room temperature for 4 hours: as the reaction did not evolve anymore, some fresh sodium borohydride was added (0.02 g; 0.530 mmol) to the reaction and the resulting mixture was left stirring overnight. The mixture was diluted in a solution of sodium hydrogencarbonate saturated in water and extracted with ethyl acetate, dried and concentrated under reduced pressure. The crude mixture was purified by flash chromatography on silica (eluent 20 to 100% ethyl acetate in heptane) to yield 0.074 g (61%) of N-(2-(5-chloro-1H-indol-3-yl)ethyl)-5-((2,5-difluorophenyl)(hydroxy)methyl)isoxazole-3-carboxamide as a white solid.

ESI/APCI (+): 432 (M+H).

Example 178

Preparation of N-(2-(5-chloro-1H-pyrrolo[2,3-b] pyridin-3-yl)ethyl)-5-(2,5-difluorobenzoyl)isoxazole-3-carboxamide A solution of tetrabutylammonium fluoride 1M in THF (1 mL; 1 mmol) was added to a solution of N-(2-(5-chloro-2-(triethylsilyl)-1H-pyrrolo[2,3-b]pyridin-3-yl)ethyl)-5-(2,5-difluorobenzoyl)isoxazole-3-carboxamide (0.105 g, 0.198 mmol) in THF (5 mL). The mixture was stirred overnight at room temperature and was evaporated. The residue was dissolved in dichloromethane, and the organic solution was washed with water and was concentrated under reduced pressure. The crude material was purified twice by flash chromatography on silica gel (eluent: 0 to 40% of ethyl acetate in dichloromethane) to give 0.019 g (22%) of N-(2-(5-chloro-1H-pyrrolo[2,3-b]pyridin-3-yl)ethyl)-5-(2,5-difluorobenzoyl)isoxazole-3-carboxamide as a white solid.

ESI/APCI (+): 431 (M+H); ESI/APCI (−): 429 (M−H).

1H NMR (d6-DMSO) d 11.6 (s, 1H); 9.1 (t, 1H); 8.16 (d, 1H); 8.09 (d, 1H); 7.7 (m, 1H), 7.63 (m, 1H), 7.57 (s, 1H); 7.55 (dt, 1H), 7.40 (br s, 1H), 3.53 (q, 2H); 2.95 (t, 2H).

Example 179

Preparation of N-(2-(5-chloro-1H-pyrrolo[2,3-b]pyridin-3-yl)ethyl)-5-(2,5-difluorobenzyl)isoxazole-3-carboxamide The mixture of 2-(5-chloro-1H-pyrrolo[2,3-b]pyridin-3-yl)ethanamine hydrochloride (0.070 g; 0.301 mmol), 5-(2,5-difluorobenzyl)isoxazole-3-carboxylic acid (0.073 g; 0.304 mmol), HATU (N,N,N',N'-Tetramethyl-O-(7-azabenzotriazol-1-yl)uronium hexafluorophosphate) (0.116 g: 0.304 mmol) and N,N-diisopropylethylamine (0.132 mL; 0.754 mmol) in DMF (3 mL) was stirred for 72 hours at room temperature and was concentrated under reduced pressure. The residue was dissolved in dichloromethane and the organic layer was washed with water and concentrated under reduced pressure. The crude material was purified by flash chromatography on silica gel (eluent: 0 to 35% of ethyl acetate in dichloromethane) to give 0.051 g (40%) of N-(2-(5-chloro-1H-pyrrolo[2,3-b]pyridin-3-yl)ethyl)-4-(3-fluorobenzyl)benzamide as a white solid.

ESI/APCI (+): 417 (M+H); 439 (M+Na).
ESI/APCI (−): 415 (M−H).

Example 180

Preparation of N-(2-(5-chloro-1H-indol-3-yl)ethyl)-5-((2,5-difluorophenyl)fluoromethyl)isoxazole-3-carboxamide Diethylaminosulfur trifluoride (0.033 mL; 0.197 mmol) was added to a solution of N-(2-(5-chloro-1H-indol-3-yl)ethyl)-5-((2,5-difluorophenyl)(hydroxy)methyl)isoxazole-3-carboxamide (0.074 g; 0.171 mmol) in dichloromethane (5 mL) at −78° C., the resulting mixture was stirred at room temperature for 3 hours, cooled to 0° C. and quenched with water. The layers were separated, the aqueous layer was extracted with dichloromethane. The organic layers rejoined were dried over magnesium sulphate and concentrated under reduced pressure. The crude material was purified by flash chromatography on silica (eluent 20 to 100% ethyl acetate in heptane) and by preparative HPLC method 2 to yield 0.005 g (7%) of N-(2-(5-chloro-1H-indol-3-yl)ethyl)-5-((2,5-difluorophenyl)fluoromethyl)isoxazole-3-carboxamide as a white solid.

ESI/APCI (+): 434 (M+H).
ESI/APCI (−): 433 (M−H).

Example 181

Preparation of 1-(3-benzylimidazolidin-1-yl)-3-(5-chloro-1H-indol-3-yl)propan-1-one The tert-butyl 3-benzylimidazolidine-1-carboxylate (0.122 g; 0.465 mmol) was dissolved in a mixture of trifluoroacetic acid (4 mL) and dichloromethane (6 mL), stirred at room temperature for 2 hours and concentrated under reduced pressure. The residue was dissolved in dichloromethane and added to a mixture of 3-(5-chloro-1H-indol-3-yl)propanoic acid (0.080 g; 0.358 mmol), HATU (0.150 g; 0.393 mmol), N,N diisopropylethylamine (0.152 mL; 0.894 mmol) in dichloromethane (5 mL) and DMF (1 mL) and stirred at room temperature overnight. The reaction mixture was concentrated underreduced pressure and dissolved in ethyl acetate, washed with sodium hydrogen sulphate, sodium carbonate, dried and concentrated under reduced pressure. The crude mixture was purified by flash chromatography on silica (0 to 10% MeOH in dichloromethane) and by preparative HPLC method 4 to yield 0.0097 g (7%) of 1-(3-benzylimidazolidin-1-yl)-3-(5-chloro-1H-indol-3-yl)propan-1-one as a solid.

ESI/APCI (+): 368 (M+H).
ESI/APCI (−): 366 (M−H).

Example 182

Preparation of (4-(5-chloro-1H-indol-3-yl)piperidin-1-yl)(5-(2,5-difluorobenzyl)isoxazol-3-yl)methanone The mixture of 5-chloro-3-(piperidin-4-yl)-1H-indole hydrochloride (0.070 g; 0.258 mmol), 5-(2,5-difluorobenzyl)isoxazole-3-carboxylic acid (0.062 g; 0.258 mmol), HATU (N,N,N'N'-tetramethyl-O-(7-azabenzotriazol-1-yl)uronium hexafluorophosphate) (0.098 g: 0.258 mmol) and N,N-diisopropylethylamine (0.113 mL; 0.634 mmol) in DMF (3 mL) was stirred for 72 hours at room temperature and was concentrated under reduced pressure. The residue was dissolved in dichloromethane and the organic layer was washed with water and concentrated under reduced pressure. The crude material was purified by flash chromatography on silica gel (eluent: 0 to 10% of ethyl acetate in dichloromethane) to give 0.0428 g (36%) of (4-(5-chloro-1H-indol-3-yl)piperidin-1-yl)(5-(2,5-difluorobenzyl)isoxazol-3-yl)methanone as a white solid.

ESI/APCI (+): 456 (M+H); 478 (M+Na).
ESI/APCI (−): 454 (M−H).

Example 183

Preparation of N-(2-(5-chloro-1H-indol-3-yl)ethyl)oxazole-5-carboxamide

A mixture of ethyl oxazole-5-carboxylate (0.167 g; 1.19 mmol) in tetrahydrofurane (5 mL) and sodium hydroxide in water (2M, 2.7 mL) was stirred at room temperature for 1 hour and diluted in water, extracted with dichloromethane and the waters acidified with HCl 6N in water to pH 2 extracted with ethyl acetate, the organic layer was dried and concentrated under reduced pressure. The residue was added to a mixture of 2-(5-chloro-1H-indol-3-yl)ethanamine hydrochloride (0.25 g; 1.08 mmol), HATU (0.411 g; 1.08 mmol), N,N diisopropylethylamine (0.466 mL; 2.70 mmol), in DMF (6 mL) and was stirred at room temperature overnight. The reaction mixture was diluted in ethyl acetate, washed with sodium disulphate, sodium carbonate and brine, dried and concentrated under reduced pressure. The crude mixture was purified by flash chromatography on silica (eluent 20 to 100% ethyl acetate in heptane) to yield 0.182 g (32%) of N-(2-(5-chloro-1H-indol-3-yl)ethyl)oxazole-5-carboxamide as a yellow solid.

ESI/APCI (+): 290 (M+H), (M+Na).
ESI/APCI (−): 288 (M−H).

Example 184

Preparation of N-(2-(5-chloro-1H-indol-3-yl)ethyl)-2-phenyloxazole-5-carboxamide Water (5 mL) was added to a pre-stirred mixture of N-(2-(5-chloro-1H-indol-3-yl)ethyl)oxazole-5-carboxamide intermediate 173 (0.107 g; 0.369 mmol), phenyl iodide (0.050 mL; 0.443 mmol), (1,1'-bis(diphenylphosphino)ferrocene)-dichloropalladium(II), complex with dichloromethane (0.015 g; 0.019 mmol), silver carbonate (0.204 g; 0.738 mmol) and triphenylphosphine (0.010 g; 0.037 mmol). The resulting mixture was stirred at 70° C. for 24 hours and after cooling down the mixture was partitioned between brine and dichloromethane. the two phases were separated and the aqueous layer was extracted with dichloromethane. The organic layer was dried and concentrated under reduced pressure. The crude mixture was purified by flash chromatography on silica (eluent 20 to 100% ethyl acetate in heptane) to yield 0.025 (19%) of the title compound as a yellow solid.

ESI/APCI (+): 366 (M+H), (M+Na).
ESI/APCI (−): 364 (M−H).

Example 185

Preparation of N-(2-(5-chloro-1H-indol-3-yl)ethyl)-5-methyl-2-phenylfuran-3-carboxamide Triethylamine (0.128 mL; 0.886 mmol) was added to a mixture of 2-(5-chloro-1H-indol-3-yl)ethanamine hydrochloride (0.082 g; 0.354 mmol) and 5-methyl-2-phenylfuran-3-carbonyl chloride (0.082 g; 0.372 mmol) in dichloromethane (7 mL) at room temperature. The reaction mixture was stirred at room temperature for 20 minutes and washed with water. The organic layer was concentrated under reduced pressure and the crude material was purified by flash chromatography on silica gel (eluent 2 to 10% ethyl acetate in dichloromethane) to afford 0.116 g (86%) of N-(2-(5-chloro-1H-indol-3-yl)ethyl)-5-methyl-2-phenylfuran-3-carboxamide as a solid.

ESI/APCI (+): 379 (M+H).

Example 186

Preparation of N-(2-(5-chloro-1H-indol-3-yl)ethyl)-4-phenylisoxazole-3-carboxamide A mixture of ethyl 4-phenylisoxazole-3-carboxylate (0.030 g; 0.130 mmol) in THF (1 mL) and sodium hydroxide in water (2M, 1 mL) was stirred at room temperature for 2.5 hours. The reaction mixture was then diluted with water and the aqueous layer was extracted with dichloromethane. The aqueous layer was acidified with HCl 6N until pH 2 and extracted with ethyl acetate. The organic layer was dried over magnesium sulphate and concentrated under reduced pressure. The crude residue was added to a mixture of 2-(5-chloro-1H-indol-3-yl)ethanamine hydrochloride (0.030 g; 0.130 mmol), HATU (0.50 g; 0.130 mmol), N,N diisopropylethylamine (0.055 mL; 0.324 mmol), in DMF (2 mL) and was stirred at room temperature for 72 hours. The reaction mixture was diluted with ethyl acetate and was washed with sodium hydrogensulphate, sodium carbonate and brine. The organic layer was dried over magnesium sulphate and concentrated under reduced pressure. The crude material was purified by flash chromatography on silica (eluent 20 to 100% ethyl acetate in heptane) and then by preparative HPLC method 2 to yield 0.0136 g (30%) of the title compound as a white solid.

ESI/APCI (+): 366 (M+H).
ESI/APCI (−): 365 (M−H).

Example 187

Preparation of 5-benzyl-N-(2-(5-chloro-1H-indol-3-yl)ethyl)isothiazole-3-carboxamide The 5-Benzyl-N-(2-(5-chloro-1H-indol-3-yl)ethyl)isothiazole-3-carboxamide is prepared following method A starting from 2-(5-chloro-1H-indol-3-yl)ethanamine hydrochloride, 5-benzylisothiazole-3-carboxylic acid (which can be prepared by procedures known to the skilled in the art), HATU and N,N-diisopropylethylamine in DMF.

Example 188

Preparation of 5-benzyl-N-(2-(5-chloro-1H-indol-3-yl)ethyl)-1,2,4-thiadiazole-3-carboxamide The 5-benzyl-N-(2-(5-chloro-1H-indol-3-yl)ethyl)-1,2,4-thiadiazole-3-carboxamide is prepared following method A starting from 2-(5-chloro-1H-indol-3-yl)ethanamine hydrochloride, 5-benzyl-1,2,4-thiadiazole-3-carboxylic acid (which can be prepared by procedures known to the skilled in the art), HATU and N,N-diisopropylethylamine in DMF.

Example 189

Preparation of (4-(1H-indol-3-yl)piperidin-1-yl)(5-(2,5-difluorobenzyl)isoxazol-3-yl)methanone The mixture of 3-(piperidin-4-yl)-1H-indole hydrochloride (0.060 g; 0.253 mmol), 5-(2,5-difluorobenzyl)isoxazole-3-carboxylic acid (0.061 g; 0.253 mmol), HATU (N,N,N',N'-tetramethyl-O-(7-azabenzotriazol-1-yl)uronium hexafluorophosphate) (0.096 g: 0.253 mmol) and N,N-diisopropylethylamine (0.110 mL; 0.634 mmol) in DMF (3 mL) was stirred for 72 hours at room temperature and was concentrated under reduced pressure. The residue was dissolved in dichloromethane and the organic layer was washed with water and concentrated under reduced pressure. The crude material was purified by flash chromatography on silica gel (eluent: 0 to 10% of ethyl acetate in dichloromethane) to give 0.069 g (65%) of (4-(1H-indol-3-yl)piperidin-1-yl)(5-(2,5-difluorobenzyl)isoxazol-3-yl)methanone as a white solid.

ESI/APCI (+): 422 (M+H); 444 (M+Na).
ESI/APCI (−): 420 (M−H).

Example 190

Preparation of N-(2-(1H-indazol-3-yl)ethyl)-5-(2,5-difluorobenzyl)isoxazole-3-carboxamide A mixture of 2-(1H-indazol-3-yl)ethanamine hydrochloride (0.040 g; 0.202 mmol), 5-(2,5-difluorobenzyl)isoxazole-3-carboxylic acid (0.053 g; 0.223 mmol) N,N-diisopropylethylamine (0.87 mL; 0.506 mmol) and HATU (0.84 g; 0.223 mmol) in DMF (5 mL) was stirred at room temperature for 18 hours. The reaction mixture was diluted with ethyl acetate and washed with sodium hydrogen sulphate, sodium carbonate and brine. The organic layer was dried and concentrated under reduced pressure. The crude material was purified by flash chromatography on silica (eluent 1 to 10% methanol in dichloromethane) and by preparative HPLC method 4 to yield 0.007 g (9%) of the title compound as a white solid.

ESI/APCI (+): 383 (M+H).

Example 191

Preparation of N-(2-(5-chloro-1H-indol-3-yl)ethyl)-5-(furan-2-yl)-1-methyl-1H-pyrazole-3-carboxamide This compound was obtained following Method B starting from 2-(5-chloro-1H-indol-3-yl)ethanamine hydrochloride (0.100 g, 0.432 mmol), 5-(furan-2-yl)-1-methyl-1H-pyrazole-3-carbonyl chloride (0.096 g; 0.454 mmol), and triethylamine (0.156 mL; 1.08 mmol) in dichloromethane (2.87 mL). Flash chromatography on silica gel eluting with 5% of ethyl acetate in dichloromethane gave 0.121 g (98%) of N-(2-(5-chloro-1H-indol-3-yl)ethyl)-5-(furan-2-yl)-1-methyl-1H-pyrazole-3-carboxamide as a solid.

ESI/APCI (+): 369 (M+H).

Example 192

Preparation of N-(2-(5-fluoro-1H-indol-3-yl)ethyl)-4-methyl-2-p-tolylthiazole-5-carboxamide This compound was prepared following Method A starting from 2-(5-fluoro-1H-indol-3-yl)ethanamine (0.030 g; 0.168 mmol), 4-methyl-2-p-tolylthiazole-5-carboxylic acid (0.043 g; 0.185 mmol), HATU (0.070 g; 0.185 mmol) and N,N-diisopropylethylamine (0.78 mL; 0.420 mmol) in DMF (5 mL). Flash chromatography on silica gel eluting with 1 to 5% of ethyl acetate in dichloromethane gave 0.018 g (27%) of N-(2-(5-fluoro-1H-indol-3-yl)ethyl)-4-methyl-2-p-tolylthiazole-5-carboxamide as a solid.

ESI/APCI (+): 394 (M+H).

Example 193

Preparation of N-(2-(5-chloro-1H-indol-3-yl)ethyl)-5-(ethoxymethyl)-4,5-dihydroisoxazole-3-carboxamide This compound was prepared following Method A starting from 2-(5-chloro-1H-indol-3-yl)ethanamine hydrochloride (0.073 g; 0.311 mmol), 5-(ethoxymethyl)-4,5-dihydroisoxazole-3-carboxylic acid (0.054 g; 0.311 mmol), HATU (0.130 g; 0.343 mmol) and N,N-diisopropylethylamine (1.36 mL; 0.779 mmol) in DMF (3 mL). Flash chromatography on silica gel eluting with 1 to 10% of ethyl acetate in dichloromethane gave 0.070 g (64%) of N-(2-(5-chloro-1H-indol-3-yl)ethyl)-5-(ethoxymethyl)-4,5-dihydroisoxazole-3-carboxamide as a solid.

ESI/APCI (+): 350 (M+H).
ESI/APCI (−): 348 (M−H).

Part B

Example 194

Construction of a TAU Gene Over-Expressing Cell Line

A TAU expression plasmid was constructed by sub-cloning the cDNA of human TAU-P301 L (encoding for TAU with proline 301 substituted by a leucine residue) into mammalian expression vector pcDNA3.1 resulting in plasmid pcDNA3.1-TAU P301L. Plasmids pcDNA3.1 and pcDNA3.1-TAU P301L were transfected to human neuroblastoma cells (BM17; ATCC No. CRL-2267) and independent clonal lines with the plasmids stably integrated into the genome were selected. These resulted in cell lines named M17-3.1 and M17-TAU(P301L) (transfected with pcDNA3.1 and pcDNA3.1-TAU P301L, respectively). Expression of the TAU P301L genes in the cell lines was confirmed by Western analysis.

Example 195

Use of TAU Expressing Cells as a Model of Neuronal Degradation

The expression of TAU P301L in M17-TAU(P301L) cells was found to confer increased toxicity relative to control cells expressing wild type TAU (M17-TAUwt). In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining TAU cytotoxicity was as follows: From appropriate precultures of M17-3.1 and M17-TAU(P301L) cells were seeded at 2500 cells/cm2 in Optimem Reduced Serum without phenol red (Gibco, Cat. 31985-047) supplemented with 1% fetal calf serum, 1 mM sodium pyruvate, 1× non-essential amino acids, 500 µg/ml G418 0.5× antibiotic/antimycotic. After 3 h of incubation at 37° C./5% CO2 1 volume of Optimem Reduced Serum (same as described above; except without fetal calf serum) supplemented with 2.5 µM retinoic acid (RA) was added. The cells were further incubated for 7 days. Subsequently, LDH activity was determined using Promega Cytotox 96 Non-Radioactive cytotoxicity assay, (Cat. G1780) according the supplier's instructions. FIG. 1 shows that of M17-TAU P301L cells, but not of M17-3.1 cells display a relatively high level of LDH leaked into the medium demonstrating toxicity specifically provoked by TAU P301.

Example 196

Use of the TAU Expressing Cells the Testing of Exemplary Compounds of this Invention The M17-TAU P301L cell line made it possible to assess the ability of novel compounds to counteract TAU cytotoxicity. Active inhibitors of TAU cytotoxicity were found to inhibit LDH leakage of M17-TAU P301L cells treated as described in Example 195 Efficacy (potency) of the compounds was determined by testing compounds at different concentrations ranging from non-effective (thus at a relatively low concentration) to an effective concentration for their ability to reduce LDH activity of retinoic acid incubated M17-TAU P301L cells. These measurements were used to calculate EC50 values of table 2.

Example 197

In-Vivo Inhibition of Pathological TAU-Phosphorylation

Human TAU R406W transgenic mice (Zhang et al, J. of Neuroscience 24(19):4657-4667, 2004) were treated once-a-day subcutaneously for 4 weeks with compound D5 (see table 1) dissolved in arachidin oil at a dose of 35 mg/kg. Correspondingly vehicle treated transgenics were included as controls. At the end of the treatment period mice were sacrificed and brainstem was stereotactically collected. Soluble protein fractions were prepared (Terwel et al, J Biol Chem 280(5): 3963-73, 2005) from the brain stem and subjected to Western analysis using antibodies directed against TAU and several different phospho-isoforms thereof.

Figure 3:
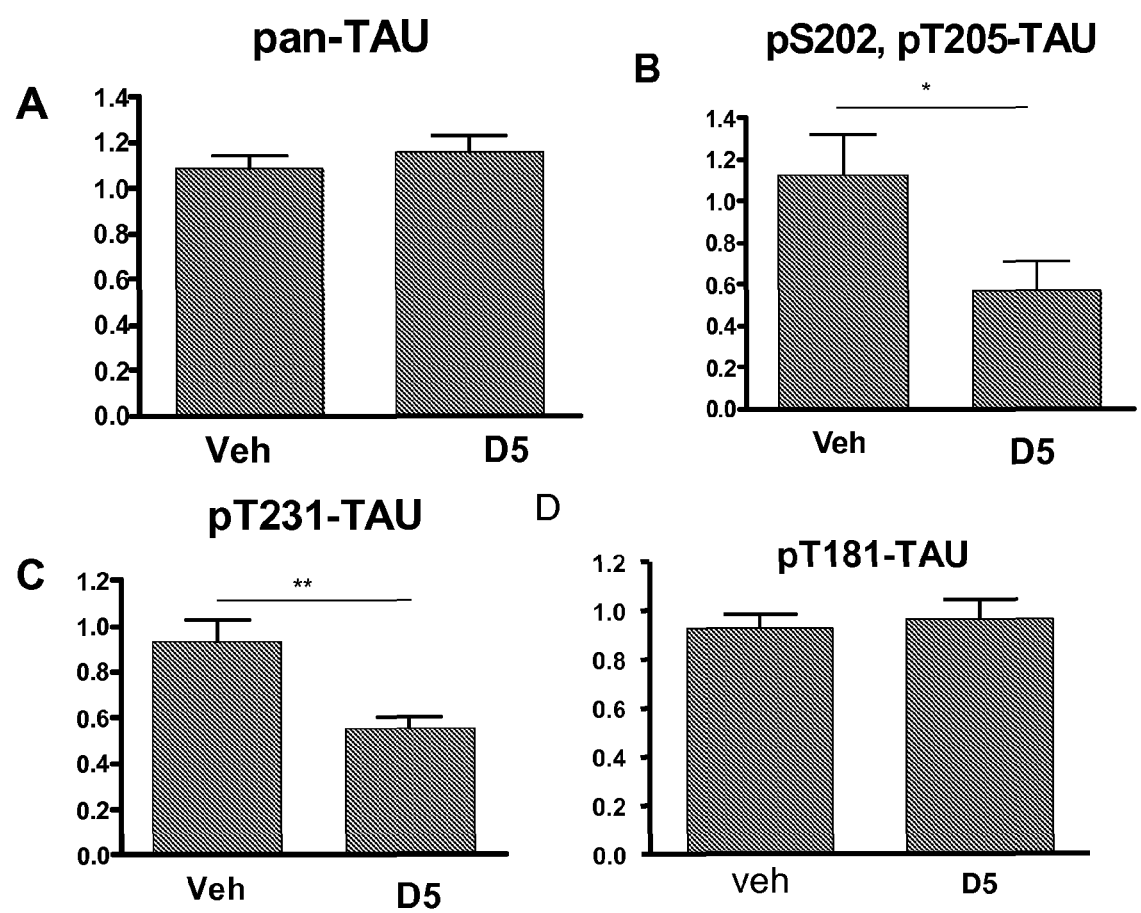
FIG. 3 shows that compound D5 (see table 1) reduces pathological TAU-species in-vivo. Quantification of Western analyses of TAU and phospho-TAU species of the soluble protein fraction prepared from cortex of all individual mice used in this study (n=10 for each treatment group). TAU signals of all individual mice were normalized against neuron specific enolase (NSE) using antibodies (monoclonal anti-NSE antibody, clone 37E4, Abcam) to correct for possible loading control differences. The graphs depict the mean normalised TAU signals±SEM. The TAU signals were obtained by using antibodies directed against.

Quantitative analysis of the Western blots revealed that total TAU levels were not statistically significant affected in treated animals (FIG. 3 A) indicating that treatment does not affect the overall levels of TAU. However, in treated animals a robust and statistically significant reduction was detected for TAU phosphorylated at serine 202 and tyrosine 205 (FIG. 3 B) or at tyrosine residue 231 (FIG. 3 C). These phospho-epitopes are pathologically relevant for disease since in Alzheimer's disease patients TAU is hyperphosphorylated at and hyperphosphorylation at these sites has been implicated in aggregation and toxicity of TAU (Bertrand et al, Neuroscience 168(2):323-34, 2010; Luna-Muños et al, J Alzheimers Dis. 12(4):365-75, 2007, Augustinack et al, Acta Neuropathol. 103(1):26-35, 2002). Phosphorylation of tyrosine residue 181 was not affected (FIG. 3 D).

Collectively, these data revealed that treatment of transgenic TAU mice with compound D5 modulates disease relevant species of TAU in-vivo. These effects on TAU are highly specific and involve specific phospho species of TAU. The overall expression of TAU is not decreased by the treatment. Hence the overall TAU activity in the cell remains fully intact by treatment of D5 and excludes the possibility of undesired toxicity or side effects in treated patients due to reduction of TAU functionality.

Example 198

In Vivo Inhibition of TAU-Instigated Pathologies

Human TAU R406W transgenic mice (J. of Neuroscience 24(19): 4657-4667, 2004) are chronically treated between 2 weeks and 12 months with either an exemplary compound of this invention or vehicle only. The compound treated mice possess a longer average lifespan and display a delayed onset or progression of motor weakness compared to the vehicle controls. In addition compound treated mice have improved learning and memory capabilities when performing the Morris water maze test.

At the end of the treatment period, mice are sacrificed and the corresponding brains are used for biochemical and immunohistochemical analysis. The brains of compound treated mice are heavier than brains of the control group. In compound treated mice Western analysis shows that TAU phosphorylation is reduced suggesting lowered formation of pathological TAU species. Also a reduced accumulation of TAU is found in the insoluble fraction of total brain extracts and/or the cerebral spine fluid (CSF) of compound treated mice. Immunohistochemical analysis showed that compound treated mice have reduced accumulation of filamentous TAU aggregates in cerebral cortex, hippocampus, cerebellum, and spinal cord neurons.

Example 199

Construction of an α-Synuclein Over-Expressing Cell Line

An α-synuclein expression plasmid was constructed by sub-cloning the NcoI/XhoI fragment from 212T-SYN(WT) (Griffioen et al., Biochem Biophys Acta (2006) 1762(3):312-318) containing the cDNA of human wild type α-synuclein correspondingly into a standard mammalian expression vector pcDNA3.1 resulting in plasmid pcDNA3.1-SYNwt. Plasmid pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Over-expression of α-synuclein in M17-SYNwt cell lines was confirmed by Western analysis.

Example 200

Use of α-Synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining α-synuclein cytotoxicity was as follows: From appropriate precultures of M17 and M17-SYN cells were seeded at 50000 cells/cm$^2$ in Optimem Reduced Serum without phenol red (InVitrogen, Cat. 31985-047) supplemented with 5% fetal calf serum, 1 mM sodium pyruvate, 1× non-essential amino acids, 500 µg/ml G418 0.5× antibiotic/antimycotic. After 3 h of incubation at 37° C./5% $CO_2$ paraquat was added to the cells (final concentration of 32 mM), together with the test compound and the cells were further incubated for 40 hours. Subsequently, LDH activity was determined using Promega Cytotox 96 Non-Radioactive cytotoxicity assay, (Cat. G1780) according the supplier's instructions.

Figure 2:
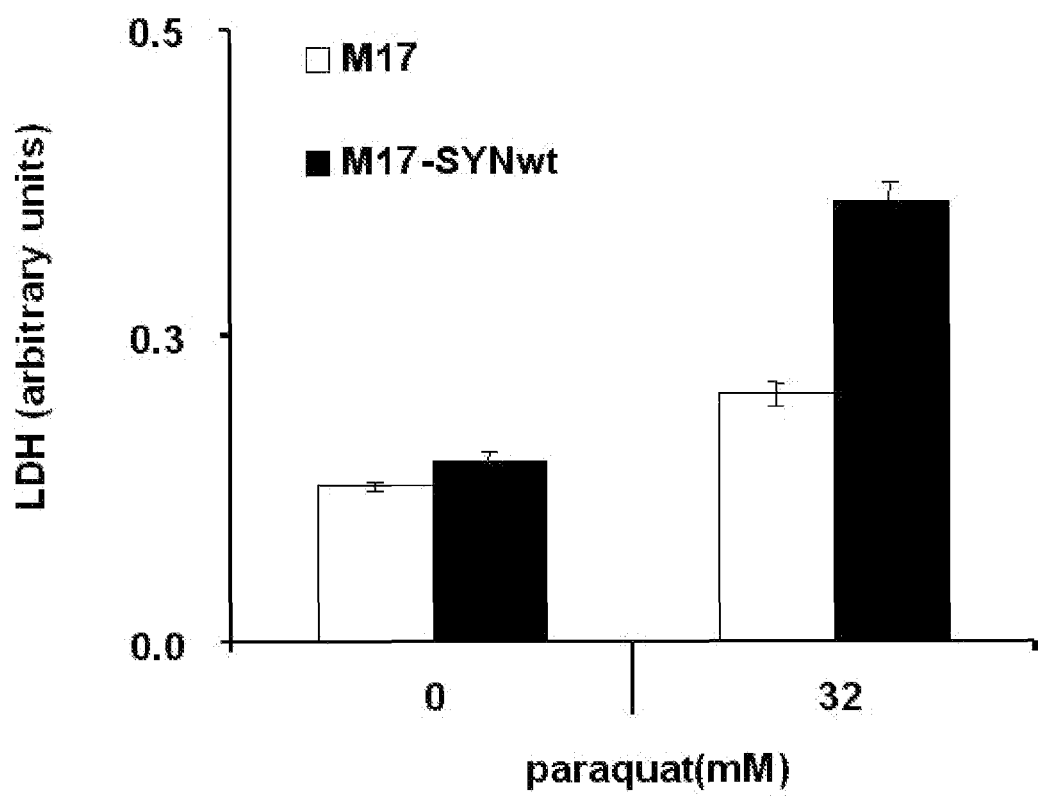
FIG. 2 shows the sensitivity of an α-synuclein expressing neuroblastoma cell line to paraquat.

FIG. 2 shows that treatment of M17-SYNwt cells, but not of M17 cells with paraquat led to a relatively high level of LDH leaked into the medium demonstrating that α-synuclein mediates cellular degeneration or cell death in response to paraquat.

Example 201

Use of the α-Synuclein Expressing Cells in Screening Compounds

This α-synuclein expressing neuroblastoma cells make it possible to assess the ability of novel compounds to counteract α-synuclein cytotoxicity. Active inhibitors of α-synuclein cytotoxicity are found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be used as a medicament to patients in need. A compound is considered to be active in this test when it inhibits α-synuclein cytotoxicity by more than 25% relative to untreated M17-SYNwt cells at a concentration of 20 µg/mL or lower. In the experiments, the control group consists of M17-SYNwt cells treated with DMSO, the untreated paraquat group consists of M17-SYNwt cells treated with paraquat and DMSO, and the treated paraquat group consists of M17-SYNwt cells to be treated with paraquat and the test compound dissolved in DMSO.

In order to determine $EC_{50}$ compounds are tested at different concentrations ranging from non-effective (thus at a relatively low concentration) to an effective (relatively high) concentration of test compound. These data are also used for calculation of percent inhibition (% I). Percent inhibition is calculated as the synuclein toxicity inhibition by the compound in treated paraquat cells, relative to the synuclein cytotoxicity in untreated paraquat cells. This corresponds to the following equation:

(LDH release of treated paraquat cells at non-effective concentration of test cmpd)−(LDH release of treated paraquat cells at most effective concentration of test cmpd)/(LDH release of untreated paraquat cells)−(LDH release control cells) *100%

Example 202

Inhibition of Synuclein-Mediated Toxicity

The compounds are screened for activity using the α-synuclein cytotoxicity assay as described above. Dose responses are carried out on all compounds found to be active (10 point curves in duplicate). Although the pharmacological properties of the compounds disclosed in this invention vary with structural change, active compounds most particularly possess $EC_{50}$ in a cell-based assay of synuclein cytotoxicity in a range from about 0.0001 to 10 μM.

Example 203

In Vivo Inhibition of Synuclein-Mediated Instigated Loss of Substantia Nigra Neurons In order to model neuronal loss in the substantia nigra region of the brain, mice are treated with paraquat (intraperitoneal) at a dose not higher than 8 mg/kg/day for a continuous period of 15-100 days. These mice are also chronically co-treated during that period with a compound from table 1 administered at a dose not higher than 20 mg/kg body weight/day), or by vehicle only (no active compound). Mice treatment by means of vehicle or a compound of the invention start 2 days before administration of paraquat.

At the end of the treatment period, mice are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains are detected. Quantitative and comparative analysis of the tyrosin hydroxylase-positive stained substantia nigra areas reveal a significantly larger TH-positive area in mice treated with compound versus vehicle treated mice.

Example 204

In Vivo Inhibition of 6-Hydroxydopamine (6-OHDA) Instigated Loss of Substantia Nigra Neurons Unilateral substantia nigra lesions are obtained by stereotactic striatal injections of 6-hydroxydopamine in brains of living rats as described by Vercammen et al. in *Molecular Therapy*, 14 (5) 716-723 (2006). These rats are also chronically co-treated with a compound of table 1 and at the same dose as mentioned in example 203 or by vehicle only (no active compound). Daily treatment of compound or vehicle is started preferably 1 or 2 days before administration of 6-OHDA and lasts between 7 to 30 days after the 6-OHDA injection.

At the end of the treatment period, rats are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains are detected. The nigral lesion volumes and/or the tyrosine hydroxylase positive cell numbers are quantified as described in Vercammen et al. (cited supra). This analysis reveals that:

the nigral lesion volumes are significantly reduced in rats treated with a compound according to this invention, as compared to vehicle treated rats, thus indicating that the compound is able to inhibit 6-OHDA triggered degeneration of substantia nigra cells in vivo; and tyrosine hydroxylase positive cell numbers are higher in rats treated with a compound according to this invention as compared to vehicle treated rats, thus providing confirmation that the compound is able to inhibit 6-OHDA triggered degeneration of substantia nigra cells in vivo.

Example 205

In Vitro Inhibition of α-Synuclein Aggregation

α-synucleinopathies are characterised by aggregation of α-synuclein in neurons. Aggregation of purified α-synuclein is performed essentially as described by Gerard et al. *FASEB*. 20(3):524-6 (2006). 20-100 μg purified α-synuclein (Sigma; S7820) at a concentration of about 2.5 μg/mL is incubated in the presence of spermin (250 μM) or paraquat (32 mM) or 6-hydroxydopamine (400 μM) or vehicle in a 384 well plate. Spermin, paraquat and 6-hydroxydopamine promote the α-synuclein aggregation process. Aggregation kinetics is determined by measuring turbidity at 340 nm, every 1-15 minutes for at least one hour. The same compounds, or vehicle only, is added to the different α-synuclein mixtures described above. This analysis reveals that, when a compound is present, the measured turbidity is lower compared to reactions containing vehicle only. This finding shows that the compound is able to inhibit aggregation of α-synuclein.

Exemplary compounds of the present invention are shown in table 2, with their chemical name and their $EC_{50}$ value (expressed in nM) as determined from example 196 in the Tau-induced toxicity experiment.

TABLE 2

| Compound code | Chemical name | EC50 (TAU assay) in nM |
|---|---|---|
| D1 | N-(2-(5-chloro-1H-indol-3-yl)ethyl)-5-(3-methoxybenzyl)isoxazole-3-carboxamide | 2 |

TABLE 2-continued

| Compound code | Chemical name | EC50 (TAU assay) in nM |
|---|---|---|
| D2 | N-(2-(5-chloro-1H-indol-3-yl)ethyl)-5-cyclopentylisoxazole-3-carboxamide | 3 |
| D3 | N-(2-(5-chloro-1H-indol-3-yl)ethyl)-5-(3-cyanobenzyl)isoxazole-3-carboxamide | 6 |
| D4 | N-(2-(5-chloro-1H-indol-3-yl)ethyl)-5-(4-cyanobenzyl)isoxazole-3-carboxamide | 9 |
| D5 | N-(2-(5-chloro-1H-indol-3-yl)ethyl)-5-(2,5-difluorobenzyl)isoxazole-3-carboxamide | 12 |
| D6 | N-(2-(5-chloro-1H-indol-3-yl)ethyl)-5-cyclopropylisoxazole-3-carboxamide | 13 |
| D7 | 5-benzyl-N-(2-(5-chloro-1H-indol-3-yl)ethyl)isoxazole-3-carboxamide | 15 |
| D8 | N-(2-(5-chloro-1H-indol-3-yl)ethyl)-5-(2-methoxybenzyl)isoxazole-3-carboxamide | 16 |
| D9 | N-(2-(5-chloro-1H-indol-3-yl)ethyl)-5-(4-(trifluoromethyl)benzyl)isoxazole-3-carboxamide | 16 |
| D10 | N-(2-(5-chloro-1H-indol-3-yl)ethyl)-5-(4-methoxybenzyl)isoxazole-3-carboxamide | 17 |
| D11 | N-(2-(5-chloro-1H-indol-3-yl)ethyl)-5-(furan-2-yl)isoxazole-3-carboxamide | 17 |
| D12 | N-(2-(5-chloro-1H-indol-3-yl)ethyl)-5-(4-methylbenzyl)isoxazole-3-carboxamide | 17 |
| D13 | N-(2-(5-chloro-1H-indol-3-yl)ethyl)-5-cyclohexylisoxazole-3-carboxamide | 18 |
| D14 | 5-(3-fluorobenzyl)-N-(2-(5-methyl-1H-indol-3-yl)ethyl)isoxazole-3-carboxamide | 19 |
| D15 | N-(2-(5-chloro-1H-indol-3-yl)ethyl)-1-methyl-5-(thiophen-2-yl)-1H-pyrazole-3-carboxamide | 21 |
| D16 | N-(2-(5-chloro-1H-indol-3-yl)ethyl)-5-(thiophen-2-yl)isoxazole-3-carboxamide | 21 |
| D17 | N-(2-(5-chloro-1H-indol-3-yl)ethyl)-5-(furan-2-ylmethyl)isoxazole-3-carboxamide | 22 |
| D19 | N-(2-(5-chloro-1H-indol-3-yl)ethyl)-5-(furan-2-yl)-1-methyl-1H-pyrazole-3-carboxamide | 23 |
| D20 | N-(2-(5-chloro-1H-indol-3-yl)ethyl)-5-(3-methylbenzyl)isoxazole-3-carboxamide | 23 |
| D21 | N-(2-(5-chloro-1H-indol-3-yl)ethyl)-5-(2-fluoro-3-methoxybenzyl)isoxazole-3-carboxamide | 25 |
| D22 | N-(2-(5-chloro-1H-indol-3-yl)ethyl)-5-(furan-3-ylmethyl)isoxazole-3-carboxamide | 28 |
| D23 | N-(2-(5-chloro-1H-indol-3-yl)ethyl)-5-(3-fluorobenzyl)isoxazole-3-carboxamide | 30 |
| D24 | N-(2-(1H-indol-3-yl)ethyl)-4-methyl-2-p-tolylthiazole-5-carboxamide | 34 |
| D25 | N-(2-(5-chloro-1H-indol-3-yl)ethyl)-5-(thiophen-3-ylmethyl)isoxazole-3-carboxamide | 35 |
| D26 | N-(2-(5-chloro-1H-indol-3-yl)ethyl)-1-methyl-5-phenyl-1H-pyrazole-3-carboxamide | 38 |
| D27 | N-(2-(5-chloro-1H-indol-3-yl)ethyl)-5-(thiophen-2-ylmethyl)isoxazole-3-carboxamide | 38 |
| D28 | N-(2-(5-fluoro-1H-indol-3-yl)ethyl)-5-(3-fluorobenzyl)isoxazole-3-carboxamide | 41 |
| D29 | tert-butyl 3-(2-(5-chloro-1H-indol-3-yl)ethylcarbamoyl)isoxazol-5-ylcarbamate | 42 |
| D30 | N-(2-(5-chloro-1H-indol-3-yl)ethyl)-5-(3-(trifluoromethyl)benzyl)isoxazole-3-carboxamide | 42 |
| D31 | N-(2-(1H-indol-3-yl)ethyl)-5-(3-fluorobenzyl)isoxazole-3-carboxamide | 44 |
| D32 | N-(2-(5-methoxy-1H-indol-3-yl)ethyl)-4-methyl-2-p-tolylthiazole-5-carboxamide | 50 |
| D33 | N-(2-(1H-indol-3-yl)ethyl)-4-methyl-2-(2-propylpyridin-4-yl)thiazole-5-carboxamide | 56 |
| D34 | N-((5-chloro-1H-indol-3-yl)methyl)-5-(3-fluorobenzyl)isoxazole-3-carboxamide | 59 |
| D35 | N-(3-(5-chloro-1H-indol-3-yl)propyl)-5-(3-fluorobenzyl)isoxazole-3-carboxamide | 60 |
| D36 | N-(2-(5-chloro-1H-indol-3-yl)ethyl)-5-phenylisoxazole-3-carboxamide | 61 |
| D37 | N-(2-(5-fluoro-1H-indol-3-yl)ethyl)-4-methyl-2-p-tolylthiazole-5-carboxamide | 61 |
| D38 | N-(2-(5-chloro-1H-indol-3-yl)ethyl)-5-(2,3-dihydrobenzo[b][1,4]dioxin-5-yl)isoxazole-3-carboxamide | 80 |
| D39 | N-(2-(1H-indol-3-yl)ethyl)-4-methyl-2-(phenethylamino)thiazole-5-carboxamide | 87 |

TABLE 2-continued

| Compound code | Chemical name | EC50 (TAU assay) in nM |
|---|---|---|
| D40 | N-(2-(5-chloro-1H-indol-3-yl)ethyl)-1-(4-ethylphenyl)-2-oxopyrrolidine-3-carboxamide | 91 |
| D41 | N-(2-(5-chloro-1H-indol-3-yl)ethyl)-5-(pyridin-4-ylmethyl)isoxazole-3-carboxamide | 91 |
| D42 | 5-((1H-pyrazol-1-yl)methyl)-N-(2-(5-chloro-1H-indol-3-yl)ethyl)isoxazole-3-carboxamide | 92 |
| D43 | 5-benzyl-N-(2-(5-chloro-1H-indol-3-yl)ethyl)-4,5-dihydroisoxazole-3-carboxamide | 94 |
| D44 | N-(2-(5-chloro-1H-indol-3-yl)ethyl)-1-cyclohexyl-1H-1,2,3-triazole-4-carboxamide | 108 |
| D45 | N-(2-(5-chloro-1H-indol-3-yl)ethyl)-4-methyl-2-p-tolylthiazole-5-carboxamide | 113 |
| D46 | N-(2-(5-chloro-1H-indol-3-yl)ethyl)-4-methyl-2-phenylthiazole-5-carboxamide | 123 |
| D47 | N-(2-(6-fluoro-1H-indol-3-yl)ethyl)-5-(3-fluorobenzyl)isoxazole-3-carboxamide | 132 |
| D48 | 1-(4-ethylphenyl)-N-(2-(5-methyl-1H-indol-3-yl)ethyl)-2-oxopyrrolidine-3-carboxamide | 138 |
| D49 | N-(2-(5-chloro-1H-indol-3-yl)ethyl)-5-(4-methoxyphenyl)isoxazole-3-carboxamide | 140 |
| D50 | N-(2-(5-chloro-1H-indol-3-yl)ethyl)-3-phenyl-4,5-dihydroisoxazole-5-carboxamide | 151 |
| D51 | N-(2-(5-chloro-1-methyl-1H-indol-3-yl)ethyl)-5-(3-fluorobenzyl)isoxazole-3-carboxamide | 157 |
| D52 | N-(2-(5-chloro-1H-indol-3-yl)ethyl)-5-phenyl-1,3,4-oxadiazole-2-carboxamide | 158 |
| D53 | N-(2-(5-chloro-1H-indol-3-yl)ethyl)-5-phenyloxazole-2-carboxamide | 171 |
| D54 | 1-benzyl-N-(2-(5-chloro-1H-indol-3-yl)ethyl)-1H-1,2,3-triazole-4-carboxamide | 173 |
| D55 | N-(2-(5-chloro-1H-indol-3-yl)ethyl)-5-phenyl-4,5-dihydroisoxazole-3-carboxamide | 189 |
| D56 | N-(2-(5-chloro-1H-indol-3-yl)ethyl)-5-(4-chlorophenyl)isoxazole-3-carboxamide | 190 |
| D57 | N-(2-(5-chloro-1H-indol-3-yl)ethyl)-5-p-tolylisoxazole-3-carboxamide | 195 |
| D58 | (R)-N-(2-(5-chloro-1H-indol-3-yl)ethyl)-4-cyclohexyl-4,5-dihydrooxazole-2-carboxamide | 202 |
| D59 | (S)-N-(2-(5-chloro-1H-indol-3-yl)ethyl)-4-cyclohexyl-4,5-dihydrooxazole-2-carboxamide | 211 |
| D60 | 5-benzyl-N-(2-(5-chloro-1H-indol-3-yl)ethyl)-1,3,4-oxadiazole-2-carboxamide | 213 |
| D61 | N-(2-(5-chloro-1H-indol-3-yl)ethyl)-5-(pyrrolidin-1-ylmethyl)isoxazole-3-carboxamide | 227 |
| D62 | N-(2-(5-chloro-1H-indol-3-yl)ethyl)-5-methyl-2-phenyloxazole-4-carboxamide | 237 |
| D63 | N-(2-(5-chloro-1H-indol-3-yl)ethyl)-3-phenylpyrrolidine-1-carboxamide | 304 |
| D64 | N-(2-(5-chloro-1H-indol-3-yl)ethyl)-2-oxo-1-phenylpyrrolidine-3-carboxamide | 313 |
| D65 | N-(2-(5-chloro-1H-indol-3-yl)ethyl)-1-(3-fluorophenyl)-2-oxopyrrolidine-3-carboxamide | 321 |
| D66 | N-(2-(5-chloro-1H-indol-3-yl)ethyl)-5-((ethylamino)methyl)isoxazole-3-carboxamide | 327 |
| D67 | N-(2-(5-chloro-1H-indol-3-yl)ethyl)-2-phenylthiazole-4-carboxamide | 333 |
| D68 | N-(2-(5-chloro-1H-indol-3-yl)ethyl)-5-(4-chlorophenyl)-2-(trifluoromethyl)furan-3-carboxamide | 337 |
| D69 | 3-benzyl-N-(2-(5-chloro-1H-indol-3-yl)ethyl)imidazolidine-1-carboxamide | 357 |
| D70 | N-(2-(5-chloro-1H-indol-3-yl)ethyl)-1-(4-methoxyphenyl)-2-oxopyrrolidine-3-carboxamide | 408 |
| D71 | N-(2-(5-chloro-1H-indol-3-yl)ethyl)-1-(4-isopropylphenyl)-2-oxopyrrolidine-3-carboxamide | 413 |
| D72 | N-(2-(1H-indol-3-yl)ethyl)-1-cyclopropyl-2,5-dimethyl-1H-pyrrole-3-carboxamide | 453 |
| D73 | N-(2-(5-chloro-1H-indol-3-yl)ethyl)-4-methyl-2-(pyrazin-2-yl)thiazole-5-carboxamide | 515 |
| D74 | 5-(3-fluorobenzyl)-N-(2-(6-methoxy-1H-indol-3-yl)ethyl)isoxazole-3-carboxamide | 534 |
| D75 | 3-benzyl-N-(2-(5-chloro-1H-indol-3-yl)ethyl)pyrrolidine-1-carboxamide | 534 |
| D76 | N-(2-(5-chloro-1H-indol-3-yl)ethyl)-1-cyclohexyl-2-oxopyrrolidine-3-carboxamide | 571 |

TABLE 2-continued

| Compound code | Chemical name | EC50 (TAU assay) in nM |
|---|---|---|
| D77 | N-(2-(5-chloro-1H-indol-3-yl)ethyl)-5-cyclohexyl-1,3,4-oxadiazole-2-carboxamide | 595 |
| D78 | N-(2-(5-chloro-1H-indol-3-yl)ethyl)-1-(4-fluorophenyl)-2-oxopyrrolidine-3-carboxamide | 691 |
| D79 | N-(2-(5-chloro-1H-indol-3-yl)ethyl)-1-(2-fluorophenyl)-2-oxopyrrolidine-3-carboxamide | 857 |
| D80 | (S)-4-benzyl-N-(2-(5-chloro-1H-indol-3-yl)ethyl)-4,5-dihydrooxazole-2-carboxamide | 915 |
| D81 | (R)-4-benzyl-N-(2-(5-chloro-1H-indol-3-yl)ethyl)-4,5-dihydrooxazole-2-carboxamide | 917 |
| D82 | N-(2-(5-chloro-1H-indol-3-yl)ethyl)-1-(3-ethylphenyl)-2-oxopyrrolidine-3-carboxamide | 939 |
| D83 | N-(2-(5-chloro-1H-indol-3-yl)ethyl)-4-phenyl-4,5-dihydrooxazole-2-carboxamide | 979 |
| D109 | N-(2-(5-methoxy-1H-indol-3-yl)ethyl)-5-methyl-3-phenylisoxazole-4-carboxamide | 3112 |
| D110 | N-(2-(1H-indol-3-yl)ethyl)-2-(p-tolylamino)thiazole-4-carboxamide | 274 |
| D111 | N-(2-(5-chloro-1H-indol-3-yl)ethyl)-5-methyl-3-phenylisoxazole-4-carboxamide | 582 |
| D112 | N-(2-(5-chloro-1H-indol-3-yl)ethyl)-4-methyloxazole-5-carboxamide | 1254 |
| D114 | N-(2-(5-chloro-1H-indol-3-yl)ethyl)-5-methylisoxazole-3-carboxamide | 30 |
| D115 | N-(2-(5-chloro-1H-indol-3-yl)ethyl)-3-methyl-5-phenylisoxazole-4-carboxamide | 269 |
| D116 | N-(2-(5-chloro-1H-indol-3-yl)ethyl)-2,5-dimethyloxazole-4-carboxamide | 306 |
| D117 | N-(2-(5-chloro-1H-indol-3-yl)ethyl)-1-phenyl-1H-pyrazole-5-carboxamide | 979 |
| D118 | N-(2-(5-chloro-1H-indol-3-yl)ethyl)-1-methyl-1H-pyrazole-3-carboxamide | 332 |
| D119 | N-(2-(5-chloro-1H-indol-3-yl)ethyl)-1-methyl-1H-pyrazole-5-carboxamide | 1026 |
| D120 | 1-benzyl-3-tert-butyl-N-(2-(5-chloro-1H-indol-3-yl)ethyl)-1H-pyrazole-5-carboxamide | 868 |
| D121 | N-(2-(5-chloro-1H-indol-3-yl)ethyl)-5-(hydroxymethyl)isoxazole-3-carboxamide | 105 |
| D123 | N-(2-(5-chloro-1H-indol-3-yl)ethyl)-5-(ethoxymethyl)isoxazole-3-carboxamide | 19 |
| D124 | N-(2-(5-chloro-1H-indol-3-yl)ethyl)-5-(dimethylamino)isoxazole-3-carboxamide | 5291 |
| D125 | N-(2-(5-chloro-1H-indol-3-yl)ethyl)-5-((diethylamino)methyl)isoxazole-3-carboxamide | 347 |
| D126 | 1-(3-benzylimidazolidin-1-yl)-3-(5-chloro-1H-indol-3-yl)propan-1-one | 357 |
| D127 | N-(2-(5-chloro-1H-pyrrolo[2,3-b]pyridin-3-yl)ethyl)-5-(2,5-difluorobenzoyl)isoxazole-3-carboxamide | 436 |
| D128 | N-(2-(5-chloro-1H-pyrrolo[2,3-b]pyridin-3-yl)ethyl)-5-(2,5-difluorobenzyl)isoxazole-3-carboxamide | 105 |
| D129 | N-(2-(5-chloro-1H-indol-3-yl)ethyl)-5-(3,4-difluorobenzyl)isoxazole-3-carboxamide | 8 |
| D130 | N-(2-(5-chloro-1H-indol-3-yl)ethyl)-5-(2,3-difluorobenzyl)isoxazole-3-carboxamide | 20 |
| D131 | N-(2-(5-chloro-1H-indol-3-yl)ethyl)-5-(3,5-difluorobenzyl)isoxazole-3-carboxamide | 13 |
| D132 | N-(2-(5-chloro-1H-indol-3-yl)ethyl)-2-oxo-1-(4-(trifluoromethyl)phenyl)pyrrolidine-3-carboxamide | 57 |
| D133 | N-(2-(5-chloro-1H-indol-3-yl)ethyl)-2-oxo-1-p-tolylpyrrolidine-3-carboxamide | 46 |
| D134 | 1-(4-acetylphenyl)-N-(2-(5-chloro-1H-indol-3-yl)ethyl)-2-oxopyrrolidine-3-carboxamide | 86 |
| D135 | 5-(2,5-difluorobenzyl)-N-(2-(5-(trifluoromethyl)-1H-indol-3-yl)ethyl)isoxazole-3-carboxamide | 144 |
| D136 | N-(2-(6-chloro-5-methyl-1H-indol-3-yl)ethyl)-5-(2,5-difluorobenzyl)isoxazole-3-carboxamide | 741 |
| D137 | N-(2-(5-cyano-1H-indol-3-yl)ethyl)-5-(2,5-difluorobenzyl)isoxazole-3-carboxamide | 32 |
| D138 | (4-(1H-indol-3-yl)piperidin-1-yl)(5-(2,5-difluorobenzyl)isoxazol-3-yl)methanone | 418 |
| D139 | (4-(5-chloro-1H-indol-3-yl)piperidin-1-yl)(5-(2,5-difluorobenzyl)isoxazol-3-yl)methanone | 186 |
| D140 | 5-(2,5-difluorobenzyl)-N-(2-(5-phenyl-1H-indol-3-yl)ethyl)isoxazole-3-carboxamide | 316 |

TABLE 2-continued

| Compound code | Chemical name | EC50 (TAU assay) in nM |
|---|---|---|
| D141 | N-(2-(5-chloro-7-fluoro-1H-indol-3-yl)ethyl)-5-(2,5-difluorobenzyl)isoxazole-3-carboxamide | 233 |
| D142 | N-(2-(5-chloro-1H-indol-3-yl)ethyl)-1-(4-chloro-3-fluorophenyl)-2-oxopyrrolidine-3-carboxamide | 561 |
| D143 | N-(2-(5-chloro-1H-indol-3-yl)ethyl)-1-(3,4-dimethylphenyl)-2-oxopyrrolidine-3-carboxamide | 1024 |
| D145 | N-(2-(5-chloro-1H-indol-3-yl)ethyl)-1-(2,3-dihydro-1H-inden-5-yl)-2-oxopyrrolidine-3-carboxamide | 137 |
| D146 | N-(2-(5-chloro-1H-indol-3-yl)ethyl)-1-(1,3-dihydroisobenzofuran-5-yl)-2-oxopyrrolidine-3-carboxamide | 1165 |
| D147 | N-(2-(5-chloro-1H-indol-3-yl)ethyl)-1-(3-fluoro-4-methoxyphenyl)-2-oxopyrrolidine-3-carboxamide | 379 |
| D148 | N-(2-(5-chloro-1H-indol-3-yl)ethyl)-1-(3,4-difluorophenyl)-2-oxopyrrolidine-3-carboxamide | 691 |
| D149 | N-(2-(5-chloro-1H-indol-3-yl)ethyl)-1-cyclopropyl-2-oxopyrrolidine-3-carboxamide | 2088 |
| D150 | N-(2-(5-chloro-1H-indol-3-yl)ethyl)-1-(3-fluoro-4-(trifluoromethyl)phenyl)-2-oxopyrrolidine-3-carboxamide | 23310 |
| D151 | N-(2-(5-chloro-1H-indol-3-yl)ethyl)-1-(2,6-difluorophenyl)-2-oxopyrrolidine-3-carboxamide | 561 |
| D152 | N-(2-(5-chloro-1H-indol-3-yl)ethyl)-1-(3-fluoro-4-methylphenyl)-2-oxopyrrolidine-3-carboxamide | 99 |
| D153 | N-(2-(5-chloro-1H-indol-3-yl)ethyl)-1-(4-chlorophenyl)-2-oxopyrrolidine-3-carboxamide | 365 |
| D155 | 1-(3-(1H-pyrrol-1-yl)phenyl)-N-(2-(5-chloro-1H-indol-3-yl)ethyl)-2-oxopyrrolidine-3-carboxamide | 1370 |
| D156 | N-(2-(5-chloro-1H-indol-3-yl)ethyl)-2-oxo-1-(1-phenylethyl)pyrrolidine-3-carboxamide | Fraction A: 819 Fraction B: 1180 |
| D157 | N-(2-(5-chloro-1H-indol-3-yl)ethyl)-1-(2-ethylphenyl)-2-oxopyrrolidine-3-carboxamide | 1213 |
| D158 | N-(2-(5-chloro-1H-indol-3-yl)ethyl)-2-oxo-1-o-tolylpyrrolidine-3-carboxamide | 1031 |
| D159 | N-(2-(5-chloro-1H-indol-3-yl)ethyl)-2-oxo-1-m-tolylpyrrolidine-3-carboxamide | 900 |
| D160 | N-(2-(5-chloro-1H-indol-3-yl)ethyl)-1-(1-methyl-1H-pyrazol-3-yl)-2-oxopyrrolidine-3-carboxamide | 1041 |
| D162 | N-(2-(5-chloro-1H-indol-3-yl)ethyl)-1-(3-methoxyphenyl)-2-oxopyrrolidine-3-carboxamide | 233 |
| D163 | N-(2-(5-chloro-1H-indol-3-yl)ethyl)-1-(2-methoxyphenyl)-2-oxopyrrolidine-3-carboxamide | 1859 |
| D164 | N-(2-(5-chloro-1H-indol-3-yl)ethyl)-1-(cyclohexylmethyl)-2-oxopyrrolidine-3-carboxamide | 320 |
| D165 | N-(2-(5-chloro-1H-indol-3-yl)ethyl)-1-p-tolylpyrrolidine-3-carboxamide | 188 |
| D166 | N-(2-(1H-indazol-3-yl)ethyl)-5-(2,5-difluorobenzyl)isoxazole-3-carboxamide | 631 |
| D167 | N-(2-(5-chloro-1H-indol-3-yl)ethyl)-1-(1-methyl-1H-indol-5-yl)-2-oxopyrrolidine-3-carboxamide | 506 |
| D168 | 5-benzyl-N-(2-(5-chloro-1H-indol-3-yl)ethyl)-1,2,4-oxadiazole-3-carboxamide | 77 |
| D169 | N-(2-(5-chloro-1H-indol-3-yl)ethyl)-5-(3-fluorobenzyl)-1,2,4-oxadiazole-3-carboxamide | 26 |
| D170 | N-(2-(5-chloro-1H-indol-3-yl)ethyl)-5-(2-fluorobenzyl)-1,2,4-oxadiazole-3-carboxamide | 45 |
| D171 | N-(2-(5-chloro-1H-indol-3-yl)ethyl)-5-(4-fluorobenzyl)-1,2,4-oxadiazole-3-carboxamide | 32 |
| D172 | N-(2-(5-chloro-1H-indol-3-yl)ethyl)-5-(4-chlorobenzyl)-1,2,4-oxadiazole-3-carboxamide | 34 |
| D173 | N-(2-(5-chloro-1H-indol-3-yl)ethyl)-5-(4-methoxybenzyl)-1,2,4-oxadiazole-3-carboxamide | 60 |
| D174 | N-(2-(5-chloro-1H-indol-3-yl)ethyl)-5-(3,4-dichlorobenzyl)-1,2,4-oxadiazole-3-carboxamide | 282 |
| D175 | N-(2-(5-chloro-1H-indol-3-yl)ethyl)-5-(4-chloro-3-fluorobenzyl)-1,2,4-oxadiazole-3-carboxamide | 94 |
| D176 | 5-(4-tert-butylbenzyl)-N-(2-(5-chloro-1H-indol-3-yl)ethyl)-1,2,4-oxadiazole-3-carboxamide | 100 |
| D177 | N-(2-(5-chloro-1H-indol-3-yl)ethyl)-5-(3-methoxybenzyl)-1,2,4-oxadiazole-3-carboxamide | 29 |
| D178 | N-(2-(5-chloro-1H-indol-3-yl)ethyl)-5-(3,4-dimethoxybenzyl)-1,2,4-oxadiazole-3-carboxamide | 125 |
| D179 | N-(2-(5-chloro-1H-indol-3-yl)ethyl)-5-(2,5-dimethoxybenzyl)-1,2,4-oxadiazole-3-carboxamide | 51 |

TABLE 2-continued

| Compound code | Chemical name | EC50 (TAU assay) in nM |
|---|---|---|
| D180 | N-(2-(5-chloro-1H-indol-3-yl)ethyl)-5-(thiophen-2-ylmethyl)-1,2,4-oxadiazole-3-carboxamide | 103 |
| D181 | N-(2-(5-chloro-1H-indol-3-yl)ethyl)-5-(4-methylbenzyl)-1,2,4-oxadiazole-3-carboxamide | 48 |
| D182 | N-(2-(5-chloro-1H-indol-3-yl)ethyl)-5-(3,5-difluorobenzyl)-1,2,4-oxadiazole-3-carboxamide | 11 |
| D183 | N-(2-(5-chloro-1H-indol-3-yl)ethyl)-5-(2-methoxybenzyl)-1,2,4-oxadiazole-3-carboxamide | 47 |
| D184 | N-(2-(5-chloro-1H-indol-3-yl)ethyl)-5-(3-methylbenzyl)-1,2,4-oxadiazole-3-carboxamide | 26 |
| D185 | N-(2-(5-chloro-1H-indol-3-yl)ethyl)-5-(4-(trifluoromethoxy)benzyl)-1,2,4-oxadiazole-3-carboxamide | 42 |
| D186 | N-(2-(5-chloro-1H-indol-3-yl)ethyl)-5-(3-(trifluoromethyl)benzyl)-1,2,4-oxadiazole-3-carboxamide | 119 |
| D187 | N-(2-(5-chloro-1H-indol-3-yl)ethyl)-5-(4-(trifluoromethyl)benzyl)-1,2,4-oxadiazole-3-carboxamide | 32 |
| D188 | N-(2-(5-chloro-1H-indol-3-yl)ethyl)-5-(2,6-difluorobenzyl)-1,2,4-oxadiazole-3-carboxamide | 41 |
| D189 | N-(2-(5-chloro-1H-indol-3-yl)ethyl)-5-(2,4-difluorobenzyl)-1,2,4-oxadiazole-3-carboxamide | 15 |
| D190 | N-(2-(5-chloro-1H-indol-3-yl)ethyl)-5-(3-chlorobenzyl)-1,2,4-oxadiazole-3-carboxamide | 25 |
| D191 | N-(2-(5-chloro-1H-indol-3-yl)ethyl)-5-(2-chlorobenzyl)-1,2,4-oxadiazole-3-carboxamide | 25 |
| D192 | N-(2-(5-chloro-1H-indol-3-yl)ethyl)-5-(2-methylbenzyl)-1,2,4-oxadiazole-3-carboxamide | 53 |
| D193 | N-(2-(5-chloro-1H-indol-3-yl)ethyl)-5-(thiophen-3-ylmethyl)-1,2,4-oxadiazole-3-carboxamide | 49 |
| D194 | N-(2-(5-chloro-1H-indol-3-yl)ethyl)-5-(2,5-difluorobenzoyl)isoxazole-3-carboxamide | 113 |
| D195 | N-(2-(5-chloro-1H-indol-3-yl)ethyl)-5-(hydroxy(phenyl)methyl)isoxazole-3-carboxamide | 101 |
| D216 | N-(2-(5-chloro-1H-indol-3-yl)ethyl)-5-(ethoxymethyl)-4,5-dihydroisoxazole-3-carboxamide | 77 |

The invention claimed is:

1. A compound of structural formula (A5), or a stereoisomer, enantiomer, or tautomer thereof,

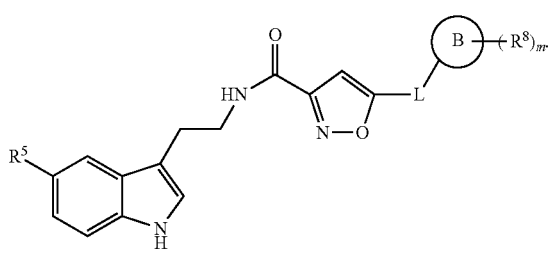

(A5)

wherein, $R^5$ is selected from the group consisting of halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

L is a single bond or is independently selected from the group consisting of —O—; —NH—; —NR$^{10}$—; C$_{1-6}$alkylene; C$_{1-6}$alkenylene; and C$_{1-6}$alkynylene, wherein each of said C$_{1-6}$alkylene, C$_{1-6}$alkenylene or C$_{1-6}$alkynylene optionally includes one or more heteroatoms, said heteroatoms being selected from the heteroatoms consisting of S and N, and wherein each of said C$_{1-6}$alkylene, C$_{1-6}$alkenylene or C$_{1-6}$alkynylene, can be unsubstituted or substituted; and wherein a carbon atom or heteroatom of said C$_{1-6}$alkylene, C$_{1-6}$alkenylene or C$_{1-6}$alkynylene, can be oxidized to form a C=O, C=S, N=O, N=S, S=O or S(O)$_2$;

B is cyclic structure selected from the group consisting of cycloalkyl; cycloalkenyl; cycloalkynyl; aryl; and heterocycle;

$R^8$ is independently selected from the group consisting of hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; and —C(O)R$^{11}$;

m is selected from the group consisting of 0; 1; 2; 3; 4 and 5;

each R$^{10}$ is independently selected from the group consisting of alkyl; alkenyl; alkynyl; aryl; heterocycle; arylalkylene; arylalkenylene; arylalkynylene; heterocycle-alkylene; heterocycle-alkenylene; and heterocycle-alkynylene;

each R$^{11}$ is independently selected from the group consisting of hydroxyl; alkyl; alkenyl; alkynyl; aryl; heterocycle; arylalkylene; arylalkenylene; arylalkynylene; heterocycle-alkylene; heterocycle-alkenylene; and heterocycle-alkynylene;

each $R^{12}$ and $R^{13}$ is independently selected from the group consisting of hydrogen; alkyl; alkenyl; alkynyl; aryl; heterocycle; arylalkylene; arylalkenylene; arylalkynylene; heterocycle-alkylene; heterocycle-alkenylene; and heterocycle-alkynylene;

or wherein $R^{12}$ and $R^{13}$ are taken together to form a 5-, 6-, or 7-membered unsubstituted or substituted heterocycle;

or a solvate, hydrate, salt or prodrug thereof, wherein the compound is not 3-isoxazolecarboxamide, 5-(4-chlorophenyl)-N-[2-(5-methyl-1H-indol-3-yl) ethyl]-.

2. The compound of claim 1, wherein L is an unsubstituted or substituted $C_{1-6}$alkylene, $C_{1-6}$alkenylene or $C_{1-6}$alkynylene and wherein the $C_{1-6}$alkylene, $C_{1-6}$alkenylene or $C_{1-6}$alkynylene includes one or more heteroatoms, heteroatoms being selected from the group consisting of S and N.

3. The compound of claim 1, wherein L is a $C_{1-6}$alkylene, $C_{1-6}$alkenylene or $C_{1-6}$alkynylene and wherein a carbon atom or heteroatom of the $C_{1-6}$alkylene, $C_{1-6}$alkenylene or $C_{1-6}$alkynylene, is oxidized to form a C=O, C=S, N=O, N=S, S=O or S(O)$_2$.

4. The compound of claim 1, wherein L is a single bond, or $C_{1-6}$alkylene optionally substituted by one or more substituents each independently selected from halogen; $C_{1-6}$alkyl; halo$C_{1-6}$alkyl; and halo$C_{1-6}$alkyloxy.

5. The compound of claim 1, wherein L is a single bond.

6. The compound of claim 1, wherein L is —CH$_2$—.

7. The compound of claim 1, wherein B is $C_{3-8}$cycloalkyl; $C_{6-10}$aryl or heterocycle; and $R^8$ is selected from hydrogen, halogen, cyano, $C_{1-6}$alkyl, $C_{1-6}$alkoxy, trifluoromethyl, trifluoromethoxy.

8. The compound of claim 1, wherein $R^8$ is selected from hydrogen; halogen; linear alkyl; linear alkenyl; linear alkynyl; —OH; —OR$^{10}$; —SH; —SR$^{10}$; trifluoromethyl; trifluoromethoxy; —NR$^{12}$R$^{13}$; -cyano.

9. The compound of claim 1, wherein $R^5$ is selected from halogen or $C_{1-6}$alkyl; B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazolyl, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; m is 0, 1, or 2; $R^8$ is independently selected from hydrogen; halogen; $C_{1-6}$alkyl; —OH; —OR$^{10}$; —SH; trifluoromethyl; trifluoromethoxy; nitro; —NR$^{12}$R$^{13}$; -cyano; —COOH; and L is $C_{1-6}$alkylene or a single bond.

10. The compound of claim 1, wherein $R^8$ is selected from hydrogen and halogen.

11. The compound of claim 1, wherein $R^5$ is halogen.

12. The compound of claim 1, wherein $R^5$ is chloro.

13. The compound of claim 1, wherein L is selected from the group consisting of —O—; —NH—; —NR$^{10}$—; $C_{1-6}$alkylene; $C_{1-6}$alkenylene; and $C_{1-6}$alkynylene, wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted; and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or S(O)$_2$.

14. The compound of claim 1 having structural formula (A6)

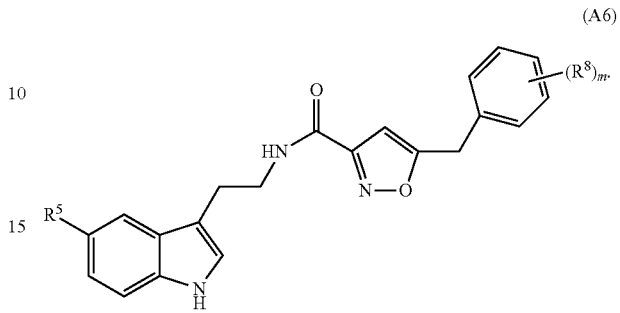

(A6)

15. The compound of claim 1, wherein said compound is selected from:

N-(2-(5-chloro-1H-indol-3-yl)ethyl)-5-(3-methoxybenzyl)isoxazole-3-carboxamide;

N-(2-(5-chloro-1H-indol-3-yl)ethyl)-5-cyclopentylisoxazole-3-carboxamide;

N-(2-(5-chloro-1H-indol-3-yl)ethyl)-5-(3-cyanobenzyl)isoxazole-3-carboxamide;

N-(2-(5-chloro-1H-indol-3-yl)ethyl)-5-(4-cyanobenzyl)isoxazole-3-carboxamide;

N-(2-(5-chloro-1H-indol-3-yl)ethyl)-5-(2,5-difluorobenzyl)isoxazole-3-carboxamide;

N-(2-(5-chloro-1H-indol-3-yl)ethyl)-5-cyclopropylisoxazole-3-carboxamide;

5-benzyl-N-(2-(5-chloro-1H-indol-3-yl)ethyl)isoxazole-3-carboxamide;

N-(2-(5-chloro-1H-indol-3-yl)ethyl)-5-(2-methoxybenzyl)isoxazole-3-carboxamide;

N-(2-(5-chloro-1H-indol-3-yl)ethyl)-5-(4-(trifluoromethyl)benzyl)isoxazole-3-carboxamide;

N-(2-(5-chloro-1H-indol-3-yl)ethyl)-5-(4-methoxybenzyl)isoxazole-3-carboxamide;

N-(2-(5-chloro-1H-indol-3-yl)ethyl)-5-(furan-2-yl)isoxazole-3-carboxamide;

N-(2-(5-chloro-1H-indol-3-yl)ethyl)-5-(4-methylbenzyl)isoxazole-3-carboxamide;

N-(2-(5-chloro-1H-indol-3-yl)ethyl)-5-cyclohexylisoxazole-3-carboxamide;

5-(3-fluorobenzyl)-N-(2-(5-methyl-1H-indol-3-yl)ethyl)isoxazole-3-carboxamide;

N-(2-(5-chloro-1H-indol-3-yl)ethyl)-5-(thiophen-2-yl)isoxazole-3-carboxamide;

N-(2-(5-chloro-1H-indol-3-yl)ethyl)-5-(furan-2-ylmethyl)isoxazole-3-carboxamide;

N-(2-(5-chloro-1H-indol-3-yl)ethyl)-5-(3-methylbenzyl)isoxazole-3-carboxamide;

N-(2-(5-chloro-1H-indol-3-yl)ethyl)-5-(2-fluoro-3-methoxybenzyl)isoxazole-3-carboxamide;

N-(2-(5-chloro-1H-indol-3-yl)ethyl)-5-(furan-3-ylmethyl)isoxazole-3-carboxamide;

N-(2-(5-chloro-1H-indol-3-yl)ethyl)-5-(3-fluorobenzyl)isoxazole-3-carboxamide;

N-(2-(5-chloro-1H-indol-3-yl)ethyl)-5-(thiophen-3-ylmethyl)isoxazole-3-carboxamide;

N-(2-(5-chloro-1H-indol-3-yl)ethyl)-5-(thiophen-2-ylmethyl)isoxazole-3-carboxamide;

N-(2-(5-fluoro-1H-indol-3-yl)ethyl)-5-(3-fluorobenzyl)isoxazole-3-carboxamide;
N-(2-(5-chloro-1H-indol-3-yl)ethyl)-5-(3-(trifluoromethyl)benzyl)isoxazole-3-carboxamide;
N-(2-(5-chloro-1H-indol-3-yl)ethyl)-5-phenylisoxazole-3-carboxamide;
N-(2-(5-chloro-1H-indol-3-yl)ethyl)-5-(2,3-dihydrobenzo[b][1,4]dioxin-5-yl)isoxazole-3-carboxamide;
N-(2-(5-chloro-1H-indol-3-yl)ethyl)-5-(pyridin-4-ylmethyl)isoxazole-3-carboxamide;
5-((1H-pyrazol-1-yl)methyl)-N-(2-(5-chloro-1H-indol-3-yl)ethyl)isoxazole-3-carboxamide;
N-(2-(5-chloro-1H-indol-3-yl)ethyl)-5-(4-methoxyphenyl)isoxazole-3-carboxamide;
N-(2-(5-chloro-1-methyl-1H-indol-3-yl)ethyl)-5-(3-fluorobenzyl)isoxazole-3-carboxamide;
N-(2-(5-chloro-1H-indol-3-yl)ethyl)-5-(4-chlorophenyl)isoxazole-3-carboxamide;
N-(2-(5-chloro-1H-indol-3-yl)ethyl)-5-p-tolylisoxazole-3-carboxamide;
N-(2-(5-chloro-1H-indol-3-yl)ethyl)-5-(pyrrolidin-1-ylmethyl)isoxazole-3-carboxamide;
5-(3-fluorobenzyl)-N-(2-(5-methoxy-1H-indol-3-yl)ethyl)isoxazole-3-carboxamide;
N-(2-(5-chloro-1H-indol-3-yl)ethyl)-5-(3,4-difluorobenzyl)isoxazole-3-carboxamide;
N-(2-(5-chloro-1H-indol-3-yl)ethyl)-5-(2,3-difluorobenzyl)isoxazole-3-carboxamide;
N-(2-(5-chloro-1H-indol-3-yl)ethyl)-5-(3,5-difluorobenzyl)isoxazole-3-carboxamide;
5-(2,5-difluorobenzyl)-N-(2-(5-(trifluoromethyl)-1H-indol-3-yl)ethyl)isoxazole-3-carboxamide;
N-(2-(5-cyano-1H-indol-3-yl)ethyl)-5-(2,5-difluorobenzyl)isoxazole-3-carboxamide;
5-(2,5-difluorobenzyl)-N-(2-(5-phenyl-1H-indol-3-yl)ethyl)isoxazole-3-carboxamide;
N-(2-(5-chloro-1H-indol-3-yl)ethyl)-5-(2,5-difluorobenzoyl)isoxazole-3-carboxamide;
N-(2-(5-chloro-1H-indol-3-yl)ethyl)-5-(hydroxy(phenyl)methyl)isoxazole-3-carboxamide;
N-(2-(5-chloro-1H-indol-3-yl)ethyl)-5-((2,5-difluorophenyl)difluoromethyl)isoxazole-3-carboxamide;
N-(2-(5-chloro-1H-indol-3-yl)ethyl)-5-((2,5-difluorophenyl)fluoromethyl)isoxazole-3-carboxamide;
N-(2-(5-bromo-1H-indol-3-yl)ethyl)-5-(2,5-difluorobenzyl)isoxazole-3-carboxamide; and
N-(2-(5-chloro-1H-indol-3-yl)ethyl)-5-((2,5-difluorophenyl)(hydroxy)methyl)isoxazole-3-carboxamide.

16. A pharmaceutical composition comprising one or more pharmaceutically acceptable excipients and a therapeutically effective amount of the compound of claim 1.

17. A method for treatment of Alzheimer's disease, Pick's disease, corticobasal degeneration, progressive supranuclear palsy, frontotemporal dementia or Parkinsonism (linked to chromosome 17, FTDP-17) in a subject, the method comprising:
administering to the subject an effective amount of the compound of claim 1.

18. A method for the treatment of Alzheimer's disease in a subject, the method comprising:
administering to the subject an effective amount of the compound of claim 1.

* * * * *